（12) United States Patent
Wells et al.

(10) Patent No.: US 11,767,515 B2
(45) Date of Patent: Sep. 26, 2023

(54) COLONIC ORGANOIDS AND METHODS OF MAKING AND USING SAME

(71) Applicant: Children's Hospital Medical Center, Cincinnati, OH (US)

(72) Inventors: James M. Wells, Cincinnati, OH (US); Jorge Orlando Munera, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 999 days.

(21) Appl. No.: 16/461,147

(22) PCT Filed: Dec. 5, 2017

(86) PCT No.: PCT/US2017/064600
§ 371 (c)(1),
(2) Date: May 15, 2019

(87) PCT Pub. No.: WO2018/106628
PCT Pub. Date: Jun. 14, 2018

(65) Prior Publication Data
US 2019/0367882 A1 Dec. 5, 2019

Related U.S. Application Data

(60) Provisional application No. 62/478,962, filed on Mar. 30, 2017, provisional application No. 62/429,948, filed on Dec. 5, 2016.

(51) Int. Cl.
*C12N 5/071* (2010.01)

(52) U.S. Cl.
CPC ........ *C12N 5/0679* (2013.01); *C12N 2501/11* (2013.01); *C12N 2501/113* (2013.01); *C12N 2501/115* (2013.01); *C12N 2501/117* (2013.01); *C12N 2501/119* (2013.01); *C12N 2501/155* (2013.01); *C12N 2501/415* (2013.01); *C12N 2506/02* (2013.01)

(58) Field of Classification Search
CPC .................................................. C12N 5/0679
See application file for complete search history.

(56) References Cited

U.S. PATENT DOCUMENTS

| 5,912,227 | A  | 6/1999  | Croom, Jr. et al. |
| 5,942,435 | A  | 8/1999  | Wheeler |
| 6,607,501 | B2 | 8/2003  | Gorsuch |
| 7,160,719 | B2 | 1/2007  | Nyberg |
| 7,291,626 | B1 | 11/2007 | Beachy et al. |
| 7,326,572 | B2 | 2/2008  | Fisk et al. |
| 7,510,876 | B2 | 3/2009  | D'Amour et al. |
| 7,514,185 | B2 | 4/2009  | Fukushima et al. |
| 7,541,185 | B2 | 6/2009  | D'Amour et al. |
| 7,625,753 | B2 | 12/2009 | Kelly et al. |
| 7,695,958 | B2 | 4/2010  | Funatsu et al. |
| 7,704,738 | B2 | 4/2010  | D'Amour et al. |
| 7,727,998 | B2 | 6/2010  | Moriya et al. |
| 7,776,592 | B2 | 8/2010  | Wandinger-Ness et al. |
| 7,927,869 | B2 | 4/2011  | Rosero |
| 7,985,585 | B2 | 7/2011  | D'Amour et al. |
| 7,993,916 | B2 | 8/2011  | Agulnick et al. |
| 8,187,878 | B2 | 5/2012  | Dalton et al. |
| 8,216,826 | B2 | 7/2012  | Lee et al. |
| 8,216,836 | B2 | 7/2012  | D'Amour et al. |
| 8,298,822 | B2 | 10/2012 | Kruse et al. |
| 8,318,492 | B2 | 11/2012 | Choo et al. |
| 8,501,476 | B2 | 8/2013  | Morgan et al. |
| 8,586,357 | B2 | 11/2013 | D'Amour et al. |
| 8,603,809 | B2 | 12/2013 | Kruse |
| 8,609,406 | B2 | 12/2013 | Subramanian et al. |
| 8,609,413 | B2 | 12/2013 | Suter et al. |
| 8,623,645 | B2 | 1/2014  | D'Amour et al. |
| 8,632,645 | B2 | 1/2014  | Daitou et al. |
| 8,633,024 | B2 | 1/2014  | D'Amour et al. |
| 8,642,339 | B2 | 2/2014  | Sato et al. |
| 8,647,873 | B2 | 2/2014  | D'Amour et al. |
| 8,658,151 | B2 | 2/2014  | Kelly et al. |
| 8,685,386 | B2 | 4/2014  | West et al. |
| 8,685,730 | B2 | 4/2014  | Odorico et al. |

(Continued)

FOREIGN PATENT DOCUMENTS

| CN | 101855554 A | 10/2010 |
| CN | 102459574 A | 5/2012 |

(Continued)

OTHER PUBLICATIONS

Li et al. (2015, J. Clin. Exp. Pathology, vol. 8(6), pp. 7072-7082) (Year: 2015).*
Li et al. (2015, Int. J. Clin. Exp. Pathol., vol. 8(6), pp. 7072-7082). (Year: 2015).*
Mashima et al. (2013, Biochem. Biophys. Res. Comm., vol. 432, pp. 586-592). (Year: 2013).*
Naujok et al. (2014, BMC Res. Notes, vol. 7, pp. 1-8). (Year: 2014).*
Ajmera, V., et al., "Novel Plasma Biomarkers Associated with Liver Disease Severity in Adults with Nonalcoholic Fatty Liver Disease," Hepatology, 2017, 65(1):65-77, 21 pgs.

(Continued)

*Primary Examiner* — Anoop K Singh
*Assistant Examiner* — David A Montanari
(74) *Attorney, Agent, or Firm* — Knobbe Martens Olson & Bear LLP

(57) ABSTRACT

Disclosed herein are methods for the in vitro differentiation of a precursor cell into definitive endoderm, which may further be differentiated into a human colonic organoid (HCO), via modulation of signaling pathways. Further disclosed are HCOs and methods of using HCOs, which may be used, for example, for the HCOs may be used to determine the efficacy and/or toxicity of a potential therapeutic agent for a disease selected from colitis, colon cancer, polyposis syndromes, and/or irritable bowel syndrome.

31 Claims, 31 Drawing Sheets
Specification includes a Sequence Listing.

(56) References Cited

U.S. PATENT DOCUMENTS

| | | |
|---|---|---|
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rajagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,000,740 B2 | 6/2018 | Vallier et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 10,668,108 B2 | 6/2020 | Takebe et al. |
| 10,781,425 B2 | 9/2020 | Wells et al. |
| 11,053,477 B2 | 7/2021 | Wells et al. |
| 11,066,650 B2 | 7/2021 | Wells et al. |
| 2003/0129751 A1 | 7/2003 | Grikscheit et al. |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2009/0311765 A1 | 12/2009 | Maguire et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0125286 A1 | 5/2011 | Selden et al. |
| 2011/0151564 A1 | 6/2011 | Menu et al. |
| 2011/0218512 A1 | 9/2011 | Tullis et al. |
| 2011/0231942 A1 | 9/2011 | He et al. |
| 2011/0294735 A1 | 12/2011 | Marsh et al. |
| 2012/0009086 A1 | 1/2012 | Nyberg et al. |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0264209 A1 | 10/2012 | Odorico et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1* | 5/2013 | Wells .................. C12N 5/0661 435/377 |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2014/0038279 A1 | 2/2014 | Ingberetal et al. |
| 2014/0044713 A1 | 2/2014 | De Lau et al. |
| 2014/0141509 A1 | 5/2014 | Gadue et al. |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |
| 2014/0302491 A1 | 10/2014 | Nadauld et al. |
| 2014/0308695 A1 | 10/2014 | Bruce et al. |
| 2014/0336282 A1 | 11/2014 | Ewald et al. |
| 2014/0369973 A1 | 12/2014 | Bernstein et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0273071 A1 | 10/2015 | Green et al. |
| 2015/0273127 A1 | 10/2015 | Flieg et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0186140 A1 | 6/2016 | Dalton et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0244724 A1 | 8/2016 | Ferro |
| 2016/0245653 A1 | 8/2016 | Park et al. |
| 2016/0256672 A1 | 9/2016 | Arumugaswami et al. |

(56) References Cited

U.S. PATENT DOCUMENTS

| | | |
|---|---|---|
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0298087 A1 | 10/2016 | Qu et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0202885 A1 | 7/2017 | Agulnick |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0292116 A1 | 10/2017 | Wells et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2017/0362574 A1 | 12/2017 | Sareen et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0043357 A1 | 2/2018 | Bocchi et al. |
| 2018/0059119 A1 | 3/2018 | Takats et al. |
| 2018/0112187 A1 | 4/2018 | Smith et al. |
| 2018/0250410 A1 | 9/2018 | Borros Gomez et al. |
| 2018/0258400 A1 | 9/2018 | Ng et al. |
| 2019/0031992 A1 | 1/2019 | Kerns et al. |
| 2019/0078055 A1 | 3/2019 | Wells et al. |
| 2019/0093076 A1 | 3/2019 | Schulz |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2020/0040309 A1 | 2/2020 | Takebe et al. |
| 2020/0056157 A1 | 2/2020 | Takebe et al. |
| 2020/0190478 A1 | 6/2020 | Wells et al. |
| 2020/0199537 A1 | 6/2020 | Takebe et al. |
| 2021/0008123 A1 | 1/2021 | Takebe et al. |
| 2021/0096126 A1 | 4/2021 | Takebe et al. |
| 2021/0115366 A1 | 4/2021 | Mahe et al. |
| 2021/0180026 A1 | 6/2021 | Takebe et al. |
| 2021/0189349 A1 | 6/2021 | Wells et al. |
| 2021/0292714 A1 | 9/2021 | Takebe et al. |
| 2021/0324334 A1 | 10/2021 | Takebe et al. |
| 2022/0056420 A1 | 2/2022 | Wells et al. |
| 2022/0090011 A1 | 3/2022 | Ngan et al. |

FOREIGN PATENT DOCUMENTS

| | | |
|---|---|---|
| CN | 102740888 A | 10/2012 |
| CN | 103154237 A | 6/2013 |
| CN | 10.3561751 A | 2/2014 |
| CN | 104995294 A | 10/2015 |
| CN | 105985395 A | 10/2016 |
| EP | 2393917 A2 | 12/2011 |
| EP | 2412800 A1 | 2/2012 |
| EP | 2393917 B1 | 4/2016 |
| EP | 3228306 A1 | 10/2017 |
| JP | 2003-521673 A | 7/2003 |
| JP | 2008-503203 A | 2/2008 |
| JP | 2008-505638 A | 2/2008 |
| JP | 2008539697 A | 11/2008 |
| JP | 2013-066414 A | 4/2013 |
| JP | 2013528397 A | 7/2013 |
| JP | 2014233281 A | 12/2014 |
| JP | 2016514968 A | 5/2016 |
| KR | 10-2006-0114355 A | 11/2006 |
| WO | WO 92/07615 | 5/1992 |
| WO | WO 98/21312 | 5/1998 |
| WO | WO-9949807 A2 | 10/1999 |
| WO | WO 2003/082201 A2 | 10/2003 |
| WO | WO 2005/001072 A1 | 1/2005 |
| WO | WO 2005/081970 A2 | 9/2005 |
| WO | WO 2005/097974 A2 | 10/2005 |
| WO | WO 2005/113747 A2 | 12/2005 |
| WO | WO 2006/126236 A1 | 11/2006 |
| WO | WO 2008/075339 A2 | 6/2008 |
| WO | WO 2009/022907 A2 | 2/2009 |
| WO | WO-2009086596 A1 | 7/2009 |
| WO | WO 2009/146911 A2 | 12/2009 |
| WO | WO 2010/008905 A2 | 1/2010 |
| WO | WO 2010/090513 A2 | 8/2010 |
| WO | WO 2010/094694 A1 | 8/2010 |
| WO | WO 2010/127399 A1 | 11/2010 |
| WO | WO 2010/143747 A1 | 12/2010 |
| WO | WO-2011050672 A1 | 5/2011 |
| WO | WO-2011116930 A1 | 9/2011 |
| WO | WO 2011/139628 A1 | 11/2011 |
| WO | WO 2011/140441 A2 | 11/2011 |
| WO | WO 2012/014076 A2 | 2/2012 |
| WO | WO 2012/027474 A1 | 3/2012 |
| WO | WO 2012/089669 A1 | 7/2012 |
| WO | WO 2012/118799 A2 | 9/2012 |
| WO | WO 2012/154834 A1 | 11/2012 |
| WO | WO 2012/155110 A1 | 11/2012 |
| WO | WO 2012/166903 A1 | 12/2012 |
| WO | WO 2012/168930 A2 | 12/2012 |
| WO | WO 2012/178215 A1 | 12/2012 |
| WO | WO 2013/040087 A2 | 3/2013 |
| WO | WO 2013/067498 A1 | 5/2013 |
| WO | WO 2013/086486 A1 | 6/2013 |
| WO | WO 2013/086502 A1 | 6/2013 |
| WO | WO 2013/093812 A2 | 6/2013 |
| WO | WO 2013/096741 A2 | 6/2013 |
| WO | WO 2013/127921 A1 | 9/2013 |
| WO | WO 2013/155060 A1 | 10/2013 |
| WO | WO 2013/174794 A1 | 11/2013 |
| WO | WO 2013/192290 A1 | 12/2013 |
| WO | WO 2014/013334 A2 | 1/2014 |
| WO | WO-2014018691 A1 | 1/2014 |
| WO | WO 2014/048637 A1 | 4/2014 |

(56) References Cited

FOREIGN PATENT DOCUMENTS

| | | |
|---|---|---|
| WO | WO 2014/053596 A1 | 4/2014 |
| WO | WO-2014062138 A1 | 4/2014 |
| WO | WO 2014/082096 A1 | 5/2014 |
| WO | WO 2014/090993 A1 | 6/2014 |
| WO | WO 2014/127170 A1 | 8/2014 |
| WO | WO 2014/151921 A1 | 9/2014 |
| WO | WO 2014/153230 A1 | 9/2014 |
| WO | WO 2014/153294 A1 | 9/2014 |
| WO | WO 2014/159356 A1 | 10/2014 |
| WO | WO 2014/173907 A1 | 10/2014 |
| WO | WO 2014/182885 A2 | 11/2014 |
| WO | WO 2014/197934 A1 | 12/2014 |
| WO | WO 2014/199622 A1 | 12/2014 |
| WO | WO 2015/021358 A2 | 2/2015 |
| WO | WO 2015/060790 A1 | 4/2015 |
| WO | WO 2015/075175 A1 | 5/2015 |
| WO | WO 2015/076388 A1 | 5/2015 |
| WO | WO 2015/108893 A1 | 7/2015 |
| WO | WO 2015/123183 A1 | 8/2015 |
| WO | WO 2015/129822 A1 | 9/2015 |
| WO | WO 2015/130919 A1 | 9/2015 |
| WO | WO 2015/135893 A1 | 9/2015 |
| WO | WO 2015/138032 A2 | 9/2015 |
| WO | WO 2015/152954 A1 | 10/2015 |
| WO | WO 2015/156929 A1 | 10/2015 |
| WO | WO 2015/157163 A1 | 10/2015 |
| WO | WO 2015/168022 A1 | 11/2015 |
| WO | WO 2015/0173425 A1 | 11/2015 |
| WO | WO 2015/183920 A2 | 12/2015 |
| WO | WO 2015/184273 A1 | 12/2015 |
| WO | WO 2015/184375 A2 | 12/2015 |
| WO | WO 2015/185714 A1 | 12/2015 |
| WO | WO 2015/196012 A1 | 12/2015 |
| WO | WO 2015/200901 A1 | 12/2015 |
| WO | WO 2016/011377 A1 | 1/2016 |
| WO | WO 2016/015158 A1 | 2/2016 |
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO-2016056999 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/121512 A1 | 8/2016 |
| WO | WO 2016/140716 A1 | 9/2016 |
| WO | WO 2016/141137 A1 | 9/2016 |
| WO | WO 2016/144769 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 A2 | 12/2016 |
| WO | WO 2017/009263 A1 | 1/2017 |
| WO | WO 2017/036533 A1 | 3/2017 |
| WO | WO 2017/037295 A1 | 3/2017 |
| WO | WO 2017/041041 A1 | 3/2017 |
| WO | WO 2017/048193 A1 | 3/2017 |
| WO | WO 2017/048322 A1 | 3/2017 |
| WO | WO 2017/049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 A1 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO-2017070337 A1 | 4/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO2017/115982 A1 | 6/2017 |
| WO | WO 2017/096192 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 A2 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 A1 | 10/2017 |
| WO | WO 2017/174609 A1 | 10/2017 |
| WO | WO 2017/176810 A1 | 10/2017 |
| WO | WO 2017/184586 A1 | 10/2017 |
| WO | WO-2017175876 A1 | 10/2017 |
| WO | WO 2017/192997 A1 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/094522 A1 | 5/2018 |
| WO | WO-2018085622 A1 | 5/2018 |
| WO | WO-2018085623 A1 | 5/2018 |
| WO | WO 2018/106628 A1 | 6/2018 |
| WO | WO-2018115852 A1 | 6/2018 |
| WO | WO-2018191673 A1 | 10/2018 |
| WO | WO 2018/197544 A1 | 11/2018 |
| WO | WO-2018200481 A1 | 11/2018 |
| WO | WO-2018226267 A1 | 12/2018 |
| WO | WO 2019/074793 A1 | 4/2019 |
| WO | WO-2019126626 A1 | 6/2019 |
| WO | WO-2020023245 A1 | 1/2020 |
| WO | WO-2020056158 A1 | 3/2020 |
| WO | WO-2020069285 A1 | 4/2020 |

OTHER PUBLICATIONS

Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.

Allard, J., et al., "Immunohistochemical toolkit for tracking and quantifying xenotransplanted human stem cells," Regenerative Medicine, 2014, 9(4):437-452, 11 pgs.

Arroyo, J.D., et al., "Argonaute2 complexes carry a population of circulating microRNAs independent of vescicles in human plasma," PNAS, 2011, 108(12):5003-5008, 6 pgs.

Bahar Halpern, K., et al. "Single-cell spatial reconstruction reveals global division of labour in the mammalian liver," Nature, 2017, 542:352-356, 18 pgs.

(56) References Cited

OTHER PUBLICATIONS

Bar-Ephraim, Y.E., et al., "Modelling cancer immunomodulation using epithelial organoid cultures," bioRxiv, 2018, accessed from Http://dx.doi.org/10.1101/377655v1.full, 13 pgs.
Barth, C.A., et al., "Transcellular transport of fluorescein in hepatocyte monolayers: Evidence for functional polarity of cells in culture," Proc Natl Sci USA, 1982, 79:4985-4987, 3 pgs.
Begriche, K., et al., "Drug-induced toxicity on mitochondria and lipid metabolism: Mechanistic diversity and deleterious consequences for the liver," J Hepatol, 2011, 54:773-794, 22 pgs.
Bell, L.N., et al., "Epidemiology of Idiosyncratic Drug-Induced Liver Injury," Semin Liver Dis, 2009, 29(4):337-347, 11 pgs.
Bergeles, C., et al., "From Passive Tool Holders to Microsurgeons: Safer, Smaller, Smarter Surgical Robots," IEEE Trans Biomed Eng, 2014, 61(5):1565-1576, 12 pgs.
Bernardi, P., "The permeability transition pore. Control points of a cyclosporin A-sensitive mitochondrial channel involved in cell death," Biochim Biophys Acta, 1996, 1275:5-9, 5 pgs.
Bharadwaj, S., et al., "Current status of intestinal and multivisceral transplantation," Gastroentrerol Rep (Oxf)., 2017, 5(1):20-28, 9 pgs.
Bhutani, N., et al., Reprogramming towards pluripotency requires AID-dependent DNA demethylation, Nature, 2010, 463(7284):1042-1047, 17 pgs.
Bohan, T.P., et al., "Effect of L-carnitine treatment for valproate-induced hepatotoxicity," Neurology, 2001, 56:1405-1409, 5 pgs.
Boroviak, T., et al., "Single cell transcriptome analysis of human, marmoset and mouse embryos reveals common and divergent features of preimplantation development," Development, 2018, 145(21):dev167833, 35 pgs.
Bort, R., et al., "Diclofenac Toxicity to Hepatocytes: A Role for Drug Metabolism in Cell Toxicity," J Pharmacol Exp Ther, 1998, 288(1):65-72, 8 pgs.
Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.
Bragdon, B., et al., "Bone Morphogenetic Proteins: A critical review," Cellular Signalling, 2011, 23:609-620, 12 pgs.
Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.
Broda, T.R., et al., "Generation of human antral and fundic gastric organoids from pluripotent stem cells," Nature Protocols, Nov. 2018, 14(1):28-50, 23 pgs., XP036660403.
Browning, J.D., et al., "Molecular mediators of hepatic steatosis and liver injury," J Clin Invest, 2004, 114(2):147-152, 6 pgs.
Burke, P., et al., "Towards a single-chip, implantable RFID system: is a single-cell radio possible?" Biomed Microdevices, 2010, 12:589-596, 8 pgs.
Burn, S.F., et al., "Left-right asymmetry in gut development: what happens next?" BioEssays, 2009, 31:1026-1037, 12 pgs.
Caneparo, L., et al., "Intercellular Bridges in Vertebrate Gastrulation," PloS ONE, 2011, 6(5):e20230, 6 pgs.
Capeling, M.M., et al., "Nonadhesive Alignate Hydrogels Support Growth of Pluripotent Stem Cell-Derived Intestinal Organoids," Stem Cell Reports, Feb. 2019, 12(2):381-394, 14 pgs.
Chai, P.R., et al., "Utilizing an Ingestible Biosensor to Assess Real-Time Medication Adherence," J Med Toxicol, 2015, 11:439-444, 6 pgs.
Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.
Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.
Chatterjee, S., et al., "Hepatocyte-based in vitro model for assemssment of drug-induced cholestasis," Toxicol Appl Pharmacol, 2014, 274:124-136, 13 pgs.
Chen, B., et al., "Dynamic Imaging of Genomic Loci in Living Human Cells by an Optimized CRISPR/Cas System," Cell, 2013, 155(7):1479-1491, 23 pgs.
Chen, L.Y., et al., "Mass fabrication and delivery of 3D multilayer Tags into living cells," Sci Rep, 2013, 3:2295, 6 pgs.
Chen, Y., et al., "Retinoic acid signaling is essential for pancreas development and promotes endocrine at the expense of exocrine cell differentiation in *Xenopus*," Dev Biol, 2004, 271:144-160, 17 pgs.
Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.
Christoffllrsson, J., et al., "Developing organ-on-a-chip concepts using bio-mechatronic design methodology," Biofabrication, 2017, 9:025023, 14 pgs.
Chughlay, M.F., et al., "N-acetylcysteine for non-paracetamol drug-induced liver injury: a systematic review," Br J Clin Pharmacol, 2016, 81:1021-1029, 9 pgs.
Cincinnati Children's Hospital Medical Center, "Scientists grow human esophagus in lab: Tiny organoids enable personalized disease diagnosis, regenerative therapies," CCHMC Public Press Release, Sep. 20, 2018, 2 pgs.
Clarke, L.L., "A guide to Ussing chamber studies of mouse intestine," Am J Physiol Gastrointest Liver Physiol, 2009, 296:G1151-G1166, 16 pgs.
Collier, A.J., et al., "Comprehensive Cell Surface Protein Profiling Identifies Specific Markers of Human Naïve and Primed Pluripotent States," Cell Stem Cell, 2017, 20:874-890, 25 pgs.
Cortez, et al., "Transplantation of human intestinal organoids into the mouse mesentery: A more physiological and anatomic engratment site," Surgery, 2018, 164:643-650, 8 pgs.
Crespo, M., et al., "Colonic organoids derived from human induced pluripotent stem cells for modeling colorectal cancer and drug testing," Natrue Medicine, 2017, 23(7):878-884, 11 pgs.
Crocenzi, F.A., et al., "$Ca^{2+}$-Dependent Protein Kinase C Isoforms are Critical to Estradiol 17β-D-Glucuronide-Induced Chloestasis in the Rat," Hepatology, 2008, 48:1885-1895, 12 pgs.
Cutrin, J.C., et al., "Reperfusion Damage to the Bile Canaliculi in Transplanted Human Liver," Hepatology, 1996, 24:1053-1057, 5 pgs.
Das, R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pgs. Summary only.
Dash, A., et al., "Pharmacotoxicology of clinically-relevant concentrations of obeticholic acid in an organotypic human hepatocyte system," Toxicology In Vitro, 2017, 39:93-103, 11 pgs.
Davidson, M.D., et al., "Long-term exposure to abnormal glucose levels alters drug metabolism pathways and insulin sensitivity in primary human hepatocytes," Sci Rep, 2016, 6:28178, 11 pgs.
Dekkers, J.F., et al., "A functional CFTR assay using primary cystic fibrosis intestinal organoids," Nat Med, 2013, 19(7):939-945, 9 pgs.
Demehri, F.R., et al., "Development of endoluminal intestinal attachment for clinically applicable distraction enterogenesis device," Journal of Pediatric Surgery, 2016, 51:101-106, 6 pgs.
Demehri, F.R., et al., "Development of an endoluminal intestinal lengthening device using a geometric intestinal attachment approach," Surgery, 2015, 158(3):802-811, 10 pgs.
Dumortier, G., et al., "Tolérance hépatique des antipsychotiques atypiques, [Hepatic tolerance of atypical antipsychotic drugs]," L'Encéphale, 2002, 28(1):542-551, 10 pgs.
Dvir-Ginzberg, M., et al., "Liver Tissue Engineering Within alginate Scaffolds: Effects of Cell-Seeding Density on Hepatocyte Viability, Morphology, and Function," Tissue Eng, 2003, 9(4):757-766, 10 pgs.
Edling, Y., et al., "Increased sensitivity for troglitazone-induced cytotoxicity using a human in vitro co-culture model," Toxicol In vitro, 2009, 23:1387-1395, 9 pgs.
Ekser, B., et al., "Comparable outcomes in intestinal retransplantation: Single-center cohort study," The Journal of Clinical and Translational Research, 2018, 32(7):e13290, 10 pgs.
El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.

(56) References Cited

OTHER PUBLICATIONS

El Taghdouini, A., et al., "In vitro reversion of activated primary human hepatic stellate cells," Fibrogenesis & Tissue Repair, 2015, 8:14, 15 pgs.
The Encode Project Consortium, "An integrated encyclopedia of DNA elements in the human genome," Nature, 2012, 489:57-74, 18 pgs.
Engmann, J., et al., "Fluid mechanics of eating, swallowing and digestion—overview and perspectives," Food & Function, 2013, 4:443-447, 5 pgs.
Fahrmayr, C., et al., "Phase I and II metabolism and MRP2-mediated export of bosentan in MDCKII-OATP1B1-CYP3A-UGT1A1-MRP2 quadruple-transfected cell line," Br J Pharmacol, 2013, 169:21-33, 13 pgs.
Falasca, L., et al., "The effect of retinoic acid on the re-establishment of differentiated hepatocyte phenotype in primary culture," Cell Tissue Res, 1998, 293:337-347, 11 pgs.
Finkenzeller, K., *RFID Handbook: Fundamentals and Applications in Contactless Smart Cards, Radio Frequency Identification and Near-Field Communication, Third Edition*. John Wiley & Son, Ltd., Chichester, West Sussex, 2010, 8 pgs. (Table of Contents Only).
Fisher, A., et al., "Entacapone-Induced Hepatotoxicity and Hepatic Dysfunction," Mov Disord, 2002, 17:1362-1365, 4 pgs.
Fromenty, B., "Drug-induced liver injury in obesity," J Hepatol, 2013, 58:824-826, 3pgs.
Gafni, O., et al., "Derivation of novel human ground state naïve pluripotent stem cells," Nature, 2013, 504:282-286, 20 pgs.
Geerts, A., et al., "Formation of Normal Desmin Intermediate Filaments in Mouse Hepatic Stellate Cells Requires Vimentin," Hepatology, 2001, 33:177-188 12 pgs.
Gerdes, H-H., et al., "Tunneling nanotubes, an emerging intercellular communication route in development," 2013, 130:381-387, 7 pgs.
Giles, D.A., et al., "Thermoneutral housing exacerbates nonalcoholic fatty liver disease in mice and allows for sex-independent disease modeling," Nature Medicine, 2017, 23(7):829-838, 13 pgs.
Glorioso, J.M., et al., "Pivotal Preclinical Trial of the Spheroid Reservoir Bioartificial Liver," J Hepatol, 2015, 63(2):388-398, 27 pgs.
Gomez-Pinilla, P.J., et al., "Ano1 is a selective marker of interstitial cells of Cajal in the human and mouse gastrointestinal tract," Am J Physiol Gastrointest Liver Physiol, 2009, 296:G1370-G1381, 12 pgs.
Grapin-Botton, A., "Three-dimensional pancreas organogenesis models," Diabetes Obes Metab, 2016, 18(Suppl 1):33-40, 8 pgs.
Gregersen, H., et al., "The Zero-Stress State of the Gastrointestinal Tract: Biomechanical and Functional Implications," Digestive Diseases and Sciences, 2000, 45(12):2271-2281, 11 pgs.
Guo, G., et al., "Epigenetic resetting of human pluripotency," Development, 2017, 144:2748-2763, 17 pgs.
Gurdon, J.B., "Adult Frogs Derived from the Nuclei of Single Somatic Cells," Dev Biol, 1962, 4:256-273, 18 pgs.
Gurken, A., "Advances in small bowel transplantation," Turk J Surg., 2017, 33(3):135-141, 7 pgs.
Haimovich, G., et al., "Intercellular mRNA trafficking via membrane nanotube-like extensions in mammalian cells," 2017, PNAS, pp. E9873-E9882, 10 pgs.
Han, B., et al., "Microbiological safety of a novel bio-artificial liver support system based on porcine hepatocytes: a experimental study," European Journal of Medical Research, 2012, 17:13, 8 pgs.
Hassan, W., et al., "Reduced Oxidative Stress Contributes to the Lipid Lowering Effect of Isoquercitrin in Free Fatty Acids Induced Hepatocytes," Oxid Med Cell Longev, 2014, 313602, 18 pgs.
Heidari, R., et al., "Factors affecting drug-induced liver injury: antithyroid drugs as instances," Clin Mol Hepatol, 2014, 20:237-248, 12 pgs.
Hernandez, F., et al., "Refining Indications for Intestinal Retransplantation," International Small Bowel Symposium 2013; Abstract 12.241 (online: https://www.tts.org/component/%20tts/?view=presentation &id=13241) Accessed Jun. 12, 2017, 3 pgs.

Hooton, D., et al., "The Secretion and Action of Brush Border Enzymes in the Mammalian Small Intestine," Rev Physiol Biochem Pharmacol, 2015, 168:59-118, 60 pgs.
Hou, P., et al., "Pluripotent Stem Cells Induced from Mouse Somatic Cells by Small-Molecule Compounds," Science, 2013, 341:651-654, 4 pgs.
Hsu, F., et al., "The UCSC Known Gene," Bioinformatics, 2006, 22(9):1036-1046, 11 pgs.
Hu, H., et al., "Long-Term Expansion of Functional Mouse and Human Hepatocytes as 3D Organoids," Cell, 2018, 175:1591-1606, 36 pgs.
Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.
Huch, M., et al., "Long-Term Culture of Genome-Stable Bipotent Stem Cells from Adult Human Liver," Cell, 2015, 160:299-312, 14 pgs.
Hynds, R.E., et al., "The relevance of human stem cell-derived organoid models for epithelial translational medicine," Stem Cells, 2013, 31(3):417-422, 11 pgs.
Ijpenberg, A., et al., "Wt1 and retinoic acid signaling are essential for stellate cell development and liver morphogenesis," Dev Biol, 2007, 312:157-170, 14 pgs.
Inoue, H., et al., "iPS cells: a game changer for future medicine," EMBO J, 2014, 33(5):409-417, 9 pgs.
Ito, K., et al., "Temporal Transition of Mechanical Characteristics of HUVEC/MSC Spheroids Using a Microfluidic Chip with Force Sensor Probes," Micromachines, 2016, 7:221, 14 pgs.
Jalan-Sakrikar, N., et al., "Hedgehog Signaling Overomes an EZH2-Dependent Epigenetic Barrier to Promote Cholangiocyte Expansion," PLoS One, 2016, 11(12):e0168266, 19 pgs.
Kanuri, G., et al., "In Vitro an in Vivo Models of Non-Alcoholic Fatty Liver Disease (NAFLD)," Int J Mol Sci, 2013, 14:11963-11980, 18 pgs.
Karlikow, M., et al., "*Drosophila* cells use nanotube-like structures to transfer dsRNA and RNAi machinery between cells," Scientific Reports, 2016, 6:27085, 9 pgs.
Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.
Kelly, G.M., et al., "Retinoic Acid and the Development of the Endoderm," J Dev Biol, 2015, 3:25-56, 32 pgs.
Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.
Kilens, S., et al., "Parallel derivation of isogenic human primed and naïve induced pluripotent stem cells," Nat Commun, 2018, 9:360, 13 pgs.
Kilpinen, H., et al., "Common genetic variation drives molecular heterogeneity in human iPSCs," Nature, 2017, 546(7658):370-375, 51 pgs.
Kim, D., et al., "HISAT: a fast spliced aligner with low memory requirements," Nature Methods, 2015, 12(4):357-360, 6 pgs.
Kock, K., et al., "A Perspective on Efflux Transport Proteins in the Liver," Clin Pharmacol Ther, 2012, 92(5):599-612, 29 pgs.
Koehler, E.M., et al., "Presence of Diabetes Mellitus and Steatosis Is Associated With Liver Stiffness in a General Population: The Rotterdam Study," Hepatology, 2016, 63:138-147, 10 pgs.
Kolodny, G.M., "Evidence for Transfer of Macromolecular RNA Between Mammalian Cells in Culture," Exp Cell Res, 1971, 65:313-324, 12 pgs.
Kordes, C., et al., "Hepatic stellate cells contribute to progenitor cells and liver regeneration," J Clin Invest, 2014, 124(12):5503-5515, 13 pgs
Krähenbühl, S., et al., "Toxicity of Bile Acids on the Electron Transport Chain of Isolated Rat Liver Mitochondria," Hepatology, 1994, 169:471-479, 9 pgs.
Kubal, C.A., et al., "Challenges with Intestine and Multiviseral Re-Transplantation: Importance of Timing of Re-Transplantation and Optimal Immunosuppression," Ann Transplant, 2018, 23:98-104, 7 pgs.

(56) References Cited

OTHER PUBLICATIONS

Kullak-Ublick, G.A., et al., "Drug induced liver injury: recent advantages in diagnosis and risk assessment," Gut, 2017, 66:1154-1164, 11 pgs.

Kumar, J.A., et al., "Controversies in the Mechanism of Total Parenteral Nutrition Induced Pathology," Children, 2015, 2:358-370, 13 pgs.

Kurpios, N.A., et al., "The direction of gut looping is estalished by changes in the extracellular matrix and in cell:cell adhesion," PNAS, 2008, 105(25):8499-8506, 8 pgs.

Lê, S., et al., "FactoMineR: An R Package for Multivariate Analysis," Journal of Statistical Software, 2008, 25(1):1-18, 18 pgs.

Le Vee, M., et al., "Polarized expression of drug transporters in differentiated human HepaRG cells," Toxicol In Vitro, 2013, 27:1979-1986, 8 pgs.

Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.

Lee, W.M., et al., "Intravenous N-Acetylcysteine Improves Transplant-Free Survival In Early Stage Non-Acetaminophen Acute Liver Failure," Gastroenterology, 2009, 137(3):856-864, 18 pgs.

Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.

Leung, A.A., et al., "Tolerance testing of passive radio frequency identification tags for solvent, temperature, and pressure conditions encountered in an anatomic pathology or biorepository setting," J Pathol Inform, 2010, 1:21, 6 pgs.

Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.

Lin, Y., et al., "Differentiation, Evaluation, and Application of Human Induced Pluripotent Stem Cell-Derived Endothelial Cells," Arterioscler Thromb Vasc Biol, 2017, 37:2014-2025, 12 pgs.

Liu, L., et al., "A Review of Locomotion Systems for Capsule Endoscopy," IEEE Rev Biomed Eng, 2015, 8:138-151, 14 pgs.

Loike, J.D., et al., "Opinion: Develop Organoids, Not Chimeras, for Transplantation," The Scientist Magazine, Aug. 2019, (online: https://www.the-scientist.com/news-opinion/opinion--develop-organoids--not-chimeras--for-transplantation-66339), 3 pgs.

Love, M.I., et al., "Moderated estimation of fold change and dispersion for RNA-seq data with DESeq2," Genome Biol, 2014, 15:550, 21 pgs.

Low, L.A., et al., "Organs-on-chips: Progress, challenges, and future directions," Experimental Biology and Medicine, 2017, 242:1573-1578, 6 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.

MacParland, S.A., et al., "Single cell RNA sequencing of human liver reveals distinct intrahepatic macrophage populations," Nat Commun, 2018, 9:4383, 21 pgs.

Mahe, M.M., et al., "In Vivo Model of Small Intestine," Methods Mol Biol, 2017, 1597:229-245, 17 pgs.

Makin, A.J., et al., "A 7-Year Experience of Severe Acetaminophen-Induced Hepatotoxicity (1987-1993)," Gastroenterology, 1995, 109:1907-1916, 10 pgs.

Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.

Mammoto, A., et al., "Mechanosensitive mechanisms in transcriptional regulation," Journal of Cell Science, 2012, 125:3061-3073, 13 pgs.

Marcum, Z.A., et al., "Medication Adherence to Multi-Drug Regimens," Clin Geriatr Med, 2012, 28(2):287-300, 15 pgs.

Marini, F., et al., "pcaExplorer: an R/Bioconductor package for interacting with RNA-seq principal components," BMC Bioinformatics, 2019, 20:331, 8 pgs.

Marini, F., "pcaExplorer: Interactive Visualization of RNA-seq Data Using a Principal Components Approach," bioconductor.org, R package version 2.3.0, 2017, 7 pgs.

Markova, S.M., et al., "Association of CYP2C9*2 With Bosentan-Induced Liver Injury," Clin Pharmacol Ther., Dec. 2013, 94(6):678-86, 9 pgs.

Marsh, M.N., et al., "A study of the small intestinal mucosa using the scanning electron microscope," Gut, 1969, 10:940-949, 10 pgs.

McCracken, K.W., et al., "Erratum: Wnt/β-catenin promotes gastric fundus specification in mice and humans," Nature, 2017, 543:136, 1 pg.

McKenzie, T.J., et al., "Artificial and Bioartificial Liver Support," Seminars in Liver Disease, 2008, 28(2):210-217, 8 pgs.

Mercaldi, C.J., et al., "Methods to Identify and Compare Parenteral Nutrition Administered From Hospital-Compounded and Premixed Mulitchamber Bags in a Retrospective Hospital Claims Database," J Parenter Enteral Nutr, 2012, 36(3):330-336, 7 pgs.

Michaut, A., et al., "A cellular model to study drug-induced liver injury in nonalcoholic fatty liver disease: application to acetaminophen," Toxicol Appl Pharmacol, 2016, 292:40-55, 35 pgs.

Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.

Mörk, L.M., et a., "Comparison of Culture Media for Bile Acid Transport Studies in Primary Human Hepatocytes," J Clin Exp Hepatol, 2012, 2:315-322, 8 pgs.

Nakamura, T., et al., "Advancing Intestinal Organoid Technology Toward Regenerative Medicine," Cell Mol Gastroenterol Hepatol, 2018, 5:51-60, 10 pgs.

Navarro, V.J., et al., "Drug-Related Hepatotoxicity," N Engl J Med, 2006, 354:731-739, 9 pgs.

Negishi, T., et al., "Retinoic Acid Signaling Positiviely Regulates Liver Specification by Inducing wnt2bb Gene Expression in Medaka," Hepatology, 2010, 51:1037-1045, 9 pgs.

Nelson, B.J., et al., "Microrobots for Minimally Invasive Medicine," Annual Review of Biomedical Engineering, 2010, 12(12):55-85, 33 pgs.

Nelson, C.M., "On Buckling Morphogenesis," J Biomech Eng, 2016, 138:021005-1-021005-6, 6 pgs.

Ni, X., et al., "Functional human induced hepatocytes (hiHeps) with bile acid synthesis and transport capacities: A novel in vitro cholestatic model," Sci Rep, 2016, 6:38694, 16 pgs.

Nishida, T., et al., "Rat liver canalicular membrane vesicles contain ATP-dependent bile acid transport system," Proc Natl Acad Sci USA, 1991, 88:6590-6594, 5 pgs.

Oorts, M., et al., "Drug-induced cholestasis risk assessment in sandwich-cultured human hepatocytes," Toxicol In Vitro, 2016, 34:179-186, 8 pgs.

Orso, G., et al., "Pediatric parenteral nutrition-associated liver disease and cholestasis: Novel advances in pathomechanisms-based prevention and treatment," Dig Liver Dis, 2016, 48:215-222, 8 pgs.

Ouchi, R., et al., "Modeling Steatohepatitis in Humans with Pluripotent Stem Cell-Derived Organoids," Cell Metabolism, Aug. 2019, 30:1-11, 17 pgs.

Pardal, M.L., et al., "Towards the Internet of Things: An Introduction to RFID technology," RFID Technology—Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.

Pastor, W.A., et al., "TFAP2C regulates transcription in human naïve pluripotency by opening enhancers," Nature Cell Biology, 2018, 20:553-564, 18 pgs.

Pereira, C.F., et al., "Heterokaryon-Based Reprogramming of Human B Lymphocytes for Pluripotency Requires Oct4 but Not Sox2," PLoS Genet, 2008, 4(9):e1000170, 14 pgs.

Pessayre, D., et al., "Central role of mitochondria in drug-induced liver injury," Drug Metab Rev, 2012, 44(1):34-87, 54 pgs.

(56) References Cited

OTHER PUBLICATIONS

Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.

Poling, H.M., et al., "Mechanically induced development and maturation of human intestinal organoids in vivo," Nat Biomed Eng, 2018, 2(6):429-442, 31 pgs.

Polson, J., et al., "AASLD Position Paper: The Management of Acute Liver Failure," Hepatology, 2005, 41(5):1179-1197, 19 pgs.

Purton, L.E., et al., "All-trans retinoic acid enhances the long-term repopulating activity of cultured hematopoietic stem cells," Blood, 2000, 95:470-477, 8 pgs.

Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.

Ramirez-Weber, F-A., et al., "Cytonemes: Cellular Processes that Project to the Principal Signaling Center in Drosophila Imaginal Discs," Cell, 1999, 97:599-607, 9 pgs.

Rane, A., et al., "Drug Metabolism in the Human Fetus and Newborn Infant," Pediatr Clin North Am, 1972, 19(1):37-49, 11 pgs.

Rao, R.R., et al., "Gene Expression Profiling of Embryonic Stem Cells Leads to Greater Understanding of Pluripotency and Early Development Events," Biol Reprod, 2004, 71:1772-1778, 7 pgs.

Rector, R.S., et al., "Mitochondrial dysfunction prededes insulin resistance and hepatic steatosis and contributes to the natural history of non-alcoholic fatty liver disease in an obese rodent model," J Hepatol, 2010, 52(5):727-736, 20 pgs.

Reuben, A., et al. "Drug-Induced Acute Liver Failure: Results of U.S. Multicenter, Prospective Study," Hepatology, 2010, 52:2065-2076, 12 pgs.

Riedinger, H-J, et al., "Reversible shutdown of replicon inititaion by transient hypoxia in Ehrlich ascites cells: Dependence of initiation on short-lived protein," Eur J. Biochem, 1992, 210:389-398, 10 pgs.

Roberts, A., et al., "Identification of novel transcripts in annotated genomes using RNA-Seq," Bioinformatics, 2011, 27(17):2325-2329, 5 pgs.

Roberts, A., et al., "Improving RNA-Seq expression estimated by correcting for fragment bias," Genome Biol, 2011, 12:R22, 14 pgs.

Ronn, R.E., et al., "Retinoic Acid Regulates Hematopoietic Development from Human Pluripotent Stem Cells," Stem Cell Reports, 2015, 4:269-281, 13 pgs.

Rouch, J.D., et al., "Scalability of an endoluminal spring for distraction enterogenesis," Journal of Pediatric Surgery, 2016, 51:1988-1992, 5 pgs.

Roy, S., et al., "Cytoneme-Mediated Contact-Dependent Transport of the *Drosophila* Decapentaplegic Signaling Protein," Science, 2014, 343:1244624-1, 11 pgs.

Russo, M.W., et al., "Liver Transplantation for Acute Live Failure From Drug Induced Liver Injury in the United States," Liver Transpl, 2004, 10:1018-1023 6 pgs.

Sachs, N., et al., "A Living Biobank of Breast Cancer Organoids Captures Disease Heterogeneity," Cell, 2018, 172:373-386, 25 pgs.

Saini, A., "Cystic Fibrosis Patients Benefit from Mini Guts," Cell Stem Cell, 2016, 19:425-427, 3 pgs.

Salas-Vidal, E., et al., "Imaging filopodia dynamics in the mouse blastocyst," Developmental Biology, 2004, 265:75-89, 15 pgs.

Sartori-Rupp, A., et al., "Correlative cryo-electron microscopy reveals the structure of TNTs in neuronal cells," Nature Communications, 2019, 10:342, 16 pgs.

Sasai, Y., "Cytosystems dynamics in self-organization of tissue architecture," Nature, 2013, 493:318-326, 9 pgs.

Sato, T., et al., "Snapshot: Growing Organoids from Stem Cells," Cell, 2015, 161:1700-1700e1, 2 pgs.

Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.

Shahbazi, M.N., et al., "Self-organization of human embryo in the absence of maternal tissues," Nature Cell Biology, 2016, 18(6):700-708, 20 pgs.

Shekherdimian, S., et al., "The feasibility of using an endoluminal device for intestinal lengthening," Journal of Pediatric Surgery, 2010, 45:1575-1580, 6 pgs.

Shi, X-L., et al., "Effects of Membrane Molecular Weight Cutoff on Performance of a Novel Bioartificial Liver," Artificial Organs, 2011, 35(3):E40-E46, 7 pgs.

Shi, X-L., et al., "Evaluation of a novel hybrid bioartificial liver based on a multi-layer flat-plate bioreactor," World J Gastroenterol, 2012, 18(28):3752-3760, 9 pgs.

Shyer, A.E., et al., "Villification: How the Gut Gets its Villi," Science, 2013, 342:212-218, 7 pgs.

Sim, Y-J., et al., "2i Maintains a Naïve Ground State in ESCs through Two Distinct Epigenetic Mechanisms," Stem Cell Reports, 2017, 8:1312-1328, 17 pgs.

Sitti, M., et al., "Biomedical Applications of Untethered Mobile Milli/Microrobots," Proc IEEE Inst Electr Electron Eng, 2015, 103(2):205-224, 20 pgs.

Slaymaker, I.M., et al., "Rationally engineered Cas9 nuclease with improved specificity," Science, 2016, 351(6268):84-88, 10 pgs.

Sloan, C.A., et al., "ENCODE data at the ENCODE portal," Nucleic Acids Res, 2016, 44:D726-D732, 7 pgs.

Sneddon, I.N., "The Relation Between Load and Penetration in the Axisymmetric Boussinesq Problem for a Punch of Arbitrary Profile," Int. J. Engng. Sci., 1965, 3:47-57, 11 pgs.

Soffers, J.H.M., et al., "The growth pattern of the human intestine and its mesentery," BMC Dev Biol, 2015, 15:31, 16 pgs.

Song, W., et al., "Engraftment of human induced pluripotent stem cell-derived hepatocytes in immunocompetent mice via 3D co-aggregation and encapsulation," Sci Rep, 2015, 5:16884, 13 pgs.

Song, Z., et al., "Efficient generation of hepatocyte-like cells from human induced pluripotent stem cells," Cell Res, 2009, 19:1233-1242, 10 pgs.

Spence, J.R., et al., "Vertebrate Intestinal Endoderm Development," Developmental Dynamics, 2011, 240:501-520, 20 pgs.

Stafford, D., et al., "A conserved role for retinoid signaling in vertebrate pancreas development," Dev Genes Evol, 2004, 214:432-441, 10 pgs.

Stender, S., et al., "Adiposity Amplifies the Genetic Risk of Fatty Liver Disease Conferred by Multiple Loci," Nat Genet, 2017, 49(6):842-847, 18 pgs.

Stevens, J.L., et al., "The future of drugs safety testing: expanding the view and narrowing the focus," Drug Discov Today, 2009, 14(3/4):162-167, 6 pgs.

Stuart, T., et al., "Comprehensive Integration of Single-Cell Data," Cell, 2019, 177:1888-1902, 37 pgs.

Sugimoto, S., et al., "Reconstruction of the Human Colon Epithelium In Vivo," Cell Stem Cell, 2018, 22:171-176, 16 pgs.

Suzuki, A., et al., "Clonal identification and characterization of self-renewing pluripotent stem cells in the developing liver" The Journal of Cell Biology, 2002, 156(1):173-184, 12 pgs.

Tada, M., et al., "Embryonic germ cells induce epigenetic reprogramming of somatic nucleus in hybrid cells," EMBO J, 1997, 16(21):6510-6520, 11 pgs.

Takahashi, S., et al., "Epigenetic differences between naïve and primed pluripotent stem cells," Cellular and Molecular Life Sciences, 2018, 75:1191-1203, 13 pgs.

Takashima, Y., et al., "Resetting Transcription Factor Control Circuitry toward Ground-State Pluripotency in Human," Cell, 2014, 158(6):1254-1269, 32 pgs.

Takebe, T., et al., "Human iPSC-Derived Miniature Organs: A Tool for Drug Studies," Clin Pharmacol Ther, 2014, 96(3):310-313, 4 pgs.

Takebe, T., et al., "Massive and Reproducible Production of Liver Buds Entirely from Human Pluripotent Stem Cells," Cell Reports, 2017, 21:2661-2670, 11 pgs.

Takebe, T., et al., "Vascularized and Complex Organ Buds from Diverse Tissues via Mesenchymal Cell-Driven Condensation," Cell Stem Cell, 2015, 16:556-565, 10 pgs.

(56) References Cited

OTHER PUBLICATIONS

Takebe, T., et al., "Vascularized and functional human liver from an iPSC-derived organ bud transplant," Nature, 2013, 499:481-484, 5 pgs.
Tamm, C., et al., "A Comparative Study of Protocols for Mouse Embryonic Stem Cell Culturing," PLoS ONE, 2013, 8(12):e81156, 10 pgs.
Tamminen, K., et al., "Intestinal Commitment and Maturation of Human Pluripotent Stem Cells Is Independent of Exogenous FGF4 and R-spondin1," PLOS One, Jul. 2015, 10(7):e0134551, 19 pgs.
Terry, B.S., et al., "Preliminary Mechanical Characterization of the Small Bowel for In Vivo Robotic Mobility," J. Biomech Eng, 2011, 133:091010-1-09101-7, 7 pgs.
The WNT homepage, "Small molecules in Wnt signalling," Nusse Lab, Jan. 2019, 2 pgs.
Theunissen, T.W., et al., "Systematic Identification of Culture Conditions for Induction and Maintenance of Naïve Human Pluripotency," Cell Stem Cell, 2014, 15:471-487, 47 pgs.
Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.
Tran, K., et al. "Evaluation of regional and whole gut motility using the wireless motility capsule: relevance in clinical practice," Therap Adv Gasroenterol, 2012, 5(4):249-260, 12 pgs.
Trapnell, C., et al., "Transcript assembly and quantification by RNA-Seq reveals unannotated transcripts and isoform switching during cell differentiation," Nat Biotechnol, 2010, 28(5):511-515, 8 pgs.
Troy, D.B. (ed.), Remington: The Science and Practice of Pharmacy, 21$^{st}$ Ed., 2006, Lippincott, Williams & Wilkens, Baltimore, MD, 6 pgs., Table of Contents Only.
Tsedensodnom, O., et al., "ROS: Redux and Paradox in Fatty Liver Disease," Hepatology, 2013, 58(4):1210-1212, 3 pgs.
Tsukada, N., et al., "The Structure and Organization of the Bile Canalicular Cytoskeleton With Special Reference to Actin and Actin-Binding Proteins," Hepatology, 1995, 21(4):1106-1113, 8 pgs.
Tyml, K., et al., "Lipopolysaccharide reduces intercellular coupling in vitro and arteriolar conducted response in vivo," AJP-Heart Circ Physiol, 2001, 281:H1397-H1406, 10 pgs.
The United States Pharmacopeia: The National Formulary (USP 24 NF 19), United States Pharmacopeial Convention, Inc., Rockville, MD, 1999, 4 pgs., Table of Contents Only.
Valadi, H., et al., "Exosome-mediated transfer of mRNAs and microRNAs in a novel mechanism of genetic exchange between cells," Nat Cell Biol, 2007, 9(6):654-659, 17 pgs.
Van De Garde, M.D., et al., "Liver Monocytes and Kupffer Cells Remain Transcriptionally Distinct during Chronic Viral Infection," PLoS One, 2016, 11(11):e0166094, 16 pgs.
Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.
Verma, S., et al., "Diagnosis, management and prevention of drug-induced liver injury," Gut, 2009, 58:1555-1564, 10 pgs.
Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.
Wakayama, T., et al., "Full-term development of mice from enucleated oocytes injected with cumulus cell nuclei,," Nature, 1998, 394:369-374, 6 pgs.
Wang, S., (Ed.), "The role of homologous genes in the development of appendages," in Basis of Developmental Biology, Press of East China University of Science and Technology, 2014, pp. 184-185, 4 pgs.
Wang, Y., et al., "Hepatic stellate cells, liver innate immunity, and hepatitis C virus," J Gastroenterol Hepatol, 2013, 28(Suppl 1):112-115, 8 pgs.
Want, R., "An Introduction to RFID Technology," IEEE Pervas Comput, 2006, 5:25-33, 9 pgs.
Ware, C.B., "Concise Review: Lessons from Naïve Human Pluripotent Cells," Stem Cells, 2017, 35:35-41, 7 pgs.
Warren, C.R., et al., "Induced Pluripotent Stem Cell Differentiation Enables Functional Validation of GWAS Variants in Metabolic Disease," Cell Stem Cell, 2017, 20:547-557, 18 pgs.
Warren, C.R., et al., "The NextGen Genetic Association Studies Consortium: A Foray into In Vitro Population Genetics," Cell Stem Cell, 2017, 20:431-433, 3 pgs.
Wernig, M., et al., "In vitro reprogramming of fibroblasts into a pluripotent ES-cell-like state," Nature, 2007, 448:318-324, 8 pgs.
Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388e1, 23 pgs.
Wiley, L.A., et al., "cGMP production of patient-specific iPSCs and photoreceptors precursor cells to treat retinal degenerative blindness," Scientific Reports, 2016, 6:30742, 16 pgs.
Wilmut, I., et al., "Viable offspring derived from fetal and adult mammalian cells," Nature, 1997, 385:810-813, 4 pgs.
Xu, R., et al., "Association Between Patatin-Like Phospholipase Domain Containing 3 Gene (PNPLA3) Polymorphisms and Non-alcoholic Fatty Liver Disease: A HuGE Review and Meta-Analysis," Sci Rep, 2015, 5:9284, 11 pgs.
Xu, R., et al. (Eds.), "Retinoic acid receptor" in Basis and Clinic of Receptor, Shanghai Science and Technology Press, 1992, pp. 129-131, 2 pgs.
Yanagimachi, M.D., et al., "Robust and Highly-Efficient Differentiation of Functional Monocytic Cells from Human Pluripotent Stem Cells under Serum- and Feder Cell-Free Conditions," PLoS One, 2013, 8(4):e59243, 9 pgs.
Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.
Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.
Yu, H., et al., "The Contributions of Human Mini-Intestines to the Study of Intestinal Physiology and Pathophysiology," Annu Rev Physiol, 2017, 79:291-312, 22 pgs.
Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.
Zambrano, E., et al., "Total parenteral Nutrition Induced Liver Pathology: An Autopsy Series of 24 Newborn Cases," Pediatr Dev Pathol, 2004, 7:425-432, 8 pgs.
Zborowski, J., et al., "Induction of swelling of liver mitochondria by fatty acids of various chain length," Biochim Biophys Acta, 1963, 70:596-598, 3 pgs.
Zhang, R-R., et al., "Human iPSC-Derived Posterior Gut Progenitors Are Expandable and Capable of Forming Gut and Liver Organoids," Stem Cell Reports, 2018, 10(3):780-793, 14 pgs.
Zhao, Y., et al., "A XEN-like State Bridges Somatic Cells to Pluripotency during Chemical Reprogramming," Cell, 2015, 163:1678-1691, 15 pgs.
Zhong, J., et al., "Continuous-wave laser-assisted injection of single magnetic nanobeads into living cells," Sensors and Actuators B: Chemical, 2016, 230:298-305, 8 pgs.
Chinese Office Action, the Second Office Action and Supplementary Search Report, dated Dec. 19, 2019 for Application No. CN 201580034910.4, 11 pgs.
European Search Report and Written Opinion dated Oct. 31, 2019 for Application No. EP 17793451.0, 11 pgs.
International Search Report and Written Opinion dated Jul. 9, 2018 for Application No. PCT/US2018/027585, 12 pgs.
International Search Report and Written Opinion dated May 7, 2019 for Application No. PCT/US2018/067057, 15 pgs.
International Search Report and Written Opinion dated Oct. 29, 2019 for Application No. PCT/US2019/041985, 13 pgs.
International Search Report and Written Opinion dated Dec. 5, 2019 for Application No. PCT/US2019/050846, 10 pgs.

(56) References Cited

OTHER PUBLICATIONS

International Search Report and Written Opinion dated Dec. 13, 2019 for Application No. PCT/US2019/053408, 10 pgs.
U.S. Appl. No. 16/346,190, filed Apr. 30, 2019, by Takebe et al., entitled: "Liver Organoid Disease Models and Methods of Making and Using Same."
U.S. Appl. No. 16/599,620, filed Oct. 11, 2019, by Wells et al., entitled: "Methods and Systems for Converting Precursor Cells Into Intestinal Tissues Through Directed Differentiation."
U.S. Appl. No. 16/603,611, filed Oct. 8, 2019, by Mahe et al., entitled: "Methods of Making Improved Human Intestinal Organoid Compositions Via Application of Strain and Human Intestinal Organoid Compositions Thereof."
U.S. Appl. No. 16/611,998, filed Nov. 8, 2019, by Takebe et al., entitled: "Liver Organoid Compositions and Methods of Making and Using Same."
Abe T., et al., "Reporter Mouse Lines for Fluorescence Imaging," Development, Growth & Differentiation, May 2013, vol. 55, No. 4, pp. 390-405.
Adam M., et al., "Psychrophilic Proteases Dramatically Reduce Single-Cell RNA-Seq Artifacts: a Molecular Atlas of Kidney Development," Development, Oct. 1, 2017, vol. 144, No. 19, pp. 3625-3632.
Arora R., et al., "Multiple Roles and Interactions of Tbx4 and Tbx5 in Development of the Respiratory System," PLoS Genetics, Aug. 2, 2012, vol. 8, No. 8, e1002866, 14 pages.
Asahina K., et al., "Septum Transversum-Derived Mesothelium gives rise to Hepatic Stellate Cells and Perivascular Mesenchymal Cells in Developing Mouse Liver," Hepatology, Mar. 2011, vol. 53, No. 3, pp. 983-995.
Barnes R.M., et al., "Analysis of the Hand1 Cell Lineage Reveals Novel Contributions to Cardiovascular, Neural Crest, Extra- Embryonic, and Lateral Mesoderm Derivatives," Developmental Dynamics, vol. 239, 2010, pp. 3086-3097.
Baron M., et al., "A Single-Cell Transcriptomic Map of the Human and Mouse Pancreas Reveals Inter- and Intra-cell Population Structure," Cell Systems, Oct. 26, 2016, vol. 3, No. 4, pp. 346-360.
Bauwens C.L., et al., "Control of Human Embryonic Stem Cell Colony and Aggregate Size Heterogeneity Influences Differentiation Trajectories," Stem Cells, vol. 26, No. 9, Sep. 2008, pp. 2300-2310.
Brandenberg N., et al., "High-Throughput Automated Organoid Culture via Stem-Cell Aggregation in Microcavity Arrays," Nature Biomedical Engineering, 2020, vol. 4, pp. 863-874.
Briggs J.A., et al., "The Dynamics of Gene Expression in Vertebrate Embryogenesis at Single-Cell Resolution," Science, Jun. 1, 2018, vol. 360, No. 6392, eaar5780, 23 pages.
Bult C.J., et al., "Mouse Genome Database (MGD) 2019,"Nucleic Acids Research, Jan. 8, 2019, vol. 47, No. D1, pp. D801-D806.
Calder, L.E., "Retinoic Acid-mediated Regulation of GLI3 Enables High Yield Motoneuron Derivation from Human Embryonic Stem Cells Independent of Extrinsic Activation of SHH Signaling," Dissertation, Jan. 2015, 24 pages.
Cao J., et al., "The Single-Cell Transcriptional Landscape of Mammalian Organogenesis," Nature, Feb. 2019, vol. 566, No. 7745, pp. 496-502.
Carpenedo R.L., et al., "Rotary Suspension Culture Enhances the Efficiency, Yield, and Homogeneity of Embryoid Body Differentiation," Stem Cells, 2007, vol. 25, pp. 2224-2234.
Carpenedo R.L., et al., "Homogeneous and Organized Differentiation Within Embryoid Bodies Induced by Microsphere-mediated Delivery of Small Molecules," Biomaterials, May 2009, vol. 30, No. 13, pp. 2507-2515.
Carpenedo R.L., "Microsphere-Mediated Control of Embryoid Body Microenvironments," May 2010, 24 pages.
Chambers M. S., et al., "Highly Efficient Neural Conversion of Human ES and IPS Cells by Dual Inhibition of SMAD Signaling," Nature Biotechnol., Mar. 2009, vol. 27(3), pp. 275-280.

Chen Y., et al., "Robust Bioengineered 3D Functional Human Intestinal Epithelium," Scientific Reports, vol. 5 (13708), Sep. 16, 2015, XP055454950, DOI: 10.1038/srep13708, 11 pages.
Chua C.C., et al., "Single Luminal Epithelial Progenitors Can Generate Prostate Organoids in Culture," Nature Cell Biology, Oct. 2014, vol. 16(10), 26 pages.
Cohen M., et al., "Lung Single-Cell Signaling Interaction Map Reveals Basophil Role in Macrophage Imprinting," Cell, Nov. 1, 2018, vol. 175, No. 4, pp. 1031-1044.
Conley B.J., et al., "Derivation, Propagation and Differentiation of Human Embryonic Stem Cells," The International Journal of Biochemistry & Cell Biology, 2004, vol. 36, pp. 555-567.
De Soysa T.Y., et al., "Single-cell Analysis of Cardiogenesis Reveals Basis for Organ-level Developmental Defects," Nature, Aug. 2019, vol. 572, No. 7767, pp. 120-124.
Dolle L., et al., "EpCAM and the Biology of Hepatic Stem/Progenitor Cells," American Journal of physiology gastrointestinal liver physiology, 2015, vol. 308, pp. G233-G250.
El Sebae G.K., et al., "Single-Cell Murine Genetic Fate Mapping Reveals Bipotential Hepatoblasts and Novel Multi-organ Endoderm Progenitors," Development, Oct. 1, 2018, vol. 145, No. 19, dev168658, 7 pages.
Erkan M., et al., "Organ-, Inflammation- and Cancer Specific Transcriptional Fingerprints of Pancreatic and Hepatic Stellate Cells,". Molecular Cancer, Dec. 2010, vol. 9, No. 1, pp. 1-15.
Farrell J.A., et al., "Single-Cell Reconstruction of Developmental Trajectories During Zebrafish Embryogenesis," Science, Jun. 1, 2018, vol. 360, No. 6392, eaar3131, 18 pages.
Fattahi F., et al., "Deriving Human ENS Lineages for Cell Therapy and Drug Discovery in Hirschsprung Disease," Nature, Feb. 2016, vol. 531 (7592), pp. 105-109.
Ferretti E., et al., "Mesoderm Specification and Diversification: From Single Cells to Emergent Tissues,". Current Opinion in Cell Biology, Dec. 2019, vol. 61, pp. 110-116.
Foulke-Abel J., et al., "Human Enteroids as a Model of Upper Small Intestinal Ion Transport Physiology and Pathophysiology," Gastroenterology, Mar. 2016, vol. 150, No. 3, pp. 638-649.
Francou A., et al., "Second Heart Field Cardiac Progenitor Cells in the Early Mouse Embryo," Biochimica et Biophysica Acta, Apr. 1, 2013, vol. 1833, No. 4, pp. 795-798.
Franklin V., et al., "Regionalisation of the Endoderm Progenitors and Morphogenesis of the Gut Portals of the Mouse Embryo,". Mechanisms of Development, Jul. 1, 2008, vol. 125, No. 7, pp. 587-600.
Gissen P., et al., "Structural and Functional Hepatocyte Polarity and Liver Disease," Journal of Hepatology, 2015, vol. 63, pp. 1023-1037.
Graffmann N., et al., "Modeling Nonalcoholic Fatty Liver Disease With Human Pluripotent Stem Cell-Derived Immature Hepatocyte-Like Cells Reveals Activation of PLIN2 and Confirms Regulatory Functions of Peroxisome Proliferator-Activated Receptor Alpha," Stem Cells and Development, vol. 25 (15), 2016, pp. 1119-1133.
Grand R. J., et al., "Development of the Human Gastrointestinal Tract—A Review," Gastroenterology, May 1976, vol. 70, No. 5, pp. 790-810.
Grapin-Botton A., "Antero-posterior Patterning of the Vertebrate Digestive Tract: 40 Years After Nicole Le Douarin's PhD Thesis," The International Journal of Developmental Biology, Jan. 1, 2005, vol. 49, Nos. 2-3, pp. 335-347.
Griffin O.D., et al., "Human B1 Cells in Umbilical Cord and Adult Peripheral Blood Express the Novel Phenotype CD20+CD27+CD43+ CD70-," Journal of Experimental Medicine, 2011, vol. 208(1), pp. 67-80.
Hill D R., et al., "Bacterial Colonization Stimulates a Complex Physiological Response in the Immature Human Intestinal Epithelium," Developmental Biology, Microbiology and Infectious Disease, Tools and Resources, Nov. 7, 2017, XP055822977, retrieved from the Internet: https://elifesciences.org/articles/29132, 35 pages.
Hoffmann A.D., et al., "Sonic Hedgehog is required in Pulmonary Endoderm for Atrial Septation," Development, 2009, vol. 136, p. 1761 1770.
Horie M., et al., "TBX4 is involved in the Super-Enhancer-Driven Transcriptional Programs Underlying Features Specific to Lung

(56) References Cited

OTHER PUBLICATIONS

Fibroblasts,". The American Journal of Physiology-Lung Cellular and Molecular Physiology, Jan. 1, 2018, vol. 314, No. 1, pp. L177-L191.
Ibarra-Soria X. et al., "Defining Murine Organogenesis at Single-Cell Resolution Reveals a Role for the Leukotriene Pathway in Regulating Blood Progenitor Formation,". Nature Cell Biology, Feb. 2018, vol. 20, No. 2, pp. 127-134.
Khan J.A., et al., "Fetal Liver Hematopoietic Stem Cell Niches Associate With Portal Vessels," Science, Jan. 8, 2016, vol. 351 (6269), pp. 176-180.
Kharchenko V. P., et al., "Bayesian Approach to Single-cell Differential Expression Analysis," Nature Methods, Jul. 2014, vol. 11, No. 7, pp. 740-742.
Kim E., et al., "Isl1 Regulation of Nkx2.1 in the Early Foregut Epithelium is Required for Trachea-Esophageal Separation and Lung Lobation," Developmental Cell, Dec. 16, 2019, vol. 51, No. 6, pp. 675-683.
Kimura M., et al., "Digitalized Human Organoid for Wireless Phenotyping," iScience, cell press, XP055822469, DOI: 10.1016/j.isci.2018.05.007, retrieved from the Internet: https://www.ncbi.nlm.nih.gov/pmc/articles/PMC6147234/, Jun. 29, 2018, vol. 4, pp. 294-301.
Kiselev Y. V., et al., "SCmap—A Tool for Unsupervised Projection of Single Cell RNA-seq data," Nature Methods, May 2018, vol. 15 (5), pp. 359-362.
Koike H., et al., "Engineering Human Hepato-Biliary-Pancreatic Organoids from Pluripotent Stem Cells," Nature Protocols, Feb. 2021, vol. 16(2), pp. 919-936.
Koike H., et al., "Modeling human hepato-biliary-pancreatic organogenesis from the foregut-midgut boundary," Nature, Oct. 2019, vol. 574(7776), pp. 112-116.
Langfelder P., et al., "WGCNA: An R package for weighted correlation network analysis," BMC Bioinformatics, Dec. 2008, vol. 9 (1), pp. 1-13.
Langmead B., et al., "Fast Gapped-read Alignment with Bowtie 2," Nature Methods, Apr. 2012, vol. 9(4), pp. 357-359.
Le Douarin N., et al., "Role of the Mesoderm in the Induction of the Synthesis of Glycogen During Differentiation of the Hepatic Endoderm," CR Acad Hebd Seances Acad Sci D, 1967, vol. 264, pp. 1872-1874.
Lee G., et al., "Derivation of Neural Crest Cells From Human Pluripotent Stem Cells," Nature Protocols, Mar. 18, 2010, vol. 5(4), pp. 688-701.
Li et al., "RSEM: Accurate Transcript Quantification from RNA-Seq data with or without a Reference Genome", BMC Bioinformatics Aug. 2011, vol. 12, No. 323, 16 pages.
Li L.C., et al., "Single-Cell Transcriptomic Analyses Reveal Distinct Dorsal/Ventral Pancreatic Programs,". EMBO Reports, Oct. 2018, vol. 19, No. 10, e46148, 14 pages.
Lis R., et al., "Conversion of Adult Endothelium to Immunocompetent Haematopoietic Stem Cells," Nature, May 2017, vol. 545 (7655), pp. 439-445.
Loh K. M., et al., "Mapping the Pairwise Choices Leading From Pluripotency to Human Bone, Heart, and Other Mesoderm Cell Types," Cell, Jul. 14, 2016, vol. 166, No. 2, pp. 451-467.
Manno L. G., et al., "Molecular Diversity of Midbrain Development in Mouse, Human and Stem Cells," Cell, Oct. 6, 2016, vol. 167, (2), pp. 566-580.
McCann C.J., et al., "Enteric Neural Stem Cell Therapies for Enteric Neuropathies," Neurogastroenterology and Motility, vol. 30, e13369, 2018, doi: 10.1111/nmo.13369, pp. 1-9.
McGrath P.S., et al., "The Basic Helix-Loop-Helix Transcription Factor NEUROG3 is Required for Development of the Human Endocrine Pancreas," Diabetes, Jul. 2015, vol. 6 4, pp. 2497-2505.
McIntyre B., et al., "Gli3-mediated hedgehog inhibition in human pluripotent stem cells initiates and augments developmental programming of adult hematopoiesis," The American Society of Hematology, Feb. 28, 2013, vol. 121 (9), pp. 1543-1552.
McKimpson W.M., et al., "A Fluorescent Reporter Assay of Differential Gene Expression Response to Insulin in Hepatocytes," Methods in Cell Physiology, American Journal of Physiology Cell Physiology, May 15, 2019, vol. 317, pp. C143-C151.
Menendez L., et al., "Directed differentiation of human pluripotent cells to neural crest stem cells", Nature Protocols, Jan. 2013, vol. 8 (1), pp. 203-212.
Mitaka T., "Reconstruction of Hepatic Organoid by Hepatic Stem Cells," Journal of Hepatobiliary Pancreatic Surgery, 2002, vol. 9 (6), pp. 697-703.
Moignard V., et al., "Decoding the Regulatory Network of Early Blood Development From Single-Cell Gene Expression Measurements," Nature Biotechnology, Mar. 2015, vol. 33, No. 3, pp. 269-276.
Montecino-Rodriguez E., et al., "Identification of a B-1 B Cell—Specified Progenitor," Natural Immunology, Mar. 2006, vol. 7(3), pp. 293-301.
Morrison A. J., et al., "Single-cell transcriptome analysis of avian neural crest migration reveals signatures of invasion and molecular transitions," eLife., Dec. 2017, vol. 6, 27 pages.
Nasr T., et al., "Endosome-Mediated Epithelial Remodeling Downstream of Hedgehog-Gli is Required for Tracheoesophageal Separation," Developmental Cell, Dec. 16, 2019, vol. 51, No. 6, pp. 665-674.
Ng S., et al., "Human iPSC-Derived Hepatocyte-Like Cells Support Plasmodium Liver-Stage Infection In Vitro," Stem cell reports, Mar. 10, 2015, vol. 4, pp. 348-359.
Nowotschin S., et al., "The Emergent Landscape of the Mouse Gut Endoderm at Single-Cell Resolution," Nature, May 2019, vol. 569, No. 7756, pp. 361-367.
Pedersen J.K., et al., "Endodermal Expression of Nkx6 Genes depends differentially on Pdx1," Developmental Biology, Dec. 15, 2005, vol. 288, No. 2, pp. 487-501.
Peng T., et al., "Coordination of Heart and Lung Co-development by a Multipotent Cardiopulmonary Progenitor," Nature, Aug. 2013, vol. 500, No. 7464, pp. 589-592.
Pijuan-Sala B., et al., "A Single-Cell Molecular Map of Mouse Gastrulation and Early Organogenesis," Nature, Feb. 2019, vol. 566, No. 7745, pp. 490-495.
Que J., et al., "Mesothelium Contributes to Vascular Smooth Muscle and Mesenchyme During Lung Development," Proceedings of the National Academy of Sciences USA, Oct. 28, 2008, vol. 105, No. 43, pp. 16626-16630.
Rana M.S., et al., "A Molecular and Genetic Outline of Cardiac Morphogenesis," Acta Physiologica (Oxf), Apr. 2013, vol. 207, No. 4, pp. 588-615.
Robert-Moreno A., et al., "Impaired Embryonic Haematopoiesis Yet Normal Arterial Development in the Absence of the Notch ligand Jagged1," EMBO Journal, 2008, vol. 27(13), pp. 1886-1895.
Robert-Moreno A., et al., "RBPjκ-dependent Notch Function Regulates Gata2 and is Essential for the Formation of Intra-embryonic Hematopoietic Cells," Development and disease, 2005, vol. 132(5), pp. 1117-1126.
Rothstein L.T., et al., "Human B-1 cells take the stage," Annals of the New York Academy of Sciences, May 2013, vol. 1285, pp. 97-114.
Rubin L.L., et al., "Targeting the Hedgehog Pathway in Cancer," Nature Reviews Drug Discovery, 2006, vol. 5, pp. 1026-1033.
Sander M., et al., "Homeobox Gene Nkx6.1 lies Downstream of Nkx2.2 in the major Pathway of Beta-Cell formation in the Pancreas," Development, Dec. 15, 2000, vol. 127, No. 24, pp. 5533-5540.
Sathananthan A.H., et al., "Human Embryonic Stem Cells and their Spontaneous Differentiation," Italian Journal of Anatomy and Embryology, 2005, vol. 110 (Supplement 1), No. 2, pp. 151-157.
Sauka-Spengler T. et al., "Snapshot: Neural Crest," Cell, Oct. 2010, vol. 143, No. 3, 486-486.e1.
Scialdone A., et al., "Resolving Early Mesoderm Diversification Through Single-Cell Expression Profiling," Nature, Jul. 2016, vol. 535, No. 7611, pp. 289-293.
Semrau S., et al., "Dynamics of lineage commitment revealed by single-cell transcriptomics of differentiating embryonic stem cells", Nature Communications, Oct. 2017, vol. 8 (1), pp. 1-16.

(56) References Cited

OTHER PUBLICATIONS

Simões F.C., et al., "The Ontogeny, Activation and Function of the Epicardium During Heart Development and Regeneration," Development, Apr. 1, 2018, vol. 145, No. 7, dev155994; 13 pages.
Soldatow V. Y., et al., "In Vitro Models for Liver Toxicity Testing," Toxicology Research 2.1, 2013, vol. 2, pp. 23-39.
Sugimura R., et al., "Haemotopoietic Stem and Progenitor Cells from Human Pluripotent Stem Cells," Nature, May 25, 2017, vol. 545 (7655), pp. 432-438.
Sweetman D., et al., "The Migration of Paraxial and Lateral Plate Mesoderm Cells Emerging From the Late Primitive Streak is Controlled by Different Wnt Signals," BMC Developmental Biology, Dec. 2008, vol. 8, No. 1, pp. 1-15.
Tanaka M., "Molecular and Evolutionary Basis of Limb Field Specification and Limb Initiation," Development, Growth & Differentiation, Jan. 2013, vol. 55, No. 1, pp. 149-163.
Tang X. et al. "Transcriptome Regulation and Chromatin Occupancy by E2F3 and MYC in Mice," Scientific Data, Feb. 16, 2016, vol. 3, No. 1, pp. 1-8.
Testaz S., et al., "Sonic hedgehog restricts adhesion and migration of neural crest cells independently of the Patched-Smoothened-Gli signaling pathway," PNAS, Oct. 23, 2001, vol. 98 (22), pp. 12521-12526.
Ueda T., et al., "Expansion of Human NOD/SCID-repopulating Cells by Stem Cell Factor Flk2/Flt3 ligand, thrombopoietin, IL-6, and soluble IL-6 receptor," Journal of Clinical Investment, 2000, vol. 105(7), pp. 1013-1021.
Uenishi I.G., et al., "NOTCH Signaling Specifies Arterial-type Definitive Hemogenic Endothelium from Human Pluripotent Stem Cells," Nature Communication, 2018, 14 pages.
Wagner D.E., et al., "Lineage Tracing Meets Single-cell Omics: Opportunities and Challenges," Nature Reviews Genetics, Jul. 2020, vol. 21, No. 7, pp. 410-427.
Wang J., et al., "WebGestalt 2017: A more comprehensive, powerful, flexible and interactive gene set enrichment analysis toolkit," Nucleic Acids Research, Jul. 2017, vol. 45, 8 pages.
Wang L., et al., "The Maintenance and Generation of Membrane Polarity in Hepatocytes," Hepatology, 2004, vol. 39, No. 4, pp. 892-899.
Weinreb C., et al., "Lineage tracing on transcriptional landscapes links state to fate during differentiation," Science, Feb. 14, 2020, vol. 367, ( 6479), 48 pages.
Weinreb C., et al., "SPRING: A Kinetic Interface for Visualizing High Dimensional Single-cell Expression Data," Bioinformatics, Apr. 2018, vol. 34 ( 7), pp. 1246-1248.
Wilkinson C. A., et al., "Long-term Ex-vivo Haematopoietic-stem—Cell Expansion Allows Nonconditioned Transplantation," Nature, 2019, vol. 571(7763), pp. 117-121.
Xie T., et al., "Single-Cell Deconvolution of Fibroblast Heterogeneity in Mouse Pulmonary Fibrosis," Cell Reports, Mar. 27, 2018, vol. 22, No. 13, pp. 3625-3640.
Yao S., et al., "Long-Term Self-Renewal and Directed Differentiation of Human Embryonic Stem Cells in Chemically Defined Conditions," PNAS, 2006, vol. 103, No. 18, pp. 6907-6912.
Yu G., et al., "ClusterProfiler: An R package for Comparing Biological Themes Among Gene Clusters," Omics: A Journal Integrative Biology, May 2012, vol. 16 (5), pp. 284-287.
Zaret K.S., "From Endoderm to Liver Bud: Paradigms of Cell Type Specification and Tissue Morphogenesis," Current Topics in Developmental Biology, Jan. 2016, vol. 117, pp. 647-669.
Zeltner N., et al., "Feeder-free derivation of neural crest progenitor cells from human pluripotent stem cells," Journal of Visualized Experiments, May 2014, vol. 87, 9 pages.
Zhang C., et al., "Angiopoietin-like 5 and IGFBP2 Stimulate Ex-vivo Expansion of Human Cord Blood Hematopoietic Stem Cells as Assayed by NOD/SCID transplantation," Hematopoiesis and stem Cells, 2008, vol. 111 (7), pp. 3415-3423.

Zhang X., et al., "A Comprehensive Structure-Function Study of NeurogeninS Disease-Causing Alleles during Human Pancreas and Intestinal Organoid Development," Developmental Cell, Aug. 5, 2019, vol. 50, pp. 367-380.
Bain G., "Embryonic Stem Cells Express Neuronal Properties in Vitro," Developmental Biology, 1995, vol. 168, pp. 842-357.
Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.
Burrin D., et al., "Enteral Obeticholic Acid Prevents Hepatic Cholestasis in Total Parenteral Nutrition-Fed Neonatal Pigs," Hepatology, vol. 62, Oct. 2015, p. 307A.
Chauhan R.K., et al., "Genetic and Functional Studies of Hirschsprung Disease," Doctoral Thesis: Department of Clinical Genetics, Erasmus University Rotterdam, the Netherlands, 2016, 202 pages.
Cunningham T.J., et al., "Mechanisms of Retinoic Acid Signalling and its Roles in Organ and Limb Development," Nature Reviews Molecular Cell Biology, vol. 16, No. 2, Jan. 5, 2015, pp. 110-123.
Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501 /10?clear=10&p10_accession_num=ucin1544098242321181; 160 pages.
Goldstein A.M., et al., "BMP Signaling is Necessary for Neural Crest Cell Migration and Ganglion Formation in the Enteric Nervous System," Mechanisms of Development, 2005, vol. 122, pp. 821-833.
Guan Y., et al., "Human Hepatic Organoids for the Analysis of Human Genetic Diseases," JCI Insight, Sep. 7, 2017, vol. 2, Issue 17, e94954; 17 pages.
Huang H., "Differentiation of Human Embryonic Stem Cells into Smooth Muscle Cells in Adherent Monolayer Culture," Biochemical and Biophysical Research Communications, 2006, vol. 351 pp. 321-327.
Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.
Kruitwagen H.S., et al., "SCH-O-5 Long-Term Adult Feline Liver Organoid Cultures For Disease Modelling of Hepatic Lipidosis," Research Communications of the 26th ECVIM-CA Congress, Sep. 2016, ECVIM Abstracts pp. 203-204.
Kruitwagen H.S., et al., "Long-Term Adult Feline Liver Organoid Cultures for Disease Modeling of Hepatic Steatosis," Stem Cell Reports, Apr. 2017, vol. 8(4), pp. 822-830.
Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.
Lai F.P.-L., et al., "Correction of Hirschsprung-Associated Mutations in Human Induced Pluripotent Stem Cells Via Clustered Regularly Interspaced Short Palindromic Repeats/Cas9, Restores Neural Crest Cell Function," Gastroenterology, 2017, vol. 153, No. 1, pp. 139-153.
Liu J.A-J., et al., "Identification of GLI Mutations in Patients with Hirschsprung Disease that Disrupt Enteric Nervous System Development in Mice," Gastroenterology, 2015, vol. 149, No. 7, pp. 1837-1848.
Mori R., et al., "Micropatterned Organoid Culture of Rat Hepatocytes and HepG2 Cells," Journal of Bioscience and Bioengineering, Sep. 2008, vol. 106(3), pp. 237-242.
Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.
Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, Issue 1, pp. 124-142.
Paddison P.J., et al., "Short Hairpin Activated Gene Silencing in Mammalian Cells," Methods in Molecular Biology, 2004, vol. 265, pp. 85-100.

(56) References Cited

OTHER PUBLICATIONS

Ricchi M., et al., "Differential Effect of Oleic and Palmitic Acid on Lipid Accumulation and Apoptosis in Cultured Hepatocytes," Journal of Gastroenterology and Hepatology, May 2009, vol. 24, Issue 5, pp. 830-840.
Siller R., et al., "Small-Molecule-Driven Hepatocyte Differentiation of Human Pluripotent Stem Cells," Stem Cell Reports, May 2015, vol. 4, No. 5, pp. 939-952.
Simkin J.E., et al., "Retinoic Acid Upregulates Ret and Induces Chain Migration and Population Expansion in Vagal Neural Crest Cells to Colonise the Embryonic Gut",PLoS ONE, May 2013, vol. 8(5), e64077, pp. 1-12.
Takebe T., et al., "Generation of a Vascularized and Functional Human Liver from an iPSC-derived Organ Bud Transplant," Nature Protocols, Feb. 2014, vol. 9(2), pp. 396-409.
Vu J., et al., "Regulation of Appetite, Body Composition and Metabolic Hormones by Vasoactive Intestinal Polypeptide (VIP)," Journal of Molecular Neuroscience, Apr. 23, 2015, vol. 56, No. 2, pp. 377-387.
Yamaguchi Y., et al., "Purified Interleukin 5 Supports the Terminal Differentiation and Proliferation of Murine Eosinophilic Precursors," Journal of Experimental Medicine, Jan. 1988, vol. 167, No. 1, pp. 43-56.
Zhang H., et al., "The Existence of Epithelial-to-Mesenchymal Cells with the Ability to Support Hematopoiesis in Human Fetal Liver," Cell Biology International, Mar. 2005, vol. 29, No. 3, pp. 213-219.
Alkhatatbeh M.J., et al., "Low Simvastatin Concentrations Reduce Oleic Acid-Induced Steatosis in HepG2 Cells: An In Vitro Model of Non-Alcoholic Fatty Liver Disease," Experimental and Therapeutic Medicine, 2016, vol. 11 (4), pp. 1487-1492.
Bain C.C., et al., "Constant Replenishment from Circulating Monocytes Maintains the Macrophage Pool in Adult Intestine," Nat Immunol, Oct. 2014, vol. 15 (10), pp. 929-937.
Bain C.C., et al., "Resident and Pro-Inflammatory Macrophages in the Colon Represent Alternative Context-Dependent Fates of the Same Ly6Chi Monocyte Precursors," Mucosal Immunology, May 2013, vol. 6 (3), pp. 498-510.
Bayha E., et al., "Retinoic Acid Signaling Organizes Endodermal Organ Specification Along the Entire Antero-Posterior Axis," PLoS one, Jun. 10, 2009, vol. 4 (6), e5845, 15 pages.
Bort R., et al., "Hex Homeobox Gene-Dependent Tissue Positioning is Required for Organogenesis of the Ventral Pancreas," Development, Jan. 2004, vol. 131 (4), pp. 797-806.
Bujko A., et al., "Transcriptional and Functional Profiling Defines Human Small Intestinal Macrophage Subsets," Journal of Experimental Medicine, 2018, vol. 215 (2), pp. 441-458.
Bulmer J.N., et al., "Macrophage Populations in the Human Placenta and Amniochorion," Clinical Experimental Immunology, 1984, vol. 57 (2), pp. 393-403.
Camp J.G., et al., "Multilineage Communication Regulates Human Liver Bud Development from Pluripotency," Nature, 2017, vol. 546 (7659), pp. 533-538.
Campbell E.L., et al., "Transmigrating Neutrophils Shape the Mucosal Microenvironment Through Localized Oxygen Depletion to Influence Resolution of Inflammation," Immunity, 2014, vol. 40(1), pp. 66-77.
Choi K.D., et al., "Identification of the Hemogenic Endothelial Progenitor and Its Direct Precursor in Human Pluripotent Stem Cell Differentiation Cultures," Cell Reports, Sep. 27, 2012, vol. 2(3), pp. 553-567.
Cumano A., et al., "Lymphoid Potential, Probed before Circulation in Mouse, Is Restricted to Caudal Intraembryonic Splanchnopleura," Cell, Sep. 20, 1996, vol. 86 (6), pp. 907-916.
Davies L.C., et al., "Tissue-Resident Macrophages," Nat Immunol, Oct. 2013, vol. 14 (10), pp. 986-995.
Dekkers R., et al., "A Bioassay Using Intestinal Organoids to Measure CFTR Modulators in Human Plasma," Journal of Cystic Fibrosis, 2015, vol. 14 (2), pp. 178-181.

DeSchepper S., et al., "Self-Maintaining Gut Macrophages are Essential for Intestinal Homeostasis," Cell, Oct. 4, 2018, vol. 175 (2), pp. 400-415.
Feldstein A.E., et al., "Free Fatty Acids Promote Hepatic Lipotoxicity By Stimulating TNF-$\alpha$ Expression Via a Lysosomal Pathway," Hepatology, Jul. 2004, vol. 40 (1), pp. 185-194.
Fukuda A., et al., "Ectopic Pancreas Formation in Hes1-Knockout Mice Reveals Plasticity of Endodermal Progenitors of the Gut, Bile Duct, and Pancreas," The Journal of Clinical Investigation, Jun. 2006, vol. 116 (6), pp. 1484-1493.
Glocker E.O., et al., "Inflammatory Bowel Disease and Mutations Affecting the Interleukin-10 Receptor," N Engl J Med, Nov. 19, 2009, vol. 361 (21), pp. 2033-2045.
Hentsch B., et al., "Hlx Homeo Box Gene is Essential for an Inductive Tissue Interaction that Drives Expansion of Embryonic Liver and Gut," Genes & Development, 1996, vol. 10 (1), pp. 70-79.
Higashiyama H., et al., "Embryonic Cholecystitis and Defective Gallbladder Contraction in the Sox17-Haploinsufficient Model of Biliary Atresia," Development, 2017, vol. 144 (10), pp. 1906-1917.
Hoeffel G., et al., "C-Myb+ Erythro-Myeloid Progenitor-Derived Fetal Monocytes Give Rise to Adult Tissue-Resident Macrophages," Immunity, Apr. 21, 2015, vol. 42 (4), pp. 665-678.
Iacovino M., et al., "HoxA3 is an Apical Regulator of Hemogenic Endothelium," Nat Cell Biol, Jan. 2011, vol. 13 (1), pp. 72-78.
Jørgensen M.C., et al., "Neurog3-Dependent Pancreas Dysgenesis Causes Ectopic Pancreas in Hes1 Mutant Mice," Development, 2018, vol. 145 (17), 11 pages.
Kennedy M., et al., "T Lymphocyte Potential Marks the Emergence of Definitive Hematopoietic Progenitors in Human Pluripotent Stem Cell Differentiation Cultures," Cell Reports, Dec. 27, 2012, vol. 2 (6), pp. 1722-1735.
Kuci Z., et al., "Mesenchymal Stromal Cells from Pooled Mononuclear Cells of Multiple Bone Marrow Donors as Rescue Therapy in Pediatric Severe Steroid-Refractory Graft-Versus-Host Disease: A Multicenter Survey," Haematologica, 2016, vol. 101 (8), pp. 985-994.
Lanctot P.M., et al., "The Glycans of Stem Cells," Curr Opin Chem Biol, Aug. 2007, vol. 11(4), pp. 373-380.
Maeno M., et al., "The Role of BMP-4 and GATA-2 in the Induction and Differentiation of Hematopoietic Mesoderm in Xenopus Laevis," Blood, Sep. 15, 1996, vol. 88 (6), pp. 1965-1972.
Maheshwari A., et al., "TGF-$\beta$2 Suppresses Macrophage Cytokine Production and Mucosal Inflammatory Responses In the Developing Intestine," Gastroenterology, 2011, vol. 140 (1), pp. 242-253.
Man A.L., et al., "CX3CR1+ Cell-Mediated Salmonella Exclusion Protects the Intestinal Mucosa during the Initial Stage of Infection," The Journal Immunology, 2017, vol. 198 (1), pp. 335-343.
Martin M.J., et al., "Human Embryonic Stem Cells Express An Immunogenic Nonhuman Sialic Acid," Nature Medicine, Feb. 2005, vol. 11 (2), pp. 228-232.
Miller A.J., et al., "Generation of Lung Organoids from Human Pluripotent Stem Cells in Vitro," Nature Protocols, Feb. 28, 2019, vol. 14, No. 2, pp. 518-540.
Montalbano G., et al., "Synthesis of Bioinspired Collagen/Alginate/Fibrin Based Hydrogels for Soft Tissue Engineering," Material Science & Engineering, C 91,2018, pp. 236-246.
Nissim S., et al., "Iterative Use of Nuclear Receptor Nr5a2 Regulates Multiple Stages of Liver and Pancreas Development," Development Biology, Jul. 26, 2016, vol. 418(1), pp. 108-123.
Palaria A., et al., "Patterning of the Hepato-Pancreatobiliary Boundary by BMP Reveals Heterogeneity Within the Murine Liver Bud," Hepatology, Jul. 2018, vol. 68 (1), pp. 274-288.
Perdiguero E.G., et al., "Development and Maintenance of Resident Macrophages," Nature Immunology, Jan. 2016, vol. 17 (1), pp. 2-8.
Perdiguero E.G., et al., "Tissue-Resident Macrophages Originate from Yolk-Sac-Derived Erythro-Myeloid Progenitors," Nature, Feb. 26, 2015, vol. 518 (7540), pp. 547-551.
Rankin S.A., et al., "A Retinoic Acid-Hedgehog Cascade Coordinates Mesoderm-Inducing Signals and Endoderm Competence During Lung Specification," Cell Reports, Jun. 28, 2016, vol. 16(1), pp. 66-78.

(56) References Cited

OTHER PUBLICATIONS

San Roman A.K., et al., "Boundaries, Junctions and Transitions in the Gastrointestinal Tract," Exp Cell Res, Nov. 15, 2011, vol. 317 (19), pp. 2711-2718.
Shaw T.N., et al., "Tissue-Resident Macrophages in the Intestine are Long Lived and Defined by Tim-4 and CD4 Expression," Journal of Experimental Medicine, 2018, vol. 215 (6), pp. 1507-1518.
Sheng J., et al., "Most Tissue-Resident Macrophages Except Microglia Are Derived from Fetal Hematopoietic Stem Cells," Immunity, Aug. 18, 2015, vol. 43 (2), pp. 382-393.
Shibata Y., et al., "Prediction of Hepatic Clearance and Availability by Cryopreserved Human Hepatocytes: An Application of Serum Incubation Method," Drug Metabolism and Disposition, 2002, vol. 30(8), pp. 892-896.
Shih H.P., et al., "A Gene Regulatory Network Cooperatively Controlled by Pdxland Sox9 Governs Lineage Allocation of Foregut Progenitor Cells," Cell Reports, Oct. 13, 2015, vol. 13 (2), 326-336.
Smith D.M., et al., "Roles of BMP Signaling and Nkx2.5 in Patterning at the Chick Midgut-Foregut Boundary," Development, 2000, vol. 127 (17), pp. 3671-3681.
Smith P.D., et al., "Intestinal Macrophages Lack CD14 and CD89 and Consequently are Down-Regulated for LPS- and IgA-Mediated Activities," The Journal of Immunology, 2001, vol. 167 (5), pp. 2651-2656.
Spence J.R., et al., "Sox17 Regulates Organ Lineage Segregation of Ventral Foregut Progenitor Cells," Dev Cell, Jul. 2009, vol. 17 (1), pp. 62-74.
Stresser D.M., et al., "Validation of Pooled Cryopreserved Human Hepatocytes as a Model for Metabolism Studies," BD Biosciences, Jan. 1, 2004, Retrieved from https://www.researchgate.net/profile/David-Stresser/publication/268359224_Validation_of_Pooled_Cryopreserved_Human_Hepatocytes_as_a_Model_for_Metabolism_Studies/links/54ed49710cf2465f5330eddc/Validation-of-Pooled-Cryopreserved-Human-Hepatocytes-as-a-Model-for-Metabolism-Studies.pdf on Jan. 15, 2021, 2 pages.
Sturgeon C.M., et al., "Wnt Signaling Controls the Specification of Definitive and Primitive Hematopoiesis from Human Pluripotent Stem Cells," Natural Biotechnology, Jun. 2014, vol. 32 (6), pp. 554-561.
Sumazaki R., et al., "Conversion of Biliary System to Pancreatic Tissue in Hes1-Deficient Mice," Nature Genetics, Jan. 2004, vol. 36 (1), pp. 83-87.
Takata K., et al., "Induced-Pluripotent-Stem-Cell-Derived Primitive Macrophages Provide a Platform for Modeling Tissue-Resident Macrophage Differentiation and Function," Immunity, Jul. 18, 2017, vol. 47 (1), pp. 183-198.
Tepass U., et al., "Epithelium Formation in the Drosophila Midgut Depends on the Interaction of Endoderm and Mesoderm," Development, 1994, vol. 120 (3), pp. 579-590.
Thamm K., et al., "Notch Signaling During Larval and Juvenile Development in the Polychaete Annelid *Capitella* sp. I," Developmental Biology, 2008, vol. 320 (1), pp. 304-318.
Tugizov S.M., et al., "Differential Transmission of HIV Traversing Fetal Oral/Intestinal Epithelia and Adult Oral Epithelia," Journal of Virology, 2012, vol. 86 (5), pp. 2556-2570.
Udager A., et al., "Dividing the Tubular Gut: Generation of Organ Boundaries at the Pylorus," Progress in Molecular Biology and Translational Science, 2010, vol. 96, pp. 35-62.
Uhlén M., et al., "A Human Protein Atlas for Normal and Cancer Tissues Based on Antibody Proteomics," Molecular & and Cellular Proteomics, Aug. 27, 2005, vol. 4 (12), pp. 1920-1932.
Yeung E.N.W., et al., "Fibrinogen Production is Enhanced in an In-Vitro Model of Non-Alcoholic Fatty Liver Disease: An Isolated Risk Factor for Cardiovascular Events?," Lipids in Health and Disease, 2015, vol. 14 (86), 8 pages.
Zhang Y., et al., "Development and Stem Cells of the Esophagus," Seminars in Cell & Developmental Biology, Dec. 19, 2016, vol. 66, pp. 25-35.
Zhang Y., et al., "Palmitic and Linoleic Acids Induce ER Stress and Apoptosis in Hepatoma Cells," Lipids in Health and Disease, 2012, vol. 11 (1), 8 pages.
Zhang Z., et al., "Syndecan4 Coordinates Wnt/JNK and BMP Signaling to Regulate Foregut Progenitor Development," Developmental Biology, 2016, vol. 416 (1), pp. 187-199.
Ader. M., et al., "Modeling human development in 3D culture," Current Opinion in Cell Biology, 2014, 31:23-28, 6 pgs.
Adorini, L., et al., "Farnesoid X receptor targeting to treat nonalcoholic steatohepatitis," Drag Discovery Today, Sep. 2012, 17(17/18):988-997, 10 pgs.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.
Ahnfelt-Ronne, J., et al., "An improved method for three-dimensional reconstraction of protein expression patterns in intact mouse and chicken embryos and organs," J. Histochem. Cytochem., 2007, 55:925-930, 6 pgs.
Alessi, D.R., et al., "LKB1—Dependent Signaling Pathways," Annu. Rev. Biochem., 2006, 75:137-63, 30 pgs.
Altman, G.H., et al., "Cell differentiation by mechanical stress," The FASEB Journal, 2001, 16(2):270-272, 13 pgs.
Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.
Amieva, M.R., et al. "*Helicobacter pylori* enter and survive within multivesicular vacuoles of epithelial cells," Cell. Microbiol., 2002, 4(10):677-690, 15 pgs.
An, W.F., et al., "Discovery of Potent and Highly Selective Inhibitors of GSK3b," Molecular Libraries, Probe Report, May 2014, 115 pgs.
Anderson, G., et al., "Loss of enteric dopaminergic neurons and associated changes in colon motility in an MPTP mouse model of Parkinson's disease," Exp Neurol, Sep. 2007, 207:4-12, 16 pgs.
Andrews, P.W., et al., "Embryonic stem (ES) cells and embryonal carcinoma (EC) cells: opposite sides of the same coin," Biochem Soc Trans, 2005, 33(part 6): 1526-1530, 5 Pgs.
Ang, S-L, et al., "The formation and maintenance of the definitive endoderm lineage in the mouse: involvement of HMF3/forkhead proteins," Development, 1993, 119:1301-1315, 15 pgs.
Anlauf, M., et al., "Chemical coding of the human gastrointestinal nervous system: cholinergic, VIPergic, and catecholaminergic phenotypes," The Journal of Comparative Neurology, 2003, 459:90-111, 22 pgs.
Aronson, B.E., et al., "GATA4 represses an ileal program of gene expression in the proximal small intestine by inhibiting the acetylation of histone H3, lysine 27," Biochim, Biophys. Acta, 2014, 1839(11):1273-1282, 31 pgs.
Arora, N., et al., "A process engineering approach to increase organoid yield," Development, 2017, 144:1128-1136, 9 pgs.
Asai, A., et al., "Paracrine signals regulate human liver organoid maturation from induced pluripotent stem cells," Development, 2017, 144:1056-1064, 9 pgs.
Aurora, M., et al., "hPSC-derived lung and intestinal organoids as models of human fetal tissue," Developmental Biology, 2016, 420:230-238, 9 pgs.
Avansino, J.R., et al., "Orthotopic transplantation of intestinal mucosal organiods in rodents," Surgery, Sep. 2006, 140(3):423-434, XP005610494, 12 pgs.
Baetge, G., et al., "Transient catecholaminergic (TC) cells in the vagus nerves and bowel of fetal mice: relationship to the development of enteric neurons," Developmental Biology, 1989, 132:189-211, 23 pgs.
Bajpai, R., et al., "CHD7 cooperates with PBAF to control multipotent neural crest formation," Nature, Feb. 18, 2010, 463:958-962, 7 pgs.
Bansal, D., et al., "An ex-vivo human intestinal model to study *Entamoeba histolytica* Pathogenesis," PLoS Neglected Tropical Diseases, Nov. 2009, 3(11):e551.
Baptista, P.M., et al., "The Use of Whole Organ Deceilularization for the Generation of a Vascularized Liver Organoid," Hepatology, 2011, 53(2):604-617, 14 pgs.

(56) References Cited

OTHER PUBLICATIONS

Barker, N., et ai., "Lgr5$^{+ve}$ Stem Ceils Drive Self-Renewal in the Stomach and Build Long-Lived Gastric Units In Vitro," Cell Stem Cell, 2010, 6:25-36, 12 pgs.
Barker, N., et ai., "Tissue-Resident Adult Stem Cell Populations of Rapidly Self-Renewing Organs," Cell Stem Cell, Dec. 2010, 7:656-670, 15 pgs.
Barlow, A. J., et al., "Critical Nos. of neural crest cells are required in the pathways from the neural tube to the foregut to ensure complete enteric nervous system formation," Development, 2008, 135:1681-1691, 11 pgs.
Bartfeld, S., et al., "In Vitro Expansion of Human Gastric Epithelial Stem Cells and Their Responses to Bacterial Infection," Gastroenterology, Jan. 2015, 148(1): 126-136, 22 pgs.
Bartfeld, S., et al., "Stem cell-derived organoids and their application for medical research and patient treatment," J Mol Med, 2017, 95:729-738, 10 pgs.
Bastide, P., et al. "Sox9 regulates cell proliferation and is required for Paneth cell differentiation in the intestinal epithelium," JCB, 2007, 178(4), pp. 635-648, 14 pgs.
Battle, M.A., et al., "GATA4 is essential for jejunal function in mice," Gastroenterology, 2008, 135:1676-1686, 17 pgs.
Baumann, K., "Colonic organoids for drug testing and colorectal disease modelling," Nature Reviews Molecular Cell Biolog.y, Jul. 2017, 1 pg.
Beck, F., et al., "Expression of Cdx-2 in the mouse embryo and placenta: possible tole in patterning of the extra-eeembroyonic membranes," Dev Dyn, 1995, 204:219-227.
Bergner, A.J., "Birthdating of myenteric neuron subtypes in the small intestine of the mouse," The Journal of Comparative Neurology, 2014, 522:514-527, 14 pgs.
Bernstein, B.E., et al., "The NIH Roadmap Epigenomics Mapping Consortium," Nat Biotechnol. 2010; 28(10):1045-1048, 9 pgs.
Beuling, E., et al., "Co-Localization of Gata4 and Hnflα in the Gastrointestinal Tract is Restricted to the Distal Stomach and Proximal Small Intestine," Gastroenterology, AGA Abstracts, Abstract T1933, 2007a, 132:A586, 1 pg.
Beuling, E., et al., "Conditional Gata4 deletion in mice induces bile acid absorption in the proximal small intestine," Gut, 2010, 59(7):888-895, 19 pgs.
Beuling, E., et al., "Fog Cofactors Partially Mediate Gata4 Function in the Adult Mouse Small Intestine," Gastroenterology, AGA Abstracts, Abstract W1467, 2007b, 132:A692-A693, 2pgs.
Beuling, E., et al., "GATA4 mediates gene repression in the mature mouse small intestine through interactions with Friend of GATA (FOG) cofactors," Dev Biol, 2008a, 322(1):179-189, 23 pgs.
Beuling, E., et al., "The Absence of GATA4 in the Distal Small Intestine Defines the Ileal Phenotype," Gastroenterology, ABA Abstract, Abstract 602, 2008b, 134:A83-A84, 2 pgss....
Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.
Blaugrund, E., et al., "Distinct subpopulations of enteric neuronal progenitors defined by time of development, sympathoadrenal lineage markers and Mash-1-dependence," Development 122, 1996, 309-320, 12 pgs.
Bohorquez, D.V., et al., "An Enteroendocrine Cell—Enteric Glia Connection Revealed by 3D Electron Microscopy," PLOS One, Feb. 2014, 9(2):e89881, 13 pgs.
Bonilla-Claudio, M., et al., "Bmp signaling regulates a dose-dependent transcriptional program to control facial skeletal development," Development, 2012, 139:709-719, 11 pgs.
Bosse, T., et al., "Gata4 and Hnfla are partially required for the expression of specific intestinal genes during development," Am J Physiol Gastrointest Liver Physiol, 2007, 292:G1302-G1314, 13 pgs.
Bouchi, R., et al., "FOXO1 Inhibition Yields Functional Insulin-Producing Cells In Human Gut Organoid Cultures," Nat Commun, 2014, 5:4242, 24 pgs.

Brevini, T.A.L., et al., "No shortcuts to pig embryonic stem cells," Theriogenology, 2010, 74:544-550, 7 pgs.
Bruens, L., et al., "Expanding the Tissue Toolbox: Deriving Colon Tissue from Human Pluripotent Stem Cells," Cell Stem Cell, Jul. 2017, 21(l):3-5, 3 pgs.
Brugmann, S.A., et al., "Building additional complexity to in vitro-derived intestinal tissues," Stem Cell Research & Therapy, 2013, 4(Suppl 1):S1, 5 pgs.
Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.
Burns, A.J., et al., "In ovo transplantation of enteric nervous system precursors from vagal to sacral neural crest results in extensive hindgut colonisation," Development, 2002, 129:2785-2796, 12 pgs.
Burns, A.J., et al., "Neural stem cell therapies for enteric nervous system disorders," Nature Reviews/Gastroenterology & Hepatology, May 2014, 11:317-328, 12 pgs.
Buta, C., et al., "Reconsidering pluripotency tests: Do we still need teratoma assays?" Stem Cell Research, 2013, 11:552-562, 11 pgs.
Cabezas, J., et al., "Nonalcoholic Fatty Liver Disease: A Pathological View," Liver Biopsy—Indications, Procedures, Results, Chapter 8, InTech, 2012, pp. 161-188, 29 pgs.
Campbell, F.C., et al., "Transplantation of cultured small bowel enterocytes," Gut, 1993, 34:1153-1155, 4 pgs.
Cao, L., et al., "Development of Intestinal Organoids as Tissue Surrogates: Cell Composition and the Epigenetic Control of Differentiation," Molecular Carcinogenesis, 2015, 54:189-202, 14 pgs.
Chang, H-M., et al., "BMP 15 Suppresses Progesterone production by Down-Regulating StAR via ALK3 in Human Granulosa Cells," Molecular Endocrinology, 2013, 27:2093-2104, 12 pgs.
Chen, C., et al., "Pdx1 inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.
Chen, T-W., et al., "Ultrasensitive fluorescent proteins for imaging neuronal activity," Nature, Jul. 18, 2013, 499:295-300, 8 pgs.
Cheng, X., et al., "Self-renewing endodermal progenitor lines generated from human pluripotent stem cells," Cell Stem Cell, Apr. 6, 2012, 10:371-384, 14 pgs.
Choi, E., et al., "Cell lineage distribution atlas of the human stomach reveals heterogeneous gland populations in the gastric antrum," Gut, 2014, 63(11):1711-1720, 20 pgs.
Churin, Y., et al., "*Helicobacter pylori* CagA protein targets the c-Met receptor and enhances the motogenic response," J. Cell Biol., 2003, 161:249-255, 7 pgs.
Cieslar-Pobuda, A., et al., The expression pattern of PFKFB3 enzyme distinguishes between induced-pluripotent stem cells and cancer stem cells, Oncotarget, 6(30):29753-29770, 18 pgs.
Clevers, H., "Modeling Development and Disease with Organoids," Cell, Jun. 2016, 165:1586-1597, 12 pgs.
Coghlan, M.P., et al., "Selective small molecule inhibitors of glycogen synthase kinase-3 modulate glycogen metabolism and gene transcription," Chem. Biol., 2000, 7(10):793-803, 11 pgs.
Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.
Costa, M., et al., "A method for genetic modification of human embryonic stem cells using electroporation," Nature Protocols, Apr. 5, 2007, 2:792-796, 5 pgs.
Couzin, J., "Small RNAs Make Big Splash," Science, 2002, 298:2296-2297, 2 pgs.
Covacci, A., et al., "Molecular characterization of the 128-kDa immunodominant antigen of *Helicobacter pylori* associated with cytotoxicity and duodenal ulcer," Proc Natl Acad Sci USA, Jun. 1993, 90:5791-5795, 5 pgs.
Curchoe, C.L., et al., "Early acquisition of neural crest competence during hESCs neuralization," PloS One, Nov. 2010, 5:1-17, 17 pgs..
D'Amour, K.A., et al., "Efficient differentiation of human embryonic stem cells to definitive endoderm," Nature Biotechnology, 2005, 23:1534-1541, 9 pgs.

(56) References Cited

OTHER PUBLICATIONS

D'Amour, K.A., et al., "Production of pancreatic hormone-expressing endocrine cells from human embiyonic stem cells," Nat Biotechnol, 2006, 24:1392-1401, 10 pgs.

Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484, 16 pgs.

Date, S., et al., "Mini-Gut Organoids: Reconstitution of the Stem Cell Niche," Annual Review of Cell and Developmental Biology, Nov. 2015, 31:269-289.

Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.

De Santa Barbara, P., et al., "Bone Morphogenetic Protein Signaling Pathway Plays Multiple Roles During Gastrointestinal Tract Development," Developmental Dynamics, 2005, 234:312-322, 11 pgs.

De Santa Barbara, P., et al., "Development and differentiation of the intestinal epithelium," Cell Mol Life Sci, 2003, 60(7):1322-1332, 12 pgs.

Dedhia, P.H., et al., "Organoid Models of Human Gastrointestinal Development and Disease," Gastroenterology, 2016, 150:1098-1112, 15 pgs.

Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.

Deng, H., et al., "Effects of all-trans retinoic acid on the differentiation of neural stem cells and the expression of c-myc gene," Chinese Journal of Tissue Engineering Research, Mar. 18, 2007, 11(11):2039-2042. [Reference unavailable].

Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. [Reference unavailable].

Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.

Dessimoz, J., et al., "FGF signaling is necessary for establishing gut tube domains along the anterior-posterior axis in vivo," Meeh Dev, 2006, 123:42-55, 14 pgs.

Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.

Discher, D.E., et al., "Growth Factors, Matrices, and Forces Combine and Control Stem Cells," Science, Jun. 2009, 324:1673-1677, 5 pgs.

Dobreva, G., et al., "SATB2 Is a Multifunctional Determinant of Craniofacial Patterning and Osteoblast Differentiation," Cell, 2006, 125:971-986, 16 pgs.

Driver, I., et al., "Specification of regional intestinal stem cell identity during *Drosophila* metamorphosis," Development, 2014, 141:1848-1856, 9 pgs.

Duluc, I., et al., "Fetal Endoderm Primarily Holds the Temporal and Positional Information Required for Mammalian Intestinal Development," The Journal of Cell Biology, 1994, 126(1):211-221, 11 pgs.

Eberhard, J., et al., "A cohort study of the prognostic and treatment predictive value of SATB2 expression in colorectal cancer," British Journal of Cancer, 2012, 106:931-938, 8 pgs.

Eicher, A.K., et al., "Translating Developmental Principles to Generate Human Gastric Organoids," Cellular and Molecular Gastroenterology and Hepatology, 2018, 5(3):353-363, 11 pgs.

Elbashir, S.M., et al., "Functional anatomy of siRNAs for mediating efficient RNAi in *Drosophila melanogaster* embiyo lysate," EMBO J., 2001, 20(23):6877-6888, 12 pgs.

Evans, M.J., et al., "Establishment in culture of pluripotent cells from mouse embiyos," Nature, 1981, 292:154-156, 3 pgs.

Ezashi, T., et al., "Low $O_2$ tensions and the prevention of differentiation of hES cells," PNAS, Mar. 2005, 102(13):4783-4788, 6 pgs.

Fagerberg, L., et al., "Analysis of the Human Tissue-specific Expression by Genome-wide Integration of Transcriptomics and Antibody-based Proteomics," Mol Cell Proteomics, 2014, 13:3 97-406, 10 pgs.

Fatehullah, A., et al., "Organoids as an in vitro model of human development and disease," Nature Cell Biology, Mar. 2106, 18(3):246-254, 9 pgs.

Finkbeiner, S.R., et al., "A Gutsy Task: Generating Intestinal Tissue from Human Pluripotent Stem Cells," Dig Dis Sci, 2013, 58:1176-1184, 9 pgs.

Finkbeiner, S.R., et al., "Stem Cell-Derived Human Intestinal Organoids as an Infection Model for Rotaviruses," mBio, Jul./Aug. 2012, 3(4):e00159-12, 6 pgs.

Finkbeiner, S.R., et al., "Transcriptome-wide Analysis Reveals Hallmarks of Human Intestine Development and Maturation In Vitro and In Vivo," Stem Cell Reports, 2015, 4:1140-1155, 16 pgs.

Fitzpatrick, D.R., et al., "Identification of SATB2 as the cleft palate gene on 2q32-q33," Human Molecular Genetics, 2003, 12(19):2491-2501, 11 pgs.

Fon Tacer, K., et al., "Research Resource: Comprehensive Expression Atlas of the Fibroblast Growth Factor System in Adult Mouse," Mol Endocrinol, Oct. 2010, 24(10):2050-2064, 15 pgs.

Fordham, R.P., et al., "Transplantation of expanded fetal intestinal progenitors contributes to colon regeneration after injury," Cell Stem Cell, Dec. 5, 2013, 13:734-744, 11 pgs.

Fu, M., et al., "Embryonic development of the ganglion plexuses and the concentric layer structure of human gut: a topographical study," Anatomy and Embryology, Feb. 27, 2004, 208:33-41, 10 pgs.

Fu, M., et al., "HOXB5 expression is spatially and temporarily regulated in human embryonic gut during neural crest cell colonization and differentiation of enteric neuroblasts," Developmental Dynamics, 2003, 228:1-10, 10 pgs.

Furness, J.B., "The enteric nervous system and neurogastroenterology," Nature Reviews/Gastroenterology & Hepatology, May 2012, 9:286-294, 9 pgs.

Genthe, J.R., et al., "Ventromorphins: A new class of small molecule activators of the canonical BMP signaling pathway," ACS Chem Biol, 2017, 12(9):2436-2447, 21 pgs.

Georgas, K.M., et al., "An illustrated anatomical ontology of the developing mouse lower urogenital tract," Development, 2015, 142:1893-1908, 16 pgs.

Gessner, R.C., et al., "Functional ultrasound imaging for assessment of extracellular matrix scaffolds used for liver organoid formation," Biomaterials, 2013, 34:9341-9351, 11 pgs.

Ginestet, C., Book Review in the Journal of the Royal Statistical Society. Series A (Statistics in Society) (2011), of *ggplot2: Elegant Graphics for Data Analysis*, by H. Wickham, 2009; 174(1):245, 2 pgs.

Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6 pgs.

Goldenring, J.R., et al., "Overexpression of Transforming Growth Factor-α Alters Differentiation of Gastric Cell Lineages," Dig. Dis. Sci., 1996, 41(4):773-784, 12 pgs.

Gomez, M.C., et al., "Derivation of cat embryonic stem-like cells from in vitro-produced blastocysts on homologous and heterologous feeder cells," Theriogenology, 2010, 74:498-515, 18 pgs.

Gori, M., et al., "Investigating nonalcoholic Fatty Liver Disease in a Liver-on-a-Chip Microfluidic Device," PLOS One, Jul. 2016, 11(7):e0159729, 15 pgs.

Gouon-Evans, V., et al., "BMP-4 is required for hepatic specification of mouse embryonic stem cell-derived definitive endoderm," Nature Biotechnology, Nov. 2006, 24(11):1402-1411, 10 pgs.

Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.

(56) References Cited

OTHER PUBLICATIONS

Gracz, A.D., et al., "Sox9 Expression Marks a Subset of CD24-expressing Small Intestinve Epithelial Stem Cells the Form Organoids in vitro," Am J Physiol Gastrointest Liver Physiol, 2010, 298:G590-600.
Grad Wohl, G., et al., "neurogenin3 is required for the development of the four endocrine cell lineages of the pancreas," Proc Natl Acad Sci USA, 2000, 97:1607-1611, 5 pgs.
Green, M.D., et al., "Generation of anterior foregut endoderm from human embryonic and induced pluripotent stem cells," Nature Biotechnology, Mar. 2011, 29(3):267-272, 7 pgs.
Gregorieff, A., et al., "Wnt signaling in the intestinal epithelium: from endoderm to cancer," Genes & Dev., 2005, 19:877-890, 15 pgs.
Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.
Grosse, A.S., et al., "Cell dynamics in fetal intestinal epithelium: implications for intestinal growth and morphogenesis," Development, 2011, 138:4423-4432. 10 pgs.
Guilak, F., et al., "Control of Stem Cell Fate by Physical Interactions with the Extracellular Matrix," Cell Stem Cell, Jul. 2009, 5:17-26, 10 pgs.
Guo, Z., et al., "Injury-induced BMP signaling negatively regulates *Drosophila* midgut homeostasis," J Cell Biol., 2013, 201(6):945-961, 17 pgs.
Gyorgy, A.B., et al., "SATB2 interacts with chromatin-remodeling molecules in differentiating cortical neurons" European Journal of Neuroscience, 2008, 27:865-873, 9 pgs.
Han, M-E., et al., "Gastric stem cells and gastric cancer stem cells," Anatomy & Cell Biology, 2013, 46:8-18, 11 pgs.
Hannon, G.J., "RNA interference," Nature, 2002, 418:244-251, 8 pgs.
Hannan, N.R.F., et al., "Generation of Multipotent Foregut Stem Cells from Human Pluripotent Stem Cells," Stem Cell Reports, Oct. 2013, 1:293-306, 14 pgs.
Hao, M.M., et al., "Development of enteric neuron diversity," J. Cell. Mol. Med., 2009 13:1193-1210, 18 pgs.
Haramis, A-P.G., et al., "De Novo Crypt Formation and Juvenile Polyposis on BMP Inhibition in Mouse Intestine," Science, 2004, 303:1684-1686, 4 pgs.
Hardwick, J.C.H., et al., "Bone Morphogenetic Protein 2 Is Expressed by, and Acts Upon, Mature Epithelial Cells in the Colon," Gastroenterology, 2004, 126:111-121, 11 pgs.
Hardy, T., et al., "Nonalcoholic fatty liver disease: new treatments," Curr Opin Gastroenterol, May 2015, 31(3):175-183, 9 pgs.
Haveri, H., et al., "Transcription factors GATA-4 and GATA-6 in normal and neoplastic human gastrointestinal mucosa," BMC Gastroenterlology, 2008, 8:9.
He, X.C., et al., "BMP signaling inhibits intestinal stem cell self-renewal through suppression of Wnt-β-catenin signaling," Nature Genetics, 2004, 36(10):1117-1121, 5 pgs.
Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.
Hockemeyer, D., et al., "Genetic engineering of human ES and iPS cells using TALE nucleases," Nat Biotechnol., 2012, 29:731-734, 8 pgs.
Hoffmann, W., "Current Status on Stem Cells and Cancers of the Gastric Epithelium," Int. J. Mol. Sci., 2015, 16:19153-19169, 17 pgs.
Holland, P.W.H., et al., "Classification and nomenclature of all human homeobox genes," BMC Biology, 2007, 5:47, 29 pgs.
Howell, J.C., et al., "Generating intestinal tissue from stem cells: potential for research and therapy," Regen Med., 6(6):743-755, 22 pgs.
Huch, M., et al., "Modeling mouse and human development using organoid cultures," Development, 2015, 142:3113-3125, 13 pgs.
Huch, M., et al., "Lgr5+ liver stem cells, hepatic organoids and regenerative medicine," Regen. Med., 2013, 8(4):385-387, 3 pgs.
Huebsch, N., et al., "Automated video-based analysis of contractility and calcium flux in human-induced pluripotent stem cell-derived cardiomyocytes cultured over different spatial scales," Tissue Engineering: Part C, 2015, 21:467-479, 15 pgs.
Huh, W.J., et al., "Ménétrier's Disease: Its Mimickers and Pathogenesis," Journal of Pathology and Translational Medicine, 2016; 50:10-16, 7 pgs.
Hutvagner, G., et al., "A microRNA in a Multiple-Turnover RNAi Enzyme Complex," Science, Sep. 20, 2002, 297:2056-2060, 6 pgs.
Jean, C., et al., "Pluripotent genes in avian stem cells," Develop Growth Differ, 2013, 55:41-51, 11 pgs.
Jeejeebhoy, K.N., "Short bowel syndrome: a nutritional and medical approach," CMAJ, 2002, 166(10):1297-1302, 6 pgs.
Jenny, M., et al., "Neurogenin3 is differentially required for endocrine cell fate specification in the intestinal and gastric epithelium," EMBO J, 2002, 21(23):6338-6347, 10 pgs.
Johannesson, M., et al., "FGF4 and Retinoic Acid Direct Differentiation of hESCs into PDX1-Expressing Foregut Endoderm in a Time- and Concentration-Dependent Manner," PLoS One, Mar. 2009, 4(3):1-13, 13 pgs.
Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pgs.
Johnson, L.R., et al., "Stimulation of rat oxyntic gland mucosal growth by epidermal growth factor," Am. J. Physiol., 1980, 238:G45-49, 5 pgs.
Johnston, T.B., et al., "Extroversion of the Bladder, Complicated by the Presence of Intestinal Openings on the Surface of the Extroverted Area," J Anat Physiol, 1913, 48(Pt 1):89-106, 18 pgs.
Jung, P., et al., "Isolation and in vitro expansion of human colonic stem cells," Nature Medicine, Oct. 2011, 17:1225-1227, 3 pgs.
Juno, R.J., et al., "A serum factor after intestinal resection stimulates epidermal growth factor receptor signaling and proliferation in intestinal epithelial cells," Surgery, Aug. 2002, 132:377-383, 7 pgs.
Juno, R.J., et al., "A serum factor(s) after small bowel resection induces intestinal epithelial cell proliferation: effects of timing, site, and extent of resection," Journal of Pediatric Surgeiy, Jun. 2003, 38:868-874, 7 pgs.
Kabouridis, P.S., et al., "Microbiota controls the homeostasis of glial cells in the gut lamina propria," Neuron, Jan. 21, 2015, 85:289-295, 8 pgs.
Kaji, K., et al., "Virus-free induction of pluripotency and subsequent excision of reprogramming factors," Nature, Apr. 2009, 458:771-775, 6 pgs.
Katoh, M., "WNT Signaling in Stem Cell Biology and Regenerative Medicine," Current Drug Targets, 2008, 9(7):565-570, 6 pgs.
Kawaguchi, J., et al., "Isolation and propagation of enteric neural crest progenitor cells from mouse embryonic stem cells and embryos," Development, 2010, 137:693-704, 12 pgs.
Kawaguchi, Y., et al., "The role of the transcriptional regulator Ptf1a in converting intestinal to pancreatic progenitors," Nat Genet, 2002, 32:128-134, 7 pgs.
Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.
Keung, A. J., et al., "Presentation Counts: Microenvironmental Regulation of Stem Cells by Biophysical and Material Cues," Annu. Rev. Cell Dev. Biol., 2010, 26:533-556, 26 pgs.
Kim, B-M., et al., "Regulation of mouse stomach development and Barx1 expression by specific microRNAs," Development, 2011, 138:1081-1086, 6 pgs.
Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.
Kim, T-H., et al., "Stomach development, stem cells and disease," Development, 2016, 143:554-565, 12 pgs.
Klimanskaya, I., et al., "Human embryonic stem cells derived without feeder cells," Lancet, 2005, 365:1636-1641, 6 pgs.

(56) References Cited

OTHER PUBLICATIONS

Kohlnhofer, B.M., et al., "GATA4 Regulates Epithelial Cell Proliferation to Control Intestinal Growth and Development in Mice," Cellular and Molecular Gastroenterology and Hepatology, 2016, 2(2):189-209, 21 pgs.
Koike, M., et al., "Effects of mechanical strain on proliferation and differentiation of bone marrow stromal cell line ST2," J Bone Miner Metab, 2005, 23:219-225, 7 pgs.
Kolahchi, A.R., et al., "Microfluidic-Bases Multi-Organ Platforms for Drug Discovery," Micromachines, 2016, 7(162):1-33, 33 pgs.
Koo, B-K, et al., "Controlled gene expression in primary Lgr5 organoid cultures," Nature Methods, Jan. 1, 2012, 9(1):81-83, XP055225249, 5 pgs.
Kosinski, C., et al., "Indian hedgehog regulates intestinal stem cell fate through epithelial-mesenchymal interactions during development," Gastroenterology, Sep. 2010, 139:893-903, 17 pgs.
Kostrzewski, T., et al., "Three-dimensional perfused human in vitro model of nonalcoholic fatty liver disease," World J Gastroenterol, 2017, 23(2):204-215, 13 pgs.
Kovalenko, P.L., et al., "The Correlation Between the Expression of Differentiation Markers in Rat Small Intestinal Mucosa and the Transcript Levels of Schlafen 3," JAMA Surg., Sep. 4, 2013, 148:1013-1019, 7 pgs.
Kraus, M.R.C., et al., "Patterning and shaping the endoderm in vivo and in culture," Current Opinion Genetics & Development., 2012, 22:347-353, 7 pgs.
Krausova, M., et al., "Wnt signaling in adult intestinal stem cells and cancer," Cellular Signalling, 2014, 26:570-579, 10 pgs.
Kretzschmar, K., et al., "Organoids: Modeling Development and the Stem Cell Niche in a Dish," Developmental Cell, Sep. 2016, 38:590-600, 11 pgs.
Kroon, E., et al., "Pancreatic endoderm derived from human embryonic stem cells generates glucose-responsive insulin secreting cells in vivo," Nat Biotechnol, 2008, 26(4):443-52.
Kubo, A., et al., "Development of definitive endoderm from embryonic stem cells in culture," Development, 2004, 131:1651-1662, 12 pgs.
Kudoh, T., et al., "Distinct roles for Fgf, Wnt and retinoic acid in posteriorizing the neural ectoderm," Development, 2002, 129:4335-4346, 12 pgs.
Kumar, M., et al., "Signals from lateral plate mesoderm instruct endoderm toward a pancreatic fate," Dev Biol, 2003, 259:109-122, 14 pgs.
Kuratnik, A., et al., "Intestinal organoids as tissue surrogates for toxicological and pharmacological studies," Biochemical Pharmacology, 2013, 85:1721-1726, 6 pgs.
Lahar, N., et al., "Intestinal suhepithelial myofibroblasts support in vitro and in vivo growth of human small intestinal epithelium," PLoS One, Nov. 2011, 6:e26898, 9 pgs.
Lambert, P.F., et al., "Using an immortalized cell line to study the HPV life cycle in organotypic 'raft' cultures," Methods in Molecular Medicine, 2005, 119:141-155.
Lambrecht, N.W.G., et al., "Identification of the K efflux channel coupled to the gastric H-K-ATPase during acid secretion," Physiological Genomics, 2005, 21:81-91, 11 pgs.
Lameris, A.L., et al., "Expression profiling of claudins in the human gastrointestinal tract in health and during inflammatory bowel disease," Scandinavian Journal of Gastroenterology, 2013, 48:58-69, 12 pgs.
Lancaster, M.A., et al., "Organogenesis in a dish: modeling development and disease using organoid technologies," Science, Jul. 18, 2014, 345:283 & 1247125-1-9, 11 pgs.
Langmead, G., et al., "Ultrafast and memory-efficient alignment of short DNA sequences to the human genome," Genome Biology, 2009, 10:R25, 10 pgs.
Lavial, F., et al., "Chicken embryonic stem cells as a non-mammalian embryonic stem cell model," Develop. Growth Diff, 2010, 52:101-114, 14 pgs.
Le Douarin, N.M., et al., "Neural crest cell plasticity and its limits," Development 131, 2004, 4637-4650, 14 pgs.
Lee, C. S., et al., "Neurogenin 3 is essential for the proper specification of gastric enteroendocrine cells and the maintenance of gastric epithelial cell identity," Genes Dev, 2002, 16:1488-1497, 11 pgs.
Lee, G., et al., "Isolation and directed differentiation of neural crest stem cells derived from human embryonic stem cells," Nature Biotechnology, Dec. 2007, 25:1468-1475, 9 pgs.
Lennerz, J.K.M., et al., "The Transcription Factor MIST1 is a Novel Human Gastric Chief Cell Marker Whose Expression is Lost in Metaplasia, Dysplasia, and Carcinoma," The American Journal of Pathology, 2010, 177(3):1514-1533, 20 pgs.
Levin, D.E., et al., "Human tissue-engineered small intestine forms from postnatal progenitor cells," Journal of Pediatric Surgery, 2013, 48:129-137, 9 pgs.
Li, H., et al., "TreeFam: a curated database of phylogenetic trees of animal gene families," Nucleic Acids Research, 2006, 34:D572-D580, 9 pgs.
Li, L., "BMP Signaling Inhibits Intestinal Stem Cell Self-Renewal Through Antagonizing Wnt Signaling," Gastroenterology, AASLD Abstracts, Abstract S1223, 2005, 128:A702, 1 pg.
Li, Y., et al., "In vitro organogenesis from pluripotent stem cells," Organogenesis, Jun. 2014, 10(2):159-163, 5 pgs.
Li, Z., et al., "SATB2 is a sensitive marker for lower gastrointestinal well-differentiated neuroendocrine tumors," Int J Clin Exp Pathol, 2015, 8(6):7072-7082, 11 pgs.
Lim, D.A., et al., "Noggin Antagonizes BMP Signaling to Create a Niche for Adult Neurogenesis," Neuron, Dec. 2000, 28:713-726, 14 pgs.
Lin, C., et al., "The application of engineered liver tissues for novel drug discovery," Expert Opinion on Drug Discovery, 2015, 10(5):519-540.
Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.
Liu, J., et al., "A Small-Molecule Agonist of the Wnt Signaling Pathway," Angew Chem Int Ed Engl., 2005, 44(13): 1987-1990, 4 pgs.
Logan, C.Y., et al., "The Wnt Signaling Pathway in Development and Disease," Annu. Rev. Cell Dev. Biol., 2004, 20:781-810, 32 pgs.
Longmire, T.A., et al., "Efficient Derivation of Purified Lung and Thyroid Progenitors from Embryonic Stem Cells," Stem Cell, 2012, 10:398-411, 14 pgs.
López-Díaz, L., et al., "Intestinal Neurogenin 3 directs differentiation of a bipotential secretory progenitor to endocrine cell rather than goblet cell fate," Dev Biol. 2007, 309:298-305, 8 pgs.
Lu, Y., et al., "A Novel 3D Liver Organoid System for Elucidation of Hepatic Glucose Metabolism," Biotechnol Bioeng., Feb. 2012, 109(2):595-604, 21 pgs.
Ludwig, T.E., et al., "Derivation of human embryonic stem cells in defined conditions," Nat Biotechnol, 2006, 24:185-187, 3 pgs.
Ludwig, T.E., et al., "Feeder-independent culture of human embryonic stem cells," Nat Methods, 2006, 3:637-646, 10 pgs.
Lui, V.C., et al., "Perturbation of hoxb5 signaling in vagal neural crests down-regulates ret leading to intestinal hypoganglionosis in mice," Gastroenterology, 2008, 134:1104-1115, 12 pgs.
Luo, X., et al., "Generation of endoderm lineages from pluripotent stem cells," Regenerative Medicine, 2017, 12(1):77-89, 13 pgs.
Mahe, M.M., et al., "Establishment of gastrointestinal epithelial organoids," Current Protocols in Mouse Biology, 2013, 3(4):217-240, XP002750112, 31 pgs.
Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.
Martin, G.R., "Teratocarcinomas and mammalian embryogenesis," Science, 1980, 209:768-776, 9pgs.
Martín, M., et al., "Dorsal pancreas agenesis in retinoic acid-deficient Raldh2 mutant mice," Dev Biol., 2005, 284:399-411, 13 pgs.
McCauley, H.A., et al., "Pluripotent stem cell-derived organoids: using principles of developmental biology to grow human tissues in a dish," Development, 2017, 144:958-962, 5 pgs.

(56) References Cited

OTHER PUBLICATIONS

McCracken, K. W., et al., "Generating human intestinal tissue from pluripotent stem cells in vitro," Nature Protocols, 2011, 6(12):1920-1928, 19 pgs.
McCracken, K.W., et al., "Mechanisms of embryonic stomach development," Seminars in Cell & Development Biology, 2017, 66:36-42, 7 pgs.
McCracken, K. W., et al., "Modelling human development and disease in pluripotent stem-cell-derived gastric organoids," Nature, Oct. 29, 2014, 516(7531):400-404, XP055210509, 30 pgs.
McCracken, K.W., et al., "Wnt/β-catenin promotes gastric fundus specification in mice and humans," Nature, Jan. 2017, 541(7636):182-187, 31 pgs.
McCracken, K.W., "Mechanisms of endoderm patterning and directed differentiation of human stem cells into foregut tissues," Dissertation, Graduate School of the University of Cincinnati, Jun. 19, 2014, 185 pgs.
McGovern, D.P.B., et al., "Genome-wide association identifies multiple ulcerative colitis susceptibility loci," Nature Genetics, 2010, 42(4):332-337, 8 pgs.
McKeown, S.J., et al., "Hirschsprung disease: a developmental disorder of the enteric nervous system," Wiley Interdisciplinary Reviews Developmental Biology, Jan./Feb. 2013, 2:113-129, 17 pgs.
McLin, V.A., et al., "Repression of Wnt/β-catenin signaling in the anterior endoderm is essential for liver and pancreas development," Development, 2007, 134:2207-2217, 11 pgs.
McLin, V. A et al., "The Role of the Visceral Mesoderm in the Development of the Gastrointestinal Tract," Gastroenterology, 2009, 136:2074-2091, 18 pgs.
McMahon, J. A., et al., "Noggin-mediated antagonism of BMP signaling is required for growth and patterning of the neural tube and somite," Genes & Development, May 1998, 12:1438-1452, 15 pgs.
McManus, M.T., et al., "Gene Silencing in Mammals by Small Interfering RNAs," Nat. Rev. Genet, Oct. 2002, 3:737-747, 13 pgs.
Meerbrey, K.L., et al., "The pINDUCER lentiviral toolkit for inducible RNA interference in vitro and in vivo," Proc Natl Acad Sci USA, 2011, 108:3665-3670, 6 pgs.
Merker, S.R., et al., "Gastrointestinal organoids: How they gut it out," Developmental Biology, 2016, 420:239-250, 12 pgs.
Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.
Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.
Mills, J.C., et al., "Gastric Epithelial Stem Cells," Gastroenterology, 2011, 140:412-424, 13 pgs.
Miyabayashi, T., et al., "Wnt/β-catenin/CBP signaling maintains long-term murine embryonic stem cell pluripotency," Proc Natl Acad Sci USA, 2007, 104(13):5668-5673, 6 pgs.
Molodecky, N.A., et al., "Increasing Incidence and Prevalence of the Inflammatory Bowel Diseases With Time, Based on Systematic Review," Gastroenterology, 2012, 142:46-54, 51 pgs.
Molotkov, A., et al., "Retinoic Acid Generated by Raldh2 in Mesoderm is Required for Mouse Dorsal Endodermal Pancreas Development," Dev Dyn, 2005, 232:950-957, 8 pgs.
Moser, A.R., et al., "A dominant mutation that predisposes to multiple intestinal neoplasia in the mouse," Science, 1990, 247(4940):322-324, 3 pgs.
Mosher, J.T., et al., "Intrinsic differences among spatially distinct neural crest stem cells in terms of migratory properties, fate-determination, and ability to colonize the enteric nervous system," Dev. Biol., Mar. 2007, 303(1):1-15, 29 pgs.
Mou, H., et al., "Generation of Multipotent Lung and Airway Progenitors from Mouse ESCs and Patient-Specific Cystic Fibrosis iPSCs," Stem Cell, 2012, 10:385-397, 13 pgs.

Muudaliarr, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.
Mullin, E., "Tiny Human Esophagus Grown in the Lab—Here's Why: Miniature versions of the organ that guides food to the stomach could help scientists treat a variety of medical ailments," National Geographic, Sep. 20, 2018, downloaded from https://www.nationalgeographic.com/science/2018/09/news-human-esophagus-grown-lab-stem-cells-cancer-health.html, 5 pgs.
Munera, J.O., et al., "Differentiation of Human Pluripotent Stem Cells into Colonic Organoids via Transient Activation of BMP Signaling," Cell Stem Cell, Jul. 2017, 21(1):51-64.e6, 21pgs.
Munera, J.O., et al., "Generation of Gastrointestinal Organoids from Human Pluripotent Stem Cells," Organ Regeneration, In: Tsuji, T., (eds), Organ Regeneration. Methods in Molecular Biology, vo. 1597, Humana Press, New York, NY, 2017, 11 pgs.
Muñoz, M., et al., "Conventional pluripotency markers are unspecific for bovine embiyonic-derived cell-lines," Theriogenology, 2008, 69:1159-1164, 6 pgs.
Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.
Neiiendam, J.L., et al., "An NCAM-derived FGF-receptor agonist, the FGL-peptide, induces neurite outgrowth and neuronal survival in primary rat neurons," J. Neurochem., 2004, 91(4):920-935, 17 pgs.
Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 100 pgs.
Nielsen, C., et al., "Gizzard Formation and the Role of Bapx1," Developmental Biology, 2001, 231:164-174, 11 pgs.
Noguchi, T-A.K., et al., "Generation of stomach tissue from mouse embryonic stem cells," Nature Cell Biology, 2015, 17(8):984-993, XP055225165, 20 pgs.
Nomura, S., et al., "Evidence for Repatterning of the Gastric Fundic Epithelium Associated With Ménétrier's Disease and TGFa Overexpression," Gastroenterology, 2005, 128:1292-1305, 14 pgs.
Obermayr, F., et al., "Development and developmental disorders of the enteric nervous system," Nature Reviews/Gastroenterology & Hepatology, Jan. 2013, 10:43-57, 15 pgs.
Ogaki, S., et al., "Wnt and Notch Signals Guide Embryonic Stem Cell Differentiation into the Intestinal Lineages," Stem Cells, 2013, 31:1086-1096, 11 pgs.
Okita, K., et al., "An Efficient Nonviral Method to Generate Integration-Free Human-Induced Pluripotent Stem Cells from Cord Blood and Peripheral Blood Cells," Stem Cells, 2013, 31:458-466, 9 pgs.
Okita, K., et al., "Generation of Mouse Induced Pluripotent Stem Cells Without Viral Vectors," Science, 2008, 322(5903):949-953, 6 pgs.
Olbe, L., et al., "A Mechanism by Which Helicobacter pylori Infection of the antrum Contributes to the Development of Duodenal Ulcer," Gastroenterology, 2001, 110:1386-1394, 9 pgs.
Ootani, A. et al., "Sustained in vitro intestinal epithelial culture within a Wnt-dependent stem cell niche," Nat Med, 2009, 15:701-706, 14 pgs.
Ornitz, D.M., et al., "FGF signaling pathways in endochondral and intramembranous bone development and human genetic disease," Genes & Development, Jun. 2002, 16:1446-1465, 21 pgs.
Ornitz, D.M., et al., "The Fibroblast Growth Factor signaling pathway," WIREs Dev Biol, 2015, 4:215-266, 52 pgs.
Paddison, P.J., et al., "RNA interference: the new somatic cell genetics?", Cancer Cell, 2002, 2:17-23, 7 pgs.
Pai, R., et al., "Deoxycholic Acid Activates β-Catenin Signaling Pathway and Increases Colon Cell Cancer Growth and Invasiveness," Mol Biol Cell., 2004, 15(5):2156-2163, 8 pgs.
Pan, Q., *Physiology*, University of Science and Technology of China Press, Jan. 31, 2014, pp. 149-150. [Reference unavailable].
Paris, D.B.B.P., et al., "Equine embryos and embryonic stem cells: Defining reliable markers of pluripotency," Theriogenology, 2010, 74:516-524, 9 pgs.

(56) References Cited

OTHER PUBLICATIONS

Park, H.R., et al., "Lipotoxicity of Palmaitic Acid on Neural Progenitor Cells and Hippocampal Neurogenesis," Toxicol Res, 2011, 27(2):103-110, 8 pgs.
Park, J.S., et al., "Differential Effects of Equiaxial and Uniaxial Strain on Mesenchymal Stem Cells," Biotechnology and Bioengineering, Nov. 2004, 88(3):359-368, 10 pgs.
Park, J.S., et al., "The effect of matrix stiffness on the differentiation of mesenhymal stem cells in response to TGF-β," Biomaterials, 2011, 32:3921-3930, 10 pgs.
Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.
Park, Y.H., et al., "Review of Atrophic Gastritis and Intestinal Metaplasia as a Premalignant Lesion of Gastric Cancer," Journal of Cancer Prevention, 2015, 20(1):25-40, 16 pgs.
Parkin, D.M., "The global health burden of infection-associated cancers in the year 2002," Int. J. Cancer, 2006, 118:3030-3044, 15 pgs.
Pastula, A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pgs.
Patankar, J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, 56:S496, 1 pg.
Patankar, J.V., et al., "Intestinal GATA4 deficiency protects from diet-induced hepatic steatosis," Journal of Hepatology, 2012, 57:1061-1068, 8 pgs.
Peek, R.M., Jr., et al., "*Helicobacter pylori* cagA+ Strains and Dissociation of Gastric Epithelial Cell Proliferation From Apoptosis," J. Natl. Cancer Inst., 1997, 89:863-868, 7 pgs.
Peek, R.M., Jr., "*Helicobacter pylori* infection and disease: from humans to animal models," Dis Model Meeh, 2008, 1:50-55, 6 pgs.
Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.
Petitte, J.N., et al., "Avian pluripotent stem cells," Meeh, of Develop., 2004, 121:1159-1168, 10 pgs.
Pompaiah, M., et al., "Gastric Organoids: An Emerging Model System to Study *Helicobacter pylori* Pathogenesis," Molecular Pathogenesis and Signal Transduction by *Helicobacter pylori*, Current Topics in Microbiology and Immunology, N. Tegtmeyer, et al., (eds.), 2017, pp. 149-168.
Prakash, R., "Regulation of WNT Genes in Stem Cells Development and Organogenesis," IJP, Jun. 2014, 1(6):366-372, 7 pgs.
Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).
Qi, M-C., et al., "Mechanical strain induces osteogenic differentiation: Cbfa1 and Ets-1 expression in stretched rat mesenchymal stem cells," Int J Oral Maxillofac Surg, 2008, 37:453-458, 6 pgs.
Que, J., et al., "Morphogenesis of the trachea and esophagus: current players and new roles for noggin and Bmps," Differentiation, 2006, 74:422-437, 16 pgs.
Raju, R., et al., "A Network Map of FGF-1/FGFR Signaling System," Journal of Signal Transduction, Apr. 2014, 2014:1-16, Article ID 962962, 16 pgs.
Ramachandran, S.D., et al., "In Vitro Generation of Functional Liver Organoid-Like Structures Using Adult Human Cells," Pios One, Oct. 2015, 14 pgs.
Ramalingam, S., et al., "Distinct levels of Sox9 expression mark colon epithelial stem cells that form colonoids in culture," Am J Physiol Gastrointest Liver Physiol,, 2012, 302:G10-G20, 11 pgs.
Ramsey, V.G., et al., "The maturation of mucus-secreting gastric epithelial progenitors into digestive-enzyme secreting zymogenic cells requires Mist1," Development, 2007, 134:211-222, 12 pgs.
Rankin, S.A., et al., "A Molecular Atlas of Xenopus Respiratory System Development," Developmental Dynamics, 2015, 244:69-85, 17 pgs.
Rankin, S.A., et al., "Suppression of Bmp4 signaling by the zinc-finger repressors Osr1 and Osr2 is required for Wnt/β-catenin-mediated lung specification in Xenopus," Development, 2012, 139:3010-3020, 11 pgs.
Rankin, S.A., et al., "Timing is everything: Reiterative Wnt, BMP and RA signaling regulate developmental competence during endoderm organogenesis," Developmental Biology, Feb. 1, 2018, 434(1): 121-132,12 pgs.
Ratineau, C., et al., "Endoderm- and mesenchyme-dependent commitment of the differentiated epithelial cell types in the developing intestine of rat," Differentiation, 2003, 71:163-169, 7 pgs.
Ray, K., "Engineering human intestinal organoids with a functional ENS," Nature Reviews Gastroenterology & Hepatology, Nov. 2016, 1 pg.
Reilly, G.C., et al., "Intrinsic extracellular matrix properties regulate stem cell differentiation," Journal of Biomechanics, 2010, 43:55-62, 8 pgs.
Rennert, K., et al., "A microfluidically perfused three dimensional human liver model," Biomaterials, 2015, 71:119-131, 13 pgs.
Richards, M., et al., "The Transcriptome Profile of Human Embryonic Stem Cells as Defined by SAGE," Stem Cells, 2004, 22:51-64, 14 pgs.
Roberts, D.J., et al., "Sonic hedgehog is an endodermal signal inducing Bmp-4 and Hox genes during induction and regionalization of the chick hindgut," Development, 1995, 121:3163-3174, 12 pgs.
Rodriguez-Pineiro, A.M., et al., "Studies of mucus in mouse stomach, small intestine, and colon. II. Gastrointestinal mucus proteome reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Rohrschneider, M.R., et al., "Polarity and cell fate specification in the control of *C. elegans* gastrulation," Dev. Dyn., 2009, 238(4):789-796, 15 pgs.
Roth, R.B., et al., "Gene expression analyses reveal molecular relationships among 20 regions of the human CNS," Neurogenetics, 2006, 7:67-80, 14 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saffrey, M.J., "Cellular changes in the enteric nervous system during ageing," Developmental Biology. 2013, 382:344-355, 12 pgs.
Saha, S., et al., "Inhibition of Human Embryonic Stem Cell Differentiation by Medical Strain," Journal of Cellular Physiology, 2006, 206:126-137, 12 pgs.
Saito, M., et al., "Reconstruction of liver organoid using a bioreactor," World J Gastroenterol, Mar. 2006, 12(12):1881-1888, 8 pgs.
Sampaziotis, F., et al., "Potential of Human Induced Pluripotent Stem Cells in Studies of Liver Disease," Hepatology, Jul. 2015, 62(1):303-311, 9 pgs.
Sancho, E., et al., "Signaling Pathways in Intestinal Development and Cancer," Annu. Rev. Cell Dev. Biol., 2004, 20:695-723, 31 pgs.
Sandoiu, A., "Scientists create human esophagus in stem cell first," Medical News Today, Sep. 21, 2018, downloaded from https://www.medicalnewstoday.com/articles/323118.php, 4 pgs.
Sasai, Y., "Next-Generation Regenerative Medicine: Organogenesis from Stem Cells in 3D Culture," Cell Stem Cell, May 2013, 12:520-530, 11 pgs.
Sasselli, V., et al., "The enteric nervous system," Developmental Biology, Jan. 2012, 366:64-73, 10 pgs.

(56) References Cited

OTHER PUBLICATIONS

Sato, T., et al., "Long-term expansion of epithelial organoids from human colon, adenoma, adenocarcinoma, and Barrett's epithelium," Gastroenterology, Nov. 2011, 141:1762-1772, 11 pgs.
Sato, T., et al., "Single Lgr5 stem cells build crypt-villus structures in vitro without a mesenchymal niche," Nature, 2009, 459:262-265, 5 pgs.
Savidge, T.C., et al., "Human intestinal development in a severe-combined immunodeficient xenograft model," Differentiation, 1995, 58:361-371, 11 pgs.
Savin, T., et al., "On the growth and form of the gut," Nature, 2011, 476:57-62, 7 pgs.
Schlieve. C.R., et al., "Created of Warm Blood and Nerves: Restoring an Enteric Nervous System in Organoids," Cell Stem Cell, Jan. 2017, 20:5-7, 3 pgs.
Schmelter, M., et al., "Embryonic stem cells utilize reactive oxygen species as transducers of mechanical strain-induced cardiovascular differentiation," The FASEB Journal, Jun. 2006, 20(8):1182-1184, 16 pgs.
Schonhoff, S.E., et al., "Neurogenin 3-expressing progenitor cells in the gastrointestinal tract differentiate into both endocrine and non-endocrine cell types," Dev Biol, 2004, 270:443-454, 12 pgs.
Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Schumacher, M.A., et al., "The use of murine-derived fundic organoids in studies of gastric physiology," J. Physiol., 2015, 593(8): 1809-1827, 19 pgs.
Schuppan, D., et al., "Non-alcoholic steatohepatitis: Pathogenesis and novel therapeutic approaches," Journal of Gastroenterology and Hepatology, 2013, 28(Suppl 1):68-76, 9 pgs.
Shah, S.B., et al., "Cellular self-assembly and biomaterials-based organoid models of development and diseases," Acta Biomaterialia, 2017, 53:29-45, 17 pgs.
Shan, J., et al., "Identification of a Specific Inhibitor of the Dishevelled PDZ Domain," Biochemistry, 2005, 44(47):15495-15503, 9 pgs.
Sheehan-Rooney, K., et al., "Bmp and Shh Signaling Mediate the Expression of satb2 in the Pharyngeal Arches," PLoS One, Mar. 2013, 8(3):e59533, 10 pgs.
Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shimizu, N., et al., "Cyclic strain induces mouse embryonic stem cell differentiation into vascular smooth muscle cells by activating PDGF receptor β," J Appl Physiol, 2008, 104:766-772, 7 pgs.
Shyer, A.E., et al., "Bending Gradients: How the Intestinal Stem Cell Gets Its Home," Cell, 2015, 161:569-580, 13 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Siegel, R., et al., "Colorectal Cancer Statistics, 2014," CA Cancer J Clin, 2014, 64:104-117, 14 pgs.
Sigalet, D.L., "The Role of the Enteric Neuronal System In Controlling Intestinal Function," Clinical Surgery Society Magazine, 2003,64:214, 1 pg. [Reference unavailable].
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.
Simon-Assmann, P., et al., "In vitro models of intestinal epithelial cell differentiation," Cell Biol. Toxicol., 2007, 23:241-256, 16 pgs.
Sinagoga, K.L., et al., "Generating human intestinal tissues from pluripotent stem cells to study development and disease," The EMBO Journal, 2015, 34(9):1149-1163, 15 pgs.
Skardal, A., et al., "Organoid-on-a-chip and body-on-a-chip systems for drug screening and disease modeling," Drug Discovery Today, Sep. 2016, 21(9):1399-1411, 13 pgs.
Snoeck, H-W., "Generation of Anterior Foregut Derivatives from Pluripotent Stem Cells," Stem Cells Handbook, S. Sell (ed.), 2013, pp. 161-175.
Snykers, S., et al., "In Vitro Differentiation of Embryonic and Adult Stem Cells into Hepatocytes: State of the Art," Stem Cells, 2009, 27:577-605, 29 pgs.
Sonntag, F., et al., "Design and prototyping of a chip-based multi-micro-organoid culture system for substance testing, predictive to human (substance) exposure," Journal of Biotechnology, 2010, 148:70-75, 6 pgs.
Soto-Gutierrez, A., et al., "Engineering of an Hepatic Organoid to Develop Liver Assist Devices," Cell Transplant., 2010, 19(6):815-822, 12 pgs.
Spear, P.C., et al., "Interkinetic nuclear migration: A mysterious process in search of a function," Develop. Growth Differ., 2012, 54:306-316, 12 pgs.
Speer, A.L., et al., "Fibroblast Growth Factor 10-Fibroblast Growth Factor Receptor 2b Mediated Signaling is Not Required for Adult Glandular Stomach Homeostasis," PLoS ONE, 2012, 7(ll):e49127, 12 pgs.
Speer, A.L., et al., "Murine Tissue-Engineered Stomach Demonstrates Epithelial Differentiation," Journal of Surgical Research, Mar. 22, 2011, 171(1):6-14, XP028317226, 9 pgs.
Spence, J.R., et al., "Directed differentiation of human pluripotent stem cells into intestinal tissue in vitro," Nature, 2011, 470:105-109, 13 pgs.
Spence, J.R., et al., "Translational Embryology: Using Embryonic Principles to Generate Pancreatic Endocrine Cells from Embryonic Stem Cells," Developmental Dynamics, 2007, 236:3218-3227, 10 pgs.
Stadtfeld, M., et al., "Induced pluripotent stem cells generated without viral integration," Science, 2008, 322(5903):945-949, 12 pgs.
Stange, D.E., et al., "Differentiated Troy$^+$ chief cells act as 'reserve' stem cells to generate all lineages of the stomach epithelium," Cell, 2013, 155(2):3 57-368, 26 pgs.
Stark, R., et al., "Development of an endoluminal intestinal lengthening capsule," Journal of Pediatric Surgeiy, 2012, 47:136-141, 6 pgs.
Su, N., et al., "Role of FGF/FGFR signaling in skeletal development and homeostasis: learning from mouse models," Bone Research, 2014, 2:14003, 24 pgs.
Sugawara, T., et al., "Organoids recapitulate organs?" Stem Cell Investig, 2018, vol. 5, Iss. 3, 4 pgs.
Sui, L., et al., "Signaling pathways during maintenance and definitive endoderm differentiation of embryonic stem cells," Int J Dev Bio, 2013, 57:1-12, 12 pgs.
Sun, Y., et al., "Genome engineering of stem cell organoids for disease modeling," Protein Cell, 2017, 8(5):315-327, 13 pgs.
Taipale, J., et al., "The Hedgehog and Wnt signalling pathways in cancer," Nature, 2001, 411:349-354, 8 pgs.
Tait, I.S., et al., "Colonic mucosal replacement by syngeneic small intestinal stem cell transplantation," The American Journal of Surgery, Jan. 1994, 167:67-72, 6 pgs.
Tait, I.S., et al., "Generation of neomucosa in vivo by transplantation of dissociated rat postnatal small intestinal epithelium," Differentiation, 1994 56:91-100, 10 pgs.
Takahashi, K. et al., "Induction of Pluripotent Stem Cells from Adult Human Fibroblasts by Defined Factors," Cell, 2007, 131:861-872, 12 pgs.
Takahashi, K., et al., "Induction of Pluripotent Stem Cells from Mouse Embryonic and Adult Fibroblast Cultures by Defined Factors," Cell, 2006, 126:663-676, 14 pgs.
Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.

(56) References Cited

OTHER PUBLICATIONS

Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.
Teo, A.K.K., et al., "Activin and BMP4 Synergistically Promote Formation of Definitive Endoderm in Human Embryonic Stem Cells," Stem Cells, 2012, 30:631-642, 12 pgs.
Thanasupawat, T., et al., "INSL5 is a novel marker for human enteroendocrine cells of the large intestine and neuroendocrine tumours," Oncology Reports, 2013, 29:149-154, 6 pgs.
Thomson, J.A., et al., "Embryonic Stem Cell Lines Derived from Human Blastocysts," Science, 1998, 282(5391):1145-1147, 4 pgs.
Tiso, N., et al., "BMP signalling regulates anteroposterior endoderm patterning in zebrafish," Meeh Dev, 2002, 118:29-37, 9 pgs.
Toivonen, S., et al., "Activin A and Wnt-dependent specification of human definitive endoderm cells," Experimental Cell Research, 2013, 319:2535-2544, 10 pgs.
Trapnell, C., et al., "Differential gene and transcript expression analysis of RNA-seq experiments with TopHat and Cufflinks," Nat Protoc, 2013, 7(3):562-578, 39 pgs.
Trisno, S.L., et al., "Esophageal Organoids from Human Pluripotent Stem Cells Delineate Sox2 Functions during Esophageal Specification," Cell Stem Cell, 2018, 23:501-515, 23 pgs.
Tsakmaki, A., et al., "3D intestinal organoids in metabolic research: virtual reality in a dish," Current Opinion in Pharmacology, 2017, 37:51-58, 8 pgs.
Tuschl, T., et al., "Targeted mRNA degradation by double-stranded RNA in vitro," Genes Dev., 1999, 13:3191-3197, 8 pgs.
Uppal, K., et al., "Meckel's Diverticulum: A Review," Clinical Anatomy, 2011, 24:416-422, 7 pgs.
Van Breemen, R.B., et al., "Caco-2 cell permeability assays to measure drug absorption," Expert Opin. Drug Metab. Toxicol., Aug. 2005, 1(2):175-185, 11 pgs.
Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.
Van Klinken, B.J-W., et al., "MUC5B is the prominent mucin in human gallbladder and is also expressed in a subset of colonic goblet cells," The American Journal of Physiology, 1998, 274:G871-G878, 8 pgs.
Verzi, M.P., et al., "Role of the Homeodomain Transcription Factor Bapx1 in Mouse Distal Stomach Development," Gastroenterology, 2009, 136:1701-1710, 10 pgs.
Walker, E.M., et al., "GATA4 and GATA6 regulate intestinal epithelia! cytodifferentiation during development," Developmental Biology, 2014, 392:283-294, 12 pgs.
Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.
Walton, K.D., et al., "Epithelial Hedgehog signals direct mesenchymal villus patterning through BMP," Abstracts / Developmental Biology, Program/Abstract # 354, 2009,331:489, 1 pg.
Walton, K.D., et al., "Hedgehog-responsive mesenchymal clusters direct patterning and emergence of intestinal villi," PNAS, 2012, 109(39):15817-15822, 6 pgs.
Walton, K.D., et al., "Villification in the mouse: Bmp signals control intestinal villus patterning," Development, 2016, 143:427-436, 10 pgs.
Wan, W., et al., "The Role of Wnt Signaling in the Development of Alzheimer's Disease: A Potential Therapeutic Target?", BioMed Research International, 2014, 2014:1-9, Article ID 301575, 9 pgs.
Wang, A., et al., "Generating cells of the gastrointestinal system: current approaches and applications for the differentiation of human pluripotent stem cells," J Mol Med, 2012, 90:763-771, 9 pgs.
Wang, F., et al., "Isolation and characterization of intestinal stem cells based on surface marker combinations and colony-formation assay," Gastroenterology, 2013, 145:383-395.e1-e21, 34 pgs.

Wang, J., et al., "Mutant Neurogenin-3 in Congenital Malabsorptive Diarrhea," New England Journal of Medicine, 2006, 355:270-280, 11 pgs.
Wang, X., et al., "Cloning and variation of ground state intestinal stem cells," Nature, 2015, 522:173-178, 18 pgs.
Wang, Z., et al., "Retinoic acid regulates morphogenesis and patterning of posterior foregut derivatives," Dev Biol, 2006, 297:433-445.
Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.
Warlich, E., et al., "Lentiviral vector design and imaging approaches to visualize the early stages of cellular reprogramming," Mol. Ther., Apr. 2011, 19:782-789, 9 pgs.
Watson, C.L., et al., "An in vivo model of human small intestine using pluripotent stem cells," Nature Medicine, Oct. 19, 2014, 20(11):1310-1314, XP055241417, 7 pgs.
Wehkamp, J., et al., "Paneth cell antimicrobial peptides: Topographical distribution and quantification in human gastrointestinal tissues," FEBS Letters, 2006, 580:5344-5350, 7 pgs.
Weis, V.G., et al., "Current understanding of SPEM and its standing in the preneoplastic process," Gastric Cancer, 2009, 12:189-197, 9 pgs.
Wells, J.M., et al., "Early mouse endoderm is patterned by soluble factors from adjacent germ layers," Development, 2000, 127:1563-1572, 10 pgs.
Wells, J.M., et al., "How to Make an intestine," Development, Feb. 15, 2014, 141(4):752-760, XP055241409, 9 pgs.
Wen, S. et al., "*Helicobacter pylori* virulence factors in gastric carcinogenesis," Cancer Lett, 2009, 282:1-8, 8 pgs.
Whissell, G., et al., "The transcription factor GATA6 enables self-renewal of colon adenoma stem cells by repressing BMP gene expression," Nature Cell Biology, 2014, 16(7):695-707, 24 pgs.
Willet, S.G., et al., "Stomach Organ and Cell Lineage Differentiation: From Embryogenesis to Adult Homeostasis," Cellular and Molecular Gastroenterology and Hepatology, 2016, 2(5):546-559, 14 pgs.
Williamson, R.C.N., et al., "Humoral stimulation of cell proliferation in small bowel after transection and resection in rats," Gastroenterology, 1978, 75:249-254, 6 pgs.
Wills, A., et al., "Bmp signaling is necessary and sufficient for ventrolateral endoderm specification in *Xenopus*" Dev Dyn., 2008, 237(8):2177-2186, 18 pgs.
Woltjen, K., et al., "*piggyBac* transposition reprograms fibroblasts to induced pluripotent stem cells," Nature, 2009, 458:766-770, 8 pgs.
Workman, M.J., et al., "Engineered human pluripotent-stem-cell-derived intestinal tissues with a functional enteric nervous system," Nat Med, Jan. 2017, 23(1):49-59, 29 pgs.
Workman, M.J., "Generating 3D human intestinal organoids with an enteric nervous system," Thesis, Graduate School of the University of Cincinnati, Oct. 2014, 61 pgs.
Xia, H.H-X., et al. "Antral-Type Mucosa in the Gastric Incisura, Body, and Fundus (Antralization): A Link Between *Helicobacter pylori* Infection and Intestinal Metaplasia?", Am. J. Gastroenterol., 2000, 95:114-121, 8ps.
Xinaris, C., et al., "Organoid Models and Applications in Biomedical Research," Nephron, 2015, 130:191-199, 9 pgs.
Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of Hox genes along the gastrointestinal tract," Congenital Anomalies, 2004, 44:18-26, 9 pgs.
Yamada, S., et al. "Differentiation of immature enterocytes into enteroendocrine cells by Pdx1 overexpression," Am. J. Physiol. Gastrointest. Liver Pyshiol., 2001, 281:G229-G236, 8 pgs.
Yanagita, M., "Modulator of bone morphogenetic protein activity in the progression of kidney diseases," Kidney International, 2006, 70:989-993, 5 pgs.

(56) References Cited

OTHER PUBLICATIONS

Yin, C., et al., "Hepatic stellate cells in liver development, regeneration, and cancer," The Journal of Clinical Investigation, May 2013, 123(5):1902-1910, 9 pgs.
Young, H.M., et al., "Expression of Ret-, p75$^{NTR}$-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M., et al., "GDNF is a chemoattractant for enteric neural cells," Developmental biology, Dec. 19, 2000, 229:503-516, 14 pgs.
Yu, Y., *Chinese Studies on Disease Signaling Pathway and Targeted Therapy*, Anhui Science and Technology Press, May 31, 2013, p. 363. [Reference unavailable].
Yuan, Y., et al., "Peptic ulcer disease today," Nat Gin Pract Gastroenterol Hepatol, 2006,3:80-89 10 pgs.
Yui, S., et al., "Functional engraftment of colon epithelium expanded in vitro from a single adult Lgr5(+) stem cell," Nature Medicine, Apr. 2012, 18:618-623, 8 pgs.
Zachos, N.C., et al., "Human Enteroids/Colonoids and Intestinal Organoids Functionally Recapitulate Normal Intestinal Physiology and Pathophysiology," The Journal of Biological Chemistiy, Feb. 2016, 291(8):3759-3766, 8 pgs.
Zbuk, K.M., et al., "Hamartomatous polyposis syndromes," Gastroenterology & Hepatology, 2007, 4(9):492-502, 12 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
Zhang, Q, et al., "Small-molecule synergist of the Wnt/β-catenin signaling pathway," Proc Natl Acad Sci USA, 2007, 104(18):7444-7448, 6 pgs.
Zhang, W., et al., "Elastomeric Free-Form Blood Vessels for Interconnecting Organs on Chip Systems," Lab Chip, Apr. 2016, 16(9):1579-1586, 19 pgs.
Zhang, Y.S., et al., "Multisensor-integrated organs-on-chips platforms for automated and continual in situ monitoring of organoid behaviors," PNAS Early Edition, 2017, 10 pgs.
Zhang, Y.S., et al., "Seeking the right context for evaluating nanomedicine: from tissue models in petri dishes to microfluidic organs-on-a-chip," Nanomedicine (Lond.), 2015, 10(5):685-688, 4 pgs.
Zhou, H., et al., "Generation of Induced Pluripotent Stem Cells Using Recombinant Proteins," Cell Stem Cell, 2009, 4(5):381-384, 4 pgs.
Zhou, J., et al., "The Potential for Gut Organoid Derived Interstitial Cells of Cajal in Replacement Therapy," International Journal of Molecular Sciences, Sep. 2017, 18:1-17, 17 pgs.
Zhou, Q., et al., "In vivo reprogramming of adult pancreatic exocrine cells to β-cells," Nature, 2008, 455: 627-632, 6 pgs.
Zorn, A.M., et al., "Vertebrate endoderm development and organ formation," Annu Rev Cell Dev Biol, 2009, 25:221-251, 36 pgs.
Chinese Office Action, and Preliminary Search Report, dated Jan. 30, 2019 for Application No. CN 201580034910.4, 11 pgs.
European Exam Report dated Sep. 28, 2017 for Application No. EP 15728704.6, 4 pgs.
European Exam Report dated Jul. 4, 2018 for Application No. EP 15728704.6, 3 pgs.
European Exam Report dated May 18, 2018 for Application No. EP 15791404.5, 3 pgs.
International Search Report dated Feb. 9, 2012 for Application No. PCT/US2011/035518, 7Pgs-.
International Preliminary Report on Patentability and Written Opinion dated Nov. 6, 2012 for Application No. PCT/US2011/035518, 5 pgs.
International Search Report and Written Opinion dated Dec. 15, 2015 for Application No. PCT/US2015/032626, 19 pgs.
International Search Report and Written Opinion dated Jan. 25, 2016 for Application No. PCT/US2015/055956, 16 pgs.
International Preliminary Report on Patentability dated Apr. 18, 2017 for Application No. PCT/US2015/055956, 8 pgs.
International Search Report and Written Opinion dated Aug. 14, 2017 for Application No. PCT/US2017/013109, 17 pgs.
International Search Report and Written Opinion dated Jan. 19, 2018 for Application No. PCT/US2017/059845, 13 pgs.
International Search Report and Written Opinion dated Jan. 29, 2018 for Application No. PCT/US2017/059860, 13 pgs.
International Search Report and Written Opinion dated Jan. 18, 2018 for Application No. PCT/US2017/059865, 12 pgs.
International Search Report and Written Opinion dated Feb. 21, 2018 for Application No. PCT/US2017/064600, 15 pgs.
International Search Report and Written Opinion dated Jun. 14, 2018 for Application No. PCT/US2018/018585, 14 pgs.
International Search Report and Written Opinion dated Sep. 28, 2018 for Application No. PCT/US2018/029083, 14 pgs.
International Search Report and Written Opinion dated Jan. 8, 2019 for Application No. PCT/US2018/054635, 16 pgs.
International Searching Authority Invitation to Pay Additional Fees, Where Applicable, Protest Fee, dated Jun. 27, 2018 for Application No. PCT/US2018/029083, 3 pgs.
Israeli Office Action dated Nov. 29, 2018 for Application No. IL 249253, 8 pgs.
Japanese Office Action, Notification of Reasons for Refusal, and First Search Report by Registered Search Organization, dated May 14, 2019 for Application JP 2017-520900, 65 pgs.
Japanese Office Action, Notice of Reasons for Refusal, and Search Report by Registered Search Organization, dated Apr. 2, 2019 for Application No. JP 2016-569618, 42 pgs.
Singaporean Written Opinion dated Oct. 19, 2017 for Application No. SG11201609953X, 8 pgs.
Singaporean Second Written Opinion dated Sep. 4, 2018 for Application No. SG11201609953X, 6 pgs.
Singaporean Office Action, Third Written Opinion, dated May 3, 2019 for Application No. 11201609953X, 5 pgs.
U.S. Appl. No. 61/332,178, filed May 6, 2010.
U.S. Appl. No. 62/003,719, filed May 28, 2014.
U.S. Appl. No. 62/065,131, filed Oct. 17, 2014.
U.S. Appl. No. 62/332.194, filed May 5, 2016.
U.S. Appl. No. 62/429.948, filed Dec. 5, 2016.
U.S. Appl. No. 62/478,962, filed Mar. 30, 2017.
U.S. Appl. No. 62/730,061, filed Sep. 12, 2018.
Forster R., et al., "Human Intestinal Tissue with Adult Stem Cell Properties Derived from Pluripotent Stem Cells," Stem Cell Reports, Jun. 3, 2014, vol. 2, No. 6, pp. 838-852.
Gao S., et al., Fetal Liver: An Ideal Niche for Hematopoietic Stem Cell Expansion, Science China, Life Sciences, Review, Aug. 2018, vol. 61 (8), pp. 885-892.
Huss J. M., et al., "Constitutive Activities of Estrogen-Related Receptors: Transcriptional Regulation of Metabolism by the ERR Pathways in Health and Disease," Biochimica et Biophysica Acta, 2015, vol. 1852, 2015, pp. 1912-1927.
Huynh N., et al., "61.06 Feasibility and Scalability of Spring Parameters in Distraction Enterogenesis in a Murine Model," 2017, 3 pages, Retrieved from Internet: URL: https://www.asc-abstracts.org/abs2017/61-06-feasibility-and-scalability-of-spring-parameters-in-distraction-enterogenesis-in-a-murine-model/, Retrieved on Jun. 4, 2022.
Moschidou D., et al., "Human Mid-Trimester Amniotic Fluid Stem Cells Cultured under Embryonic Stem Cell Conditions with Valproic Acid Acquire Pluripotent Characteristics," Stem Cells and Development, Feb. 1, 2013, vol. 22, No. 3, pp. 444-458.
Nantasanti S., et al., Disease Modeling and Gene Therapy of Copper Storage Disease in Canine Hepatic Organoids, Stem Cell Reports, 2015, vol. 5, pp. 895-907.
Ogaki S., et al., A Cost-Effective System for Differentiation of Intestinal Epithelium from Human Induced Pluripotent Stem Cells, Scientific Reports, Nov. 30, 2015, 11 pages.
Payushina O.V., Hematopoietic Microenvironment in the Fetal Liver: Roles of Different Cell Populations, Review Article, International Scholarly Research Network Cell Biology, 2012, 8 pages.
Riehl T., et al., "CD44 and TLR4 Mediate Hyaluronic Acid Regulation of Lgr5+ Stem Cell Proliferation, Crypt Fission, and Intes-

(56) References Cited

OTHER PUBLICATIONS tinal Growth in Postnatal and Adult Mice," The American Journal of Physiology-Gastrointestinal and Liver Physiology, Dec. 1, 2015, vol. 309, No. 11, pp. G874-G887.

Scott A., et al., "Repeated Mechanical Lengthening of Intestinal Segments in a Novel Model," Journal of Pediatric Surgery, Jun. 2015, vol. 50, No. 6, pp. 954-957.

Seet C.S., et al., Generation of Mature T Cells from Human Hematopoietic Stem/Progenitor Cells in Artificial Thymic Organoids, Nature Methods, May 2017, vol. 14 (5), pp. 521-530.

Sullins V. F., et al., "Intestinal Lengthening in an Innovative Rodent Surgical Model," Journal of Pediatric Surgery, Dec. 2014, vol. 49, No. 12, pp. 1791-1794.

\* cited by examiner

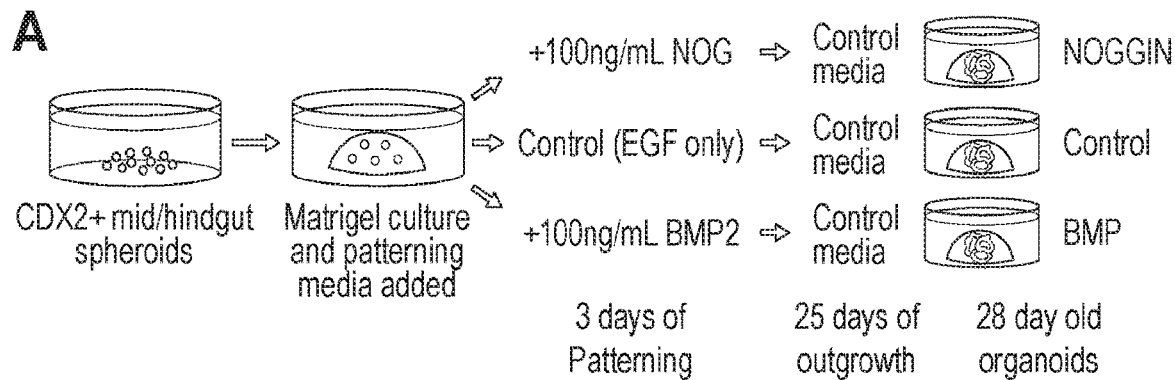
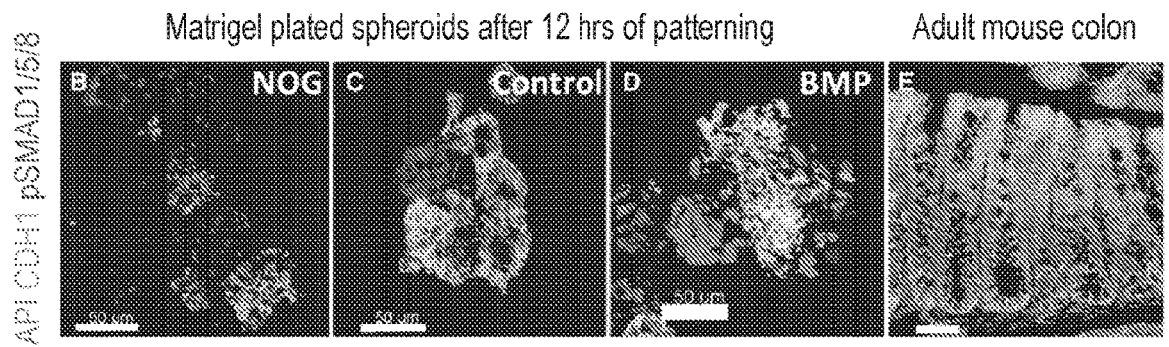
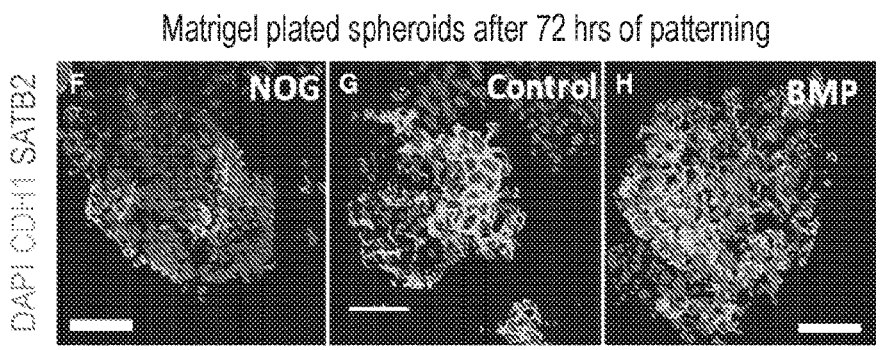
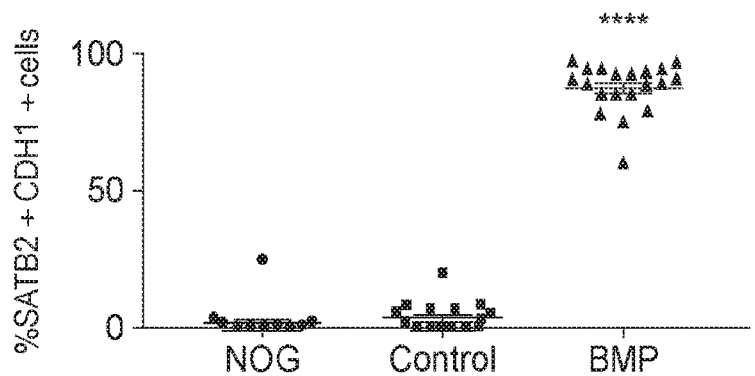
FIG. 2A

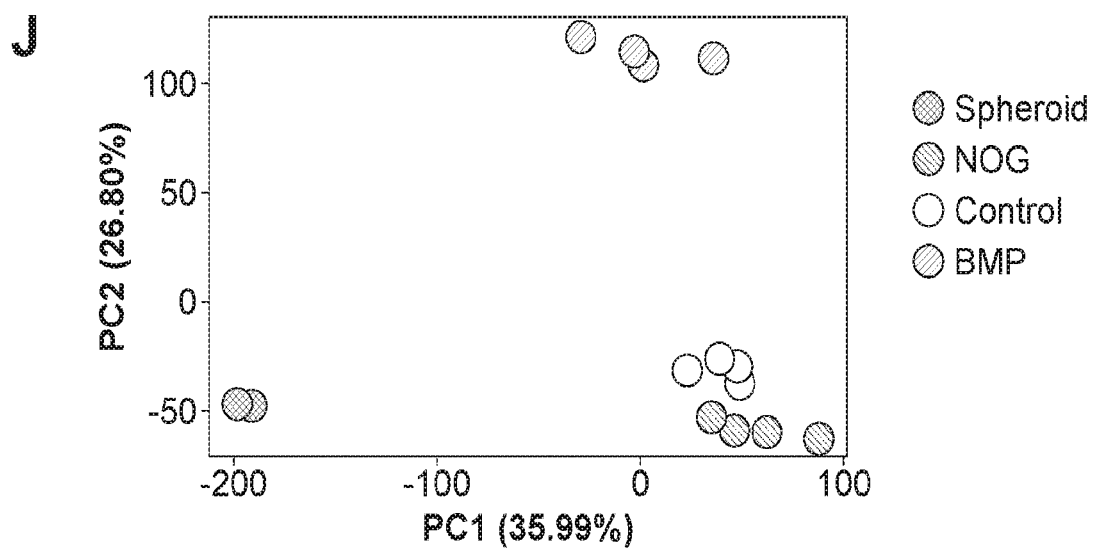
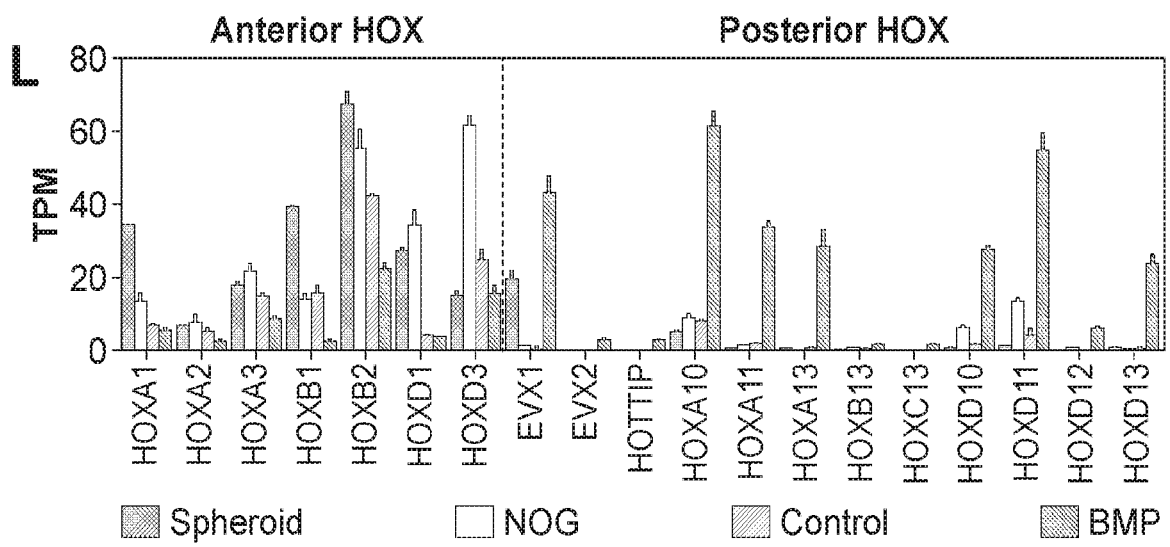
FIG. 2B

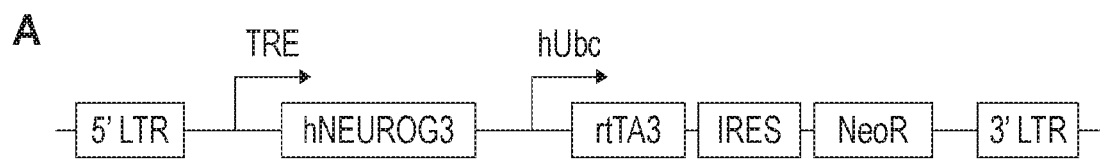
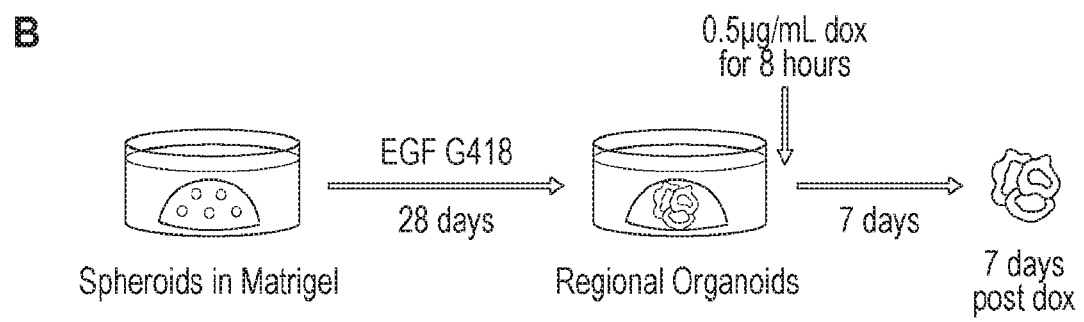
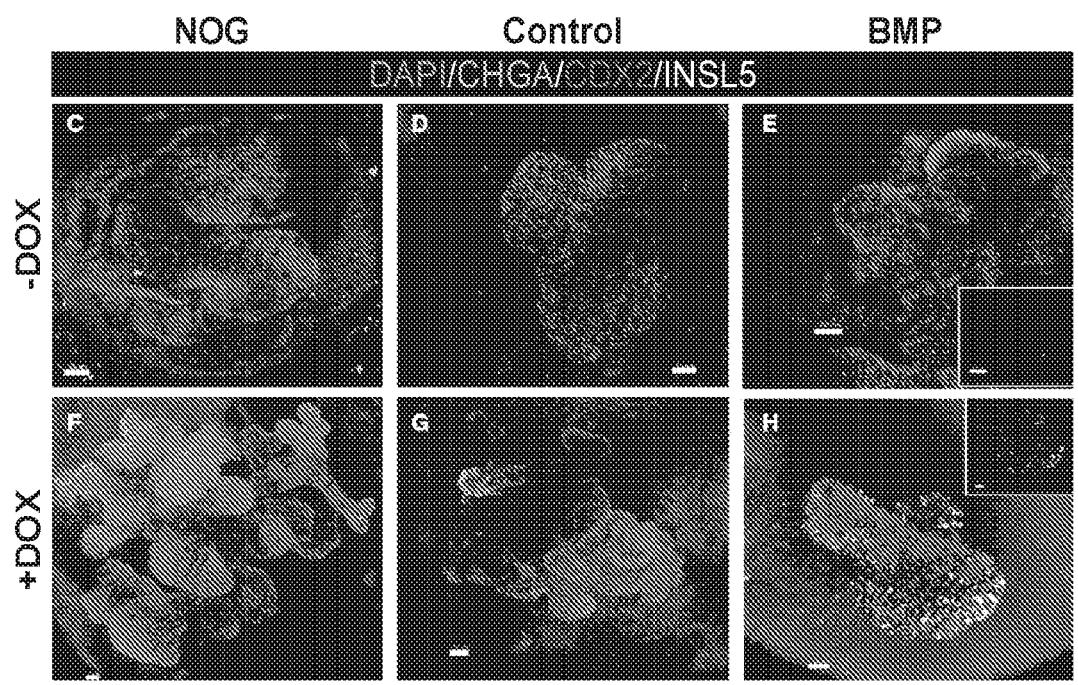
FIG. 4A

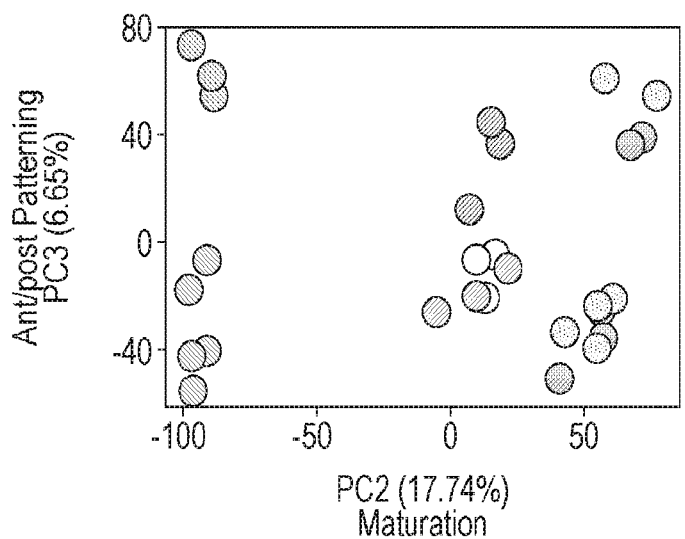
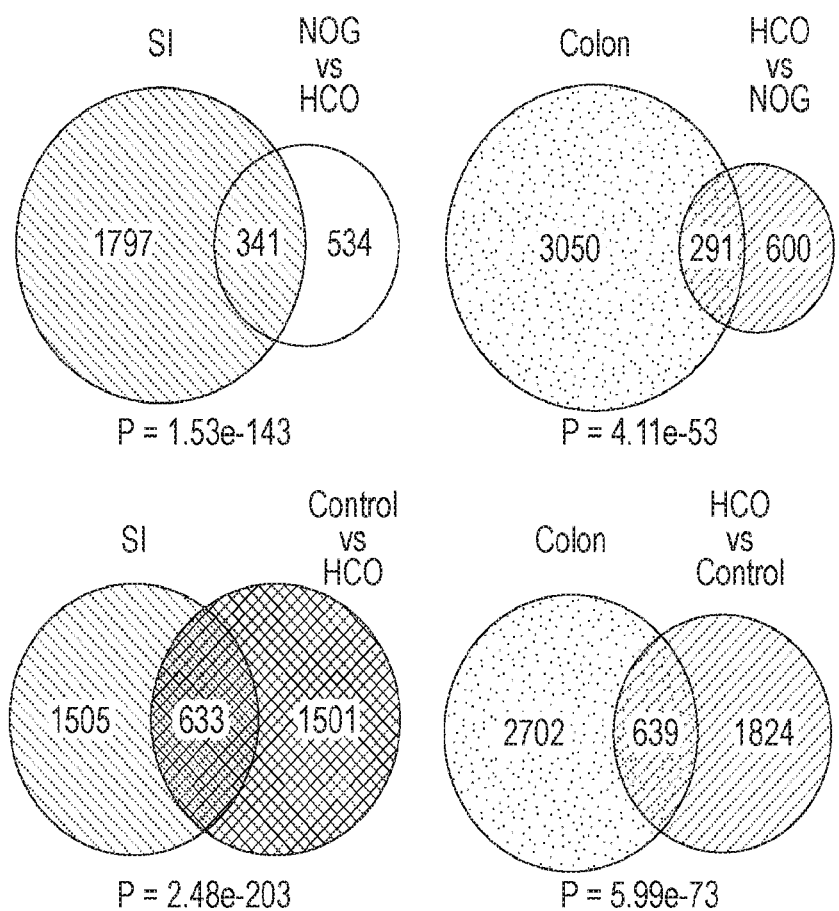
FIG. 7A

A
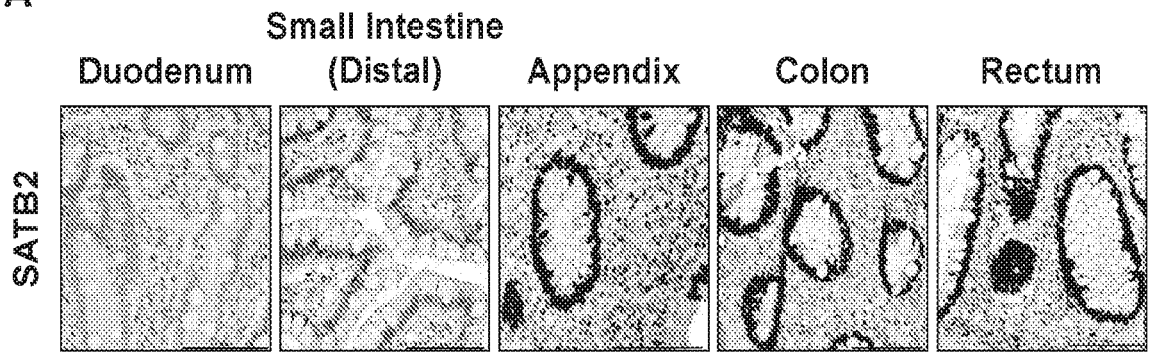
B
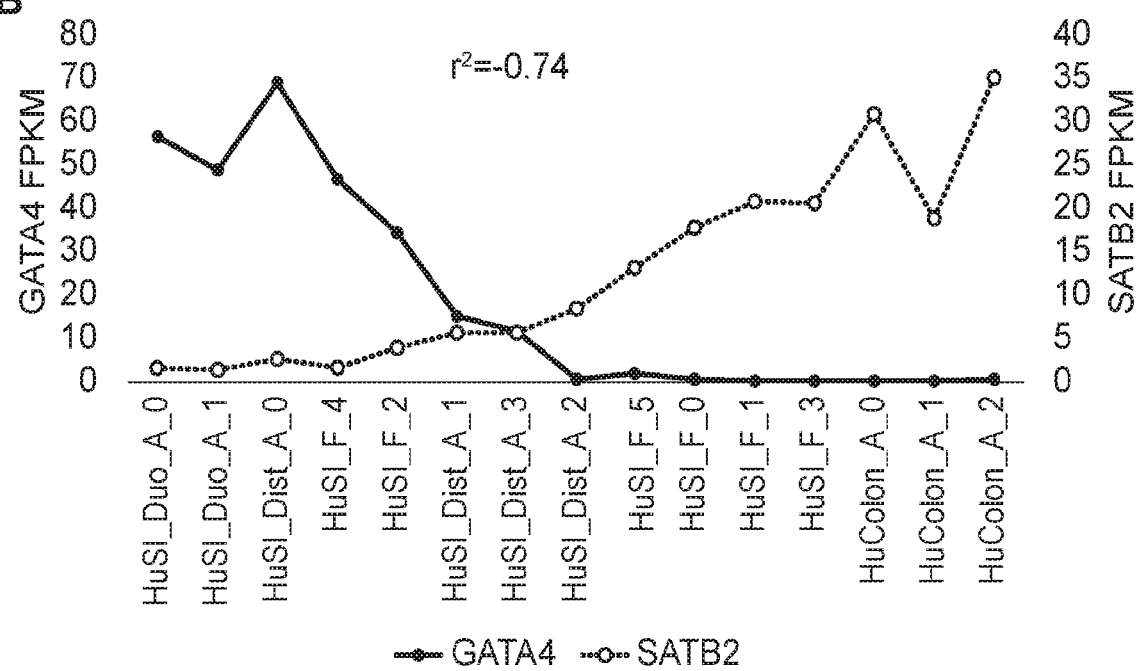
FIG. 9A

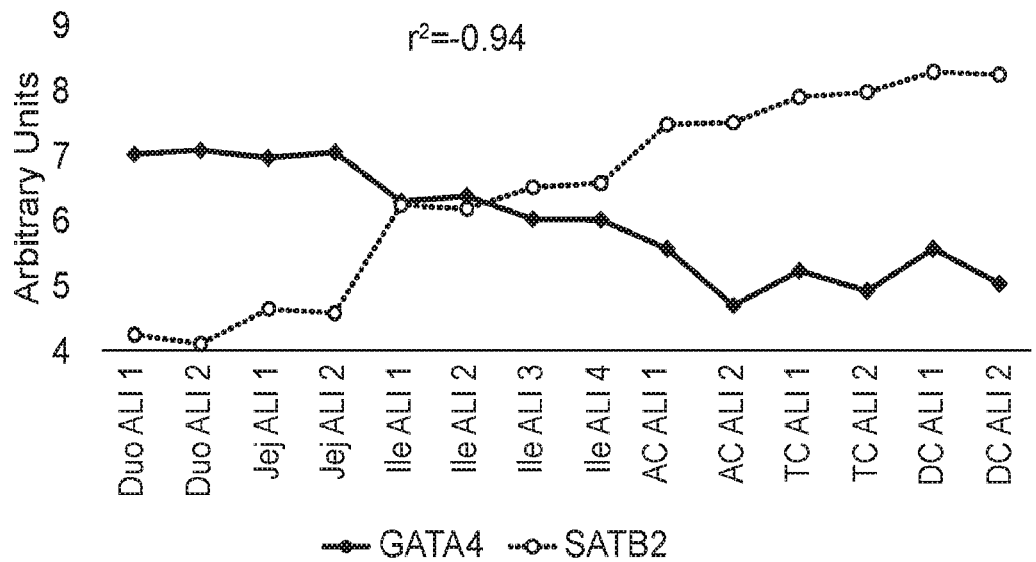
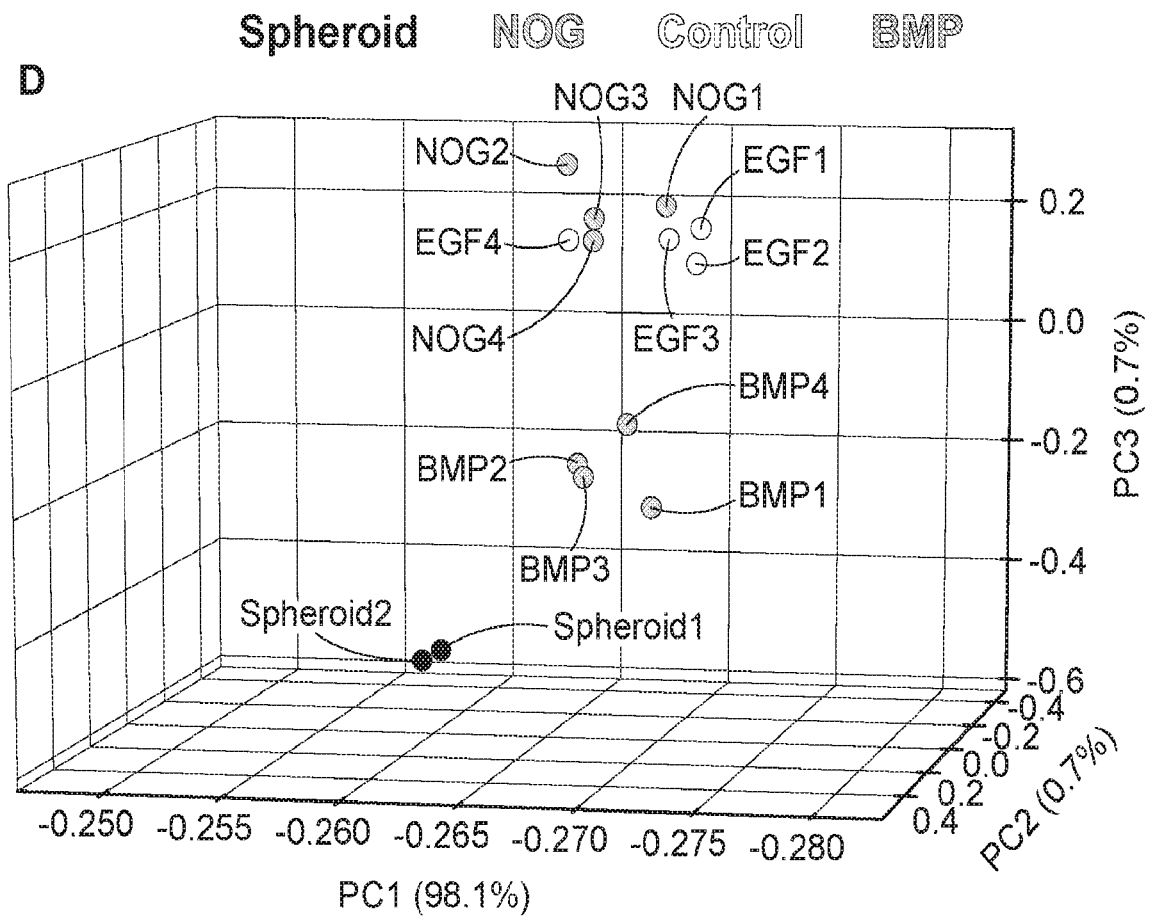
FIG. 9B

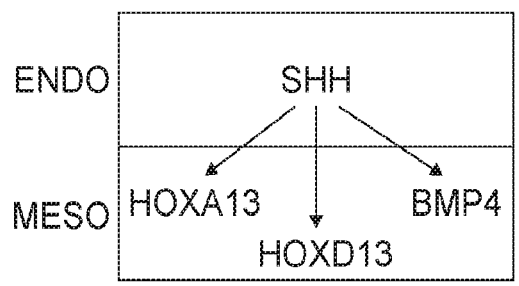
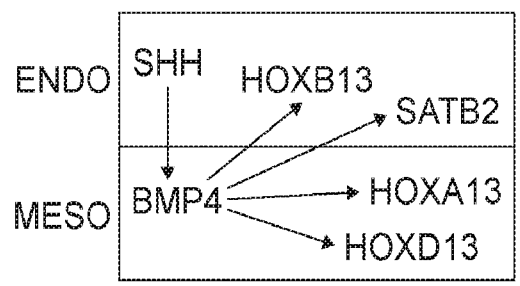
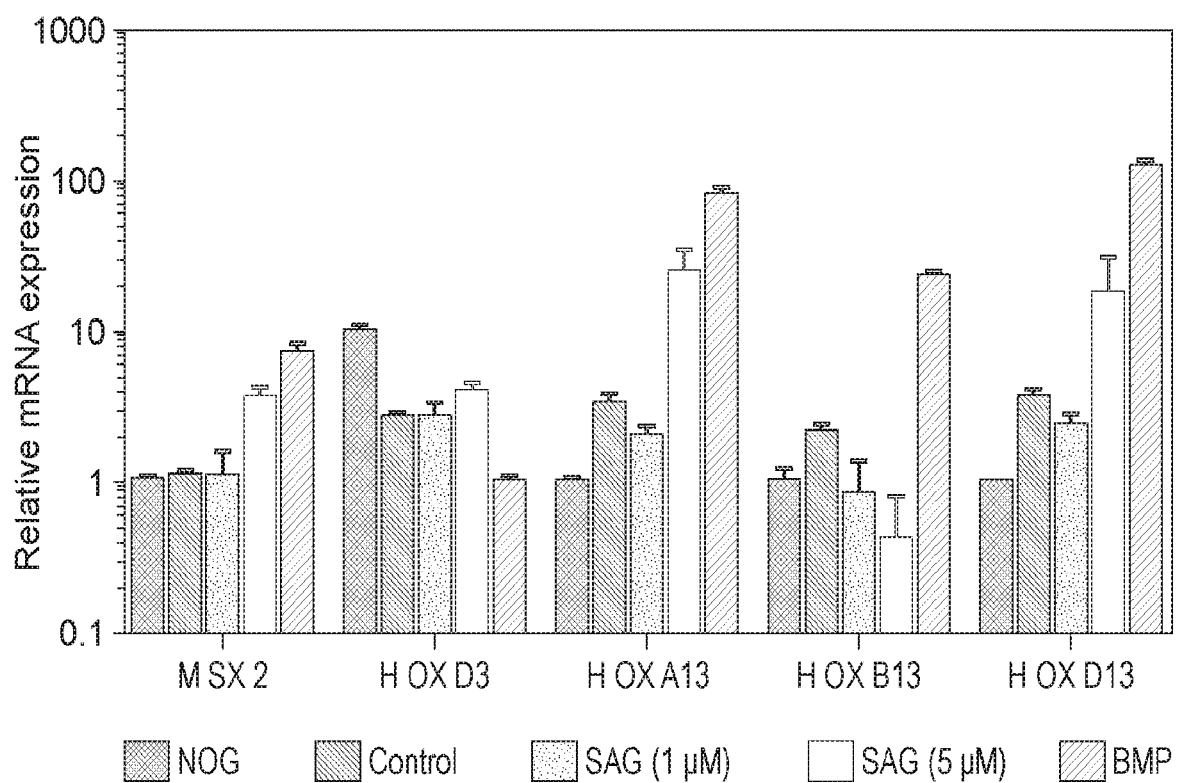
FIG. 10A

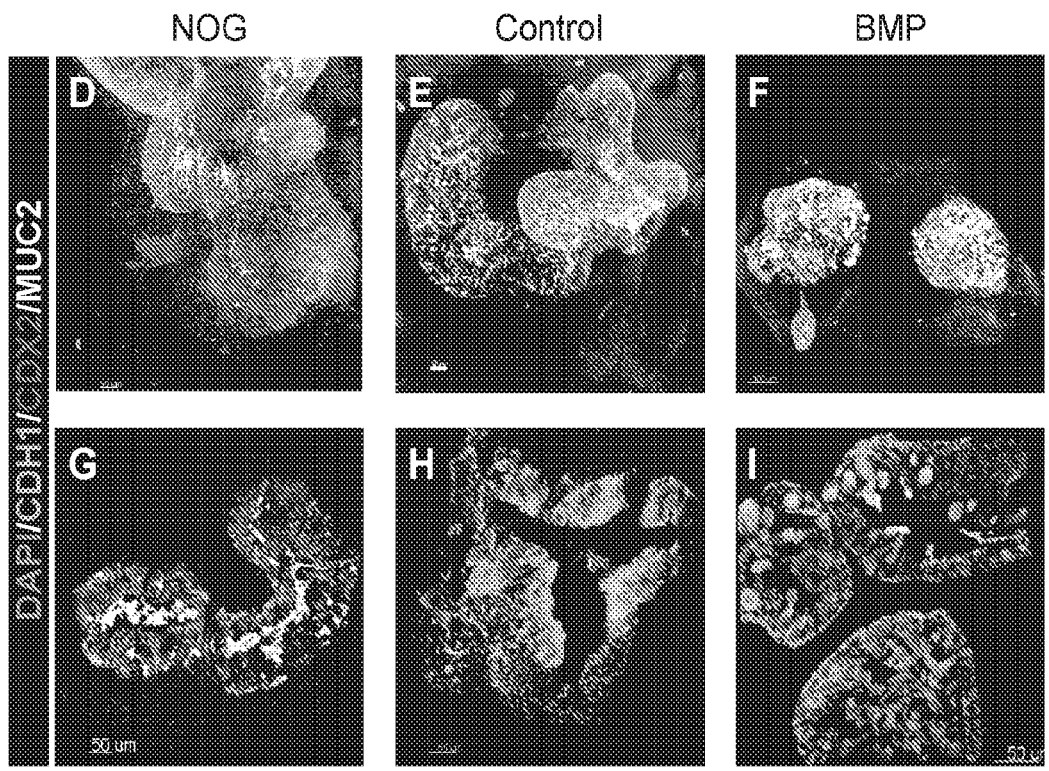
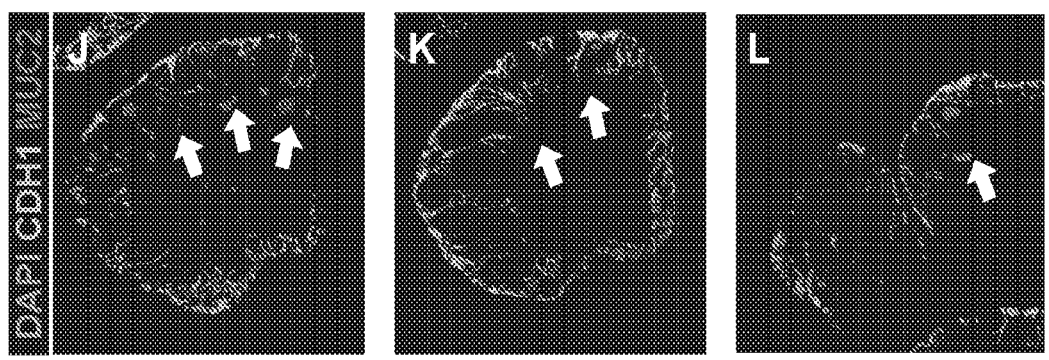
FIG. 11B

Graft derived enteroids
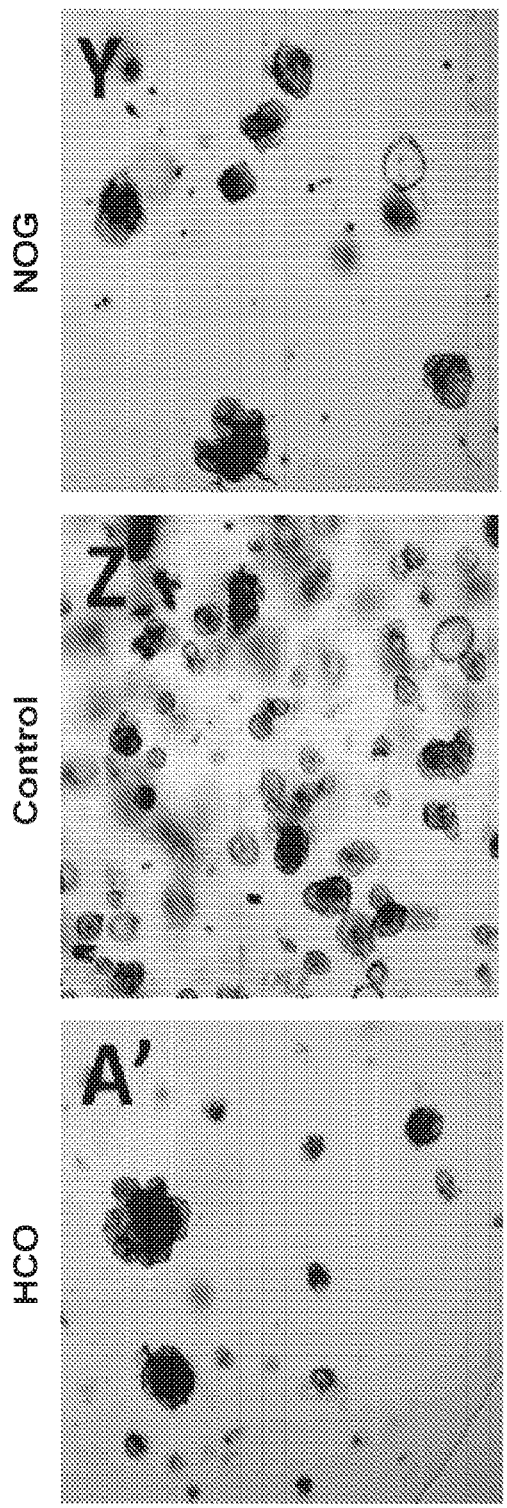
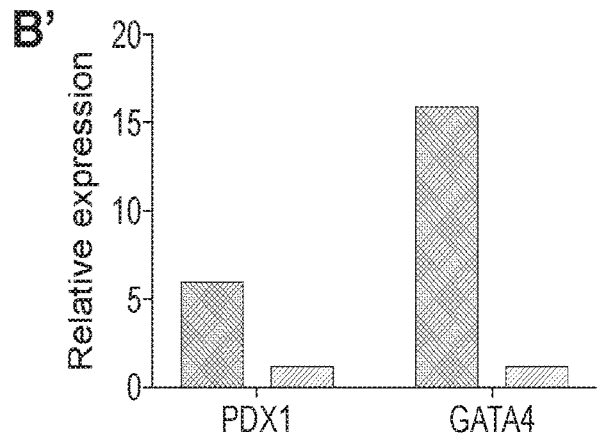
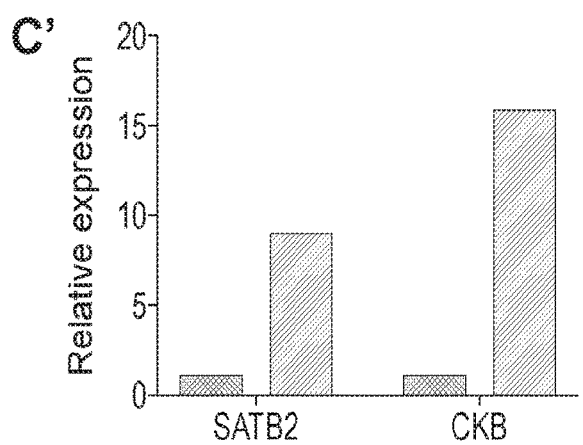
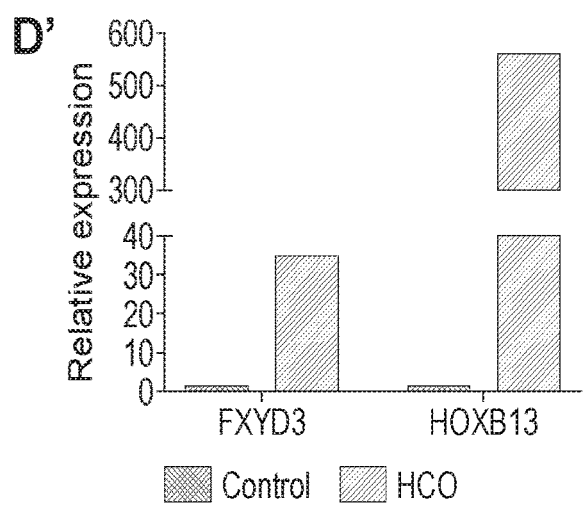
FIG. 13C

A

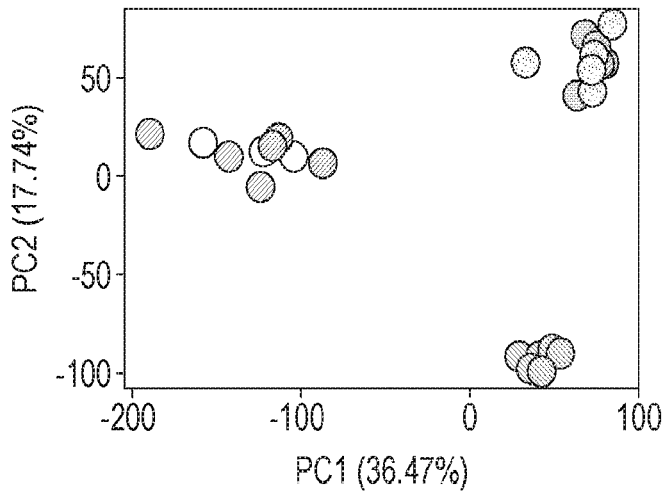

- Adult colon
- Adult SI
- Fetal colon
- Fetal SI
- HCO-TXP
- Control-TXP
- NOG-TXP B  Up in TXP's vs primary tissues

| Category | Name | p-value |
| --- | --- | --- |
| Pathway | Ribosome | 2.20E-57 |
| GO: Cellular Component | ribosomal subunit | 3.20E-55 |
| GO: Cellular Component | ribosome | 2.61E-48 |
| GO: Molecular Function | structural constituent of ribosome | 5.07E-26 |
| GO: Cellular Component | cytosolic ribosome | 1.66E-41 |
| GO: Cellular Component | large ribosomal subunit | 2.43E-39 |
| GO: Biological Process | SRP dependent cotranslational protein targeting to membrane | 8.02E-39 |
| GO: Biological Process | protein targeting to ER | 1.14E-36 |
| GO: Cellular Component | mitochondrion | 7.71E-36 |
| GO: Biological Process | cotranslational protein targeting to membrane | 1.57E-35 |

FIG. 14A

C                  Up primary tissues vs in TXP's

| Category | Name | p-value |
| --- | --- | --- |
| GO: Biological Process | leukocyte activation | 2.26E-22 |
| GO: Biological Process | immune system process | 3.25E-22 |
| GO: Biological Process | cell activation | 1.46E-21 |
| GO: Biological Process | positive regulation of immune system process | 2.72E-19 |
| GO: Cellular Component | plasma membrane part | 1.89E-18 |
| GO: Biological Process | lymphocyte activation | 3.14E-18 |
| GO: Biological Process | leukocyte cell-cell adhesion | 6.71E-18 |
| GO: Biological Process | single organism cell-cell adhesion | 8.69E-18 |
| GO: Biological Process | immune response | 8.81E-18 |
| GO: Biological Process | intracellular signal transduction | 2.82E-17 |

FIG. 14B

A  Patient colon biopsy        28 day old Human Colonic Organoid
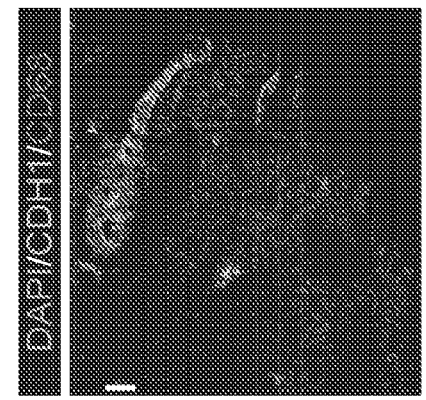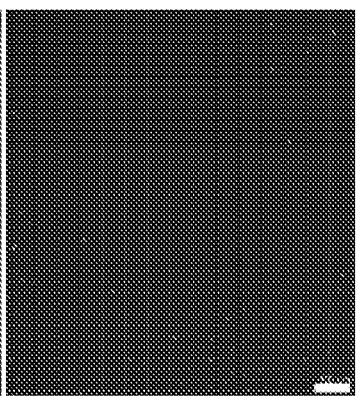
B
Live                                    Live
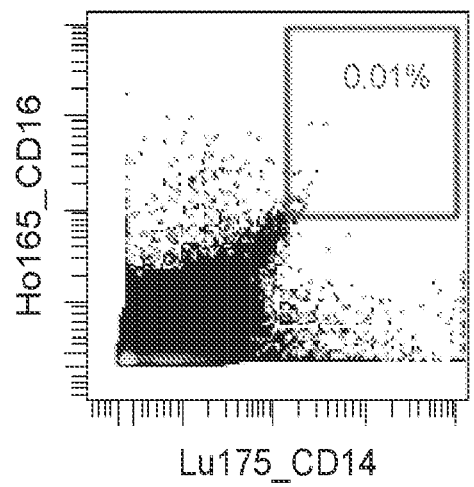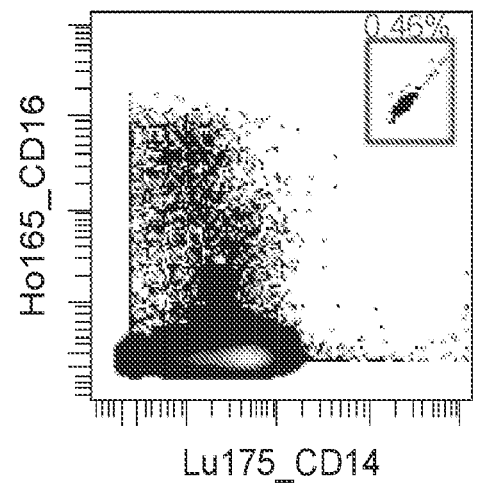
FIG. 16A

SEQUENCE LISTING

<160> NUMBER OF SEQ ID NOS: 32

<210> SEQ ID NO 1
<211> LENGTH: 19
<212> TYPE: DNA
<213> ORGANISM: Artificial Sequence
<220> FEATURE:
<223> OTHER INFORMATION: CDH1 Forward

<400> SEQUENCE: 1
gaccggtgca atcttcaaa                                               19

<210> SEQ ID NO 2
<211> LENGTH: 19
<212> TYPE: DNA

```
<213> ORGANISM: Artificial Sequence
<220> FEATURE:
<223> OTHER INFORMATION: CDH1 Reverse

<400> SEQUENCE: 2
ttgacgccga gagctacac                                                    19

<210> SEQ ID NO 3
<211> LENGTH: 20
<212> TYPE: DNA
<213> ORGANISM: Artificial Sequence
<220> FEATURE:
<223> OTHER INFORMATION: CHGA Forward

<400> SEQUENCE: 3
tgtgtcggag atgacctcaa                                                   20

<210> SEQ ID NO 4
<211> LENGTH: 20
<212> TYPE: DNA
<213> ORGANISM: Artificial Sequence
<220> FEATURE:
<223> OTHER INFORMATION: CHGA Reverse

<400> SEQUENCE: 4
gtcctggctc ttctgctctg                                                   20

<210> SEQ ID NO 5
<211> LENGTH: 20
<212> TYPE: DNA
<213> ORGANISM: Artificial Sequence
<220> FEATURE:
<223> OTHER INFORMATION: CKB Forward

<400> SEQUENCE: 5
cccacaccag gaaggtctta                                                   20

<210> SEQ ID NO 6
<211> LENGTH: 18
<212> TYPE: DNA
<213> ORGANISM: Artificial Sequence
<220> FEATURE:
<223> OTHER INFORMATION: CKB Reverse

<400> SEQUENCE: 6
cctcttcgac aagcccgt                                                     18

<210> SEQ ID NO 7
<211> LENGTH: 20
<212> TYPE: DNA
<213> ORGANISM: Artificial Sequence
<220> FEATURE:
<223> OTHER INFORMATION: FXYD3 Forward

<400> SEQUENCE: 7
agggtcacct tctgcatgtc                                                   20

<210> SEQ ID NO 8
<211> LENGTH: 20
<212> TYPE: DNA
<213> ORGANISM: Artificial Sequence
<220> FEATURE:
<223> OTHER INFORMATION: FXYD3 Reverse

<400> SEQUENCE: 8
cttcggataa acgcaggact                                                   20
```

<210> SEQ ID NO 9
<211> LENGTH: 20
<212> TYPE: DNA
<213> ORGANISM: Artificial Sequence
<220> FEATURE:
<223> OTHER INFORMATION: GATA4 Forward

<400> SEQUENCE: 9
tagccccaca gttgacacac                                                      20

<210> SEQ ID NO 10
<211> LENGTH: 17
<212> TYPE: DNA
<213> ORGANISM: Artificial Sequence
<220> FEATURE:
<223> OTHER INFORMATION: GATA4 Reverse

<400> SEQUENCE: 10
gtcctgcaca gcctgcc                                                         17

<210> SEQ ID NO 11
<211> LENGTH: 20
<212> TYPE: DNA
<213> ORGANISM: Artificial Sequence
<220> FEATURE:
<223> OTHER INFORMATION: HOXA13 Forward

<400> SEQUENCE: 11
gcaccttggt ataaggcacg                                                      20

<210> SEQ ID NO 12
<211> LENGTH: 20
<212> TYPE: DNA
<213> ORGANISM: Artificial Sequence
<220> FEATURE:
<223> OTHER INFORMATION: HOXA13 Reverse

<400> SEQUENCE: 12
cctctggaag tccactctgc                                                      20

<210> SEQ ID NO 13
<211> LENGTH: 20
<212> TYPE: DNA
<213> ORGANISM: Artificial Sequence
<220> FEATURE:
<223> OTHER INFORMATION: HOXB13 Forward

<400> SEQUENCE: 13
gctgtacgga atgcgtttct                                                      20

<210> SEQ ID NO 14
<211> LENGTH: 19
<212> TYPE: DNA
<213> ORGANISM: Artificial Sequence
<220> FEATURE:
<223> OTHER INFORMATION: HOXB13 Reverse

<400> SEQUENCE: 14
aacccaccag gtccctttt                                                       19

<210> SEQ ID NO 15
<211> LENGTH: 20
<212> TYPE: DNA
<213> ORGANISM: Artificial Sequence
<220> FEATURE:

<223> OTHER INFORMATION: HOXD13 Forward

<400> SEQUENCE: 15
cctcttcggt agacgcacat                                              20

<210> SEQ ID NO 16
<211> LENGTH: 20
<212> TYPE: DNA
<213> ORGANISM: Artificial Sequence
<220> FEATURE:
<223> OTHER INFORMATION: HOXD13 Reverse

<400> SEQUENCE: 16
caggtgtact gcaccaagga                                              20

<210> SEQ ID NO 17
<211> LENGTH: 20
<212> TYPE: DNA
<213> ORGANISM: Artificial Sequence
<220> FEATURE:
<223> OTHER INFORMATION: HOXD3 Forward

<400> SEQUENCE: 17
cacctccaat gtctgctgaa                                              20

<210> SEQ ID NO 18
<211> LENGTH: 23
<212> TYPE: DNA
<213> ORGANISM: Artificial Sequence
<220> FEATURE:
<223> OTHER INFORMATION: HOXD3 Reverse

<400> SEQUENCE: 18
caaaattcaa gaaaacacac aca                                          23

<210> SEQ ID NO 19
<211> LENGTH: 19
<212> TYPE: DNA
<213> ORGANISM: Artificial Sequence
<220> FEATURE:
<223> OTHER INFORMATION: INSL5 Forward

<400> SEQUENCE: 19
gaaggttttg cgctggatt                                               19

<210> SEQ ID NO 20
<211> LENGTH: 20
<212> TYPE: DNA
<213> ORGANISM: Artificial Sequence
<220> FEATURE:
<223> OTHER INFORMATION: INSL5 Reverse

<400> SEQUENCE: 20
gatccctcaa gctcagcaag                                              20

<210> SEQ ID NO 21
<211> LENGTH: 20
<212> TYPE: DNA
<213> ORGANISM: Artificial Sequence
<220> FEATURE:
<223> OTHER INFORMATION: MSX2 Forward

<400> SEQUENCE: 21
ggtcttgtgt ttcctcaggg                                              20

```
<210> SEQ ID NO 22
<211> LENGTH: 20
<212> TYPE: DNA
<213> ORGANISM: Artificial Sequence
<220> FEATURE:
<223> OTHER INFORMATION: MSX2 Reverse

<400> SEQUENCE: 22
aaattcagaa gatggagcgg                                              20

<210> SEQ ID NO 23
<211> LENGTH: 20
<212> TYPE: DNA
<213> ORGANISM: Artificial Sequence
<220> FEATURE:
<223> OTHER INFORMATION: MUC2 Forward

<400> SEQUENCE: 23
tgtaggcatc gctcttctca                                              20

<210> SEQ ID NO 24
<211> LENGTH: 20
<212> TYPE: DNA
<213> ORGANISM: Artificial Sequence
<220> FEATURE:
<223> OTHER INFORMATION: MUC2 Reverse

<400> SEQUENCE: 24
gacaccatct acctcacccg                                              20

<210> SEQ ID NO 25
<211> LENGTH: 20
<212> TYPE: DNA
<213> ORGANISM: Artificial Sequence
<220> FEATURE:
<223> OTHER INFORMATION: ONECUT1 Forward

<400> SEQUENCE: 25
tttttgggtg tgttgcctct                                              20

<210> SEQ ID NO 26
<211> LENGTH: 19
<212> TYPE: DNA
<213> ORGANISM: Artificial Sequence
<220> FEATURE:
<223> OTHER INFORMATION: ONECUT1 Reverse

<400> SEQUENCE: 26
agaccttccg gaggatgtg                                               19

<210> SEQ ID NO 27
<211> LENGTH: 18
<212> TYPE: DNA
<213> ORGANISM: Artificial Sequence
<220> FEATURE:
<223> OTHER INFORMATION: PDX1 Forward

<400> SEQUENCE: 27
cgtccgcttg ttctcctc                                                18

<210> SEQ ID NO 28
<211> LENGTH: 20
<212> TYPE: DNA
<213> ORGANISM: Artificial Sequence
<220> FEATURE:
<223> OTHER INFORMATION: PDX1 Reverse
```

```
<400> SEQUENCE: 28
cctttcccat ggatgaagtc                                              20

<210> SEQ ID NO 29
<211> LENGTH: 21
<212> TYPE: DNA
<213> ORGANISM: Artificial Sequence
<220> FEATURE:
<223> OTHER INFORMATION: PPIA (CPHA)  Forward

<400> SEQUENCE: 29
cccaccgtgt tcttcgacat t                                            21

<210> SEQ ID NO 30
<211> LENGTH: 22
<212> TYPE: DNA
<213> ORGANISM: Artificial Sequence
<220> FEATURE:
<223> OTHER INFORMATION: PPIA (CPHA) Reverse

<400> SEQUENCE: 30
ggacccgtat gctttaggat ga                                           22

<210> SEQ ID NO 31
<211> LENGTH: 19
<212> TYPE: DNA
<213> ORGANISM: Artificial Sequence
<220> FEATURE:
<223> OTHER INFORMATION: SATB2 Forward

<400> SEQUENCE: 31
ccaccttccc agcttgatt                                               19

<210> SEQ ID NO 32
<211> LENGTH: 20
<212> TYPE: DNA
<213> ORGANISM: Artificial Sequence
<220> FEATURE:
<223> OTHER INFORMATION: SATB2 Reverse

<400> SEQUENCE: 32
ttagccagct ggtggagact                                              20
```

COLONIC ORGANOIDS AND METHODS OF MAKING AND USING SAME

CROSS REFERENCE TO RELATED APPLICATIONS

This application claims the benefit of International Application No. PCT/US17/64600 filed Dec. 5, 2017, which claims the benefit of U.S. Provisional Application Ser. No. 62/478,962 filed Mar. 30, 2017 and U.S. Provisional Application Ser. No. 62/429,948 filed Dec. 5, 2016, which are incorporated herein by reference in their entirety for all purposes.

GOVERNMENT SUPPORT CLAUSE

This invention was made with government support under EB021780. DK103117 and AI116491 awarded by the National Institutes of Health. The government has certain rights in the invention.

BACKGROUND

While the generation of gastric and small intestinal organoids from pluripotent stem cells (PSCs) has revolutionized the study of human gastrointestinal (GI) development and disease, the efforts to generate large intestinal organoids have lagged behind, in part due to the lack of a robust understanding of posterior gut tube development.

BRIEF SUMMARY

Disclosed herein are methods for the in vitro differentiation of a precursor cell into definitive endoderm, which may further be differentiated into a human colonic organoid (HCO), via modulation of signaling pathways. Further disclosed are HCOs and methods of using HCOs, which may be used, for example, for the HCOs may be used to determine the efficacy and/or toxicity of a potential therapeutic agent for a disease selected from colitis, colon cancer, polyposis syndromes, and/or irritable bowel syndrome.

BRIEF DESCRIPTION OF THE DRAWINGS

Those of skill in the art will understand that the drawings, described below, are for illustrative purposes only. The drawings are not intended to limit the scope of the present teachings in any way.

FIG. 2. BMP2 induces SATB2 and a posterior HOX code in human gut tube spheroids. (A) Schematic of gut tube spheroid patterning protocol. (B-D) BMP signaling levels as measured by pSMAD1/5/8 (red) staining of spheroids treated with NOGGIN (B), no treatment (C) and BMP2 (D) for 12 hours. (E) pSmad1/5/8 staining of adult mouse colon showing increased BMP signaling at to the top of crypts. (F-H) SATB2 expression in spheroids treated with NOGGIN (F), no treatment (G) and BMP2 (H) for 72 hours. (I) Quantification of the percentage of SATB2+ CDH1+ epithelium following patterning. (J) Principal component analysis of nascent spheroids and spheroids after 3 days of patterning. (K) Gene ontology analysis of differentially expressed genes between BMP vs NOG treated spheroids. (L) Graph of TPM (Transcripts per million) values of spheroids before and after patterning. Samples analyzed were spheroids before patterning (n=2), and NOGGIN, Control and BMP2 treated spheroids 3 days after patterning (n=4 for each group). For quantification in I, 20 organoids from at least 3 experiments were examined. Error bars represent SD. Scale bars=50 microns. ****p s 0.0001 determined by 2 tailed t-test.

FIG. 9. SATB2 is expressed in GATA4 negative human small and large intestine. SATB2 staining in human adult duodenum, small intestine, appendix, colon and rectum showing that SATB2 expression is present in distal small intestine and the entire large intestine. Analysis of GATA4 and SATB2 from published RNA-seq data from human adult and fetal intestinal samples. Samples plotted include human adult duodenum (HuSI_Duo_A), human adult small intestine distal to duodenum (HuSI_Dist_A), human adult colon (HuColon_A) and human fetal small intestine (HuSI_F). (C) Analysis of GATA4 and SATB2 expression from microarray data generated by Wang et al. 2015 on fetal intestinal stem cells from duodenum (Duo), jejunum (Jej), ileum (lle), ascending colon (AC), transverse colon (TC) and Descending colon grown in Air Liquid Interface (ALI). r2 values were determined using CORREL function in Excel.

FIG. 14. Ribosome and immune cell signatures are differentially expressed between transplanted organoids and primary human tissues. (A) Principal component analysis of patterned transplanted organoids and human adult and fetal small intestine and colon. (B) Gene ontology analysis of genes upregulated in transplants versus human primary tissues. (C) Gene ontology analysis of genes upregulated in human primary tissues versus transplants.

DETAILED DESCRIPTION

Definitions

Figure 1A:
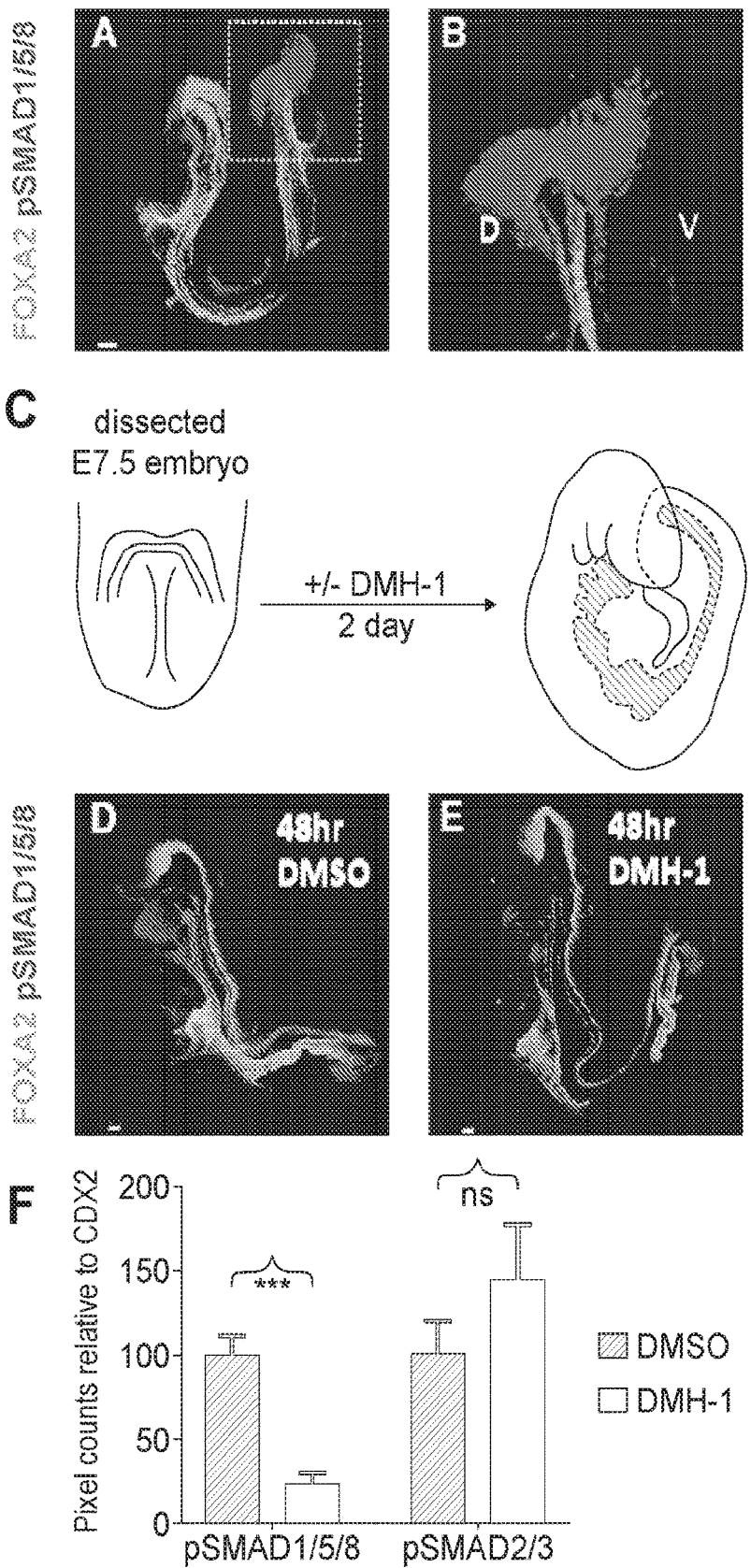
FIG. 1. Bmp signaling regulates Satb2 expression in mouse and frog embryos. (A) Whole-mount pSmad158 (red) and Foxa2 (green) staining of e8.5 mouse embryo showing nuclear staining around the developing hindgut (n=6). (B) Inset of optical slices from boxed region in (A) showing pSmad1/5/8 staining in the hindgut mesoderm and endoderm (D, dorsal; V, ventral). (C) Schematic of mouse embryo isolated at the headfold stage and cultured for 2 days +/− Bmp inhibition with DMH-1. (D,E) Whole-mount pSmad1/5/8 (red) and Foxa2 (green) staining of DMSO (0) and DMH-1 (E) treated embryos after 48 hours of culture. (F) Quantification of pSmad1/5/8 and pSmad2/3 staining in relative to Cdx2 in embryos cultured in DMSO or DMH-1 (n=3 embryos per condition). (G-J) Whole-mount immunostaining of Cdx2 (green), Satb2 (red) and Foxa2 (white) of mouse embryos (n=6 for each condition) following 2 days of culture in DMSO (G,H) or DMH-1 (I,J). Arrows in H-J point to the approximate location of the yolk stalk (BA1, first brachial arch). (K) Quantification of Satb2 expression in mouse embryos treated with DMSO or DMH-1. (L) Schematic of Bmp inhibition in *Xenopus tropicalis* embryos. In situ hybridization of Satb2 in *Xenopus tropicalis* embryos treated with DMSO (M) or DMH-1 (R). The white dotted line in (M) and (R) depict the plane of section used subsequent analysis. Mx and md=maxillary and mandibular processes of first brachial arch. Cba=Caudal brachial arches. Immunofluorescence of Satb2 (red), pSmad1/5/8 (green), DAPI (blue), and color merged images from *Xenopus tropicalis* embryos treated with DMSO (N-Q) or DMH-1 (S-V). Scale bars for=100 μm in G-H and 50 μm in all other panels. p<0.01 and *p 0.001 for 2 tailed t-test.

Unless otherwise noted, terms are to be understood according to conventional usage by those of ordinary skill in the relevant art.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryonic stem cells (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "embryonic stem cells (ESCs)," also commonly abbreviated as ES cells, refers to cells that are pluripotent and derived from the inner cell mass of the blastocyst, an early-stage embryo. For purpose of the present invention, the term "ESCs" is used broadly sometimes to encompass the embryonic germ cells as well.

As used herein, the term "precursor cell" encompasses any cells that can be used in methods described herein, through which one or more precursor cells acquire the ability to renew itself or differentiate into one or more specialized cell types. In some aspects, a precursor cell is pluripotent or has the capacity to becoming pluripotent. In some aspects, the precursor cells are subjected to the treatment of external factors (e.g., growth factors) to acquire pluripotency. In some aspects, a precursor cell can be a totipotent (or omnipotent) stem cell; a pluripotent stem cell (induced or non-induced); a multipotent stem cell; an oligopotent stem cells and a unipotent stem cell. In some aspects, a precursor cell can be from an embryo, an infant, a child, or an adult. In some aspects, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

As described herein, methods and systems are established using a temporal series of growth factor manipulations to mimic embryonic intestinal development in culture. In particular, methods and systems are established to direct in vitro differentiation of PSCs, both human embryonic stem cells (hESC) and induced pluripotent stem cells (iPSC), into intestinal tissue The generation of gastric and small intestinal organoids from pluripotent stem cells (PSCs) has revolutionized the study human gastrointestinal (GI) development and disease. However, efforts to generate large intestinal organoids have lagged behind, in part due to a robust molecular understanding of posterior gut tube development. Here, Applicant has found that the intestinal epithelium posterior to the umbilical cord expresses Satb2 throughout development and postnatally. Applicant has further found that BMP signaling establishes the Satb2+ domain in frog and mouse embryos, and that brief activation of BMP signaling was sufficient to activate a posterior HOX code and direct human PSC-derived gut tube cultures into colonic organoids (HCOs). HCOs grown in vitro had a marker profile and unique cell types consistent with colonic identity. Following transplantation into mice, HCOs underwent morphogenesis and maturation forming tissue with molecular, cellular and morphologic properties of the human colon. The disclosed colonic organoids may be used in future studies of colitis and colon cancer.

In one aspect, a method of inducing formation of a human colon organoid is disclosed. The method may comprise the steps of (a) contacting a definitive endoderm (DE) with an FGF signaling pathway activator and a WNT signaling pathway activator (for example, CHIRON/GSK2 inhibitor) for a period of time sufficient for said DE to form a mid-hindgut spheroid, and (b) contacting the mid-hindgut spheroid of step (a) with a BMP activator and an EGF signaling pathway activator for a period of time sufficient to form said human colon organoid, wherein said human colon organoid expresses SATB2.

In one aspect, the DE may be derived from a precursor cell selected from an embryonic stem cell, an embryonic germ cell, an induced pluripotent stem cell, a mesoderm cell, a definitive endoderm cell, a posterior endoderm cell, a hindgut cell or combinations thereof.

In one aspect, the FGF signaling pathway activator may be selected from a small molecule or protein FGF signaling pathway activator, FGF1, FGF2, FGF3, FGF4, FGF10, FGF11, FGF12, FGF13, FGF14, FGF15, FGF16, FGF17, FGF18, FGF19, FGF20, FGF21, FGF22, FGF23, or combinations thereof. The WNT signaling pathway activator may be selected from a small molecule or protein Wnt signaling pathway activator, preferably Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine, Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSK3 inhibitor, preferably CHIRON, or combinations thereof. In one aspect, the BMP activator may be selected from BMP2, BMP4, BMP7, BMP9, small molecules that activates the BMP pathway, proteins that activate the BMP pathway, and may include the following: Noggin, Dorsomorphin, LDN189, DMH-1, ventromophins, and combinations thereof.

In one aspect, the period of time sufficient for said DE to form a mid-hindgut spheroid may be determined by expression of CDX2 by said mid-hindgut spheroid of step (a). Such measurement is within the ability of one of ordinary skill in the art using routine methods.

In one aspect, the period of time sufficient for the mid-hindgut spheroid to form a human colon organoid is determined by expression of SATB2 and CDX2 by a cell of said human colon organoid, wherein when SATB2 and CDX2 is expressed, the mid-hindgut spheroid has formed a human colon organoid. Such measurement may be used in lieu of a temporal measurement, in that expression of the genes listed above indicates that steps (a) and (b) have been carried out for a sufficient duration of time.

In one aspect, an HCO obtained according to the methods described herein are disclosed. The HCOs of the instant invention may be characterized in a variety of different ways. In one aspect, the HCO may be characterized by the presence of colonic enteroendocrine cells (EEC). In one aspect, the HCO may be characterized by the presence of crypts and is substantially free of villi. In one aspect, the HCO may be characterized by the presence of colon-specific goblet cells. In one aspect, the HCO may be characterized by being substantially free of Paneth cells. In one aspect, the HCO may be characterized by the ability to secrete colon-specific hormone INSL5. The intestinal organoid may be free of one or more of an immune function, innervation, blood vessels, villi, and Paneth cells.

In one aspect, a method of forming colonic tissue is disclosed, wherein the HCO of the described invention may be engrafted under a kidney capsule of a mammal, preferably a rodent, preferably an immunocompromised rodent, preferably an immunocompromised mouse.

In one aspect, the HCOs disclosed herein may be used to determine the efficacy and/or toxicity of a potential therapeutic agent for a disease selected from colitis, colon cancer, polyposis syndromes, and/or irritable bowel syndrome. The method may comprise the step of contacting a potential therapeutic agent with an HCO as described herein, for a period of time sufficient to determine the efficacy and/or toxicity of said potential therapeutic agent.

In one aspect, an intestinal colonoid derived from the HCO of any preceding claim is contemplated.

In some aspects, stem cells that are pluripotent or can be induced to become pluripotent may be used. In some aspects, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. For example, three cell lines (H1, H13, and H14) had a normal XY karyotype, and two cell lines (H7 and H9) had a normal XX karyotype. Human embryonic stem cells H9 (H9-hESCs) are used in the exemplary aspects described in the present application, but it would be understood by one of skill in the art that the methods and systems described herein are applicable to any stem cells.

Additional stem cells that can be used in aspects in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in aspects in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

In some aspects, the stem cells are further modified to incorporate additional properties. Exemplary modified cell lines include but not limited to H1 OCT4-EGFP; H9 Cre-LoxP; H9 hNanog-pGZ; H9 hOct4-pGZ; H9 inGFPhES; and H9 Syn-GFP.

More details on embryonic stem cells can be found in, for example, Thomson et al., 1998, "Embryonic Stem Cell Lines Derived from Human Blastocysts," *Science* 282 (5391):1145-1147; Andrews et al., 2005, "Embryonic stem (ES) cells and embryonal carcinoma (EC) cells: opposite sides of the same coin," *Biochem Soc Trans* 33:1526-1530; Martin 1980, "Teratocarcinomas and mammalian embryogenesis,". *Science* 209 (4458):768-776; Evans and Kaufman, 1981, "Establishment in culture of pluripotent cells from mouse embryos," *Nature* 292(5819): 154-156; Klimanskaya et al., 2005, "Human embryonic stem cells derived without feeder cells," *Lancet* 365 (9471): 1636-1641; each of which is hereby incorporated herein in its entirety.

Alternatively, pluripotent stem cells can be derived from embryonic germ cells (EGCs), which are the cells that give rise to the gametes of organisms that reproduce sexually. EGCs are derived from primordial germ cells found in the gonadal ridge of a late embryo, have many of the properties of embryonic stem cells. The primordial germ cells in an embryo develop into stem cells that in an adult generate the reproductive gametes (sperm or eggs). In mice and humans, it is possible to grow embryonic germ cells in tissue culture under appropriate conditions. Both EGCs and ESCs are pluripotent. For purpose of the present invention, the term "ESCs" is used broadly sometimes to encompass EGCs.

Induced Pluripotent Stem Cells (iPSCs)

In some aspects, iPSCs are derived by transfection of certain stem cell-associated genes into non-pluripotent cells, such as adult fibroblasts. Transfection may be achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells.

In some aspects, non-viral based technologies may be employed to generate iPSCs. In some aspects, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some aspects, reprogramming can be accomplished via plasmid without any virus transfection system at all, although at very low efficiencies. In other aspects, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some aspects, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," *Nature* 458:771-775; Woltjen et al., 2009, *"piggyBac* transposition reprograms fibroblasts to induced pluripotent stem cells," *Nature* 458:766-770; Okita et al., 2008, "Generation of Mouse Induced Pluripotent Stem Cells Without Viral Vectors," *Science* 322(5903):949-953; Stadtfeld et al., 2008, "Induced Pluripotent Stem Cells Generated without Viral Integration," *Science* 322(5903):945-949; and Zhou et al., 2009, "Generation of Induced Pluripotent Stem Cells Using Recombinant Proteins," *Cell Stem Cell* 4(5):381-384; each of which is hereby incorporated herein in its entirety.

In some aspects, exemplary iPS cell lines include but not limited to iPS-DF19-9; iPS-DF19-9; iPS-DF4-3; iPS-DF6-9; iPS (Foreskin); iPS (IMR90); and iPS (IMR90).

Definitive Endoderm

The HCOs of the instant disclosure may be derived from a simple sheet of cells called the definitive endoderm (DE). Methods for deriving definitive endoderm from precursor cells are well known in the art, as taught by D'Armour et al. 2005 and Spence et al. The anterior DE forms the foregut and its associated organs including the liver and pancreas and the posterior DE forms the midgut and hindgut, which forms the small and large intestines and parts of the genitourinary system. Studies using mouse, chick and frog embryos suggest that establishing the anterior-posterior pattern in DE at the gastrula stage is a prerequisite for subsequent foregut and hindgut development. The Wnt and FGF signaling pathways are believed to be critical for this process and act to promote posterior endoderm and hindgut fate and suppress anterior endoderm and foregut fate. The simple cuboidal epithelium of the hindgut first develops into a pseudostratified columnar epithelium, then into villi containing a polarized columnar epithelium and a proliferative zone at the base of the villi, which corresponds with the presumptive progenitor domain.

Applicant describes herein a robust and efficient process to direct the differentiation of DE into intestinal tissue, in particular human colon tissue, in vitro. Directed differentiation may be achieved by selectively activating certain signaling pathways in the iPSCs and/or DE cells.

Additional details of pathways relating to intestinal development in general are found in, for example, Sancho et al., 2004, "Signaling Pathways in Intestinal Development and Cancer," *Annual Review of Cell and Developmental Biology* 20:695-723; Logan and Nusse, 2004, "The Wnt Signaling Pathway in Development and Disease," *Annual Review of Cell and Developmental Biology* 20:781-810; Taipalel and Beachyl, 2001, "The Hedgehog and Wnt signalling pathways in cancer," *Nature* 411:349-354; Gregorieff and Clevers, 2005, "Wnt signaling in the intestinal epithelium: from endoderm to cancer," *Genes & Dev.* 19: 877-890; each of which is hereby incorporated by reference herein in its entirety. More details on the functions of signaling pathways relating to DE development can be found in, for example, Zorn and Wells, 2009, "Vertebrate endoderm development and organ formation," *Annu Rev Cell Dev Biol* 25:221-251; Dessimoz et al., 2006, "FGF signaling is necessary for establishing gut tube domains along the anterior-posterior axis in vivo," *Mech Dev* 123:42-55; McLin et al., 2007, "Repression of Wnt/{beta}-catenin signaling in the anterior endoderm is essential for liver and pancreas development. Development," 134:2207-2217; Wells and Melton, 2000, *Development* 127:1563-1572; de Santa Barbara et al., 2003, "Development and differentiation of the intestinal epithelium," *Cell Mol Life Sci* 60(7): 1322-1332; each of which is hereby incorporated herein in its entirety.

Any methods for producing definitive endoderm from pluripotent cells (e.g., iPSCs or ESCs) are applicable to the methods described herein. In some aspects, pluripotent cells are derived from a morula. In some aspects, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some aspects, human embryonic stem cells are used to produce definitive endoderm. In some aspects, human embryonic germ cells are used to produce definitive endoderm. In some aspects, iPSCs are used to produce definitive endoderm.

In some aspects, one or more growth factors are used in the differentiation process from pluripotent stem cells to DE cells. The one or more growth factors used in the differentiation process can include growth factors from the TGF-beta superfamily. In such aspects, the one or more growth factors may comprise the Nodal/Activin and/or the BMP subgroups of the TGF-beta superfamily of growth factors. In some aspects, the one or more growth factors are selected from the group consisting of Nodal, Activin A, Activin B, BMP4, Wnt3a or combinations of any of these growth factors. In some aspects, the embryonic stem cells or germ cells and iPSCs are treated with the one or more growth factors for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; or 240 or more hours. In some aspects, the embryonic stem cells or germ cells and iPSCs are treated with the one or more growth factors at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some aspects, concentration of the growth factor is maintained at a constant level throughout the treatment. In other aspects, concentration of the growth factor is varied during the course of the treatment. In some aspects, the growth factor is suspended in media that include fetal bovine serine (FBS) with varying HyClone concentrations. One of skill in the art would understand that the regimen described herein is applicable to any known growth factors, alone or in combination. When two or more growth factors are used, the concentration of each growth factor may be varied independently.

In some aspects, populations of cells enriched in definitive endoderm cells are used. In some aspects, the definitive endoderm cells are isolated or substantially purified. In some aspects, the isolated or substantially purified definitive endoderm cells express the SOX17, FOXA2, and/or the CXRC4 marker to a greater extent than the OCT4, AFP, TM, SPARC and/or SOX7 markers. Methods for enriching a cell population with definitive endoderm are also contemplated. In some aspects, definitive endoderm cells can be isolated or substantially purified from a mixed cell population by contacting the cells with a reagent that binds to a molecule that is present on the surface of definitive endoderm cells but which is not present on the surface of other cells in the mixed cell population, and then isolating the cells bound to the reagent. In certain aspects, the cellular constituent that is present on the surface of definitive endoderm cells is CXCR4.

Additional methods for obtaining or creating DE cells that can be used in the present invention include but are not limited to those described in U.S. Pat. No. 7,510,876 to D'Amour et al.; U.S. Pat. No. 7,326,572 to Fisk et al.; Kubol et al., 2004, "Development of definitive endoderm from embryonic stem cells in culture," Development 131:1651-1662; D'Amour et al., 2005, "Efficient differentiation of human embryonic stem cells to definitive endoderm," Nature Biotechnology 23:1534-1541; and Ang et al., 1993, "The formation and maintenance of the definitive endoderm lineage in the mouse: involvement of HNF3/forkhead proteins," *Development* 119:1301-1315; each of which is hereby incorporated by reference herein in its entirety.

Definitive Endoderm to Mid/Hindgut Spheroids

In some aspects, posteriorized endoderm cells of the DE are further developed into one or more specialized cell types. Activin-induced definitive endoderm (DE) can further undergo FGF/Wnt induced posterior endoderm pattering, hindgut specification and morphogenesis, and finally a pro-intestinal culture system that promoted intestinal growth, morphogenesis and cytodifferentiation into functional intestinal cell types including enterocytes, goblet, Paneth and enteroendocrine cells. In some aspects, human PSCs are efficiently directed to differentiate in vitro into intestinal epithelium that may include secretory, endocrine and absorptive cell types. It will be understood that molecules such as growth factors may be added to any stage of the development to promote a particular type of intestinal tissue formation.

PSCs, such as ESCs and iPSCs, undergo directed differentiation in a step-wise or non-step-wise manner first into definitive endoderm (DE) then into mid/hindgut epithelium and mesenchyme (e.g., hindgut spheroids), and then into intestinal tissue. In some aspects, definitive endoderm cells and hESCs are treated with one or more growth factors.

In some aspects, soluble FGF and Wnt ligands are used to mimic early hindgut specification in culture to convert, through directed differentiation, DE developed from iPSCs or ESCs into hindgut epithelium that efficiently gives rise to all the major intestinal cell types. In human, directed differentiation of DE is achieved through selective activating certain signaling pathways that are important to intestinal development. It will be understood by one of skill in the art that altering the expression of any Wnt signaling protein in combination with any FGF ligand can give rise to directed differentiation as described herein.

More details are found, for example, in Liu et al., "A small-molecule agonist of the Wnt signaling pathway," *Angew Chem Int Ed Engl.* 44(13): 1987-1990 (2005); Miyabayashi et al., "Wnt/beta-catenin/CBP signaling maintains long-term murine embryonic stem cell pluripotency," *Proc Natl Acad Sci USA.* 104(13):5668-5673 (2007); Zhang et al., "Small-molecule synergist of the Wnt/beta-catenin signaling pathway," *Proc Natl Acad Sci US A.* 104(18):7444-7448 (2007); Neiiendam et al., "An NCAM-derived FGF-receptor agonist, the FGL-peptide, induces neurite outgrowth and neuronal survival in primary rat neurons," *J Neurochem.* 91(4):920-935 (2004); Shan et al., "Identification of a specific inhibitor of the dishevelled PDZ domain," *Biochemistry* 44(47):15495-15503 (2005); Coghlan et al., "Selective small molecule inhibitors of glycogen synthase kinase-3 modulate glycogen metabolism and gene transcription," *Chem Biol.* 7(10):793-803 (2000); Coghlan et al., "Selective small molecule inhibitors of glycogen synthase kinase-3 modulate glycogen metabolism and gene transcription," Chemistry & Biology 7(10):793-803; and Pai et al., "Deoxycholic acid activates beta-catenin signaling pathway and increases colon cell cancer growth and invasiveness," *Mol Biol Cell.* 15(5):2156-2163 (2004); each of which is hereby incorporated by reference in its entirety.

In some aspects, siRNA and/or shRNA targeting cellular constituents associated with the Wnt and/or FGF signaling pathways are used to activate these pathways.

Modulators/activators of the Wnt signaling pathway include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16. In some aspects, the modulation of the pathway may be through the use of small molecule modulators or protein modulators that activate the aforementioned pathways or proteins that activate the aforementioned pathways. For example, Small molecule modulators of the Wnt pathway included, but is not limited to Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine. Exemplary natural inhibitors of Wnt signaling include but are not limited to Dkk1, SFRP proteins and FrzB. In some aspects, the extrinsic molecules include but are not limited to small molecules such as WAY-316606; SB-216763; or BIO (6-bromoindirubin-3'-oxime). In some aspects, siRNA and/or shRNA targeting cellular constituents associated with the Wnt and/or FGF signaling pathways may be used to activate these pathways. It would be understood by one of skill in the art that the target cellular constituents include but are not limited to SFRP proteins; GSK3, Dkk1, and FrzB. Additional modulators include molecules or proteins that inhibit GSK3, which activates the Wnt signaling pathway. Exemplary GSK3 inhibitors include, but are not limited to: Chiron/CHIR99021, for example, which inhibits GSK30. One of ordinary skill in the art will recognize GSK3 inhibitors suitable for carrying out the disclosed methods. The GSK3 inhibitor may be administered in an amount of from about 1 uM to about 100 uM, or from about 2 uM to about 50 uM, or from about 3 uM to about 25 uM. One of ordinary skill in the art will readily appreciate the appropriate amount and duration.

Fibroblast growth factors (FGFs) are a family of growth factors involved in angiogenesis, wound healing, and embryonic development. In some aspects, it will be understood by one of skill in the art that any of the FGFs can be used in conjunction with a protein from the Wnt signaling pathway. In some aspects, soluble FGFs include and but are not limited to FGF4, FGF2, and FGF3. In some embodiments, the FGF signaling pathway is activated by contacting the precursor cell with one or more molecules selected from the group consisting of FGF1, FGF2, FGF3, FGF4, FGF10, FGF11, FGF12, FGF13, FGF14, FGF15, FGF16, FGF17, FGF18, FGF19, FGF20, FGF21, FGF22, and FGF23. In some embodiments, siRNA and/or shRNA targeting cellular constituents associated with the FGF signaling pathway may be used to activate these pathways. It will be understood by one of skill in the art that the methods and compositions described herein in connection with the Wnt and FGF signaling pathways are provided by way of examples. Similar methods and compositions are applicable to other signaling pathways disclosed herein.

In some aspects, DE culture is treated with the one or more modulators of a signaling pathway described herein for 6 or more hours; 12 or more hours; 18 or more hours; 24 or more hours; 36 or more hours; 48 or more hours; 60 or more hours; 72 or more hours; 84 or more hours; 96 or more hours; 120 or more hours; 150 or more hours; 180 or more hours; 200 or more hours; 240 or more hours; 270 or more hours; 300 or more hours; 350 or more hours; 400 or more hours; 500 or more hours; 600 or more hours; 700 or more hours; 800 or more hours; 900 or more hours; 1,000 or more hours; 1,200 or more hours; or 1,500 or more hours.

In some aspects, DE culture is treated with the one or more modulators of a signaling pathway described herein at a concentration of 10 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher. In some aspects, concentration of signaling molecule is maintained at a constant throughout the treatment. In other aspects, concentration of the modulators of a signaling pathway is varied during the course of the treatment. In some aspects, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known modulators of the signaling pathways described herein, alone or in combination, including but not limited to any molecules in the Wnt and FGF signaling pathways.

In aspects where two or more signaling molecules are used to treat the DE culture, the signaling molecules can be added simultaneously or separately. When two or more molecules are use, the concentration of each may be varied independently.

Expression of CDX2 may be used to reveal tendency of hindgut formation after DE have been incubated with an FGF signaling activator and a Wnt signaling activator, for example, FGF4 and Wnt3a, for a period of time, for example, for 12 hours or longer; 18 hours or longer; 24 hours or longer; 36 hours or longer; 48 hours or longer; 60 hours or longer; or 90 hours or longer. In some aspects, longer periods of incubation are needed to achieve a stable posterior endoderm phenotype as measured by prolonged expressed of CDX2. In such aspects, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

Alternatively, in some aspects, the absence of cellular constituents, such as foregut markers Sox2, Pdx1, Cldn18, and Albumin, can be used to reveal directed hindgut formation. In some aspects, intestinal transcription factors CDX2, KLF5 and SOX9 can be used to represent intestinal development. In some aspects, GATA6 protein expression can be used to represent intestinal development. In these aspects, the periods of incubation can be for 12 hours or longer; 18 hours or longer; 24 hours or longer; 36 hours or longer; 48 hours or longer; 60 hours or longer; or 90 hours or longer. Alternatively, the periods of incubation can be for 60 hours or longer; 72 hours or longer; 84 hours or longer; 96 hours or longer; 108 hours or longer; 120 hours or longer; 140 hours or longer; 160 hours or longer; 180 hours or longer; 200 hours or longer; 240 hours or longer; or 300 hours or longer.

In some aspects, abundance data of cellular constituents, for example, protein and/or gene expression levels, are determined by immunohistochemistry using primary and/or secondary antibodies targeting molecules in the relevant signaling pathways. In other aspects, abundance data of cellular constituents, for example, protein and/or gene expression levels, are determined by microarray analyses.

Still alternatively, morphological changes can be used to represent the progress of directed differentiation. In some aspects, hindgut spheroids are further subject to 3-dimensional culture conditions for further maturation. In other aspects, a highly convoluted epithelium surrounded by mesenchymal cells can be observed following hindgut spheroids formation. Additionally, intestinal organoids; polarized columnar epithelium; goblet cells; or smooth muscle cells can be observed in 6 days or longer; 7 days or longer; 9 days or longer; 10 days or longer; 12 days or longer; 15 days or longer; 20 days or longer; 25 days or longer; 28 days or longer; 32 days or longer; 36 days or longer; 40 days or longer; 45 days or longer; 50 days or longer; or 60 days or longer.

Mid/Hindgut Spheroids to Colon Organoids

It has been identified that, in addition to FGF and WNT signaling, Bone Morphogenetic Proteins (BMP) specifically BMP2 and BMP4, are capable of promoting a posterior/hindgut fate and repressing foregut fate. Additionally, BMP signaling regulates formation of distinct regional types of intestine. Inhibition of BMP with noggin after the hindgut stage promotes a proximal intestinal fate (duodenum/jejunum). Activation of BMP signaling after the hindgut stage promotes a more distal intestinal cell fate (cecum/colon).

Activation of BMP can be carried out by contacting the mid/hindgut spheroids with a BMP activator and an EGF signaling pathway activator for a period of time sufficient to form said human colon organoid. The demarcation of the incubation period may be defined by the point in time in which the human colon organoid expresses SATB2. Suitable BMP activators and EGF signaling pathway activators will be readily appreciated by one of ordinary skill in the art. Suitable BMP activators may include, for example BMP2, BMP4, BMP7, BMP9 and protein or small molecule agonists such as ventromorphins (Genthe et al. 2017) or proteins that serve as agonists. The BMP activator and EGF signaling pathway activator may be contacted with the mid-/hindgut spheroids for from about 1 day to about 3 days. BMP signaling may be activated within the first three days. In one aspect, the contacting step of the BMP activator and EGF signaling pathway activator is from 24 hours to about 10 days, or from about 48 hours to about 9 days, or from about 3 days to about 8 days, or from about 4 days to about 8 days, or from about 5 days to about 7 days. Suitable EGF activators may include, for example TGF alpha, HB-EGF, Amphiregulin, Epigen, Betacellulin and small molecules such as db-cAMP. The EGF activator may be contacted with the mid-/hindgut spheroids at a concentration of from about 10 ng/mL to 10,000 ng/ML, for a time period of from about 24 hours to about 10 days, or from about 48 hours to about 9 days, or from about 3 days to about 8 days, or from about 4 days to about 8 days, or from about 5 days to about 7 days.

The mid/hindgut spheroids may be contacted with a BMP activator and/or EGF activator at a concentration of 5 ng/ml or higher; 20 ng/ml or higher; 50 ng/ml or higher; 75 ng/ml or higher; 100 ng/ml or higher; 120 ng/ml or higher; 150 ng/ml or higher; 200 ng/ml or higher; 500 ng/ml or higher; 1,000 ng/ml or higher; 1,200 ng/ml or higher; 1,500 ng/ml or higher; 2,000 ng/ml or higher; 5,000 ng/ml or higher; 7,000 ng/ml or higher; 10,000 ng/ml or higher; or 15,000 ng/ml or higher, alone or combined. In some embodiments, concentration of signaling molecule is maintained at a constant throughout the treatment. In other embodiments, concentration of the molecules of a signaling pathway is varied during the course of the treatment. In some embodiments, a signaling molecule in accordance with the present invention is suspended in media comprising DMEM and fetal bovine serine (FBS). The FBS can be at a concentration of 2% and more; 5% and more; 10% or more; 15% or more; 20% or more; 30% or more; or 50% or more. One of skill in the art would understand that the regiment described herein is applicable to any known molecules of the signaling pathways described herein, alone or in combination Examples The following non-limiting examples are provided to further illustrate aspects of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific aspects that are disclosed and still obtain a like or similar result without departing from the spirit and scope of the invention.

The epithelium of the gastrointestinal tract is derived from the definitive endoderm, one of the primary germ layers that are established during gastrulation. The process of gut tube morphogenesis transforms the definitive endoderm into a primitive gut tube with a foregut, midgut and hindgut. The midgut gives rise to the small and proximal large intestine and the hindgut gives rise to the distal large intestine and rectum (Zorn and Wells, 2009). The small intestine is further subdivided into 3 segments: The duodenum which is involved in absorption of nutrients and uptake of iron, the jejunum which is involved in the digestion and absorption of nutrients and the ileum which is involved in the absorption of bile acids and vitamin-B12 (Jeejeebhoy, 2002). The large intestine is subdivided in to the cecum, colon and rectum which are all involved in absorption of water and electrolytes (Jeejeebhoy, 2002). Although recent advances have shed light into the development of the small intestine (Finkbeiner et al., 2015; Spence et al., 2011; Watson et al., 2014), little is known about development of human large intestine/colon. Furthermore, diseases affecting this region of the gastrointestinal (GI) tract, colitis, colon cancer, polyposis syndromes and Irritable Bowel Syndrome are prevalent (Molodecky et al., 2012; Siegel et al., 2014; Zbuk and Eng, 2007). Animal models of polyposis syndromes and intestinal cancer are limited since polyps and tumors preferentially form in the small intestine and rarely in the colon or rectum (Haramis et al., 2004; He et al., 2004; Moser et al., 1990).

Applicant previously described a method in which human pluripotent stem cells can be differentiated into intestinal tissue through steps of directed differentiation that approximate embryonic development of the small intestine. First, pluripotent stem cells are differentiated into definitive endoderm by treatment with Activin A. Exposure of definitive endoderm to high levels of Wnt and FGF induces morphogenesis into mid/hindgut tube spheroids. Once formed, these midgut/hindgut spheroids, when grown in 3-dimensional culture under conditions that favor intestinal growth, transition through stages that approximate small intestinal development in vivo and form human intestinal organoids (HIOs) (Spence et al., 2011). HIOs have a small intestinal identity and have proven extremely useful for modeling small intestinal biology (Bouchi et al., 2014; Finkbeiner et al., 2015; Watson et al., 2014; Xue et al., 2013). However, until now, PSC-derived large intestinal organoids have not been developed, and given the prevalence of disease in the large intestine, such a system would allow for interrogation of development and disease mechanisms in this region of the GI tract.

To develop a method for generating large intestinal organoids, Applicant first identified Satb2 as a definitive marker of the presumptive large intestinal epithelium in frogs, mice, and humans. Using Satb2 as a marker, Applicant has shown that BMP signaling is required for specification of posterior gut endoderm of frogs and mice, consistent with the known role of BMP in posterior-ventral development (Kumar et al., 2003; Roberts et al., 1995; Sherwood et al., 2011; Tiso et al., 2002; Wills et al., 2008). Moreover, stimulation of BMP signaling in PSC-derived gut tube cultures for 3 days is sufficient to induce a posterior HOX code and the formation of SATB2-expressing colonic organoids. Human colonic organoids (HCOs) had a marker profile and cell types consistent with large intestine. Furthermore, HCOs, but not HIOs, formed colonic enteroendocrine cells (EEC) in response to expression of NEUROG3, demonstrating that HCOs were functionally committed to the colonic region. In addition, HCOs engrafted under the kidney capsule of immunocompromised mice and grown in vivo for 8-10 weeks, maintain their regional identify, formed tissues with colonic morphology, contained colon-specific cell types, had zones of proliferation and differentiation, as well as well-formed smooth muscle layers. Intestinal enteroids and colonoids that were derived from in vivo grown organoids maintained regional identify. Lastly, RNA-seq analysis demonstrated that HIOs and HCOs underwent substantial maturation and express regional markers consistent with a small and large intestinal identity respectively. In summary, Applicant identified an evolutionarily conserved BMP-HOX pathway in frogs and mice and used this to direct hindgut patterning and formation of human colonic organoids.

Results

SATB2 expression marks the gut endoderm of posterior embryonic and adult intestine.

The molecular pathways that establish the mid and hindgut, the presumptive small and large intestine, are poorly understood, in part due to a paucity of well-defined markers. This has limited the ability to direct the differentiation of human PSCs into regionally distinct intestinal organoids, in particular large intestinal organoids. Applicant therefore identified markers that distinguish different domains of the mouse embryonic gut tube and used these to interrogate signaling pathways that pattern the early intestine. Consistent with previous reports Applicant found that in e9.5 mouse embryos, Gata4 marked the gut endoderm from the posterior foregut to the yolk stalk (FIG. 8A) (Aronson et al., 2014; Battle et al., 2008; Beuling et al., 2008a; Beuling et al., 2007a; Beuling et al., 2007b; Beuling et al., 2010; Beuling et al., 2008b; Bosse et al., 2007; Kohlnhofer et al., 2016; Patankar et al., 2012a; Patankar et al., 2012b; Sherwood et al., 2009; Walker et al., 2014). At later stages of development (e11.5-e16.5), Gata4 continued to distinctly mark the anterior but not the posterior intestine (FIG. 8B-D,I-J). This expression domain remains intact into adulthood in both mice (not shown) and humans (FIG. 8K-L).

Figure 8:
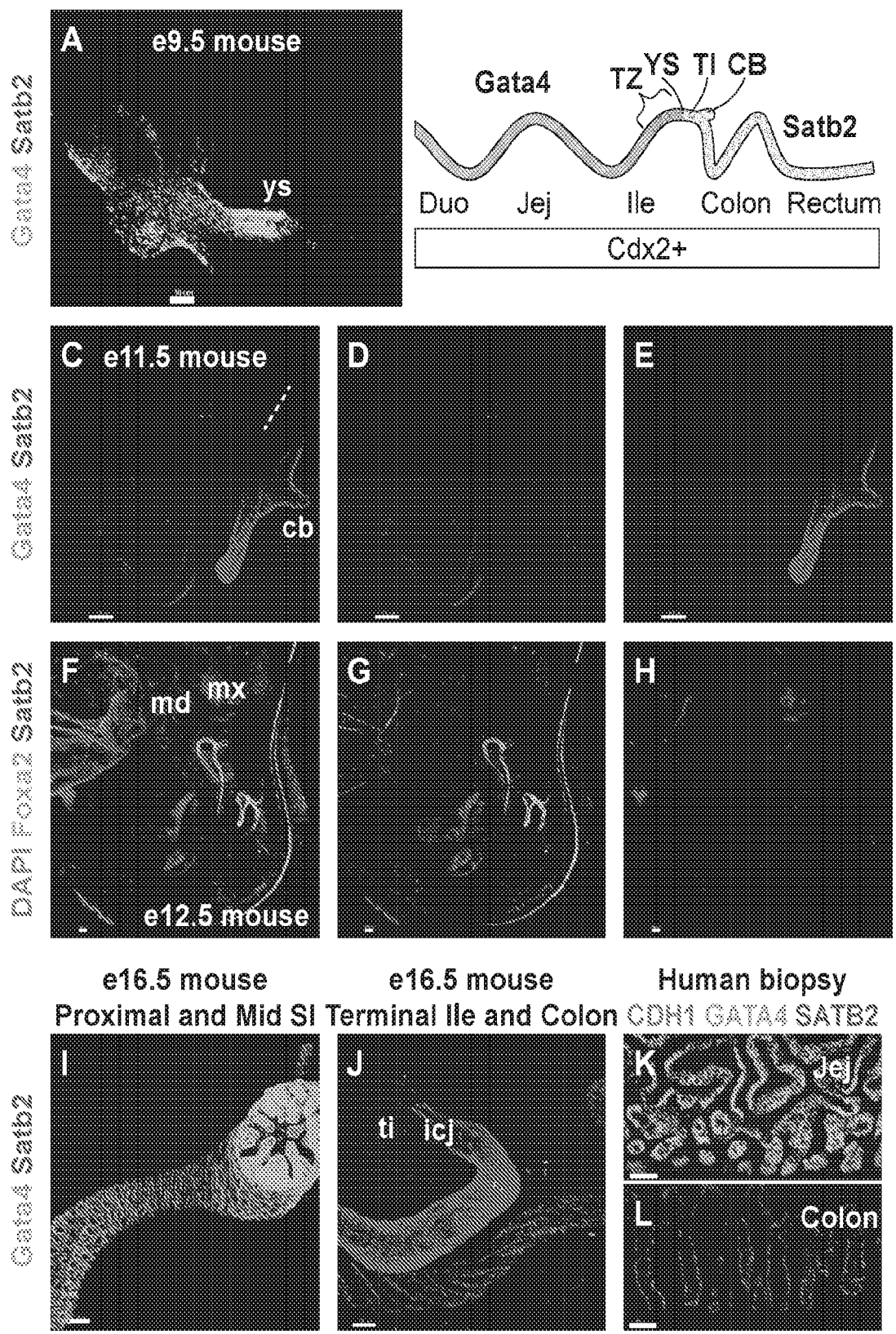
FIG. 8. Gata4 and Satb2 mark discreet regional boundaries during development of the small and large intestines. (A) Whole-mount staining of Gata4 (green) and Satb2 (red) in an e9.5 mouse embryo showing expression boundary at the yolk stalk (n=9). (B) Model depicting Gata4 and Satb2 expression domains el 1.5 intestine showing a transitional zone of low Gata4 and low Satb2 expression. (C¬E) Whole-mount staining of Gata4 and Satb2 in an e11.5 mouse embryo showing posterior boundary of Gata4 and anterior boundary of Satb2 at the yolk stalk (n=3). (F-H) Whole-mount staining of Satb2 and Foxa2 in an e12.5 mouse embryo showing that the anterior boundary of Satb2 expression is maintained (n=3). (I) Whole-mount staining of Gata4 and Satb2 in proximal intestine isolated from an e16.5 mouse embryo (n=6). (J) Whole-mount staining of Gata4 and Satb2 in distal small intestine and large intestine isolated from an e16.5 mouse embryo (n=6). Staining of GATA4 and SATB2 in section of (K) human jejunum (n=2) and (L) colon (n=2). Scale bars=50 am (B-D) and 100 1 Am (E-M). Dotted lines in (C) and (F) mark the approximate location of the umbilicus. Abbreviations: ys, yolk stalk; cb, cecal bud; tz, transition zone; mx, maxilliary; and md, mandibular portion of first brachial arch; ti, terminal ileum; icj, ileocecal junction.

In order to identify markers of the posterior fetal intestine, Applicant mined public expression databases such as GNCPro™, TiGER and Human Protein Atlas for colon enriched genes (described in the Materials and Methods section) and found Satb2 as a potential marker of large intestine. Satb2 is a member of the CUT-class of homeobox genes (Holland et al., 2007), which binds nuclear matrix attachment regions and is involved in chromatin remodeling (Gyorgy et al., 2008). Immunostaining showed that Satb2 protein was first detected in the posterior endoderm of mouse embryos at e9-9.5 and formed a discreet expression boundary with Gata4 (FIG. 8A) at the yolk stalk, suggesting that the Satb2+ domain marks the posterior intestine, a broader expression domain than previously identified (Dobreva et al., 2006). Satb2 expression continued to mark the posterior intestinal endoderm throughout development (e11.5-16.5) (FIG. 8 B, C, E, F, H, J) and in the postnatal colon in mice (not shown) and humans (FIG. 8L). Using published human proteome and RNA-seq data, Applicant confirmed that GATA4 and SATB2 differentially mark proximal and distal regions of the human fetal and adult intestinal tract respectively (Bernstein et al., 2010; Fagerberg et al., 2014) (Wang et al., 2015) (FIG. 9A-C). These data demonstrate that the Gata4 and Satb2 expression boundaries are established early during development of mouse and marks future boundaries of the developing small and large intestine in mice and humans.

BMP Signaling is Required for Satb2 Expression in the Embryonic Hindgut Endoderm.

Figure 1B:
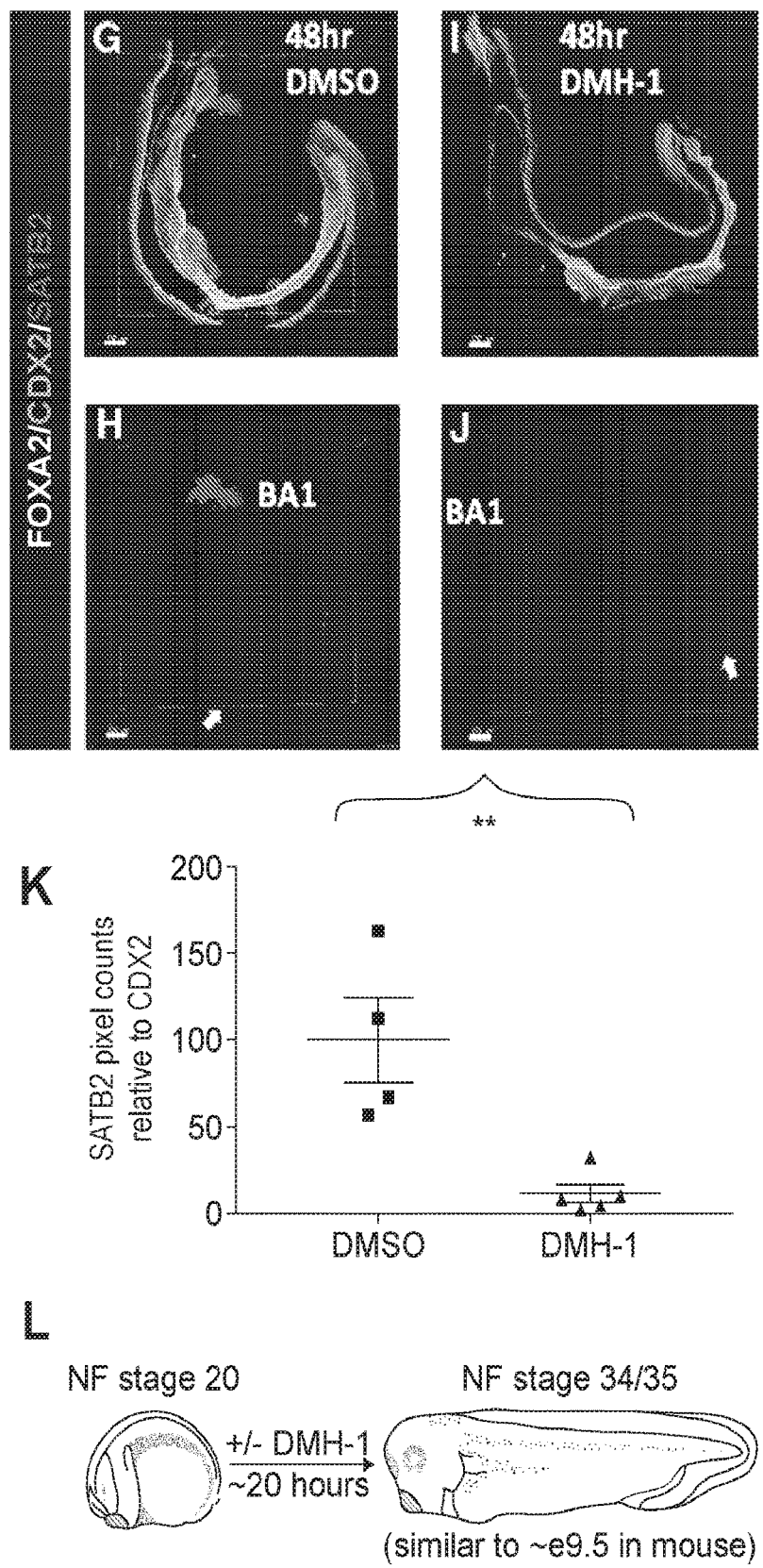
Figure 1C:
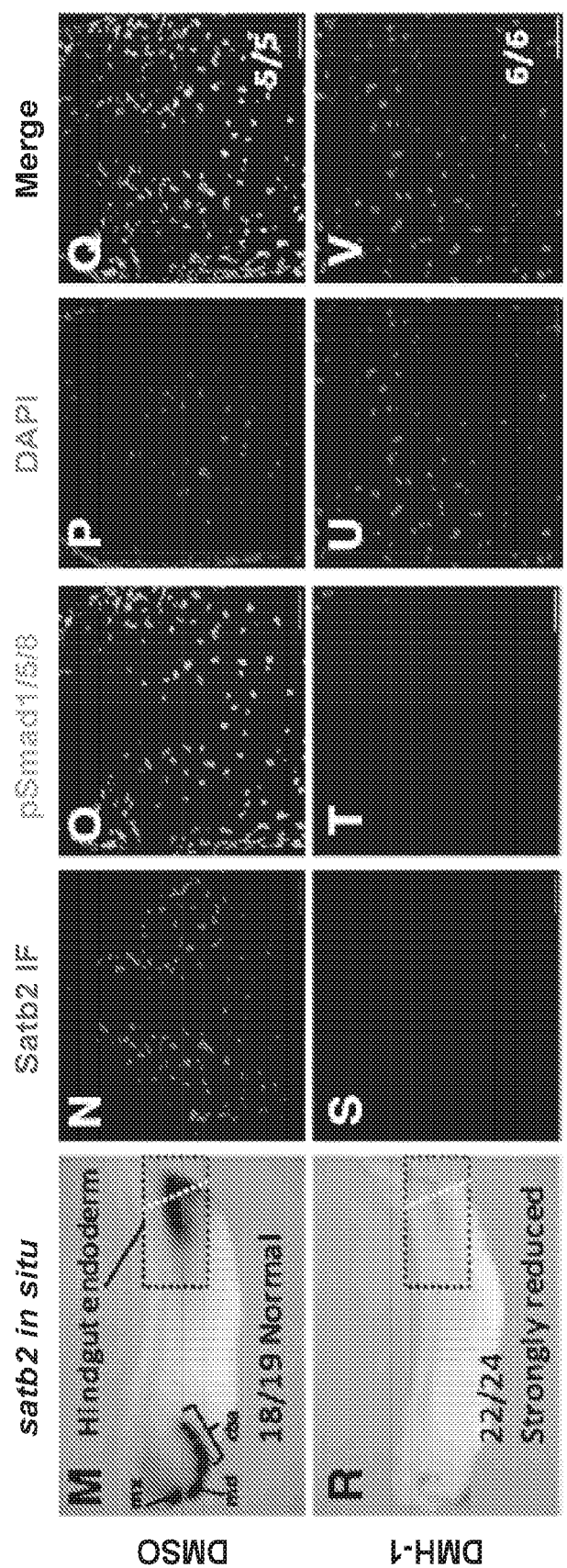

Applicant next used Satb2 as a marker to identify pathways that promote posterior intestinal fate in embryos. Applicant first determined if BMP signaling was active in the posterior gut tube, given its known role in patterning endoderm at several stages of development in zebrafish, *Xenopus*, chick and mouse (Kumar et al., 2003; Roberts et al., 1995; Sherwood et al., 2011; Tiso et al., 2002; Wills et al., 2008). Applicant observed that BMP signaling was highly active in the endoderm and mesoderm of the posterior gut tube of e8.5 mouse embryos as measured by phosphorylated Smad1/5/8 (pSMAD1/5/8) (FIG. 1A-B). To determine if BMP signaling is required for patterning of the posterior gut tube, Applicant cultured early headfold stage mouse embryos (e7.5) in the BMP signaling inhibitor DMH-1 (FIG. 1C). After 48 hours of DMH-1 treatment, Applicant saw a significant reduction in pSmad1/5/8 levels and a loss of Satb2 expression in the posterior gut tube (FIG. 2D-K). In addition, Satb2 expression was lost in the first brachial arch of DMH-1 treated embryos consistent with previous studies in Zebrafish (Sheehan-Rooney et al., 2013). DMH-1 had no impact on TGFβ signaling as measured by pSmad2/3 levels (FIG. 1F). Given the evolutionary conservation of the Satb2 across vertebrate species (Li et al., 2006) Applicant investigated if BMP is required for Satb2 expression in the hindgut of frog embryos (FIG. 2L). Similar to mice, treatment of *Xenopus* embryos with DMH-1 (FIG. 1M-V), or transgenic expression of the BMP-antagonist Noggin (not shown) resulted in a loss of Satb2 expression in the hindgut and brachial arches. BMP signaling has been shown to directly regulate Satb2 expression in mouse embryonic mandibles through direct binding of Smad1/5 to a conserved enhancer (Bonilla-Claudio et al., 2012), suggesting that Satb2 may be a direct BMP target in the gut as well. Taken together these results revealed a conserved pathway in vertebrates whereby BMP signaling is required for defining the posterior most region of the developing gut tube that gives rise to the distal ileum and large intestine.

BMP Signaling Promotes Posterior Fate in Human Gut Tube Cultures.

Applicant next investigated if BMP signaling could be used to promote a posterior gut tube fate in humans using nascent CDX2+ gut tube spheroids derived from human PSCs as previously described (Spence et al., 2011). Applicant either inhibited or activated BMP signaling using the BMP inhibitor NOGGIN or BMP2 respectively (FIG. 2A) and monitored BMP signaling levels by accumulation of nuclear pSMAD1/5/8. Control cultures had low levels of pSMAD1/5/8 protein and addition of NOGGIN abolished this staining (FIG. 2B-D). In contrast, addition of BMP2 caused a rapid accumulation of pSMAD158 in both epithelial and mesodermal cells suggesting both cell types respond to BMP signals similar to what Applicant observed in mouse embryos (FIG. 1A-B). The specificity of pSmad1/5/8 staining was confirmed using adult mouse colon, which showed pSmad1/5/8 staining restricted to the differentiated compartment of the upper crypt (FIG. 2E) as previously reported (Hardwick et al., 2004; van Dop et al., 2009; Whissell et al., 2014). Further analysis of organoids revealed that 3 days of BMP2 treatment was sufficient to induce high levels of SATB2 protein in the epithelium compared to NOGGIN and control cultures (FIG. 2F-I). This suggests that a short pulse of BMP activity is sufficient to pattern spheroid endoderm into a posterior gut tube fate.

While BMP signaling is known to regulate anterior-posterior patterning of the endoderm, little is known about the transcriptional networks that ultimately confer positional identity along the A-P axis in mammals. Applicant used human gut tube spheroids and RNA-seq to identify how BMP signaling establishes posterior domains in the developing human gut. Principal component analysis revealed that gut tube spheroids treated with BMP for 3 days clustered separately from NOGGIN and control treated organoids (FIG. 2J). Examination of gene ontology terms (GO terms) revealed that modulation of BMP signaling affects multiple biological processes including organ morphogenesis, cell-cell signaling, pattern specification and cellular response to BMP signaling (FIG. 2K). The most definitive regulators of A-P patterning are HOX genes, and Applicant found that BMP activation resulted in down regulation of anterior HOX genes and up regulation of posterior HOX genes (FIG. 2L). In particular Applicant saw BMP-mediated increases in multiple paralogs of HOX10, 11, 12 and 13 groups. These results demonstrate that BMP signaling broadly regulates A-P hox code during patterning of the human gut tube and suggest a mechanism by which the distal GI tract is initially specified.

BMP Signaling Acts Downstream of SHH to Induce a Posterior Hox Code.

Figure 10B:
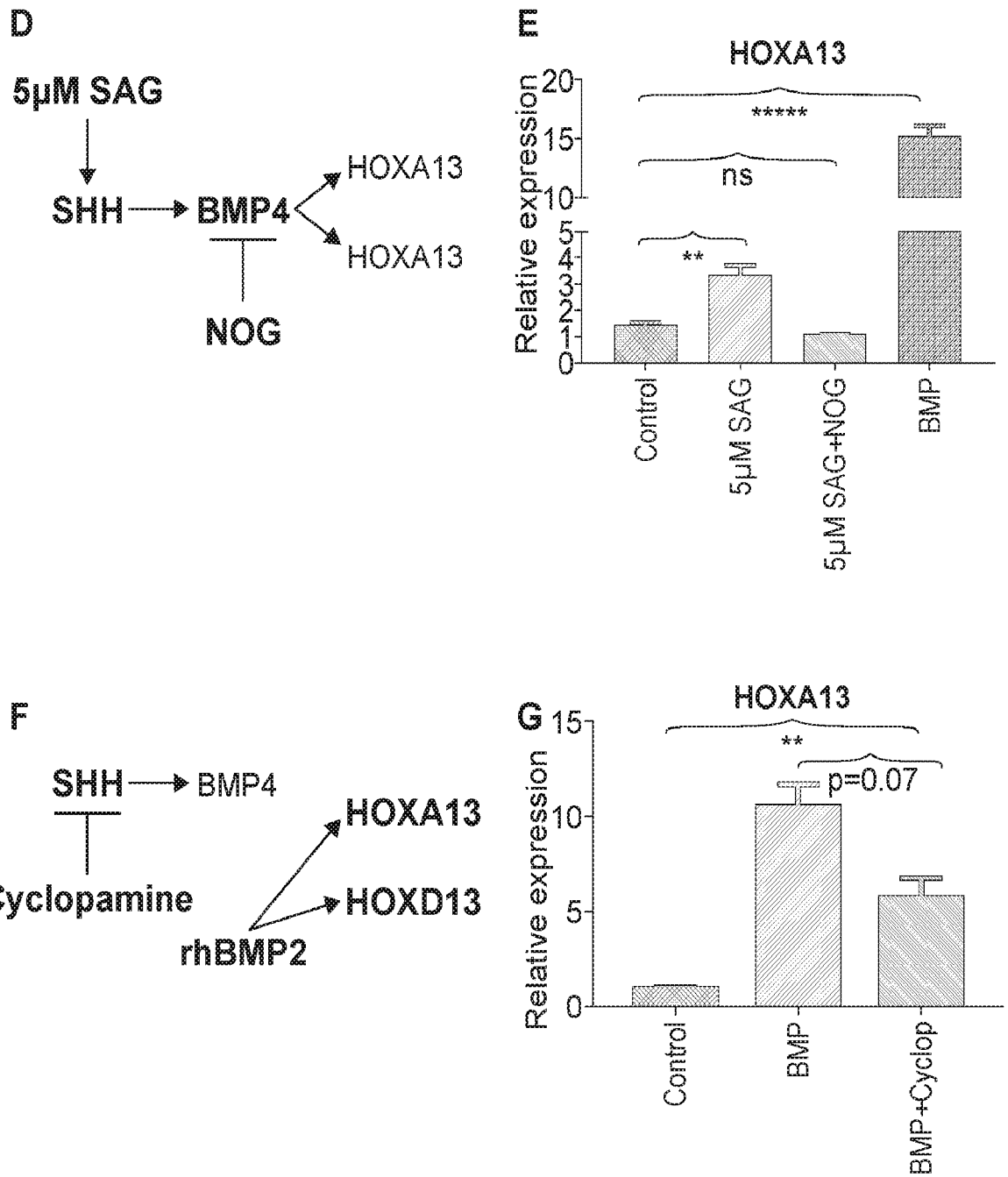
FIG. 10. BMP mediates SHH activation of posterior HOX genes. (A) Previous model of SHH-mediated activation of posterior HOX genes. (B) New model of SHH mediated activation of posterior HOX genes and BMP-mediated activation of endoderm HOX genes. (C) QPCR analysis of HOX factors following treatment with NOGGIN, control, Smoothened agonist (SAG), or BMP2. (D) Model of BMP4 dependent activation of HOX13 genes induced by SAG. (E) QPCR analysis of HOXA13 in control, 5 µM SAG, 5 µM SAG+NOG and BMP2 treated organoids after 3 days. (F) Model of SHH independent activation of HOX13 genes induced by exogenous recombinant human BMP2. (G) QPCR analysis of HOXA13 in control, BMP, and BMP+ Cyclopamine treated organoids after 3 days (n=6 per condition).
Figure 11A:
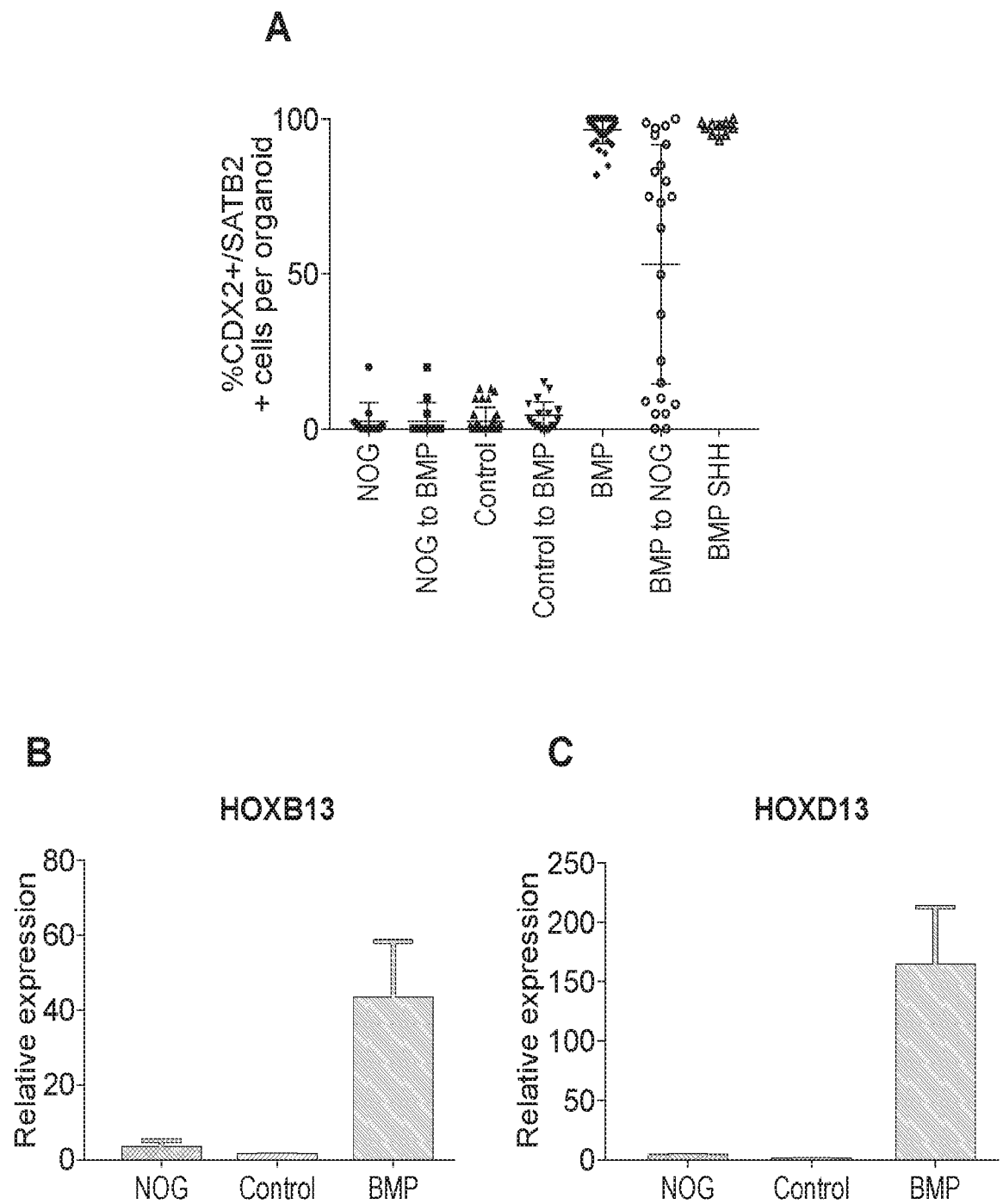
FIG. 11. Extended in vitro culture allows maturation of goblet cells. (A) Quantitation of the percentage of CDX2+ SATB2+ cells in organoids which were patterned and were then re-patterned. QPCR analysis of HOXB13 (B) and HOXD13 (C) in 28-day old organoids. (D-F) Whole-mount and (G-I) cross section staining with CDH1 (green), CDX2 (red), and MUC2 (white) from 44-day old NOGGIN, Control, and BMP treated organoids. (J-L) Staining of sections from 44-day old BMP2 treated organoids. White arrows points to goblet cells which were in the process of secreting Mucin 2. For QPCR a minimum of 5 biological replicates from 2 separate experiments were examined. For IF a minimum of 10 organoids per condition were examined. Scale bars=50 pm.

Previous studies suggest that Sonic Hedgehog (Shh) acts upstream of Bmp4 and Hox13 expression during posterior gut patterning in chick embryos (FIG. 10A) (Roberts et al., 1995). However, the relative epistatic relationship between BMP and Hox13 (FIG. 10B) was not investigated due to embryonic lethality caused by Bmp4 overexpression in the midgut and hindgut (De Santa Barbara et al., 2005; Roberts et al., 1995). Applicant used human gut tube cultures to better model the epistatic relationship of SHH-BMP-HOX13 during posterior gut tube patterning. Activation of hedgehog signaling with the smoothened agonist SAG led to a concentration dependent activation of the BMP signaling target gene MSX2 and the mesenchymal HOX factors, HOXA13 and HOXD13 (FIG. 10C). However, SAG-mediated activation of these factors was only a fraction of the activation mediated by BMP2 (FIG. 10C). Applicant further showed that the ability of HH signaling to activate HOXA13 was entirely dependent on BMP (FIG. 10D-E), confirming that BMP signaling functions downstream of SHH as previously reported (Shyer et al., 2015; Walton et al., 2012; Walton et al., 2009; Walton et al., 2016). It has not been determined if BMP signaling is sufficient to activate the posterior HOX program downstream of HH signaling. Applicant therefore examined HOXA13 induction by BMP in the presence of the SHH inhibitor Cyclopamine and found that BMP2 was sufficient to induce HOXA13 when SHH signaling is inhibited (FIG. 10F-G). Consistent with this, activation of SHH signaling during BMP patterning did not improve SATB2 expression (FIG. 11A). Experiments in *Xenopus* confirmed this epistatic relationship between SHH and BMP (data not shown) suggesting that this mechanism is evolutionarily conserved. Taken togetherApplicant's data suggest that BMP signaling is sufficient to activate the posterior HOX code and does so downstream of HH signaling.

BMP-Derived Organoids Cultured In Vitro Maintain a Distal Identity.

Figure 3A:
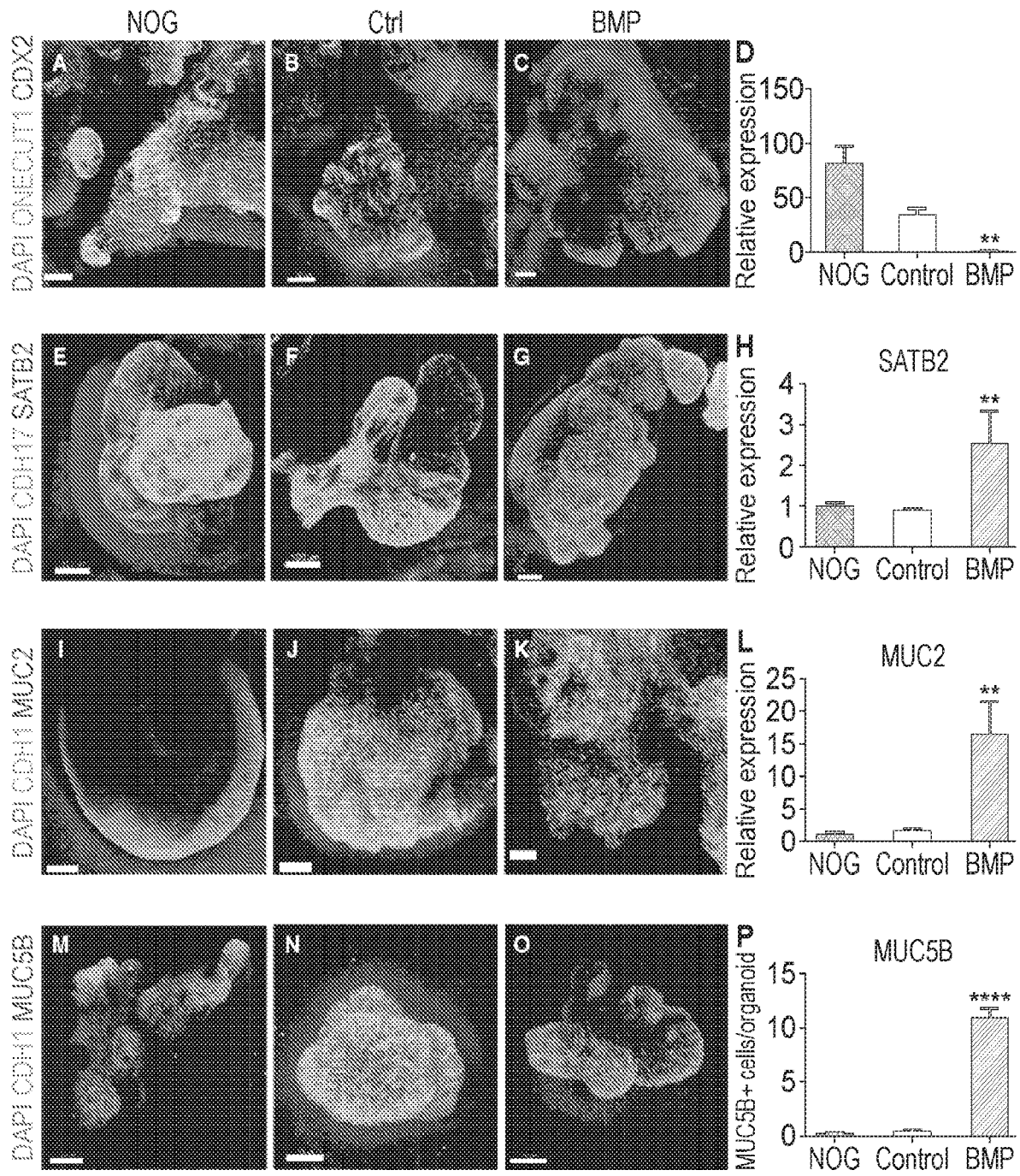
FIG. 3. Regional patterning is maintained in human intestinal organoids following prolonged in vitro culture. (A-D) Whole-mount immunofluorescence and QPCR analysis with the proximal marker ONECUT1 (green) of 28-day old organoids that resulted from the initial 3 day treatment of spheroids with NOGGIN, control, or BMP2. Staining with CDX2 (red) and DAPI (blue) were also used to detect the epithelium and mesenchyme. (E-H) Expression of the posterior marker SATB2 (red) detected by IF and by QPCR. (I-L) Analysis of the pan-goblet cell marker MUC2 (red) by IF and by QPCR. (M-P) Analysis of the colon-specific goblet cell marker MUC5B (red) by IF. The number of MUC5B+ cells was quantified in (P). (Q-S) Analysis of patterning markers in isolated mesenchyme cultures relative to whole organoids. QPCR analysis of CDH1 (Q), the proximal HOX gene HOXD3 (R), and the distal HOX gene HOXA13 (S) in whole organoids and in mesenchyme cultures derived from NOGGIN, control, or BMP2 treated organoids. CDH1 was only observed in whole organoids that contained epithelial cells. Error bars represent SEM. For IF minimum of 10 organoids from at least 3 different experiments were examined for each condition. For QPCR a minimum of 5 biological replicates from 2 separate experiments were examined. Scale bars=100 microns. p 5 0.01 and **p 5 0.0001 determined by 2 tailed t-test.
Figure 3B:
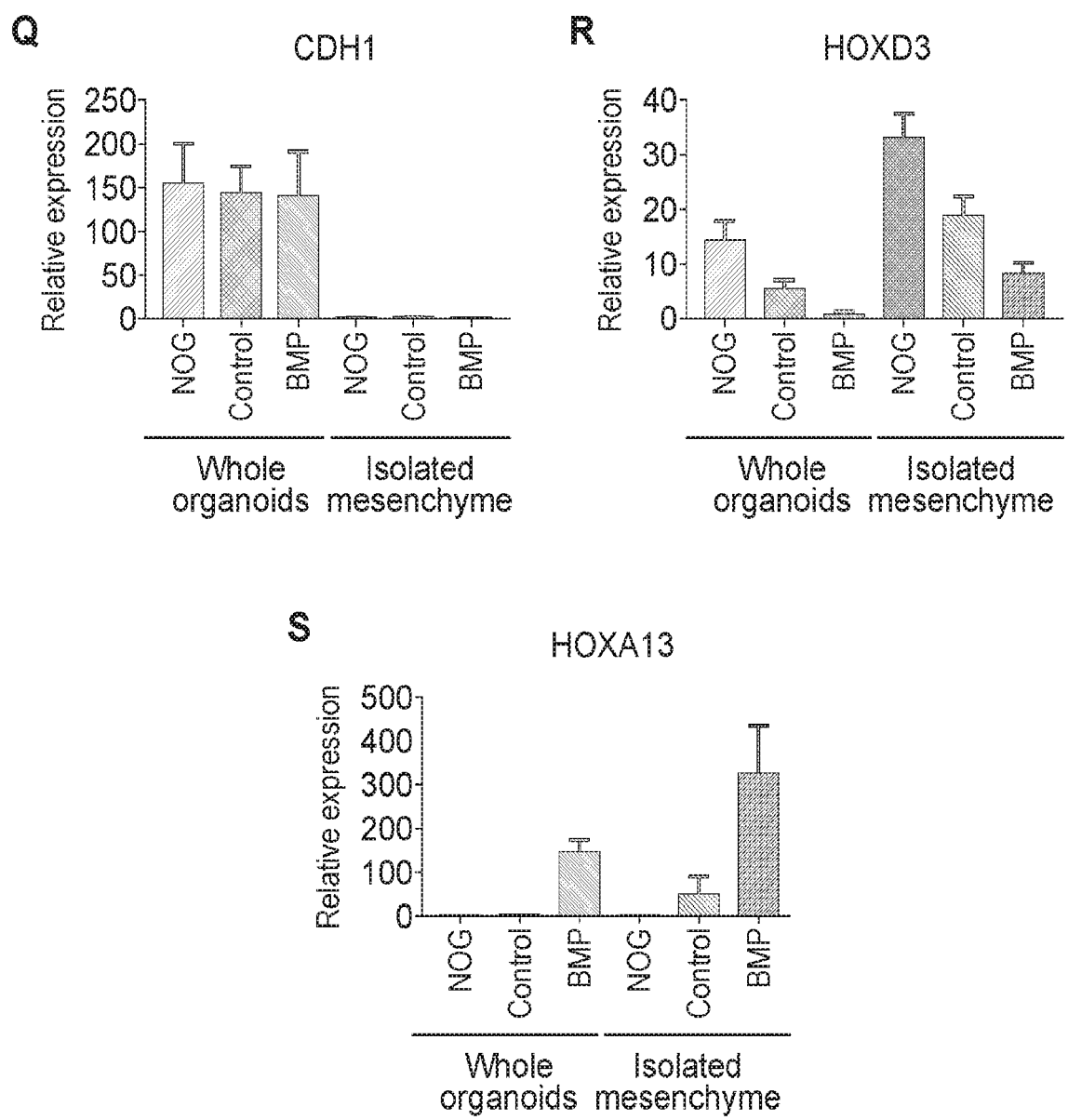
Figure 4B:
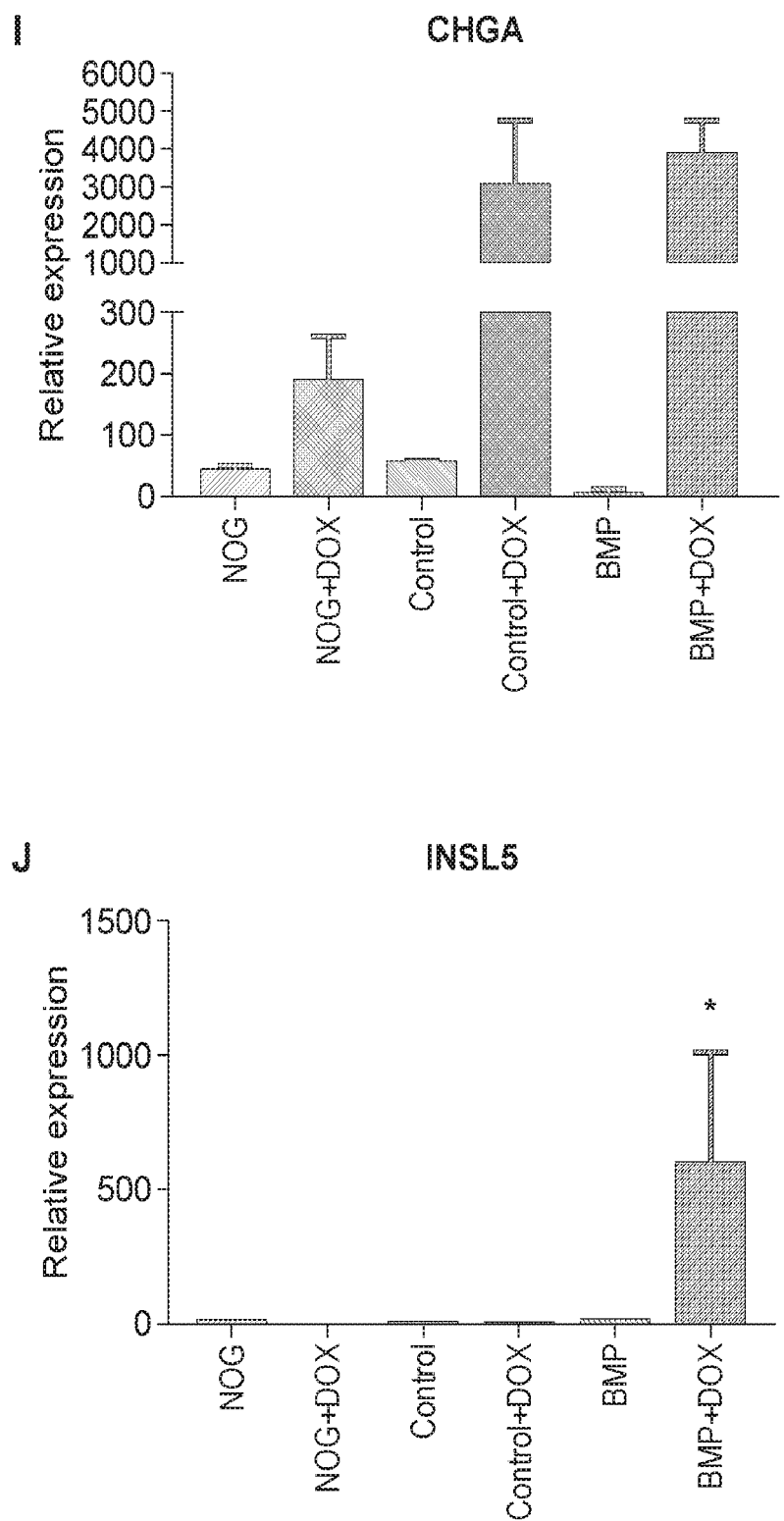
FIG. 4. HCOs but not HIOs gave rise to colon-specific enteroendocrine cells in response to expression of the proendocrine transcription factor NEUROGENIN 3. (A-B) Schematic of the doxycycline inducible NEUROG3 lentiviral construct used to generate the IPSC72.3 inducible NEUROG3 line, and the doxycycline induction protocol. Whole-mount staining with Chromagranin A (green), CDX2 (red) and INSL5 (white) of 35 day old organoids patterned with NOGGIN (C,F), untreated (D,G) or BMP (E,H). (C-E) Untreated organoids (−Dox) and (F-H) organoids with expressed NEUROG3 (+Dox). Insets in E and H show a magnified view of INSL5 staining. (I, J) QPCR analysis of NEUROG3 induction of enteroendocrine cells in HIOs and HCOs as measured by CHGA (I) and for INSL5 (J) expression. Data is representative of 2 different experiments with NOGGIN (n=3), Control (n=3) or BMP (n=6) treated organoids. Error bars represent SEM. Scale bars=50 microns. *p<0.05 determined by 2 tailed t-test.
Figure 5:
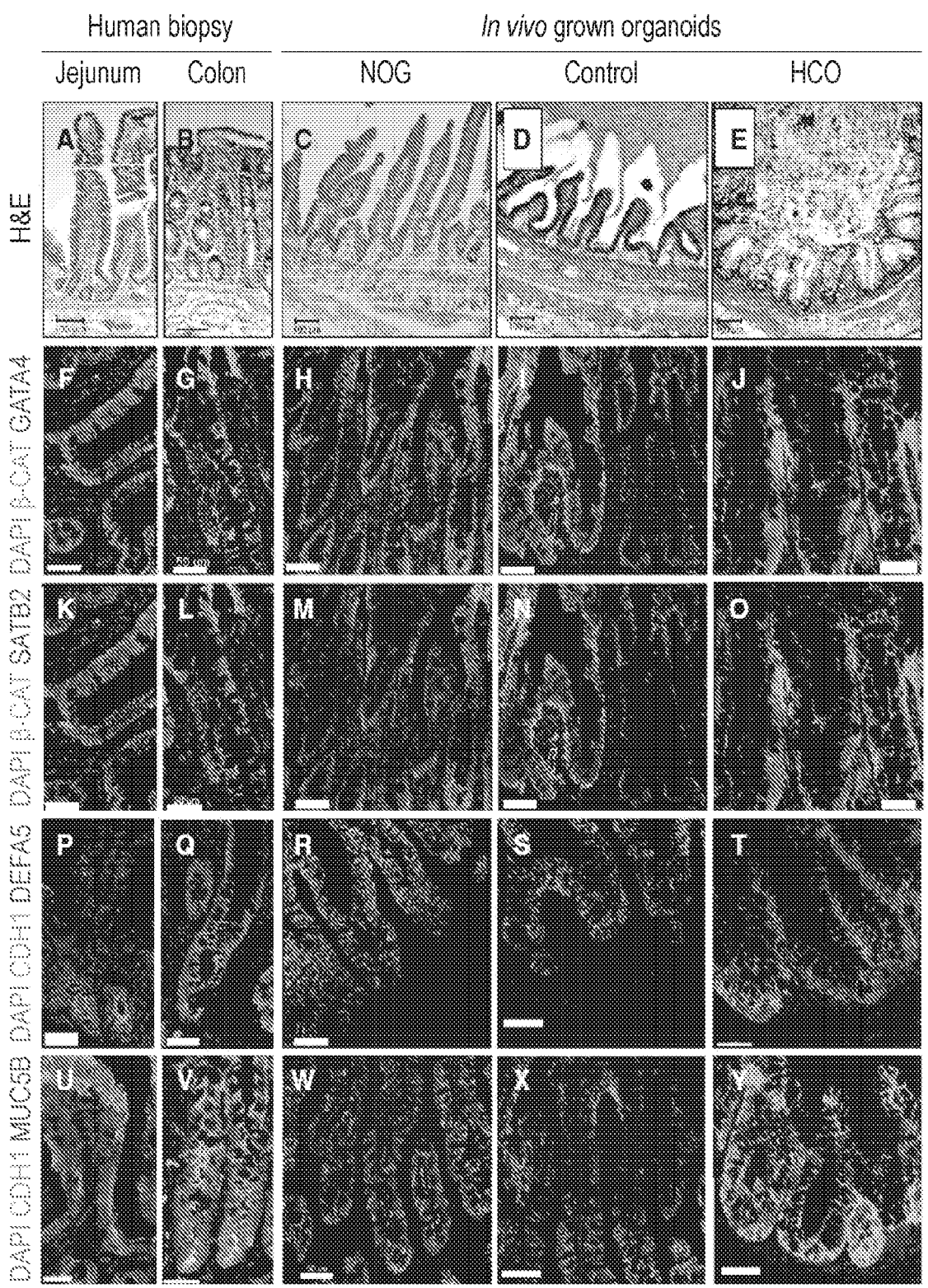
FIG. 5. HIOs and HCOs maintained regional identity following transplantation in vivo. (A-E) H&E staining of biopsies from human jejunum and colon and of NOGGIN-derived HIOs, control HIOs, and BMP2-derived HCOs that were transplanted underneath the mouse kidney capsule and grown for 8-10 weeks in vivo. The samples of the same conditions were stained with the proximal intestinal marker GATA4 (F-J), the distal intestinal marker SATB2 (K-0), the Paneth cell marker DEFA5 (P-T), and the colon-specific goblet cell marker MUC5B (U-Y). Note that although GATA4 and SATB2 double staining was done in different channels but on the same slides for panels (F-0), they are shown as individual pseudo-colored (red) images. For human biopsies n=2. For transplanted NOGGIN treated organoids n=12, for control organoids n=7, and for BMP2 treated organoids n=16. Scale bars=50 pm.
Figure 6:
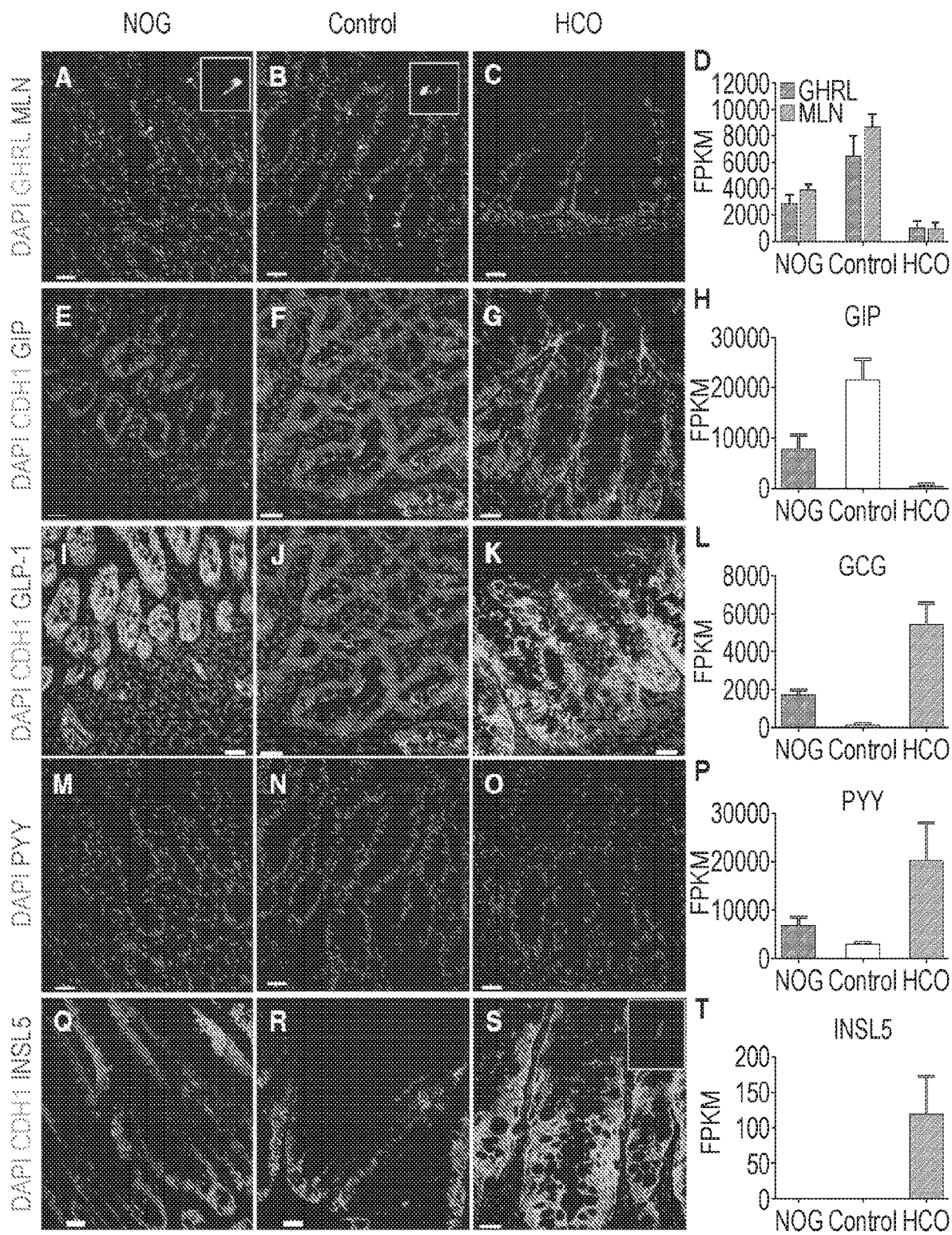
FIG. 6. In vivo grown organoids express region-specific hormones. Analysis of expression of the regionally expressed hormones (A-D) Ghrelin (GHRL), Motilin (MLN), (E-H) GIP, (I-L) GLP-1, (M-P) PYY and (Q-T) INSL5 in HIOs and HCOs grown for 8-10 weeks underneath the mouse kidney capsule. The proximally enriched hormones GHRL, GIP and MLN were enriched in NOGGIN and control HIOs (A-H). The distally enriched hormones GLP-1 and PYY were enriched in BMP2-derived HCOs (1-0). The colon specific hormone INSL5 was only present in HCO (Q-T). Data is representative of a minimum of 5 transplanted organoids per condition. Insets in (A) and (B) show GHRL and MLN double positive cells. (D, H, L, P, T) FPKM values for GHRL, MLN, GIP, GLP1, PYY, and INSL5 are from RNA-seq data. FPKM values represent 3 biological replicates per condition. Scale bars=30 microns.

Applicant next investigated if 3 days of BMP treatment is sufficient to confer stable regional identity following extended culture of organoids for 25 days (FIG. 3). Levels of ONECUT1 (a marker of proximal small intestine) were highest in NOGGIN and control treated organoids and absent in BMP2 treated organoids (FIG. 3A-D). Conversely, SATB2 was absent in the epithelium of NOGGIN and control treated organoids but broadly expressed in nearly all of the CDX2+ epithelial cells of BMP2 treated organoids (FIG. 3 E-H, FIG. 11A). Importantly, modulation of BMP signaling had similar proximal-distal patterning effects on multiple human PSC lines, including embryonic stem cell lines H1 and H9 and induced pluripotent stem cell lines (IPSC 54.1 and IPSC 72.3) (shown below). Applicant frequently observed non-epithelial SATB2 expression in NOGGIN and control organoids (data not shown) possibly due to the presence of other cell types that are known to be present in HIOs in vitro (Spence et al., 2011). Examination of HOXB13 and HOXD13, which is expressed in posterior epithelium and mesenchyme respectively, further revealed that BMP treated organoids maintained posterior patterning following prolonged culture in vitro (FIG. 11B-C).

Goblet cells are distributed in a low-to-high gradient from proximal small intestine to distal large intestine (Rodriguez-Pineiro et al., 2013), and Applicant investigated if goblet cell numbers were lower in proximal and higher in distal organoids. Analysis of MUC2 staining at 28 days revealed that BMP2 treated organoids had high numbers of goblet cells as visualized by intracellular MUC2 (FIG. 3I-L) as compared to more proximal NOGGIN treated and control organoids, which only had rare intracellular MUC2 staining. Applicant further confirmed the regional identity of goblet cells using the marker MUC5B, which is expressed by a subset of goblet cells in the colon but not in the small intestine (van Klinken et al., 1998). MUC5B staining was absent in Noggin and control treated 28-day organoids but was present in BMP2 treated organoids (FIG. 4M-P). Goblet cell morphology became more mature in older organoids (FIG. 11D-I), where in 44-day old BMP treated organoids Applicant observed goblet cells in the process of secreting mucus into the lumen of the organoids (FIG. 11J-L). The ability to observe mucus secretion in BMP treated organoids suggests that this organoid system would be useful to study mucus secretion and the roles of mucus in intestinal pathophysiology.

While the regional pattern of organoids is stable after 28 days in culture, Applicant wanted to investigate if early patterning was fully established after the initial 3-day treatment. To do so, Applicant shifted 3-day NOGGIN-treated spheroids to BMP2-containing media for 3 days and conversely shifted 3-day BMP treated spheroids to NOGGIN-containing media for 3 days. Proximal organoids generated with NOGGIN did not express SATB2 in response to BMP2 demonstrating that proximal fate was stable following 3 days of patterning (FIG. 11A). In the converse experiment, while 3 days of BMP2 treatment was sufficient to induce a stable distal fate, a subset of organoids lost SATB2 expression in response to NOGGIN treatment (FIG. 11A). While 3 days of BMP2 treatment is sufficient to induce a colonic fate that is stable in vitro and in vivo (FIG. 12), there remains plasticity in the early posterior gut tube. This is consistent with the observation that the colonic endoderm of midgestation rat embryos is more regionally plastic than the small intestinal endoderm (Ratineau et al., 2003).

Patterning of Organoid Mesenchyme by BMP Signaling.

While stimulation of BMP signaling conferred regional identity to organoid epithelium, Applicant also observed pSMAD1/5/8 in the non-epithelial compartment of BMP2 treated organoids during patterning, and upregulation of posterior HOX factors known to be expressed in the mesenchyme. To determine if mesenchymal patterning was stable, or required continued patterning input from epithelium, Applicant isolated and expanded mesenchymal cell cultures for 2-3 weeks and analyzed them for expression of regional HOX genes. Mesenchymal cultures were lacking E-cadherin expressing cells, suggesting that they were primarily comprised of mesenchyme (FIG. 3Q). Analysis of HOXD3, which is enriched in proximal intestinal mesenchyme (Yahagi et al., 2004), confirmed that the mesenchyme from NOGGIN and control treated organoids have a stable proximal identity while BMP treated organoids had decreased expression of HOXD3 (FIG. 3R) and high levels HOXA13 (FIG. 3S), which continues to be expressed in human colon fibroblasts (Higuchi et al., 2015). Taken together, these data suggest that early modulation of BMP signaling patterns both the epithelium and the mesenchyme and that mesenchymal patterning is stable even in the absence of epithelium.

Induction of Colonic Enteroendocrine Cells is Restricted to BMP2 Treated Organoids.

The development of several ECC subtypes is regionally restricted to specific segments of small and large intestine. For example, expression of the protein INSL5 is restricted to colonic EECs (Burnicka-Turek et al., 2012; Thanasupawat et al., 2013). As a functional test of colonic identity, Applicant determined if experimental induction of the colonic EEC marker INSL5 was restricted to BMP2-treated distal organoids. To do this Applicant inducibly expressed the proendocrine transcription factor NEUROG3 using an iPSC line harboring a doxycycline (DOX) inducible NEUROG3 expression cassette (FIG. 4A) as previously described (McCracken et al., 2017; McCracken et al., 2014). Applicant performed a 6-hour pulse of DOX and after an additional 7 days in culture observed a robust induction of EECs as measured by CHGA positive cells (FIG. 4B-I). However, Applicant only observed INSL5 positive cells in BMP2 treated organoids and confirmed this by QPCR analysis (FIG. 4C-H,J). Given that INSL5-expressing cells are only in the colon, Applicant's data strongly suggest that BMP2-treated organoids are functionally committed to the colonic fate. The expression of distal markers like SATB2, MUC5B and HOXA13 and the competence to generate colon specific ECCs support the conclusion that BMP2 treated organoids are colonic, and thus will be referred to as human colonic organoids (HCOs).

Regional Identity of Patterned Organoids is Maintained In Vivo.

Figure 12A:
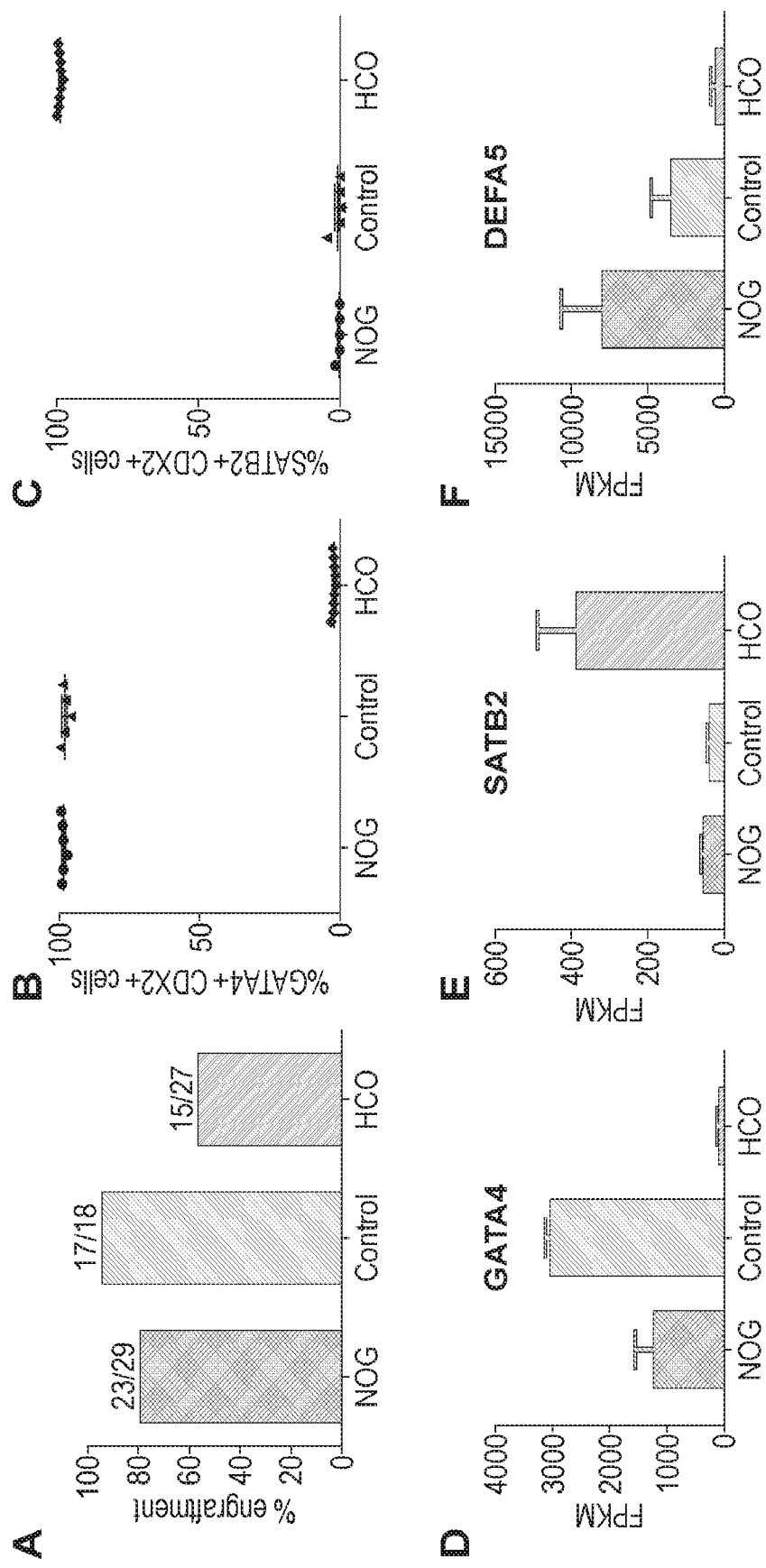
FIG. 12. BMP patterning of organoids is stable in vitro and in vivo. (A) Efficiency of organoid engraftment of NOGGIN, Control, and BMP patterned organoids. Quantitation of the percentage of GATA4+ CDX2+ cells (B) and SATB2+ CDX2+ cells (C) in transplanted patterned organoids. FPKM values from RNA-seq data for GATA4 (D) SATB2 (E) DEFA5 (F) and MUCSB (G) in transplanted organoids. MUC2 (red) staining of (H-I) human jejunum and colon biopsies (n=2 per region) and (J-L) transplanted organoids (n=5 per condition). Scale bars=50 microns.
Figure 12B:
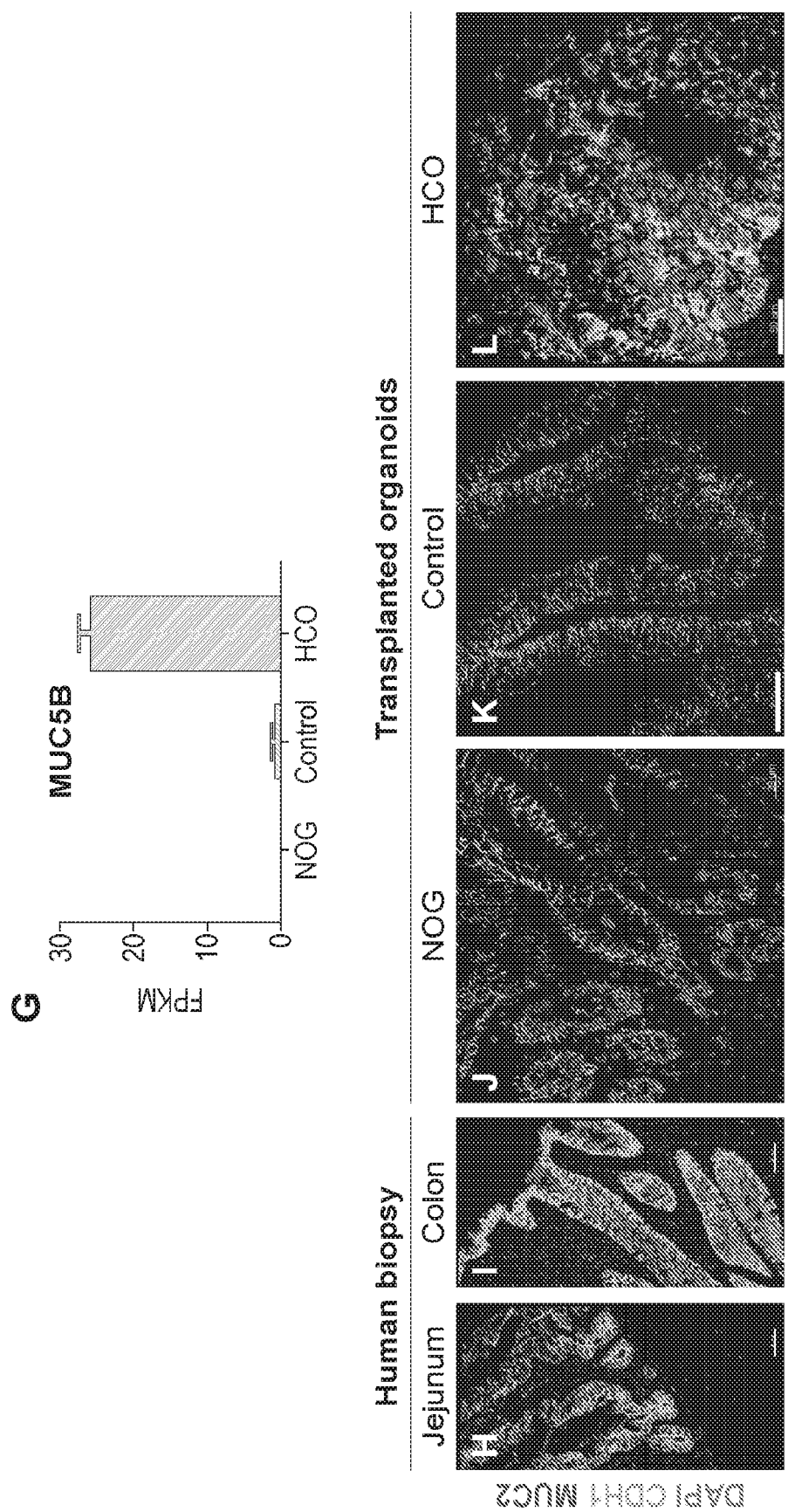

Previous studies of mouse and human fetal intestine have demonstrated that regional identity and tissue morphology of different regions of the intestine were maintained following orthotopic transplantation and growth in immunocompromised mice (Duluc et al., 1994; Savidge et al., 1995). To determine if HIOs and HCOs that were patterned in vitro would maintain regional identity and grow into small and large intestinal tissue, Applicant transplanted them under the mouse kidney capsule for 6-10 weeks, which Applicant previously demonstrated results in HIO maturation into small intestinal tissue (Watson et al., 2014). Applicant observed that the engraftment of NOGGIN and control HIOs was more efficient than HCOs (FIG. 12A). Consistent with their regional identity, transplanted HIOs and HCOs developed into mature tissues that morphologically resembled either small or large intestine, respectively (FIG. 5A-E). The epithelium of NOGGIN and control organoids formed well-defined crypts and tall villi, comparable to human small intestine. In contrast BMP2-treated organoids contained crypts but lacked villi, similar to colon.

In addition to their morphological resemblance to either small or large intestine, transplanted HIOs and HCOs expressed distinct regional markers and contained regionally enriched cell types. For example, the majority of the epithelium of NOGGIN and control HIOs expressed the proximal marker GATA4 and did not express the large intestinal marker SATB2 (FIG. 5F-I, K-N, FIG. 12B-E). Conversely HCO epithelia were uniformly SATB2+ but did not express GATA4 (FIG. 5J,O, FIG. 12B-E). In addition, Paneth cells expressing DEFA5 were present in the crypts of NOGGIN and control HIOs, but were absent HCOs (FIG. 5P-T, FIG. 12F) similar to the human colon (Wehkamp et al., 2006). Applicant further confirmed the colonic identity of HCOs using the colonic goblet cell marker MUC5B (van Klinken et al., 1998), which is expressed by a subset of goblet cells of HCOs but is not detectible in NOGGIN or control HIOs (FIG. 5U-Y, FIG. 12G). Additionally, the number of MUC2+ goblet cells was vastly higher in HCOs compared HIOs consistent with the abundance of goblet cells seen in the human colon (FIG. 12H-L). The patterning markers, the presence of MUC5B-expressing goblet cells, and the absence of Paneth cells all support the conclusion that transplanted HCOs have colonic epithelium.

In Vivo Matured HIOs and HCOs Express Regional Enteroendocrine Hormones.

There are at least 12 major EEC subtypes that are found in different regions of the gastrointestinal tract and Applicant analyzed HIOs and HCOs for the presence of regional EECs. Ghrelin and Motilin are found predominantly in the proximal intestine, and correspondingly these hormones were largely expressed in NOGGIN and control HIOs but not HCOs (FIG. 6A-D). Similarly, GIP, which is found in K-cells of the small intestine but is absent in the colon, were found in NOGGIN and control HIOs but not in HCOs (FIG. 6E-H). Applicant then examined presence of distally enriched EECs in HCOs by analyzing for expression of GLP-1 and PYY, which are more abundant in the colon. Applicant observed higher numbers of GLP-1 and PYY cells and higher expression of preproglucagon and PYY in HCOs than in HIOs (FIG. 6I-P). In addition, Applicant found expression of the colon specific hormone INSL5 (Burnicka-Turek et al., 2012; Thanasupawat et al., 2013), only in HCOs (FIG. 6Q-T).

Analysis of Stem and Progenitor Cells in HIOs and HCOs In Vitro and In Vivo.

To determine if in vitro-derived HIOs and HCOs express markers of stem and progenitor cells, Applicant used the H9-BAC-LGR5-eGFP transgenic line that has been described previously (McCracken et al., 2014; Watson et al., 2014). Examination of LGR5-eGFP expression in organoids revealed expression in broad epithelial domains similar to the expression patterns in Lgr5-eGFP mice as early as e13.5 (Shyer et al., 2015) (FIG. 13 A, B, F, G, K, L). GFP expression was also evident outside the epithelium of organoids as determined by histology and FACS analysis which revealed a population of GFP+ EPCAM-cells (data not shown). In addition, Applicant examined the expression of SOX9, which is a marker of progenitor cells in the fetal and adult intestine and found it expressed in the epithelium of both HIOs and HCOs (FIG. 13C-E, H-J, M-0). These data suggest that embryonic/fetal intestinal progenitor cells, marked by LGR5-eGFP and SOX9, are present in HIOs and HCOs in vitro.

Figure 13A:
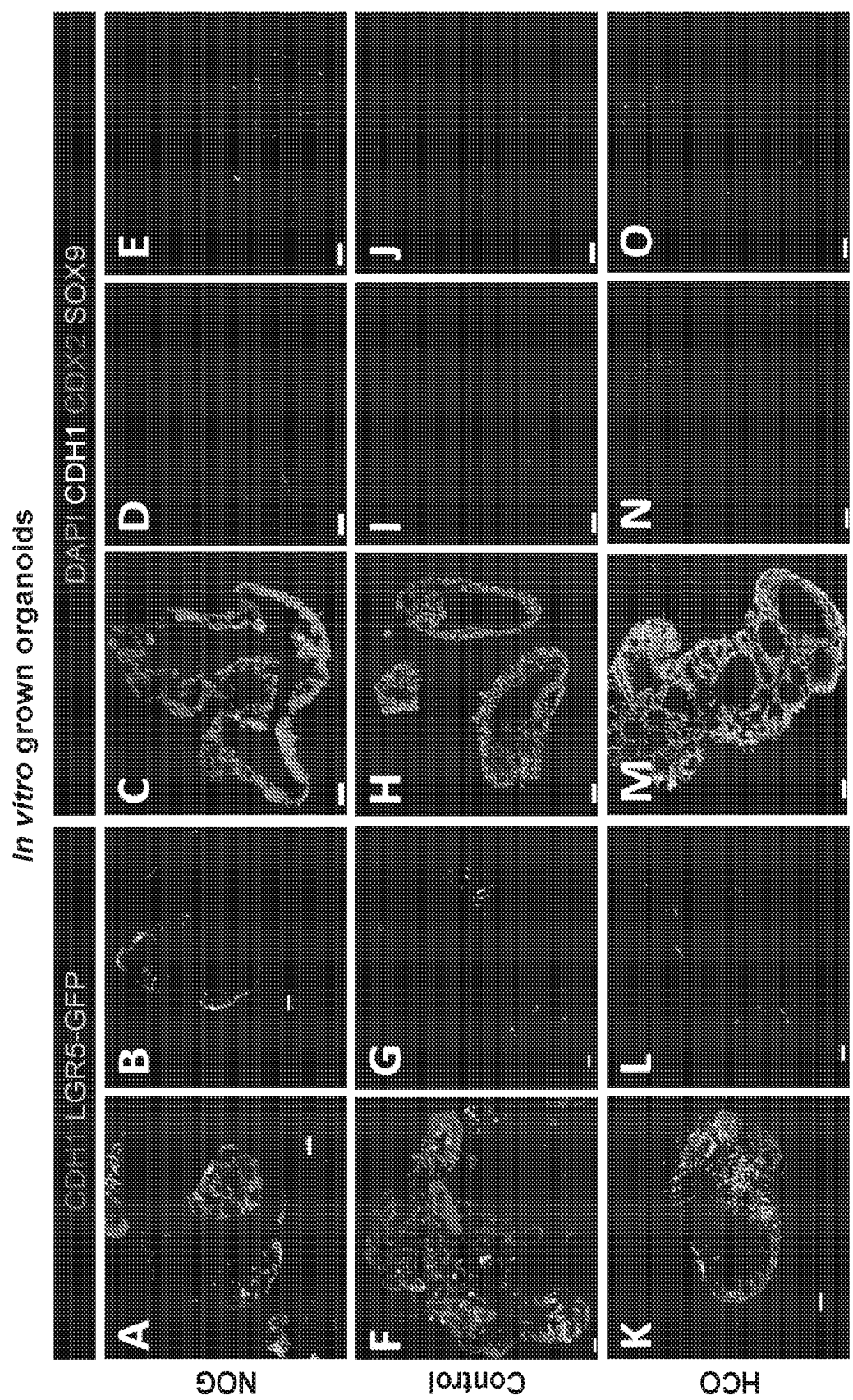
FIG. 13. In vitro and in vivo grown organoids contain intestinal progenitors. Representative whole-mount (A,F,K) and slice section (B,G,L) images of CDH1 and GFP from H9-LGR5-GFP derived organoids treated with NOGGIN, control, or BMP. CDX2 (red) and SOX9 (green) staining on sections from (C-E) NOGGIN, (H-J) control, or (M-O) BMP2 treated organoids. Representative images of CDX2 and LGR5-GFP (P, S,V), CDX2 and SOX9 (Q,T, W), and CDH1 and KI67 (R,U,X) stained in vivo organoids derived from H9-LGR5-GFP organoids treated with NOGGIN, control, or BMP. (Y-A') Stereomicrographs showing enteroids derived from NOGGIN, control or BMP transplants respectively. (B'-D') QPCR analysis of proximal and distal genes in control enteroids (>100 pooled enteroids from 2 transplants) and BMP2 treated colonoids (>50 colonoids from 1 transplant). Scale bars=50 µm.
Figure 13B:
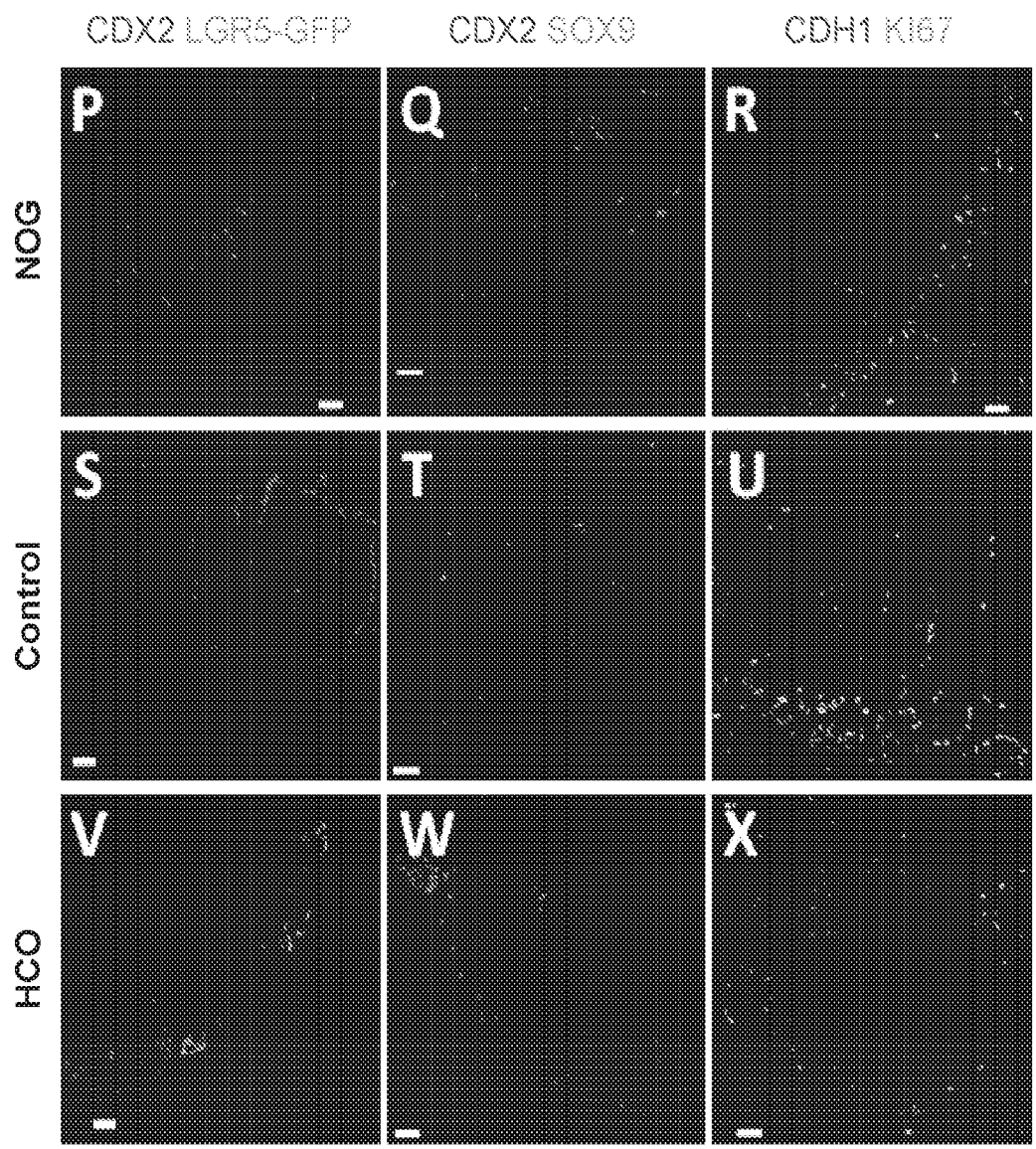
Figure 15A:
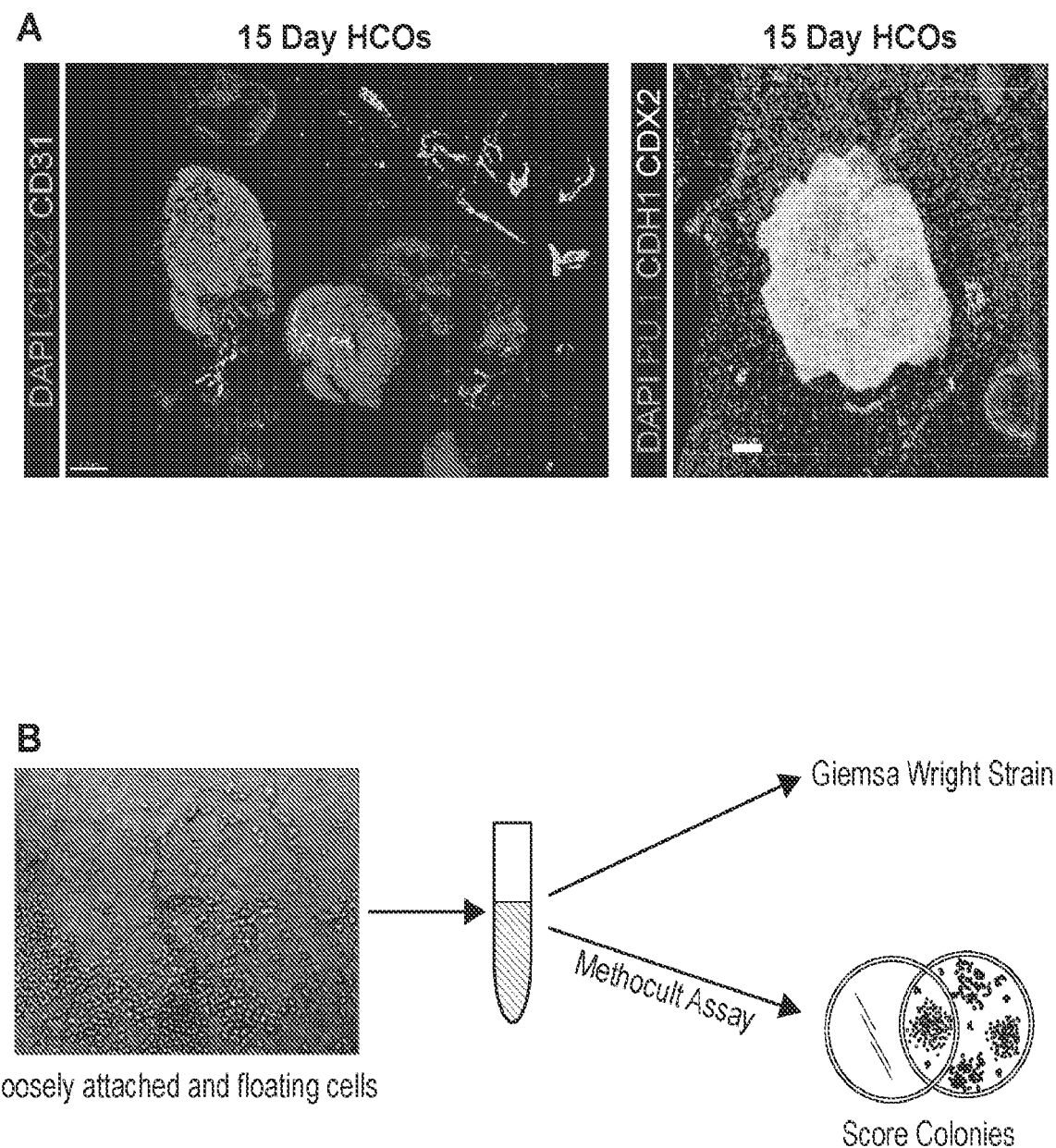
FIG. 15. (A) Wholemount immunofluorescence staining of HCOs after 15 days of growth in Matrigel. HCO cultures were stained for the endothelial marker CD31 (green) and the hindgut epithelium marker CDX2 (red). Cultures were also stained for the hematopoietic cell marker PU.1 (red right panel). (B) Schematic of hematopoietic progenitor assays. Cells were collected from HCOs, centrifuged and either stained using Giemsa Wright Stain or plated in Methocult media to assay for hematopoietic cell differentiation. (C) Representative images of Giemsa Wright stained cells with morphologies consistent with differentiation into Macrophages, Neutrophils, Basophils and Eosinophils. (D) Representative images of colonies formed after 14 days in Methocult. Erythrocyte, macrophage and granulocyte colonies were present in cells derived from HCOs but not those derived from NOGGIN treated HIOs.
Figure 15B:
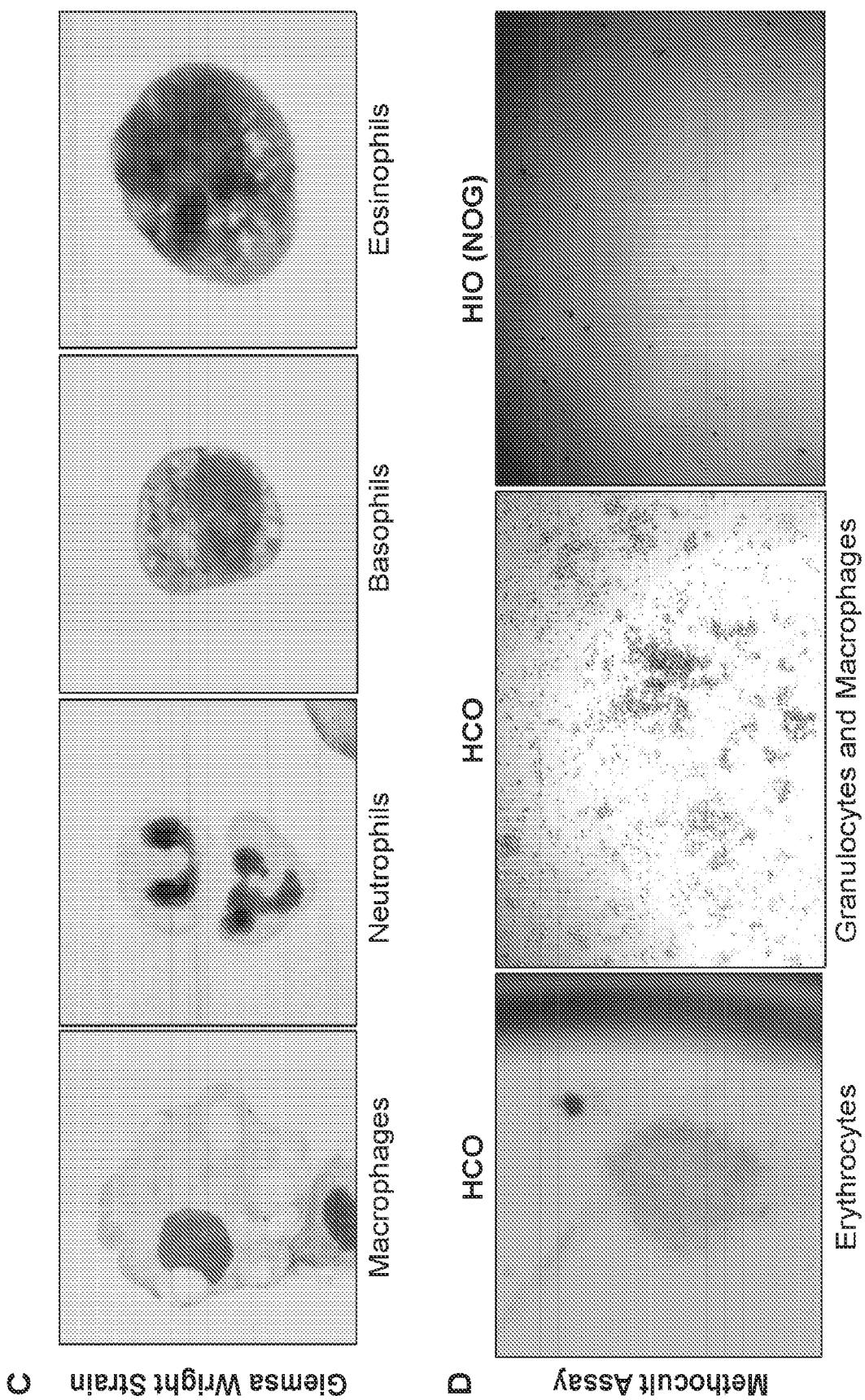
Figure 16B:
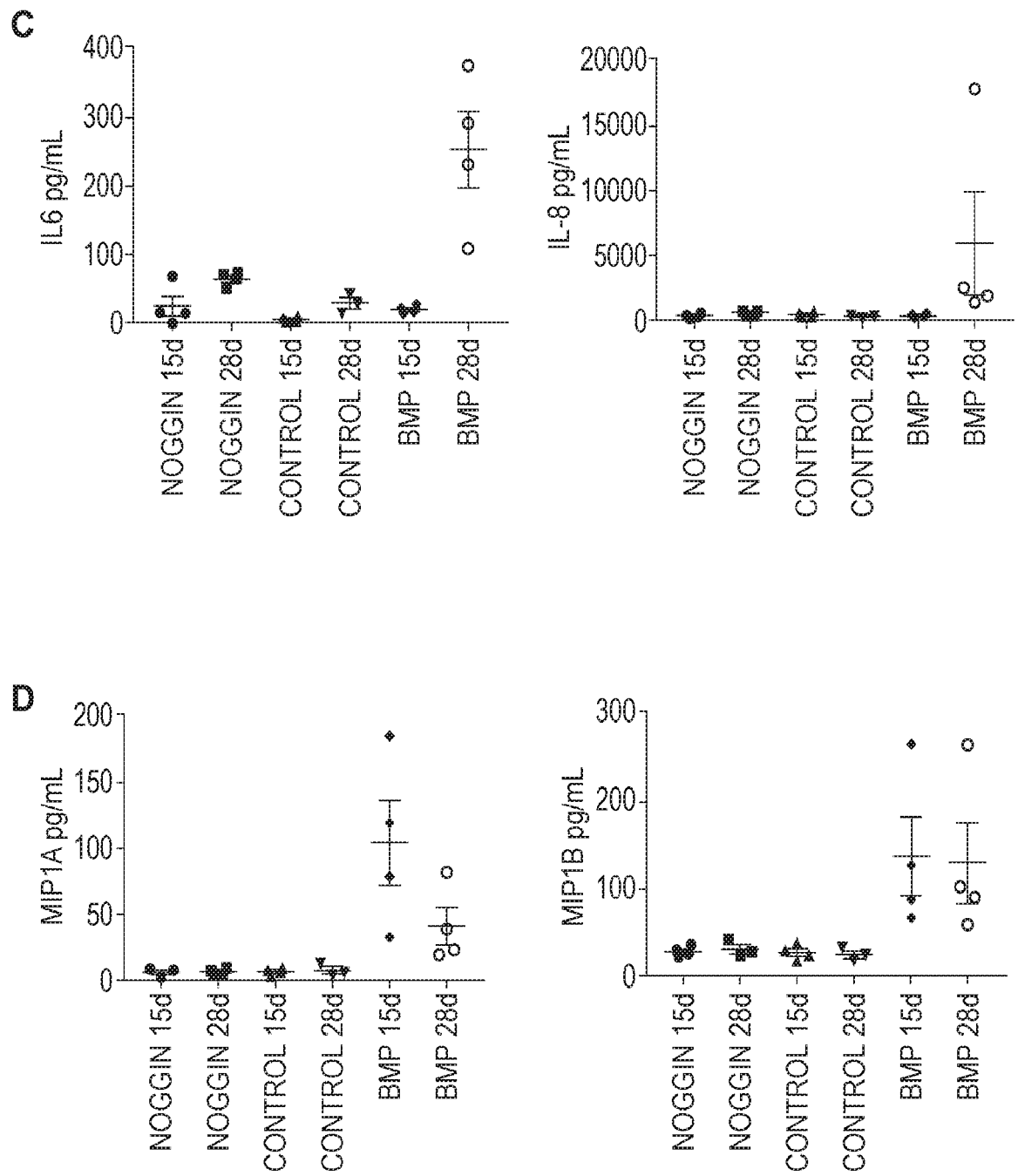
FIG. 16. (A) Immunofluorescence staining of a human colon biopsy or an HCO grown for 28 days in Matrigel. Staining was done for CD68 a marker of macrophages. (B) Plots of CYTOF analysis of CD14 and CD16 in HIOs and HCOs. A small percentage of CD14+/CD16+ cells are present in HCOs (blue square) but not HIOs. Additionally, CD16 single positive cells were present in HCOs suggesting monocytes are present within the culture. (C) Luminex array analysis of supernatant collected from 14 and 28-day old HIOs and HCOs. IL6 and IL8 were detected in 28-day old HCOs (BMP) but not HIOs. (D) Luminex array analysis of supernatant collected from 14 and 28-day old HIOs and HCOs. The macrophage specific cytokines MIP1A and MIP1B were detected in 14 and 28-day old HCOs (BMP) but not in 14 or 28-day old HIOs.

At later stages of intestinal development, progenitor cells become restricted to the base of developing villi, where they will eventually contribute to the intestinal stem cells (ISCs) of the crypts of Lieberkuhn. To determine if the progenitor cells that Applicant observed in vitro will undergo this this developmental transition, Applicant transplanted HIOs and HCOs and monitored LGR5-eGFP, SOX9, and KI67 protein. Following maturation of organoids in vivo, Applicant observed LGR5-eGFP, SOX9, and KI67 restricted to the base presumptive crypts (FIG. 13P-X). In addition, SOX9 was also observed in EECs in the villi of HIOs and in the cuff of the colonic epithelium transplanted HCOs consistent with SOX9 expression in these cell types. Given that Sox9 and Lgr5 mark intestinal and colonic stem cells capable of forming enteroids and colonoids in mice (Gracz et al., 2010; Ramalingam et al., 2012) Applicant investigated if the epithelium of transplanted organoids could be isolated and used to generate enteroids and colonoids. Both HIOs and HCOs gave rise to cultures of epithelial organoids that grew and could be passaged (FIG. 13Y-A'). Moreover, HCO-derived epithelial cultures expressed the colonic markers CKB, FXYD3, SATB2, and HOXB13 but did not express the proximal small intestine markers PDX1 or GATA4 suggesting that regional identity was maintained (FIG. 13B'-D'). These data suggest that HIOs and HCOs grown in vivo contain progenitor and stem cells.

Global Transcriptional Analysis of HIOs and HCOs.

In order to broadly interrogate the regional identity and maturation of HIOs and HCOs, Applicant performed RNA-seq analysis of HIOs and HCOs grown in vivo and compared them with published data sets of human fetal and adult small and large intestines. Principal component analysis revealed that primary tissues isolated from adult and fetal intestine clustered together along principle component 1 (PC1) axis, which accounted for 36.5% of the cumulative variation among samples (FIG. 14A). A GO analysis revealed that this variation was due to cell types that were present only in primary tissues and not PSC-derived transplants. For example, 6 of the top 10 biological processes present in human primary tissues and absent in transplants were related to immune cells (FIG. 14B-C). The second principle component (PC2) accounts for 17.7% of cumulative variation and separates the samples according to maturity (FIG. 7A). This component revealed that transplanted organoids are more mature than human fetal intestine and fetal colon but not as mature as adult colon and intestine. The third principle component (PC3) accounts for 6.7% of cumulative variation and separates the samples according to regional identity, and shows that HCOs are more similar to colon whereas HIOs cluster with small intestine (FIG. 7A). Interestingly, human fetal samples did not cluster based on regional identity (small intestine vs colon) suggesting that these samples may not have been cleanly isolated from the indicated region of the GI tract.

Figure 7B:
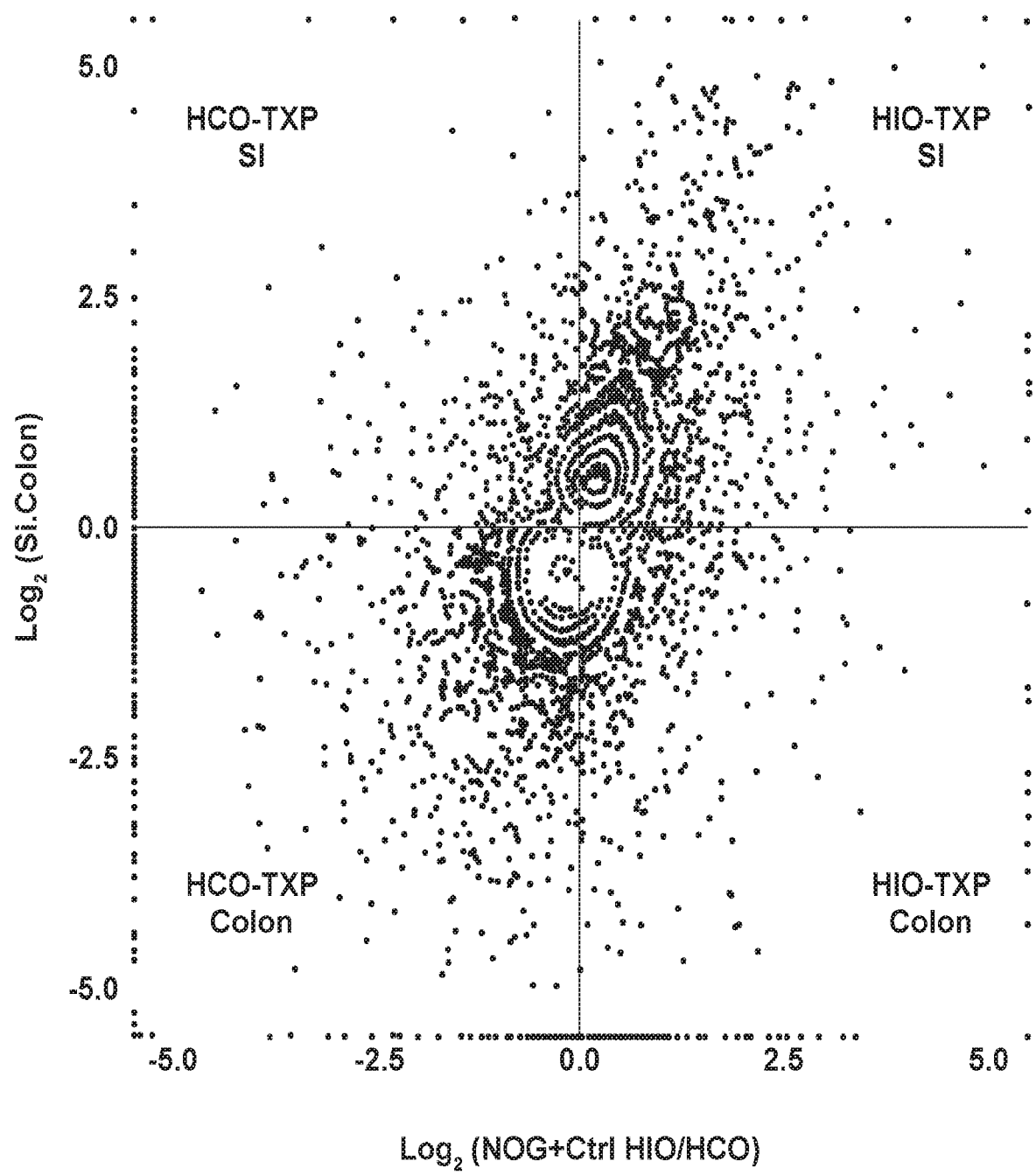
FIG. 7. Global transcriptional analysis of HIOs and HCOs and comparison with human small intestine and colon. (A) Principal component analysis human adult and fetal small intestine and colon compared with transplanted HIOs and HCOs. (B) Hypergeometric means test comparing human adult small intestine with HIOs and human adult colon with HCOs. (C) 4-way scatter plot comparing transcripts that were differentially expressed in human small intestine and colon compared to HIOs and HCOs.

Applicant next used hypergeometric means test to determine the probability that HIOs and HCOs share similar patterns of region-specific gene expression small intestine and colon (FIG. 7B). A total of 341 transcripts are expressed in the small intestine and in NOGGIN treated HIOs as compared to colon or BMP2 treated HCOs, a proportion that is exceedingly unlikely by chance alone ($P=1.5\times10-143$). Similarly, the gene set that is up-regulated in the control HIOs shares a highly significant degree of similarity with the gene set up-regulated in adult small intestine relative to the adult colon ($P=2.5\times10-203$). Conversely, the gene set up-regulated in HCOs are highly enriched for genes that are up-regulated in the colon relative to the small intestine ($P=4.1\times10-53$ and $P=6.0\times1073$, respectively). This analysis concluded that HIO patterning is most similar to human small intestine and HCO patterning is colonic. To further explore the nature of HIOs (NOG and control treated) and HCOs, Applicant conducted differential expression analysis (adult small intestine vs. adult colon; HIOs vs. HCOs). Applicant generated 4-way scatter plot, which also demonstrated that a high proportion of genes up-regulated in the colon were also up-regulated in HCOs and the majority of genes up-regulated in the small intestine were also up-regulated in HIOs (FIG. 7C, Table 1). Lastly, analysis of biological processes that were enriched revealed that adult colon and transplanted HCOs have highly active Wnt signaling and a similar HOX code (FIG. 7D). Taken together, these data suggest Applicant has developed a robust method to differentiate PSCs into human colonic tissue.

TABLE 1

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | | | |
|---|---|---|---|
| ABCA4 | AADAC | AAGAB | AAK1 |
| ABCC2 | ABCA4 | ABCA12 | ABHD10 |
| ABCC6 | ABCB8 | ACTR2 | ABHD17C |
| ABCD1 | ABCC10 | ADAM10 | ABL2 |
| ABCG8 | ABCC6 | ADAM22 | ACTR2 |
| ABHD14A, ABHD14A-ACY1, ACY1 | ABCD1 | AGPS | ACVR2B |
| ABHD6 | ABCG5 | AGTPBP1 | ACYP1 |
| ACBD4 | ABCG8 | AKAP13, MIR7706 | ADAM10 |
| ACO2 | ABHD14A, ABHD14A-ACY1, ACY1 | ALDH1B1 | ADAM17 |
| ACOT11 | ABHD16A | ALG5 | ADAM22 |
| ACP2 | ABHD4 | ANKDD1B | ADGRF4 |
| ACSL5 | ABHD6 | ANKRD30BP2 | AEBP2 |
| ACY3 | ACACB | ANTXR2 | AGPS |
| ADAMTSL5 | ACADS | ANXA3 | AHI1 |
| AGPAT3 | ACADVL | ARFGEF3 | AIDA |
| AKR1B10 | ACKR4 | ARHGAP44 | AIFM3 |
| AKR1C1 | ACO2 | ARPC5 | AKAP11 |
| AKR1C3 | ACOT11 | ASCC1 | AKAP13, MIR7706 |
| ALDOB | ACOT7 | ASIP | AKAP5 |
| ALPI | ACOX2 | ATF6 | ALG8 |
| ANGPTL4 | ACP2 | ATOH1 | ANKDD1B |
| ANXA13 | ACSL5 | ATXN3 | ANKFY1 |
| APOA1 | ACTN4 | B3GALNT2 | ANKS1B |
| APOA1-AS | ACY3 | B3GNT6 | ANP32B |
| APOA4 | ADAMTSL5 | B4GALNT3 | ANTXR2 |
| APOBEC1 | ADGRG4 | BCAS1 | AP2B1 |
| APOBEC2 | ADGRG5 | BCL10 | AP3M1 |
| APOC2, APOC4, APOC4-APOC2 | AGMO | BCLAF1 | APH1B |
| APOC3 | AGPAT1, MIR6721 | BEND3 | APOBR |
| APOL2 | AGPAT2 | BEST2 | ARFGEF3 |
| AQP3 | AGPAT3 | BTBD3 | ARHP1 |
| AQP7 | AK2 | BZW1 | ARL14EP |
| AQP7P1 | AKR1A1 | C11orf58 | ARMC8 |
| ATG4D | AKR1B10 | C12orf75 | ARPC5 |
| AVIL | AKR1C1 | CA12 | ARRDC3 |
| BAK1 | AKR1C3 | CAMSAP1 | ASB7 |
| BCRP3 | AKR1C4 | CAPN2 | ASPH |
| BRE-AS1, RBKS | AKR7A3 | CAPRIN1 | ATG4C |
| BTD | ALDH1A3 | CASC18 | ATL3 |
| BTNL3 | ALDH2 | CBFB | ATM |
| BTNL8 | ALDOB | CCPG1, DYX1C1, DYX1C1-CCPG1 | ATP13A3 |
| C10orf25 | ALPI | CD24 | ATP2A3 |
| C10orf67 | AMBRA1 | CD9 | ATR |
| C11orf24 | ANAPC2 | CDC23 | ATRX |
| C11orf86 | ANGPTL4 | CEACAM6 | ATXN1 |
| C19orf66 | ANPEP | CEP290 | ATXN3 |
| C1orf115 | ANXA13 | CFC1, CFC1B | B3GALNT2 |
| C1orf116 | ANXA4 | CLIC4 | B3GNT6 |
| C5orf56 | AP5B1 | CLMN | BAG5 |
| C6orf132 | APOA1 | CLNS1A | BAZ1B |
| C6orf136 | APOA1-AS | CLSTN1 | BBIP1 |
| C8G | APOA4 | CNTN3 | BCAS1 |
| C9orf173 | APOBEC1 | CSRNP3 | BCAT1 |
| CA13 | APOBEC2 | DAAM1 | BCLAF1 |
| CALM3 | APOC2, APOC4, APOC4-APOC2 | DDX50 | BEND3 |
| CAMKK2 | APOC3 | DGKH | BEST2 |
| CAPN10-AS1 | APOL2 | DICER1 | BIN1 |
| CAPN3 | APOM | DIP2B | BMPR2 |
| CASP1 | AQP3 | DMTN | BNC2 |
| CATSPER2 | AQP7 | EARS2 | BTBD10 |
| CBR1 | ARHGEF16 | EBPL | BTBD3 |
| CCL11 | ASAH2 | EEA1 | BTBD7 |
| CCL25 | ASB13 | EHF | BTF3L4 |
| CD82 | ASIC2 | EPHA10 | BTRC |
| CDCA3 | ASPA | EPHB4 | BZW1 |
| CDH4 | ATG4D | EXOC5 | C10orf99 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | | | |
|---|---|---|---|
| CDIP1 | ATP11A | EXOC6 | C11orf58 |
| CDR2L | ATP5SL | FAM105A | C18orf54 |
| CERK | ATXN2L | FAM169A | C3orf52 |
| CES2 | AZGP1 | FAM175A | C7orf60 |
| CGREF1 | B3GNT8 | FAM218A | CA12 |
| CHRM4 | BAG6 | FAM60A | CA4 |
| CIB2 | BAIAP2L2 | FAS | CAMKID, LOC283070 |
| CIDEB | BAIAP3 | FECH | CAMSAP2 |
| CIDEC | BAK1 | FERMT1 | CAPN8 |
| CLDN15 | BET1L | FFAR4 | CAPZA1 |
| CMTR1 | BLNK | FGF7 | CASC4 |
| CNNM3 | BRE-AS1, RBKS | FKTN | CASD1 |
| CPS1 | BTD | FMN2 | CBFB |
| CRAT | BTNL3 | FRMPD3 | CBX5, MIR3198-2 |
| CREB3L3 | BTNL8 | G3BP1 | CCDC132 |
| CRIP3 | BUD13 | GARS | CCDC88A |
| CTD-3080P12.3 | C10orf54 | GCSH | CCND1 |
| CYP27A1 | C11orf24 | GGH | CCNJL |
| CYP2B7P | C11orf86 | GJB4 | CCNT1 |
| CYP2C9 | C15orf62 | GLIS3 | CD24 |
| CYP2S1 | C16orf58 | GLUL | CD59 |
| CYP3A5 | C17orf78 | GMNN | CD9 |
| CYTH2 | C18orf8 | GNE | CDC42 |
| DBP | C19orf12 | GNPTAB | CDHR1 |
| DCAF11 | C19orf54 | GOT2 | CDK19 |
| DECR1 | C1orf116 | GP9 | CEACAM5 |
| DGAT1, MIR6848 | C2CD2L | GRSF1 | CEACAM6 |
| DGAT2 | C5orf56 | GSPT1 | CEBPZ |
| DGKA | C6orf132 | GYG2 | CELF2 |
| DHDH | C6orf136 | HDAC1 | CENPO |
| DHRS1 | C8G | HIATL1 | CEP250 |
| DHRS11 | CALCOCO1 | HK2 | CHD9 |
| DHX16 | CALM3 | HMGA2 | CHIC1 |
| DMBT1 | CAMK2G | HN1L | CLIC4 |
| DNAJC22 | CAMTA2 | HNMT | CLMN |
| DNASE1 | CAPN1 | HNRNPAB | CLNS1A |
| DNPEP | CAPNS1 | HOXA10-AS | CLTC |
| DOLPP1 | CARD10 | HOXA10, HOXA10-HOXA9, HOXA9 | CMTM6 |
| DOT1L | CARD6 | HOXA11 | CNEP1R1 |
| DTX1 | CASP1 | HOXB9 | CNTN3 |
| ELMOD3 | CASP4 | HOXB-AS3 | CPM |
| EMB | CASP9 | IARS | CRK |
| ENKUR | CBLC | IFT74-AS1 | CRYM |
| EPHX2 | CBR1 | IL1R2 | CSNK1A1 |
| ERICH4 | CC2D1A | ILDR1 | CSRNP3 |
| ESPN | CCL25 | IPO5P1 | CTDSPL |
| ETV7 | CD302, LY75, LY75-CD302 | IQGAP1 | CTTNBP2NL |
| EXOC3L4 | CD68 | ITM2C | CYLD |
| F10 | CD74 | JAG1 | CYP20A1 |
| FAM102A | CD82 | JPH1 | DAAM1 |
| FAM109A | CDC42BPB | KCNJ2 | DCBLD2 |
| FBP1 | CDC42EP4 | KCNN4 | DCP2 |
| FBXO7 | CDCA3 | KCNRG, TRIM13 | DDX50 |
| FCHSD1 | CDHR5 | KCTD1 | DDX6 |
| FLJ12825 | CDIP1 | KCTD20 | DGKH |
| FLJ22763 | CDK18 | KLK15 | DHRS13 |
| FUOM | CDK2 | KNOP1 | DHRS9 |
| FXR2 | CDK20 | KPNA4 | DHX57 |
| GABRE | CDR2L | LEFTY1 | DICER1 |
| GALK1 | CEACAM18 | LIMK2 | DIO3OS |
| GALT | CELA3A | LINC00341 | DISC1, TSNAX, TSNAX-DISC1 |
| GATA4 | CENPV | LINC00858 | DNAJC3 |
| GATA5 | CERS2 | LIPH | DNAL1 |
| GATS | CES2 | LOC100507346 | DPY19L1 |
| GCHFR | CFI | LOC101928233 | DSEL |
| GIGYF1 | CFL1 | LOC101929395 | DSTYK |
| GNA11 | CGREF1 | LOC101929524 | DTD2 |
| GOLT1A | CHP2 | LRRK1 | EBPL |
| GOSR2 | CHRM4 | MAML2 | EED, MIR6755 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | | | |
|---|---|---|---|
| GPD1 | CIAO1 | MAPRE2 | EFNA5 |
| GPRIN1 | CIB2 | MARCH3 | EHF |
| GRAMD1B | CIDEB | MARCKSL1 | EI24 |
| GRIA1 | CIDEC | MBNL3 | EID1 |
| GSDMB | CISD1 | MCOLN2 | EIF4E |
| GSK3A | CLDN15 | MECOM | EIF5B |
| GSTK1 | CLDN18 | METTL5 | EMC1 |
| HADHA | CLPTM1 | MFAP3L | ENAH |
| HAGH | CMBL | MFHAS1 | ENDOD1 |
| HAPLN4 | CNNM3 | MINA | ENTPD1 |
| HEBP1 | CNPY2, PAN2 | MLLT3 | EPAS1 |
| HOPX | COASY | MPHOSPH6 | ERCC6L2 |
| HOXA4 | COMMD9 | MPLKIP | ERMP1 |
| HPS1 | COMT, MIR4761 | MPZL2 | ERN2 |
| IDH3A | CPA2 | MREG | EXOC2 |
| IFIT3 | CPPED1 | MRPL1 | EXOC4 |
| IGSF23 | CRADD | MRPL3 | EXOC5 |
| IL2RB | CRAT | MTL5 | EXOC6 |
| INTS12 | CREB3L3 | MYO3A | FAM102B |
| IRF1 | CRELD1 | MYO5C | FAM103A1 |
| IRF8 | CS | NAA15 | FAM105A |
| ISG20 | CSK | NAP1L1 | FAM120A |
| ITPK1 | CTSO | NCBP1 | FAM13B |
| KDM2A | CXCR3 | NDC1 | FAM169A |
| KDM6B | CYB5A | NEDD4L | FAM178A |
| KDM8 | CYP27A1 | NEURL1B | FAM208A |
| KHK | CYP2C19 | NLE1 | FAM46A |
| KIAA2013 | CYP2S1 | NOLC1 | FAM83H-AS1 |
| KIFC3 | CYP3A4 | NOTCH1 | FAM8A1 |
| KLC4 | CYSLTR2 | NOTCH2 | FAM98B |
| LBX2-AS1 | DBP | NRARP | FANCI |
| LINC00574 | DCAF11 | NRXN1 | FAR2P2 |
| LINC01268 | DECR1 | NSF, NSFP1 | FBXO28 |
| LOC100240735 | DEDD | NT5DC3 | FBXO45 |
| LOC284825 | DEGS2 | NUDT4 | FCF1 |
| LOC646471 | DERA | NXPE1 | FEM1B |
| LOC728989 | DESI1 | NXPE2 | FEM1C |
| LPCAT3 | DFNA5 | NXPE4 | FFAR4 |
| LPIN3 | DGAT1, MIR6848 | ODC1 | FKBP5, LOC285847 |
| LRRC75A | DGAT2 | ORC5 | FKTN |
| LRRC75B | DGKA | P4HA1 | FLOT2 |
| MALL | DGKG | PAPPA2 | FNDC3B |
| MAPKBP1 | DGKQ | PARM1 | FOCAD |
| METTL7B | DGKZ | PAWR | FOXD2 |
| MFSD2A | DHDH | PCDHB11 | FOXO3 |
| MGAM | DHRS11 | PDE3B | FOXO3B, ZNF286B |
| MICALL2 | DHRS7 | PDZK1IP1 | FRMPD3 |
| MICU1 | DHX16 | PGBD5 | FRYL |
| MIR1268A, SLC27A4 | DMBT1 | PHF20 | FSIP2 |
| MIR22, MIR22HG | DNAJC22 | PHF6 | FZD4 |
| MIR31HG | DNASE1 | PKIB | G3BP1 |
| MIR3615, SLC9A3R1 | DNPEP | PLCD3 | GGH |
| MIR5187, TOMM40L | DOLPP1 | PLSCR4 | GIN1 |
| MIR5193, UBA7 | DPP9 | POF1B | GJC1 |
| MIR6073, SOX6 | DSCR3 | POLR3B | GLB1L2 |
| MIR621, SLC25A15 | DTX1 | POSTN | GLG1 |
| MIR7703, PSME2 | E2F4 | PP14571 | GLIS3 |
| MISP | EGFR-AS1 | PPIC | GLTSCR1L |
| MME | EIF6 | PPP1R8 | GLUL |
| MMEL1 | ENPP6 | PPP2R3A | GMNN |
| MOCS1 | EPB41L3 | PPP3CA | GNAI1 |
| MOGAT3 | EPHA1 | PREP | GNAQ |
| MON1A | EPHB1 | PRKACB | GNE |
| MS4A8 | EPHX2 | PRKAR2A | GOLGA3 |
| MSRA | EPS8L2 | PRKRIR | GOPC |
| MST1 | EPSTI1 | PRMT5 | GP9 |
| MTTP | ERAL1 | PSMD6 | GPC6 |
| MUS81 | ERF | PSME4 | GPX8 |
| MYO15B | ESPN | PTAR1 | GRM7 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | | | |
|---|---|---|---|
| MYO1A | ESRRA | PTTG1IP | GRSF1 |
| NAGS | ETV3 | PUM1 | GTF2F2 |
| NELL2 | ETV7 | PYGL | GTF3C1 |
| NGEF | EWSR1 | QPCT | HABP4 |
| NOP9 | EXOC3L4 | R3HDM1 | HEATR3 |
| NPC1L1 | F10 | RAB3B | HIATL1 |
| NR0B2 | FABP2 | RABEP1 | HMG20A |
| NR1I3 | FAH | RAP1GDS1 | HMGA2 |
| NSUN6 | FAM101A, ZNF664, ZNF664-FAM101A | RAPGEF2 | HN1L |
| NUB1 | FAM102A | RBMS3 | HOXA10-AS |
| OGDH | FAM109A | RCC2 | HOXA10, HOXA10-HOXA9, HOXA9 |
| OTC | FAM32A | REXO2 | HOXB5 |
| P4HB | FAM83G | RIF1 | HOXB6 |
| PARP12 | FBLIM1 | RIMS3 | HOXB7 |
| PARP3 | FBP1 | RNASEH2B | HOXB8 |
| PATL2 | FLJ22763 | RPA2 | HOXB9 |
| PCK2 | FUOM | RSF1 | HOXB-AS3 |
| PCSK5 | FZR1 | RSL24D1 | IFFO2 |
| PDLIM2 | GABRA4 | RXFP4 | IFNAR1 |
| PDZD7 | GAL3ST1 | SATB2 | IFT74-AS1 |
| PDZK1 | GALK1 | SATB2-AS1 | IGF1R |
| PEBP1 | GALNT6 | SCLT1 | IGIP |
| PEPD | GALT | SERBP1 | IL17RD |
| PEX14 | GATA4 | SETBP1 | IL1R2 |
| PGRMC2 | GATA5 | SH3PXD2A-AS1 | IL20RB |
| PHEX | GCNT4 | SIPA1L2 | IL6ST |
| PKLR | GFI1B | SLC16A9 | ILDR1 |
| PLA2G6 | GGT1 | SLC1A3 | IMPAD1 |
| PLCB3 | GLOD5 | SLC39A8 | INPP5F |
| PLEKHS1 | GLRX | SLC7A2 | IPO11, IPO11-LRRC70, LRRC70 |
| PLIN2 | GLYCTK | SLC9A2 | IPO5 |
| PLIN3 | GNA11 | SLCO4A1-AS1 | IPO5P1 |
| PLLP | GNB1 | SMAD5 | IPO7 |
| PNP | GOLT1A | SMARCA5 | IQGAP1 |
| PP7080 | GOSR2 | SMC6 | ITGAV |
| PQLC2 | GPD1 | SNRPE | ITGB1 |
| PRAP1 | GPR108 | SNX13 | ITM2A |
| PRDM7 | GPR35 | SOCS5 | ITPRIPL2 |
| PRODH | GRAMD1B | SORBS2 | JAG1 |
| PSMB9 | GRIA1 | SPAG1 | JPH1 |
| PSMD9 | GRK5 | SRSF12 | KBTBD6 |
| PSME1 | GRTP1-AS1 | SRSF9 | KCNJ2 |
| PTPRH | GSDMB | ST6GAL2 | KCNN4 |
| PXDC1 | GSK3A | STAB2 | KCNRG, TRIM13 |
| RAB11FIP3 | GSTA1 | STMND1 | KCTD10 |
| RAB17 | GSTA2 | STS | KCTD20 |
| RAB5C | GSTK1 | STX19 | KDM5B |
| RAB8A | GSTM4 | SUSD1 | KIAA0226L |
| RARRES3 | GTF2I | SUV39H2 | KIAA0232 |
| RBP2 | GTPBP1 | TBL2 | KIAA0513 |
| REEP6 | GUCD1 | TCTA | KIAA1143 |
| REG1A | HADHB | TDGF1 | KIAA1429 |
| RPS6KA1 | HAGH | TFRC | KIAA1715 |
| RTKN | HAPLN4 | TMA16 | KLHL15 |
| RTP4 | HDAC6 | TMCC1-AS1 | KLK15 |
| SAT1 | HDGF | TMED10 | KPNA4 |
| SAT2 | HDHD3 | TMED2 | KRR1 |
| SCAMP5 | HEBP1 | TMEM123 | LAPTM4A |
| SCNN1D | HECTD3 | TMEM159 | LARS |
| SCRN2 | HIP1R | TMEM200B | LEFTY1 |
| SDHA | HLA-F | TMEM38A | LIFR |
| SEC14L2 | HMGA1 | TRABD2A | LIMD1 |
| SERP2 | HNF1A | TSN | LIMK2 |
| SFRP5 | HNF4A-AS1 | TSPAN5 | LINC00341 |
| SFXN3 | HOPX | TTC3 | LINC00482 |
| SH3BP1 | HPS1 | TTC8 | LINC00515 |
| SH3GL1 | HRASLS2 | TTPA | LINC00657 |
| SHBG | HRH2 | UBE2A | LINC01006 |
| SIDT2 | HSD3B7 | UBE2N | LMAN2L |
| SLC12A7 | HYKK | UGP2 | LOC100129550 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | | | |
|---|---|---|---|
| SLC15A1 | IDNK | UNC13B | LOC100507351 |
| SLC1A7 | IFIT3 | URB1 | LOC101929374 |
| SLC22A4 | IFNLR1 | VWA3B | LOC101929524 |
| SLC23A1 | IGSF23 | WDHD1 | LOC105372441 |
| SLC25A20 | IL22RA1 | WDR35 | LOC731424 |
| SLC25A34 | IL2RB | WDR78 | LOC93622 |
| SLC25A44 | ILVBL | WIPI1 | LRCH2 |
| SLC25A45 | IMMP2L | WNK4 | LRRC37A4P |
| SLC26A11 | INPP5J | WWP1 | LRRC58 |
| SLC2A2 | INTS12 | XPO4 | LUZP6 |
| SLC35B1 | IQSEC2 | YWHAE | LYST |
| SLC37A4 | IRF1 | ZBTB7C | MAFA |
| SLC39A5 | ISG20 | ZBTB8B | MAGEF1 |
| SLC3A2 | ITM2B | ZFHX3 | MAGT1 |
| SLC52A1 | ITPK1 | ZNF658 | MAL2 |
| SLC5A1 | ITPKA | ZNF774 | MAP3K7 |
| SLC5A9 | KALRN | ZNF780B | MARCKS |
| SLC6A19 | KDF1 | | MATR3, SNHG4 |
| SLC6A20 | KDM6B | | MBNL2 |
| SLC7A7 | KDM8 | | MBNL3 |
| SMIM24 | KHK | | MBOAT2 |
| SMIM5 | KIAA0141 | | MBTPS2 |
| SMLR1 | KIAA1551 | | MDN1 |
| SMPD3 | KIAA2013 | | MECOM |
| SOWAHA | KLC4 | | METTL8 |
| SPNS3 | KLHDC8B | | MFAP3L |
| ST7, ST7-OT3 | LASP1 | | MFSD4 |
| STRC | LBX2-AS1 | | MFSD6L |
| SULT1A1 | LEAP2 | | MIB1 |
| SULT1A2 | LHPP | | MIER1 |
| SYK | LINC00319 | | MIOS |
| SYP | LINC00330 | | MIR1244-4, PTMA |
| TAP2 | LINC00483 | | MIR4680, PDCD4 |
| TCF7 | LINC00574 | | MIR6824, SLC26A6 |
| TICAM1 | LINC00667 | | MLF1 |
| TKFC | LINC01137 | | MLLT3 |
| TM4SF20 | LINC01347 | | MLXIP |
| TM4SF4 | LIPE | | MMGT1 |
| TM4SF5 | LIPT1 | | MOB1B |
| TM6SF2 | LMBR1L | | MON2 |
| TMEM150B | LOC100093631 | | MORF4L1 |
| TMEM184A | LOC100506302 | | MPZL1 |
| TMEM253 | LOC100507334 | | MREG |
| TMEM37 | LOC101927051 | | MRPL1 |
| TMEM41A | LOC284825 | | MRPS6, SLC5A3 |
| TMEM82 | LOC90768 | | MTHFD2 |
| TMEM86B | LPCAT3 | | MTMR6 |
| TNFRSF14 | LRP5 | | MTSS1 |
| TNFRSF1A | LRRC28 | | MTURN |
| TNRC6C-AS1 | LRRC41 | | MUC1 |
| TOM1 | LRRC66 | | MUC12 |
| TREH | LRRC75A | | MYO3A |
| TRIM15 | LSMEM2 | | MYO5C |
| TRIM50 | LYRM5 | | NAA15 |
| TTC31 | LZTS3 | | NAA50 |
| TTC38 | MALL | | NAP1L1 |
| | | | NBPF10, NBPF12, NBPF20, NBPF25P, NBPF8, NBPF9 |
| UGT2B7 | MAP2K3 | | NCBP1 |
| UGT3A1 | MAP3K11 | | NCOA3 |
| USH1C | MAPK3 | | NDC1 |
| WBP2 | MAPKAPK2 | | NEK1 |
| WNT3 | MAPKBP1 | | NEURL1B |
| XAF1 | MARC2 | | NFIA |
| XDH | MBD1 | | NFYB |
| XPNPEP2 | MCRS1 | | NIFK-AS1 |
| ZMYND15 | MCUR1 | | NKIRAS1 |
| ZNF300 | MEP1A | | NOL11 |
| ZSWIM8 | MEP1B | | NOL9 |
| | METTL17 | | NOTCH1 |
| | METTL7B | | NPAS1 |
| | MFSD2A | | NRXN1 |
| | MGAM | | |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | |
|---|---|
| MGAM2 | NSF, NSFP1 |
| MGAT3 | NT5C2 |
| MGST3 | NT5DC3 |
| MICAL1, ZBTB24 | NUBPL |
| MICU1 | NUCKS1 |
| MIR1268A, SLC27A4 | NUDT4 |
| MIR22, MIR22HG | NUP133 |
| MIR3615, SLC9A3R1 | NUP205 |
| MIR5187, TOMM40L | NUS1 |
| MIR5193, UBA7 | NXPE1 |
| MIR639, TECR | NXPE4 |
| MIR7109, PISD | OPHN1 |
| MIR7703, PSME2 | ORC5 |
| MISP | PARM1 |
| MLF2 | PBRM1 |
| MLX | PCM1 |
| MLXIPL | PDE3B |
| MME | PDE4D |
| MMEL1 | PDS5A |
| MMP24 | PDS5B |
| MOCOS | PEAK1 |
| MOCS1 | PGBD5 |
| MOGAT2 | PGGT1B |
| MOGAT3 | PGM2L1 |
| MOGS | PHC3 |
| MON1A | PHF14 |
| MOV10 | PHF20 |
| MPP1 | PHF6 |
| MS4A8 | PHIP |
| MSRA | PHTF2 |
| MST1 | PIAS2 |
| MST1R | PIBF1 |
| MTTP | PIGN |
| MUC17 | PIGX |
| MYD88 | PIK3R3 |
| MYO15B | PIKFYVE |
| MYO19 | PITHD1 |
| MYRF | PJA2 |
| NAALADL1 | PKI55 |
| NAGS | PKIB |
| NAPRT | PKNOX1 |
| NCK2 | PLEKHF2 |
| NCSTN | PLXNA2 |
| NELL2 | POF1B |
| NGEF | POLR1E |
| NIT1 | POT1 |
| NLRP6 | POU2F1 |
| NOL4L | PP14571 |
| NOP9 | PPIC |
| NPC1L1 | PPIP5K2 |
| NPY6R | PPM1B |
| NQO2 | PPM1K |
| NR0B2 | PPP1R3B |
| NR1H3 | PPP2R5C |
| NR1I3 | PPP3CA |
| NUCB1 | PRKACB |
| NUTM2B-AS1 | PRKDC |
| OCIAD2 | PRKG1 |
| OGDH | PRKRIR |
| OGG1 | PRPS2 |
| OTC | PRRT3-AS1 |
| OXNAD1 | PSME4 |
| P4HB | PTAR1 |
| PAOX | PTEN |
| PARP2 | PTGDR |
| PARP3 | PTPN14 |
| PBLD | PUM1 |
| PBX2 | PURB |
| PCBP2, PCBP2-OT1 | PWWP2A |
| PCK2 | PYGB |
| PCSK5 | PYGO1 |
| PCYT1A | PYURF |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | |
|---|---|
| PDE8B | QPCT |
| PDLIM2 | RAB11FIP2 |
| PDSS1 | RAB3B |
| PDXP | RAB40B |
| PDZD7 | RABEP1 |
| PEBP1 | RABGAP1 |
| | RALGAPA1, |
| PEPD | RALGAPA1P |
| PEX14 | RANBP2 |
| PEX16 | RAP1GDS1 |
| PFKL | RAP2A |
| PFKP | RAP2B |
| PGD | RAPGEF6 |
| PGRMC2 | RASA2 |
| PGS1 | RASEF |
| PIM1 | RBFOX2 |
| PIP5K1A | RBM7 |
| PKLR | RBMS3 |
| PLCB3 | RBPJ |
| PLEK2 | RBPMS-AS1 |
| PLEKHA7 | RBSN |
| PLEKHS1 | RBX1 |
| PLIN3 | RCC2 |
| PLLP | RDX |
| PMM1 | REXO2 |
| PNLIPRP2 | RGL3 |
| PNP | RIF1 |
| POLR3H | RIMKLA |
| POMGNT1 | RLIM |
| POR | RND3 |
| PP7080 | RNF139 |
| PPIP5K1 | RNF144A |
| PPP2R5D | RNF145 |
| PPP6R1 | RNF223 |
| PQBP1 | RNMT |
| PQLC2 | RSL24D1 |
| PRAP1 | RXFP4 |
| PRDX2 | SAMD13 |
| PRKCD | SAR1A |
| PRKCZ | SARAF |
| PRKD2 | SATB2 |
| PRODH | SATB2-AS1 |
| PRR13 | SBNO1 |
| PRSS1 | SCAI |
| PRSS3P2 | SCFD1 |
| PSD4 | SDC4 |
| PSMA1 | SEC22A |
| PSMB10 | SEC23IP |
| PSMB8 | SEC62 |
| PSMB9 | SECISBP2L |
| PSMD9 | SEL1L |
| PSME1 | SEMA3C |
| PTK2B | SEMA3D |
| PTPRH | SEMA5A |
| PVRL2 | SEPT11 |
| PXDC1 | SEPT7 |
| QRICH1 | SERBP1 |
| RAB11FIP3 | SERINC5 |
| RAB17 | SERTAD2 |
| RAB5C | SESN1 |
| RAB8A | SESN3 |
| RARA | SETX |
| RARRES3 | SH3PXD2A-AS1 |
| RASSF4 | SHOC2 |
| RBP2 | SHROOM4 |
| REEP6 | SIPA1L2 |
| REG1A | SLC10A7 |
| RFX5 | SLC15A2 |
| RGN | SLC16A9 |
| RIC3 | SLC19A2 |
| RIPK3 | SLC1A3 |
| RIPK4 | SLC22A15 |
| RMDN3 | SLC25A12 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | |
|---|---|
| RMND1 | SLC25A30 |
| RNF10 | SLC2A10 |
| RNF123 | SLC30A6 |
| RNF167 | SLC35A1 |
| RRNAD1 | SLC37A3 |
| RTKN | SLC38A2 |
| RTP4 | SLC38A6 |
| SAPCD1-AS1, VWA7 | SLC39A8 |
| SAT2 | SLC44A1 |
| SCAMP5 | SLC7A2 |
| SCARB1 | SLC9A2 |
| SCML4 | SMAD5 |
| SCNN1D | SMARCA5 |
| SCRN2 | SMC6 |
| SDHD | SMG1 |
| SEC13 | SMIM14 |
| SEC14L2 | SNRPE |
| SEC16B | SNX13 |
| SFRP5 | SOCS5 |
| SFXN3 | SORBS2 |
| SH3BP1 | SPAG1 |
| SH3GL1 | SPIN2B |
| SHPK, TRPV1 | SPIRE1 |
| SIDT2 | SPTAN1 |
| SIGLEC12 | SPTSSA |
| SLC12A7 | SRSF12 |
| SLC13A2 | SSB |
| SLC16A13 | SSR1 |
| SLC16A5 | SSR3 |
| SLC19A1 | ST6GAL2 |
| SLC22A18 | ST7L |
| SLC22A4 | STAB2 |
| SLC23A1 | STAG1 |
| SLC25A20 | STMND1 |
| SLC25A44 | STRN3 |
| SLC25A45 | STS |
| SLC25A5 | STX19 |
| SLC26A11 | STX6 |
| SLC2A12 | SUMF1 |
| SLC2A5 | SUPT16H |
| SLC2A9 | SUV39H2 |
| SLC35B1 | SYT7 |
| SLC37A4 | SYTL2 |
| SLC39A5 | SYTL4 |
| SLC3A2 | TACC1 |
| SLC52A1 | TAF9B |
| SLC5A1 | TAOK1 |
| SLC5A6 | TBL1X |
| SLC6A19 | TCAM1P |
| SLC6A20 | TDGF1 |
| SLC7A7 | TEAD1 |
| SLC7A9 | TFCP2L1 |
| SLC9A3 | TFRC |
| SLX4 | TGFBR1 |
| SMAD3 | THADA |
| SMARCD1 | TICAM2, TMED7, TMED7-TICAM2 |
| SMIM24 | TINCR |
| SMLR1 | TLK1 |
| SMOX | TLN2 |
| SMPD3 | TMCC1-AS1 |
| SOAT2 | TMED10 |
| SPANXN3 | TMED9 |
| SPHK2 | TMEM106B |
| SPNS3 | TMEM123 |
| SRC | TMEM159 |
| SSTR1 | TMEM194A |
| ST7, ST7-OT3 | TMEM194B |
| STAT6 | TMEM2 |
| STAU1 | TMEM44 |
| STK24 | TMEM45A |
| SUCLG1 | TMEM87A |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

| | |
|---|---|
| SULT1A1 | TMX1 |
| SULT1A2 | TNFRSF10D |
| SULT2A1 | TNKS |
| SYP | TNRC6C |
| TAP2 | TOP2B |
| TBK1 | TP53BP1 |
| TCF7 | TP53INP1 |
| TFG | TRABD2A |
| THRA | TRIM23 |
| TIAM2 | TRIM37 |
| TICAM1 | TRIP12 |
| TJAP1 | TRMT5 |
| TKFC | TROVE2 |
| TLDC2 | TSN |
| TM4SF4 | TSPAN5 |
| TM4SF5 | TSPAN6 |
| TM6SF2 | TSPYL4 |
| TMED4 | TTC28 |
| TMEM116 | TTC3 |
| TMEM120A | TTL |
| TMEM139 | TTPA |
| TMEM150B | TTPAL |
| TMEM177 | TWISTNB |
| TMEM184A | TWSG1 |
| TMEM229B | TXNDC15 |
| TMEM253 | UBE2D1 |
| TMEM25, TTC36 | UBE2Q2 |
| TMEM37 | UBR5 |
| TMEM51 | UGGT1 |
| TMEM51-AS1 | UGGT2 |
| TMEM82 | UNC5C |
| TMEM86B | USP13 |
| TMEM92 | USP24 |
| TNFRSF14 | USP34 |
| TNFRSF1A | USP47 |
| TNIK | USP53 |
| TOM1 | UXS1 |
| TOM1L1 | VANGL1 |
| TOX4 | VKORC1L1 |
| TPI1 | VOPP1 |
| TRAF4 | VPS13B |
| TREH | VPS13C |
| TRIM14 | WAC-AS1 |
| TRIM15 | WBP5 |
| TRIM16 | WDFY1 |
| TRIM21 | WDHD1 |
| TTC38 | WDR36 |
| UBXN2A | WDR7 |
| UGT3A1 | WDR78 |
| UNC5CL | WDR89 |
| USF1 | WNK4 |
| USH1C | XIAP |
| USP10 | XPNPEP3 |
| USP2 | XPO4 |
| VRK3 | YTHDF3 |
| VRTN | ZBTB10 |
| WBP2 | ZBTB7C |
| WDR45 | ZDHHC7 |
| WDTC1 | ZFHX3 |
| WNT3 | ZFP90 |
| WWC1 | ZFX |
| XAF1 | ZMAT2 |
| XDH | ZMPSTE24 |
| XPNPEP1 | ZMYM4 |
| ZDHHC9 | ZNF148 |
| ZER1 | ZNF260 |
| ZFAND3 | ZNF264 |
| ZFYVE27 | ZNF320 |
| ZMYND15 | ZNF555 |
| ZNF384 | ZNF644 |
| ZNF782 | ZNF652 |
| ZRANB2-AS1 | ZNF678 |
| ZSWIM8 | ZNF69 |

TABLE 1-continued

Genes upregulated in adult small intestine and colon which are also upregulated in HIOs and HCOs respectively. Column 1, Commonly upregulated in NOG HIOs vs HCOs & adult small intestine vs adult colon, Column 2, Commonly upregulated in Control HIOs vs HCOs & adult small intestine vs adult colon, Column 3, Commonly upregulated in HCOs vs NOG HIOs & adult colon vs adult small intestine, Column 4, Commonly upregulated in HCOs vs Control HIOs & adult colon vs adult small intestine

ZNF704
ZNF709
ZNF766
ZNF780B
ZNF81
ZYG11B

Discussion

Historically, the classification of foregut, midgut, and hindgut are based on the development of the anterior and posterior intestinal portals and the source of mesenteric blood supply (Uppal et al., 2011). An alternative definition of midgut and hindgut have been proposed, in which the midgut is the portion of the intestine derived from the portion anterior to the umbilicus and the hindgut derives posterior to the umbilicus (Johnston, 1913; Savin et al., 2011). In either case, the historic reliance on anatomical landmarks, and lack of more precise molecular markers to distinguish fore, mid and hindgut, have made it difficult to develop methods to generate these cell/tissues in vitro from PSCs. Therefore, identification of markers that clearly demarcate regions of developing mid and hindgut is essential.

Applicant used a combination of CDX2, GATA4, ONECUT1 and SATB2 to identify that distinct molecular boundaries are established at early stages of mid and hindgut development in *Xenopus*, mouse and humans. Interestingly, GATA4 and SATB2 expression domains form a boundary at the yolk stalk/presumptive umbilical cord in mice, and this boundary is maintained throughout development and in the adult intestine. The fact that GATA4 expression marks the intestine anterior to the umbilicus, and SATB2 expression marks the domain posterior to the umbilicus, suggests that the umbilicus is the boundary between the midgut and hindgut (Johnston, 1913; Savin et al., 2011).

While ONECUT1 expression in HIOs and SATB2 expression is HCOs is consistent with their proximal and distal identify respectively, GATA4 was not as robustly expressed in proximal HIOs in vitro as would be expected given its embryonic expression (data not shown). In contrast, GATA4 was robustly expressed following in vivo maturation of HIOs and in enteroids generated from patient biopsies (data not shown). This could suggest that factors involved in expression of GATA4 are absent in culture conditions or that maturation in vivo is required for epithelial expression of GATA4. This data also suggests that high levels of GATA4 expression may be dispensable for early regionalization of the intestine, consistent with intestinal Gata4 knockout mice that retain normal Onecut factor expression (Battle et al., 2008). In addition, a small subset of BMP treated organoids lost CDX2 expression and activated expression of the bladder markers Keratin 13 and Uroplakin 1a (data not shown). This is consistent with BMP organoids having a hindgut fate since urothelial tissue is derived from the hindgut/cloaca (Georgas et al., 2015).

SATB2 is expressed throughout development of the distal ileum and large intestine, however it is not known if SATB2 is required for development of the distal intestine. Mouse knockout studies have focused on craniofacial and cortical neuronal development since mutations in SATB2 has been implicated in Cleft Palate associated with 2q32-q33 deletions and Glass Syndrome (FitzPatrick et al., 2003). However, there is indirect evidence that SATB2 may play a role human colonic physiology. SATB2 has been identified in Genome Wide Association Studies as an ulcerative colitis susceptibility gene (McGovern et al., 2010). In addition, loss of SATB2 expression has been shown to be associated with poor prognosis in colorectal cancer patients (Eberhard et al., 2012). Future studies with HCOs may allow identification of SATB2 targets in the developing colon, which could provide insight into the pathology of ulcerative colitis and colorectal cancer.

Several studies in model organisms have implicated the BMP signaling pathway in patterning endoderm during hindgut development (Kumar et al., 2003; Roberts et al., 1995; Sherwood et al., 2011; Tiso et al., 2002; Wills et al., 2008). Consistent with this, Applicant has demonstrated that posterior patterning of human definitive endoderm is dependent on BMP signaling, as inhibition of BMP abrogates the ability of WNT and FGF to promote a posterior endoderm fate (McCracken et al., 2014). However, it is not surprising that BMP signaling plays other temporally distinct roles during intestinal development. For example, after the establishment of proximal-distal regional domains, BMP signaling functions to establish the crypt-villus axis in the intestine and colon (Li, 2005). Thus, a temporal requirement for patterning allows the embryo to use the same signaling pathway for multiple purposes gut development, as has been reported in *Drosophila* midgut (Driver and Ohlstein, 2014; Guo et al., 2013). In a human disease context, mutations in BMPR1A are associated with a subset of patients with Juvenile Polyposis Syndrome. The HCO system was highly amenable for identifying the HOX code that is downstream of BMP during early development and it could be interesting to determine if hamartomatous polyps with BMPR1A mutations have altered HOX gene expression.

Applicant previously reported the in vitro directed differentiation and in vivo transplantation of HIOs (Spence et al., 2011; Watson et al., 2014), which were small intestinal. Given the unique physiology and pathological conditions that affect the large intestine, it was imperative to develop a colonic model system to interrogate pathophysiological questions specific to the colon. Developmentally, this system provides the opportunity to investigate fundamental questions about how regional identity is established. HIOs and HCOs develop unique cell types, such as Paneth cells in the HIOs and colon-specific goblet cells in HCOs. Moreover, HIOs and HCOs have a distinct set of EECs that are normally enriched in the small and large intestine, respectively. Regionalized organoids should provide a platform for future studies of how different regions of the intestine give rise to regionalized stem cells. In addition, generation of HCOs will allow for modeling of diseases that affect the colon such as ulcerative colitis and colorectal cancer.

Materials and Methods

Animals. Immune-deficient NOD-SCID IL-2Rynu" (NSG) mice, 8-16 weeks old, were used in transplantation experiments (obtained from the Comprehensive Mouse and Cancer Core Facility, Cincinnati, Ohio). Wild type mice were used for studies on mouse fetal intestine. All mice were housed in the animal facility at the Cincinnati Children's Hospital Medical Center (CCHMC). All experiments were performed with the approval of the Institutional Animal Care and Use Committee of CCHMC.

BMP inhibition in frog and mouse embryos. *Xenopus tropicalis* embryo culture and small molecule treatments were performed as previously described (Rankin et al., 2012; Rankin et al., 2015). DMH-1 (Sigma D8946) was dissolved in DMSO, and used at final concentration of 20 pM; equal concentrations of DMSO vehicle were used on sibling embryos. Inhibitor treatment experiments were repeated twice with similar effects on the markers analyzed. For *Xenopus* in-situ hybridization analyses, DIG-labeled antisense RNA probes were generated using linearized full-length cDNA plasmid templates (*X. tropicalis* satb2 was purchased from ATCC, clone 7720194; HinDIII, T7 for probe; *X. laevis* satb2 was a gift for Tyler Square and Daniel Medeiros, University of Colorado-Boulder; Xbal, Sp6 for probe). Complete details describing probe synthesis and the in-situ hybridization protocol are available on Xenbase (hftp://wiki.xenbase.orq/xenwiki/index.php/Protocols).

For mouse whole embryo cultures, e7.5 embryos were cultured in a 1:1 mixture of Ham's F12 medium and whole embryo culture rat serum (Harlan Labs) containing N-2 Supplement (Invitrogen). Vessels were placed on a roller culture apparatus (BTC Engineering, Cambridge, UK) and maintained for 2 days at 37° C. and gassed with 20% O2 and 5% CO2. BMP signaling was inhibited by treatment with 5 pM DMH-1, with DMSO serving as a vehicle control.

Generation of human midgut/hindgut spheroids. Human intestinal organoids were generated and maintained as previously described (Watson et al., 2014). Human embryonic stem cells and induced pluripotent stem cells were grown in feeder-free conditions in six-well Nunclon surface plates (Nunc) coated with Matrigel (basement membrane matrix, BD Biosciences) and maintained in mTESR1 media (Stem Cell Technologies). For induction of definitive endoderm (DE), human ES or iPS cells were passaged with Accutase (Invitrogen) and plated at a density of 100,000 cells per well in a Matrigel-coated, Nunclon surface 24-well plate. For Accutase split cells, 10 pM Y27632 compound (Sigma) was added to the media for the first day. After the first day, media was changed to mTESR1 and cells were grown for an additional 24 hours. Cells were then treated with 100 ng/mL of Activin A for 3 days as previously described (Spence et al., 2011). DE was then treated with hindgut induction medium (RPMI 1640, 2 mM L-glutamine, 2% decomplemented FBS, penicillin-streptomycin and 100 ng/mL Activin A) for 4 d with 500 ng/mL FGF4 (R&D) and 3 pM Chiron 99021 (Tocris) to induce formation of mid-hindgut spheroids.

Patterning midgut/hingut spheroids into HIOs and HCOs. Spheroids were collected from 24 well plate and plated in Matrigel (BD). To generate proximal HIOs, spheroids were overlayed with intestinal growth medium (Advanced DMEM/F-12, N2, B27, 15 mM HEPES, 2 mM L-glutamine, penicillin-streptomycin) supplemented with 100 ng/mL EGF (R&D) alone, or 100 ng/mL EGF with 100 ng/ml NOGGIN (R&D). To generate HCOs, spheroids were overlayed with 100 ng/mL EGF plus 100 ng/mL BMP (R&D). For SHH experiments, 1 pM SAG (Tocris), 5 pM SAG or 2.5 pM Cyclopamine (Tocris) were added to control media for initial 3 days after which RNA samples were collected. Media was changed at 3 days with only EGF being maintained in the media for all patterning conditions. Media was then changed twice weekly thereafter. HIOs and HCOs were replated in fresh Matrigel every 14 days.

Generation of NEUROGENIN3 inducible line. To generate a doxycycline inducible NEUROG3 line, Applicant transduced IPSC 72.3 cells with pINDUCER21-NEUROG3 lentivirus and selected using 250 g/mL of G418. Both the IPSC 72.3 cell line and the inducible NEUROG3 have been described previously (McCracken et al., 2014). Stably transduced cells were differentiated into mid/hindgut spheroids and then patterned into HIOs or HCOs. Spheroids were grown for 28 days and were pulsed with 0.5 ug/mL of doxycycline for 8 hrs. At day 35, organoids were collected and were analyzed by QPCR and IF.

Growth of organoid mesenchyme. Mesenchymal cells from organoids which attach to the bottom of the 24-well plate attach and grow in 2 dimensions. To expand mesenchymal cells from organoids, DMEM 10% FBS+L-glutamine+ penicillin-streptomycin was added to wells from which organoids had been harvested at 14 days. Media was changed twice weekly for a total of 2-3 weeks until near 100% confluence was achieved.

Transplantation of human intestinal organoids. NSG mice were kept on antibiotic chow (275 p.p.m. Sulfamethoxazole and 1.365 p.p.m. Trimethoprim; Test Diet). Food and water was provided ad libitum before and after surgeries. A single HIO, matured in vitro for 28 days, was removed from Matrigel, washed with cold phosphate-buffered saline (DPBS; Gibco), and embedded into purified type I collagen (rat tail collagen; BD Biosciences) 12 hours before surgery to allow for formation of a solidified gel plug. These plugs were then placed into standard growth media overnight in intestinal growth medium (Advanced DMEM/F-12, B27, 15 mM HEPES, 2 mM L-glutamine, penicillin-streptomycin) supplemented with 100 ng/mL EGF (R&D). HIOs were then transplanted under the kidney capsule as previously reported (Watson et al., 2014). Briefly, the mice were anesthetized with 2% inhaled isoflurane (Butler Schein), and the left side of the mouse was then prepped in sterile fashion with isopropyl alcohol and povidine-iodine. A small left-posterior subcostal incision was made to expose the kidney. A subcapsular pocket was created and the collagen-embedded HIO was then placed into the pocket. The kidney was then returned to the peritoneal cavity and the mice were given an IP flush of Zosyn (100 mg/kg; Pfizer Inc.). The skin was closed in a double layer and the mice were given a subcutaneous injection with Buprenex (0.05 mg/kg; Midwest Veterinary Supply). At 8-10 weeks following engraftment, the mice were then humanely euthanized or subjected to further experimentation.

Tissue processing, immunofluorescence and microscopy. Tissues were fixed for 1-3 hours in 4% paraformaldehyde (PFA) on ice depending on the size of the tissue. Organoids and transplant engraftments were frozen in OCT. OCT sections were blocked using donkey serum (5% serum in 1×PBS plus 0.5% Triton-X) for 30 min and incubated with primary antibody overnight at 4° C. Slides were then washed 3× with 1×PBS plus 0.5% Triton-X and incubated in secondary antibody with DAPI in blocking buffer for 2 h at room temperature. See Table 2 for a list of antibodies and respective dilutions. Slides were then washed 2× with 1×PBS plus 0.5% Triton-X followed by a final wash in 1×PBS. Coverslips were then mounted using Fluoromount-G® (SouthernBiotech). Images were captured on a Nikon A1 confocal microscope and analyzed using Imaris Imaging Software (Bitplane). For whole-mount staining, tissues were processed similarly as above and then cleared in Murray's solution. Imaging was performed with a Nikon A1 confocal microscope.

Quantification of immunofluorescence images. Image quantitation of whole embryos was done by splitting images into separated channels and then measuring pixel area using ImageJ (NIH). Pixel area was determined for each channel, the ratio between channels was determined and the ratio for control treated embryos was represented as 100. Quantitation of in vitro and in vivo grown organoids was done on sections from which images were captured as explained above. The number of CDX2, GATA4 and SATB2 positive nuclei were quantified using the spot function in [marls following calibration with human biopsy samples.

RNA isolation and QPCR. RNA was extracted using Nucleospin® RNA extraction kit (Macharey-Nagel) and reverse transcribed into cDNA using Superscript VILO (Invitrogen) according to manufacturer's protocols. QPCR primers were designed using the qPrimerDepot webased tool (primerdepot.nci.nih.gov). Primer sequences are listed in Table 3. QPCR was performed using Quantitect SYBR® Green PCR kit (Qiagen) and a QuantStudio™ 6 Flex Real-Time PCR System (Applied Biosystems).

TABLE 2

QPCR primers used. See FIGS. 3 and 4.

| GENE | Sequence |
|---|---|
| CDH1 FWD | GACCGGTGCAATCTTCAAA |
| CDH1 REV | TTGACGCCGAGAGCTACAC |
| CHGA FWD | TGTGTCGGAGATGACCTCAA |
| CHGA REV | GTCCTGGCTCTTCTGCTCTG |
| CKB FWD | CCCACACCAGGAAGGTCTTA |
| CKB REV | CCTCTTCGACAAGCCCGT |
| FXYD3 FWD | AGGGTCACCTTCTGCATGTC |
| FXYD3 REV | CTTCGGATAAACGCAGGACT |
| GATA4 FWD | TAGCCCCACAGTTGACACAC |
| GATA4 REV | GTCCTGCACAGCCTGCC |
| HOXA13 FWD | GCACCTTGGTATAAGGCACG |
| HOXA13 REV | CCTCTGGAAGTCCACTCTGC |
| HOXB13 FWD | GCTGTACGGAATGCGTTTCT |
| HOXB13 REV | AACCCACCAGGTCCCTTTT |
| HOXD13 FWD | CCTCTTCGGTAGACGCACAT |
| HOXD13 REV | CAGGTGTACTGCACCAAGGA |
| HOXD3 FWD | CACCTCCAATGTCTGCTGAA |
| HOXD3 REV | CAAAATTCAAGAAAACACACACA |
| INSL5 FWD | GAAGGTTTTGCGCTGGATT |
| INSL5 REV | GATCCCTCAAGCTCAGCAAG |
| MSX2 FWD | GGTCTTGTGTTTCCTCAGGG |
| MSX2 REV | AAATTCAGAAGATGGAGCGG |
| MUC2 FWD | TGTAGGCATCGCTCTTCTCA |
| MUC2 REV | GACACCATCTACCTCACCCG |
| ONECUT1 Fwd | TTTTTGGGTGTGTTGCCTCT |
| ONECUT1 Rev | AGACCTTCCGGAGGATGTG |
| PDX1 FWD | CGTCCGCTTGTTCTCCTC |
| PDX1 REV | CCTTTCCCATGGATGAAGTC |
| PPIA (CPHA) FWD | CCCACCGTGTTCTTCGACATT |
| PPIA (CPHA) REV | GGACCCGTATGCTTTAGGATGA |
| SATB2 FWD | CCACCTTCCCAGCTTGATT |
| SATB2 REV | TTAGCCAGCTGGTGGAGACT |

TABLE 3

Antibodies used. See FIGS. 1-6.

| ANTIBODY | HOST | Catalog number | Dilution |
|---|---|---|---|
| B-Catenin | rabbit | Santa Cruz #sc-7199 | 1:200 |
| CDH17* | rabbit | Sigma #HPA023616 | 1:1,500 |
| Cdx2 | mouse | BioGenex cdx2-88 | 1:300 |
| Cdx2 | rabbit monoclonal | Cell Marque EPR2764Y | 1:100 |
| Chr-A (C20) | goat | Santa Cruz #sc-1488 | 1:100 |
| DEFA5* | mouse monoclonal | Novus BiologicalsNB110-60002 | 1:60,000 |
| E-Cadherin | goat | R&D #AF648 | 1:400 |
| E-Cadherin (mouse-specific) | rat | R&D #MAB7481 | 1:500 |
| E-Cadherin | mouse | R&D #AF648 | 1:500 |
| FoxA2 | goat | Santa Cruz #sc-6554 | 1:500 |
| GATA4 | goat | Santa Cruz #sc-1237 | 1:100 |
| GATA4 | rabbit | Santa Cruz #sc-9053 | 1:100 |
| GFP (green fluorescent protein) | rabbit | Invitrogen #A11122 | 1:1,000 |
| Ghrelin | goat | Santa Cruz #sc-10368 | 1:500 |
| GIP (Gastric Inhibitory Polypeptide) | goat | Santa Cruz #sc-23554 | 1:500 |
| GLP-1 | mouse | BioVision #3104-100 | 1:200 |
| HNF-6 (ONECUT1) | rabbit | Santa Cruz #sc-13050 | 1:100 |
| INSL5 (H-110)* | rabbit | Santa Curz #sc-67190 | 1:100 |
| KI67 | rabbit monoclonal | Cell Marque SP6 | 1:100 |
| Motilin | mouse monoclonal | Santa Cruz #sc-376605 | 1:100 |
| Mucin 5B* | rabbit | Santa Cruz #sc-20119 | 1:100 |
| Mucin2 (MUC2) | rabbit | Santa Cruz #sc-15334 | 1:200 |
| Peptide YY | rabbit | Abcam #ab22663 | 1:1000 |
| pSmad 1/5/8 (Discontinued and replaced with 13820S) | rabbit | Cell Signaling 9511S | 1:100 |
| pSmad 2/3 | rabbit | Cell Signaling 9510S | 1:100 |
| SATB2 | rabbit monoclonal | Cell Marque EP281 | 1:100 |
| SATB2 (SATBA4610)* | mouse monoclonal | Santa Cruz #sc-81376 | 1:100 |
| Sox9 | rabbit | Millipore #AB5535 | 1:10,000 |
| Alexafluor ® Donkey anti-goat 488 | donkey | Life Technologies A-11055 | 1:500 |
| Alexafluor ® Donkey anti-goat 568 | donkey | Life Technologies A-11057 | 1:500 |

TABLE 3-continued

Antibodies used. See FIGS. 1-6.

| ANTIBODY | HOST | Catalog number | Dilution |
|---|---|---|---|
| Alexafluor ® Donkey anti-mouse 568 | donkey | Life Technologies A-10037 | 1:500 |
| Alexafluor ® Donkey anti-rabbit 647 | donkey | Life Technologies A-31573 | 1:500 |
| Alexafluor ® Donkey anti-rat 488 | donkey | Life Technologies A-21208 | 1:500 |

Identification of SATB2 as a Large Intestinal Marker.

To identify markers of large intestine, Applicant first used GNCPro http://gncpro.sabiosciences.comigncpro/expression_grapherphp to identify transcription factors upregulated in colon (compared to other tissues) based on the University of Tokyo database. Based on this search, SATB2 was the 6th ranked gene in colon. To verify that SATB2 is indeed upregulated in the colon, Applicant searched SATB2 expression using the TiGER database (hftp://bioinfo.wilmer.ihu.edu/tiger/db gene/SATB2-index.html). To further confirm the expression of SATB2 in the colon, and to examine protein expression across numerous tissues, Applicant used the Human Protein Atlas (http://www.proteinatlas.org/search/satb2). A similar approach was used to identify other markers of large intestine/colon.

Public RNA-seq accession numbers. Adult small intestine and large intestine RNA-seq data were downloaded from the public database E-MTAB-1733. These data sets represent whole organ tissue which includes the epithelium and muscle layers. Accession numbers for the small intestine samples: ERR315344, ERR315381, ERR315409, ERR315442, ERR315461. Accession numbers for the large intestine samples: ERR315348, ERR315357, ERR315484. For FIG. 9B, processed FPKM data was downloaded from https://qithub.com/hilldr/Finkbeiner StemCellReports2015. These data include adult duodenum (ERS326992, ERS326976) and small intestine samples listed above from E-MTAB-1733 as well as human fetal intestinal (also whole organ) samples from GSE18927. Accession numbers for human fetal small intestine are GSM1059508, GSM1059521, GSM1059486, GSM1059507, GSM1059517, GSM1220519. For FIG. 9C, data was obtained from GEO accession GSE66749 platform GLP5175. The following samples were used: GSM1385160, GSM1385161, GSM1385162, GSM1385163, GSM1385164, GSM1385165, GSM1385166, GSM1385167, GSM1385168, GSM1385169, GSM1385170, GSM1385171, GSM1614646, GSM1614646. Sample values were determined using the GEO2R "profile graph" function and searching for GATA4 and SATB2 by their ID numbers (U.S. Pat. Nos. 3,086,100 and 2,594,089 respectively).

RNA-seq sequence assembly abundance estimation. RNA library construction and RNA sequencing was performed by the Cincinnati Children's Hospital DNA Sequencing Core, using an Illumina HiSeq2500 platform. The quality of the Illumina sequencing run was evaluated by analyzing FASTQ data for each sample using FastQC version 0.10.1 http://www.bioinformatics.babraham.ac.uk/projects/fastqc to identify features of the data that may indicate quality problems (e.g. low-quality scores, over-represented sequences, inappropriate GC content, etc.). No major issues were identified by the QC analysis. Applicant used the software package Tuxedo Suite for alignment, differential expression analysis, and post-analysis diagnostics. Briefly, Applicant aligned reads to the reference transcriptome (UCSC hg19) using TopHat version 2.0.13 and Bowtie version 2.2.5 (Langmead et al., 2009). Applicant used default parameter settings for alignment, with the exception of: "-b2-very-sensitive" to maximize the accuracy of the read alignment, as well as "-no-coverage-search" and "-no-novel-juncs" limiting the read mapping to known transcripts. Cufflinks version 2.2.1 (Trapnell et al., 2012) was used for RNA abundance estimation. UCSC hg19.fa was used as the reference genome sequence and UCSC hg19.gtf was used for transcriptome annotation. Applicant applied the following parameters in Cufflinks: "-multi-read-correct" to adjust expression calculations for reads that map in more than one locus, and "-compatible-hits-norm" and "-upper-quartile-norm" for normalization of expression values. Normalized FPKM tables were generated using the CuffNorm function. RNA sequence assembly and transcriptional analysis was conducted using the 64-bit Debian Linux stable version 7.10 ("Wheezy") platform.

Differential Expression Analysis.

All plots and statistical analyses were conducted in R version 3.3.1 (2016-06-21). Plots were generated using the R package 'ggplot2' (Ginestet, 2011). Differential expression analysis and statistical tests of Cufflinks output were completed with the R package 'SeqRetriever' 'SeqRetriever' version 0.6 https://github.com/hilldr/SeqRetrieyer. Hypergeometric means testing was used to evaluate relative enrichment of shared gene expression signatures between groups using the R package 'GeneOverlap' http://shenlab-sinai.cithub.io/shenlab-sinai/. The complete RNA-seq FASTQ processing pipeline and analysis scripts are available at https://qithub.com/hilldr/Munera2016.

REFERENCES

Aronson, B. E., Aronson, S. R., Berkhout, R. P., Chavoushi, S. F., He, A., Pu, W. T., Verzi, M. P., and Krasinski, S. D. (2014). GATA4 represses an ileal program of gene expression in the proximal small intestine by inhibiting the acetylation of histone H3, lysine 27. Bba-Gene Regul Mech 1839, 1273-1282.

Battle, M. A., Bondow, B. J., Iverson, M. A., Adams, S. J., Jandacek, R. J., Tso, P., and Duncan, S. A. (2008). GATA4 is essential for jejuna! function in mice. Gastroenterology 135, 1676-1686 e1671.

Bernstein, B. E., Stamatoyannopoulos, J. A., Costello, J. F., Ren, B., Milosavljevic, A., Meissner, A., Kellis, M., Marra, M. A., Beaudet, A. L., Ecker, J. R., et al. (2010). The NIH Roadmap Epigenomics Mapping Consortium. Nat Biotechnol 28, 1045-1048.

Beuling, E., Bosse, T., aan de Kerk, D. J., Piaseckyj, C. M., Fujiwara, Y., Katz, S. G., Orkin, S. H., Grand, R. J., and Krasinski, S. D. (2008a). GATA4 mediates gene repression in the mature mouse small intestine through interactions with friend of GATA (FOG) cofactors. Dev Biol 322, 179-189.

Beuling, E., Bosse, T., Buckner, M. A., and Krasinski, S. D. (2007a). Co-localization of Gata4 and Hnfl alpha in the gastrointestinal tract is restricted to the distal stomach and proximal small intestine. Gastroenterology 132, A586-A586.

Beuling, E., Bosse, T., de Kerk, D. A., Piaseckyj, C. M., Fujiwara, Y., Orkin, S. H., and Krasinski, S. D. (2007b).

Fog cofactors partially mediate Gata4 function in the adult mouse small intestine. Gastroenterology 132, A692-A693.

Beuling, E., Kerkhof, I. M., Nicksa, G. A., Giuffrida, M. J., Haywood, J., aan de Kerk, D. J., Piaseckyj, C. M., Pu, W. T., Buchmiller, T. L., Dawson, P. A., et al. (2010). Conditional Gata4 deletion in mice induces bile acid absorption in the proximal small intestine. Gut 59, 888-895.

Beuling, E., Kerkhof, I. M., Piaseckyj, C. M., Dawson, P A., Pu, W. T., Grand, R. J., and Krasinski, S. D. (2008b). The absence of GATA4 in the distal small intestine defines the ilea! phenotype. Gastroenterology 134, A83-A84.

Bonilla-Claudio, M., Wang, J., Bai, Y., Klysik, E., Selever, J., and Martin, J. F. (2012). Bmp signaling regulates a dose-dependent transcriptional program to control facial skeletal development. Development 139, 709-719.

Bosse, T., Fialkovich, J. J., Piaseckyj, C. M., Beuling, E., Broekman, H., Grand, R. J., Montgomery, R. K., and Krasinski, S. D. (2007). Gata4 and Hnf1alpha are partially required for the expression of specific intestinal genes during development. Am J Physiol Gastroint Liver Physiol 292, G1302-1314.

Bouchi, R., Foo, K. S., Hua, H., Tsuchiya, K., Ohmura, Y., Sandoval, P. R., Ratner, L. E., Egli, D., Leibel, R. L., and Accili, D. (2014). FOXO1 inhibition yields functional insulin-producing cells in human gut organoid cultures. Nat Commun 5, 4242.

Burnicka-Turek, O., Mohamed, B. A., Shirneshan, K., Thanasupawat, T., Hombach-Klonisch, S., Klonisch, T., and Adham, I. M. (2012). INSL5-deficient mice display an alteration in glucose homeostasis and an impaired fertility. Endocrinology 153, 4655-4665.

De Santa Barbara, P., Williams, J., Goldstein, A. M., Doyle, A. M., Nielsen, C., Winfield, S., Faure, S., and Roberts, D. J. (2005). Bone morphogenetic protein signaling pathway plays multiple roles during gastrointestinal tract development. Developmental dynamics: an official publication of the American Association of Anatomists 234, 312-322.

Dobreva, G., Chahrour, M., Dautzenberg, M., Chirivella, L., Kanzler, B., Farinas, I., Karsenty, G., and Grosschedl, R. (2006). SATB2 is a multifunctional determinant of craniofacial patterning and osteoblast differentiation. Cell 125, 971-986.

Driver, I., and Oh!stein, B. (2014). Specification of regional intestinal stem cell identity during Drosophila metamorphosis. Development 141, 1848-1856.

Duluc, I., Freund, J. N., Leberquier, C., and Kedinger, M. (1994). Fetal endoderm primarily holds the temporal and positional information required for mammalian intestinal development. J Cell Biol 126, 211-221.

Eberhard, J., Gaber, A., Wangefjord, S., Nodin, B., Uhlen, M., Ericson Lindquist, K., and Jirstrom, K. (2012). A cohort study of the prognostic and treatment predictive value of SATB2 expression in colorectal cancer. Br J Cancer 106, 931-938.

Fagerberg, L., Hallstrom, B. M., Oksvold, P., Kampf, C., Djureinovic, D., Odeberg, J., Habuka, M., Tahmasebpoor, S., Danielsson, A., Edlund, K., et al. (2014). Analysis of the human tissue-specific expression by genome-wide integration of transcriptomics and antibody-based proteomics. Mol Cell Proteomics 13, 397-406.

Finkbeiner, S. R., Hill, D. R., Altheim, C. H., Dedhia, P. H., Taylor, M. J., Tsai, Y. H., Chin, A. M., Mahe, M. M., Watson, C. L., Freeman, J. J., et al. (2015). Transcriptome-wide Analysis Reveals Hallmarks of Human Intestine Development and Maturation In Vitro and In Vivo. Stem Cell Reports.

FitzPatrick, D. R., Carr, I. M., McLaren, L., Leek, J. P., Wightman, P., Williamson, K., Gautier, P., McGill, N., Hayward, C., Firth, H., et al. (2003). Identification of SATB2 as the cleft palate gene on 2q32-q33. Hum Mol Genet 12, 2491-2501.

Georgas, K. M., Armstrong, J., Keast, J. R., Larkins, C. E., McHugh, K. M., Southard-Smith, E. M., Cohn, M. J., Batourina, E., Dan, H., Schneider, K., et a/. (2015). An illustrated anatomical ontology of the developing mouse lower urogenital tract. Development 142, 1893-1908.

Ginestet, C. (2011). ggplot2: Elegant Graphics for Data Analysis. J R Stat Soc a Stat 174, 245-245.

Gracz, A. D., Ramalingam, S., and Magness, S. T. (2010). Sox9 expression marks a subset of CD24-expressing small intestine epithelial stem cells that form organoids in vitro. Am J Physiol-Gastr L 298, G590-G600.

Guo, Z., Driver, I., and Ohlstein, B. (2013). Injury-induced BMP signaling negatively regulates Drosophila midgut homeostasis. J Cell Biol 201, 945-961.

Gyorgy, A. B., Szemes, M., de Juan Romero, C., Tarabykin, V., and Agoston, D. V. (2008). SATB2 interacts with chromatin-remodeling molecules in differentiating cortical neurons. Eur J Neurosci 27, 865-873.

Haramis, A. P. G., Begthel, H., van den Born, M., van Es, J., Jonkheer, S., Offerhaus, G. J. A., and Clevers, H. (2004). De novo crypt formation and juvenile polyposis on BMP inhibition in mouse intestine. Science 303, 1684-1686.

Hardwick, J. C., Van Den Brink, G. R., Bleuming, S. A., Ballester, I., Van Den Brande, J. M., Keller, J. J., Offerhaus, G. J., Van Deventer, S. J., and Peppelenbosch, M. P. (2004). Bone morphogenetic protein 2 is expressed by, and acts upon, mature epithelial cells in the colon. Gastroenterology 126, 111-121.

He, X. C., Zhang, J. W., Tong, W. G., Tawfik, O., Ross, J., Scoville, D. H., Tian, Q., Zeng, X., He, X., Wiedemann, L. M., et a/. (2004). BMP signaling inhibits intestinal stem cell self-renewal through suppression of Wnt-beta-catenin signaling. Nature Genetics 36, 1117-1121.

Higuchi, Y., Kojima, M., Ishii, G., Aoyagi, K., Sasaki, H., and Ochiai, A. (2015). Gastrointestinal Fibroblasts Have Specialized, Diverse Transcriptional Phenotypes: A Comprehensive Gene Expression Analysis of Human Fibroblasts. Plos One 10.

Holland, P. W. H., Booth, H. A. F., and Bruford, E. A. (2007). Classification and nomenclature of all human homeobox genes. Bmc Biol 5.

Jeejeebhoy, K. N. (2002). Short bowel syndrome: a nutritional and medical approach. CMAJ 166, 1297-1302.

Johnston, T. B. (1913). Extroversion of the Bladder, complicated by the Presence of Intestinal Openings on the Surface of the Extroverted Area. J Anat Physiol 48, 89-106.

Kohlnhofer, B. M., Thompson, C. A., Walker, E. M., and Battle, M. A. (2016). GATA4 regulates epithelial cell proliferation to control intestinal growth and development in mice. Cell Mol Gastroenterol Hepatol 2, 189-209.

Kumar, M., Jordan, N., Melton, D., and Grapin-Botton, A. (2003). Signals from lateral plate mesoderm instruct endoderm toward a pancreatic fate. Dev Biol 259, 109-122.

Langmead, B., Trapnell, C., Pop, M., and Salzberg, S. L. (2009). Ultrafast and memory-efficient alignment of short DNA sequences to the human genome. Genome Biol 10, R25.

Li, H., Coghlan, A., Ruan, J., Coin, L. J., Heriche, J. K., Osmotherly, L., Li, R., Liu, T., Zhang, Z., Bolund, L., et al. (2006). TreeFam: a curated database of phylogenetic trees of animal gene families. Nucleic Acids Res 34, D572-580.

Li, L. H. (2005). BMP signaling inhibits intestinal stem cell self-renewal through antagonizing Wnt signaling. Gastroenterology 128, A702-A702.

McCracken, K. W., Aihara, E., Martin, B., Crawford, C. M., Broda, T., Treguier, J., Zhang, X., Shannon, J. M., Montrose, M. H., and Wells, J. M. (2017). Wnt/beta-catenin promotes gastric fundus specification in mice and humans. Nature 541, 182-187.

McCracken, K. W., Cata, E. M., Crawford, C. M., Sinagoga, K. L., Schumacher, M., Rockich, B. E., Tsai, Y. H., Mayhew, C. N., Spence, J. R., Zavros, Y., et al. (2014). Modelling human development and disease in pluripotent stem-cell-derived gastric organoids. Nature 516, 400-404.

McGovern, D. P., Gardet, A., Torkvist, L., Goyette, P., Essers, J., Taylor, K. D., Neale, B. M., Ong, R. T., Lagace, C., Li, C., et al. (2010). Genome-wide association identifies multiple ulcerative colitis susceptibility loci. Nat Genet 42, 332-337.

Molodecky, N A., Soon, I. S., Rabi, D. M., Ghali, W. A., Ferris, M., Chernoff, G., Benchimol, E. I., Panaccione, R., Ghosh, S., Barkema, H. W., et al. (2012). Increasing incidence and prevalence of the inflammatory bowel diseases with time, based on systematic review. Gastroenterology 142, 46-54 e42; quiz e30.

Moser, A. R., Pitot, H. C., and Dove, W. F. (1990). A Dominant Mutation That Predisposes to Multiple Intestinal Neoplasia in the Mouse. Science 247, 322-324.

Patankar, J., Obrowsky, S., Hoefler, G., Battle, M., Kratky, D., and Levak-Frank, S. (2012a). Intestinal Deficiency of Gata4 Protects from Diet-Induced Hepatic Steatosis by Suppressing De Novo Lipogenesis and Gluconeogenesis in Mice. J Hepatol 56, S496-S496.

Patankar, J. V., Obrowsky, S., Doddapattar, P., Hoefler, G., Battle, M., Levak-Frank, S., and Kratky, D. (2012b). Intestinal GATA4 deficiency protects from diet-induced hepatic steatosis. J Hepatol 57, 1061-1068.

Ramalingam, S., Daughtridge, G. W., Johnston, M. J., Gracz, A. D., and Magness, S. T. (2012). Distinct levels of Sox9 expression mark colon epithelial stem cells that form colonoids in culture. Am J Physiol Gastrointest Liver Physiol 302, G10-20.

Rankin, S. A., Gallas, A. L., Neto, A., Gomez-Skarmeta, J. L., and Zorn, A. M. (2012). Suppression of Bmp4 signaling by the zinc-finger repressors Osr1 and Osr2 is required for Wnt/beta-catenin-mediated lung specification in *Xenopus*. Development 139, 3010-3020.

Rankin, S. A., Thi Tran, H., Wlizla, M., Mancini, P., Shifley, E. T., Bloor, S. D., Han, L., Vleminckx, K., Wert, S. E., and Zorn, A. M. (2015). A Molecular atlas of *Xenopus* respiratory system development. Developmental dynamics: an official publication of the American Association of Anatomists 244, 69-85.

Ratineau, C., Duluc, I., Pourreyron, C., Kedinger, M., Freund, J. N., and Roche, C. (2003). Endoderm- and mesenchyme-dependent commitment of the differentiated epithelial cell types in the developing intestine of rat. Differentiation 71, 163-169.

Roberts, D. J., Johnson, R. L., Burke, A. C., Nelson, C. E., Morgan, B. A., and Tabin, C. (1995). Sonic Hedgehog Is an Endodermal Signal Inducing Bmp-4 and Hox Genes during Induction and Regionalization of the Chick Hindgut. Development 121, 3163-3174.

Rodriguez-Pineiro, A. M., Bergstrom, J. H., Ermund, A., Gustafsson, J. K., Schutte, A., Johansson, M. E., and Hansson, G. C. (2013). Studies of mucus in mouse stomach, small intestine, and colon. II. Gastrointestinal mucus proteome reveals Muc2 and Muc5ac accompanied by a set of core proteins. Am J Physiol Gastrointest Liver Physiol 305, G348-356.

Savidge, T. C., Morey, A. L., Ferguson, D. J., Fleming, K. A., Shmakov, A. N., and Phillips, A. D. (1995). Human intestinal development in a severe-combined immunodeficient xenograft model. Differentiation 58, 361-371.

Savin, T., Kurpios, N. A., Shyer, A. E., Florescu, P., Liang, H., Mahadevan, L., and Tabin, C. J. (2011). On the growth and form of the gut. Nature 476, 57-62.

Sheehan-Rooney, K., Swartz, M. E., Lovely, C. B., Dixon, M. J., and Eberhart, J. K. (2013). Bmp and Shh signaling mediate the expression of satb2 in the pharyngeal arches. PLoS One 8, e59533.

Sherwood, R. I., Chen, T. Y., and Melton, D. A. (2009). Transcriptional dynamics of endodermal organ formation. Developmental dynamics: an official publication of the American Association of Anatomists 238, 29-42.

Sherwood, R. I., Maehr, R., Mazzoni, E. O., and Melton, D. A. (2011). Wnt signaling specifies and patterns intestinal endoderm. Mech Dev 128, 387-400.

Shyer, A. E., Huycke, T. R., Lee, C., Mahadevan, L., and Tabin, C. J. (2015). Bending gradients: how the intestinal stem cell gets its home. Cell 161, 569-580.

Siegel, R., Desantis, C., and Jemal, A. (2014). Colorectal cancer statistics, 2014. CA Cancer J Clin 64, 104-117.

Spence, J. R., Mayhew, C. N., Rankin, S. A., Kuhar, M. F., Valiance, J. E., Tolle, K., Hoskins, E. E., Kalinichenko, V. V., Wells, Si., Zorn, A. M., et al. (2011). Directed differentiation of human pluripotent stem cells into intestinal tissue in vitro. Nature 470, 105-109.

Thanasupawat, T., Hammje, K., Adham, I., Ghia, J. E., Del Bigio, M. R., Krcek, J., Hoang-Vu, C., Klonisch, T., and Hombach-Klonisch, S. (2013). INSL5 is a novel marker for human enteroendocrine cells of the large intestine and neuroendocrine tumours. Oncol Rep 29, 149¬154.

Tiso, N., Filippi, A., Pauls, S., Bortolussi, M., and Argenton, F. (2002). BMP signalling regulates anteroposterior endoderm patterning in zebrafish. Mech Dev 118, 29-37.

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nat Protoc 7, 562-578.

Uppal, K., Tubbs, R. S., Matusz, P., Shaffer, K., and Loukas, M. (2011). Meckel's diverticulum: a review. Clin Anat 24, 416-422.

van Dop, W. A., Uhmann, A., Wijgerde, M., Sleddens-Linkels, E., Heijmans, J., Offerhaus, G. J., Weerman, M. A. V., Boeckxstaens, G. E., Hommes, D. W., Hardwick, J. C., et al. (2009). Depletion of the Colonic Epithelial Precursor Cell Compartment Upon Conditional Activation of the Hedgehog Pathway. Gastroenterology 136, 2195-2203.

van Klinken, B. J., Dekker, J., van Gool, S. A., van Marie, J., Buller, H. A., and Einerhand, A. W. (1998). MUCSB is the prominent mucin in human gallbladder and is also expressed in a subset of colonic goblet cells. The American journal of physiology 274, G871-878.

Walker, E. M., Thompson, C. A., and Battle, M. A. (2014). GATA4 and GATA6 regulate intestinal epithelial cytodifferentiation during development. Dev Biol 392, 283-294.

Walton, K. D., Kolterud, A., Czerwinski, M. J., Bell, M. J., Prakash, A., Kushwaha, J., Grosse, A. S., Schnell, S., and Gumucio, D. L. (2012). Hedgehog-responsive mesenchymal clusters direct patterning and emergence of intestinal villi. Proc Natl Acad Sci USA 109, 15817-15822.

Walton, K. D., Kolterud, A., Grosse, A. S., Hu, C. B., Czerwinski, M., Richards, N., and Gumucio, D. L. (2009). Epithelial Hedgehog signals direct mesenchymal villus patterning through BMP. Dev Biol 331, 489-489.

Walton, K. D., Whidden, M., Kolterud, A., Shoffner, S. K., Czerwinski, M. J., Kushwaha, J., Parmar, N., Chandhrasekhar, D., Freddo, A. M., Schnell, S., et al. (2016). Villification in the mouse: Bmp signals control intestinal villus patterning. Development 143, 427-436.

Wang, X., Yamamoto, Y., Wilson, L. H., Zhang, T., Howitt, B. E., Farrow, M. A., Kern, F., Ning, G., Hong, Y., Khor, C. C., et al. (2015). Cloning and variation of ground state intestinal stem cells. Nature 522, 173-178.

Watson, C. L., Mahe, M. M., Munera, J., Howell, J. C., Sundaram, N., Poling, H. M., Schweitzer, J. l., Valiance, J. E., Mayhew, C. N., Sun, Y., et al. (2014). An in vivo model of human small intestine using pluripotent stem cells. Nat Med 20, 1310-1314.

Wehkamp, J., Chu, H., Shen, B., Feathers, R. W., Kays, R. J., Lee, S. K., and Bevins, C. L. (2006). Paneth cell antimicrobial peptides: topographical distribution and quantification in human gastrointestinal tissues. FEBS Left 580, 5344-5350.

Whissell, G., Montagni, E., Martinelli, P., Hernando-Momblona, X., Sevillano, M., Jung, P., Cortina, C., Caton, A., Abuli, A., Castells, A., et al. (2014). The transcription factor GATA6 enables self-renewal of colon adenoma stem cells by repressing BMP gene expression. Nat Cell Biol 16, 695-707.

Wills, A., Dickinson, K., Khokha, M., and Baker, J. C. (2008). Bmp signaling is necessary and sufficient for ventrolateral endoderm specification in *Xenopus*. Developmental dynamics: an official publication of the American Association of Anatomists 237, 2177-2186.

Xue, X., Ramakrishnan, S., Anderson, E., Taylor, M., Zimmermann, E. M., Spence, J. R., Huang, S., Greenson, J. K., and Shah, Y. M. (2013). Endothelial PAS domain protein 1 activates the inflammatory response in the intestinal epithelium to promote colitis in mice. Gastroenterology 145, 831-841.

Yahagi, N., Kosaki, R., Ito, T., Mitsuhashi, T., Shimada, H., Tomita, M., Takahashi, T., and Kosaki, K. (2004). Position-specific expression of Hox genes along the gastrointestinal tract. Congenit Anom (Kyoto) 44, 18-26.

Zbuk, K. M., and Eng, C. (2007). Hamartomatous polyposis syndromes. Nat Clin Pract Gastr 4, 492-502.

Zorn, A. M., and Wells, J. M. (2009). Vertebrate endoderm development and organ formation. Annu Rev Cell Dev Biol 25, 221-251.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inducing formation of a human colon organoid (HCO), comprising the steps of
   (a) contacting a definitive endoderm (DE) with an FGF signaling pathway activator and a WNT signaling pathway activator for a period of time sufficient for said DE to form a mid-hindgut spheroid;
   (b) contacting the mid-hindgut spheroid of step (a) with a BMP activator and an EGF signaling pathway activator for about 1 day to about 3 days; and
   (c) contacting the mid-hindgut spheroid of step (b) with an EGF signaling pathway activator without a BMP activator for a period of time sufficient to form said human colon organoid, wherein said human colon organoid expresses SATB2.

2. The method of claim 1, wherein said DE is derived from a precursor cell selected from an embryonic stem cell, an induced pluripotent stem cell, a mesoderm cell, a definitive endoderm cell, a posterior endoderm cell, a hindgut cell or combinations thereof.

3. The method of claim 1, wherein said FGF signaling pathway activator is selected from a small molecule FGF signaling pathway activator, a protein-based FGF signaling pathway activator, FGF1, FGF2, FGF3, FGF4, FGF10, FGF11, FGF12, FGF13, FGF14, FGF15, FGF16, FGF17, FGF18, FGF19, FGF20, FGF21, FGF22, FGF23, or combinations thereof.

4. The method of claim 1, wherein said WNT signaling pathway activator is selected from a protein Wnt signaling pathway activator, a small molecule Wnt signaling pathway activator, or combinations thereof.

5. The method of claim 1, wherein said BMP activator is selected from BMP2, BMP4, BMP7, BMP9, a small molecule that activates the BMP pathway, a protein that activates the BMP pathway, ventromorphins, and combinations thereof.

6. The method of claim 1, wherein said period of time sufficient for said DE to form a mid-hindgut spheroid is determined by expression of CDX2 by said mid-hindgut spheroid of step (a).

7. The method of claim 1, wherein said period of time sufficient for said mid-hindgut spheroid to form said human colon organoid is determined by expression of SATB2 and CDX2 by a cell of said human colon organoid.

8. The method of claim 1, wherein said HCO comprises colonic enteroendocrine cells (EEC).

9. The method of claim 1, wherein said HCO comprises crypts and is free of villi.

10. The method of claim 1, wherein said HCO comprises colon-specific goblet cells.

11. The method of claim 1, wherein said HCO is substantially free of Paneth cells.

12. The method of claim 1, wherein said HCO secretes colon-specific hormone INSL5.

13. The method of claim 4, wherein the WNT signaling pathway activator is selected from Lithium Chloride; 2-amino-4,6-disubstituted pyrimidine (hetero) arylpyrimidines; IQ1; QS11; NSC668036; DCA beta-catenin; 2-amino-4-[3,4-(methylenedioxy)-benzyl-amino]-6-(3-methoxyphenyl) pyrimidine; Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16, a GSK3 inhibitor, and CHIR99021.

14. The method of claim 4, wherein the WNT signaling pathway activator is CHIR99021.

15. The method of claim 1, wherein said contacting the mid-hindgut spheroid of step (b) with a BMP activator and an EGF signaling pathway activator is for about 3 days.

16. The method of claim 3, wherein said FGF signaling pathway activator is FGF4.

17. The method of claim 16, wherein said FGF4 is provided at a concentration of about 200-1000 ng/ml.

18. The method of claim 16, wherein said FGF4 is provided at a concentration of about 500 ng/mL.

19. The method of claim 14, wherein said CHIR99021 is provided at a concentration of about 1-50 µM.

20. The method of claim 14, wherein said CHIR99021 is provided at a concentration of about 3 µM.

21. The method of claim 5, wherein said BMP activator is BMP2.

22. The method of claim 21, wherein said BMP2 is provided at a concentration of about 50-500 ng/ml.

23. The method of claim 21, wherein said BMP2 is provided at a concentration of about 100 ng/mL.

24. The method of claim 1, wherein said EGF signaling activator is selected from EGF, TGF alpha, HB-EGF, Amphiregulin, Epigen, Betacellulin, and small molecules such as db-cAMP, and combinations thereof.

25. The method of claim 24, wherein said EGF signaling pathway activator is EGF.

26. The method of claim 25, wherein said EGF is provided at a concentration of about 50-500 ng/mL.

27. The method of claim 25, wherein said EGF is provided at a concentration of about 100 ng/ml.

28. The method of claim 15, wherein the FGF signaling pathway activator is FGF4, the WNT signaling pathway activator is CHIR99021, the BMP activator is BMP2, and the EGF signaling pathway activator is EGF.

29. The method of claim 28, wherein the DE is derived from an induced pluripotent stem cell.

30. The method of claim 28, wherein the FGF4 is provided at a concentration of about 500 ng/ml, the CHIR99021 is provided at a concentration of about 3 µM, the BMP2 is provided at a concentration of about 100 ng/ml, and the EGF is provided at a concentration of about 100 ng/ml.

31. The method of claim 30, wherein the DE is derived from an induced pluripotent stem cell.

* * * * *